(12) United States Patent
Schaffer et al.

(10) Patent No.: US 11,680,249 B2
(45) Date of Patent: Jun. 20, 2023

(54) ADENO-ASSOCIATED VIRUS CAPSID VARIANTS AND METHODS OF USE THEREOF

(71) Applicant: The Regents of the University of California, Oakland, CA (US)

(72) Inventors: David V. Schaffer, Danville, CA (US); David Stephen Ojala, Berkeley, CA (US); Philip A. Romero, Madison, WI (US)

(73) Assignee: The Regents of the University of California, Oakland, CA (US)

( * ) Notice: Subject to any disclaimer, the term of this patent is extended or adjusted under 35 U.S.C. 154(b) by 834 days.

(21) Appl. No.: 16/500,706

(22) PCT Filed: Aug. 22, 2018

(86) PCT No.: PCT/US2018/047561
§ 371 (c)(1),
(2) Date: Oct. 3, 2019

(87) PCT Pub. No.: WO2019/046069
PCT Pub. Date: Mar. 7, 2019

(65) Prior Publication Data
US 2020/0095559 A1    Mar. 26, 2020

Related U.S. Application Data

(60) Provisional application No. 62/551,133, filed on Aug. 28, 2017.

(51) Int. Cl.
| | | |
|---|---|---|
| *C12N 7/00* | (2006.01) | |
| *A61P 25/28* | (2006.01) | |
| *A61K 35/761* | (2015.01) | |
| *C07K 14/005* | (2006.01) | |
| *C12N 15/86* | (2006.01) | |

(52) U.S. Cl.
CPC ............ *C12N 7/00* (2013.01); *A61K 35/761* (2013.01); *A61P 25/28* (2018.01); *C07K 14/005* (2013.01); *C12N 15/86* (2013.01); *C12N 2750/14122* (2013.01); *C12N 2750/14133* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,773,700 A | 6/1998 | Grinsven et al. |
| 6,096,548 A | 8/2000 | Stemmer |
| 6,482,634 B1 | 11/2002 | Wilson et al. |
| 6,491,907 B1 | 12/2002 | Rabinowitz et al. |
| 6,596,539 B1 | 7/2003 | Stemmer et al. |
| 6,703,237 B2 | 3/2004 | Samulski et al. |
| 6,710,036 B2 | 3/2004 | Kurtzman et al. |
| 6,733,757 B2 | 5/2004 | Patel et al. |
| 6,855,314 B1 | 2/2005 | Chiorini et al. |
| 6,943,153 B1 | 9/2005 | Manning, Jr. et al. |
| 6,962,815 B2 | 11/2005 | Bartlett |
| 7,172,893 B2 | 2/2007 | Rabinowitz et al. |
| 7,252,997 B1 | 8/2007 | Hallek et al. |
| 7,254,489 B2 | 8/2007 | Mossel |
| 7,285,381 B1 | 10/2007 | Hallek et al. |
| 7,314,912 B1 | 1/2008 | Hallek et al. |
| 7,368,428 B2 | 5/2008 | Serrero |
| 7,427,396 B2 | 9/2008 | Arbetman et al. |
| 7,556,965 B2 | 7/2009 | Hallek et al. |
| 7,629,322 B2 | 12/2009 | Kleinschmidt et al. |
| 7,749,492 B2 | 7/2010 | Bartlett et al. |
| 7,968,340 B2 | 6/2011 | Hallek et al. |
| 8,524,446 B2 | 9/2013 | Gao et al. |
| 8,574,583 B2 | 11/2013 | Kay et al. |
| 8,632,764 B2 | 1/2014 | Xiao et al. |
| 8,663,624 B2 | 3/2014 | Schaffer et al. |
| 9,193,956 B2 | 11/2015 | Schaffer et al. |

(Continued)

FOREIGN PATENT DOCUMENTS

| | | |
|---|---|---|
| AU | 2014331708 | 5/2016 |
| CA | 2379220 | 1/2001 |

(Continued)

OTHER PUBLICATIONS

Lee at al. Adeno-associated Virus (AAV) Vectors: Rational Design Strategies for Capsid Engineering. Current Opinion in Biomedical Engineering, 2018. 7:58-63.*

(Continued)

*Primary Examiner* — James D Schultz
*Assistant Examiner* — Kimberly A Aron
(74) *Attorney, Agent, or Firm* — Shweta Chandra; Bozicevic, Field & Francis LLP

(57) ABSTRACT

The present disclosure provides recombinant adeno-associated virus virions with variant capsid protein, where the recombinant AAV (rAAV) virions exhibit one or more of increased ability to cross neuronal cell barriers, increased infectivity of a neural stem cell, increased infectivity of a neuronal cell, and reduced susceptibility to antibody neutralization, compared to a control AAV, and where the rAAV virions comprise a heterologous nucleic acid. The present disclosure provides methods of delivering a gene product to a neural stem cell or a neuronal cell in an individual. The present disclosure also provides methods of modifying a target nucleic acid present in a neural stem cell or neuronal cell.

18 Claims, 46 Drawing Sheets

Specification includes a Sequence Listing.

(56) References Cited

U.S. PATENT DOCUMENTS

| | | | |
|---|---|---|---|
| 9,233,131 B2 | 1/2016 | Schaffer et al. | |
| 9,441,244 B2 | 9/2016 | Schaffer et al. | |
| 9,587,282 B2 | 3/2017 | Schaffer et al. | |
| 11,021,519 B2 | 6/2021 | Chalberg et al. | |
| 11,167,041 B2 | 11/2021 | Kim et al. | |
| 2002/0136710 A1 | 9/2002 | Samulskl et al. | |
| 2002/0155610 A1 | 10/2002 | Colosi | |
| 2002/0192823 A1 | 12/2002 | Bartlett | |
| 2003/0138772 A1* | 7/2003 | Gao | A61P 5/14 435/456 |
| 2003/0143732 A1 | 7/2003 | Fosnaugh et al. | |
| 2003/0171254 A1 | 9/2003 | Sasaki et al. | |
| 2003/0228284 A1 | 12/2003 | McCown et al. | |
| 2004/0180440 A1 | 9/2004 | Zolotukhin | |
| 2005/0019927 A1 | 1/2005 | Hildinger et al. | |
| 2005/0053922 A1 | 3/2005 | Schaffer | |
| 2005/0089973 A1 | 4/2005 | Yocum et al. | |
| 2005/0106558 A1 | 5/2005 | Perabo et al. | |
| 2005/0148069 A1 | 7/2005 | Gage et al. | |
| 2005/0220766 A1 | 10/2005 | Amalfitano et al. | |
| 2005/0287122 A1 | 12/2005 | Bartlett et al. | |
| 2006/0051333 A1 | 3/2006 | Arbetman et al. | |
| 2006/0292117 A1 | 12/2006 | Loiler et al. | |
| 2007/0020624 A1 | 1/2007 | Rubenfield et al. | |
| 2007/0036760 A1 | 2/2007 | Wilson et al. | |
| 2007/0172460 A1 | 7/2007 | Kleinschmidt et al. | |
| 2007/0196338 A1 | 8/2007 | Samulski et al. | |
| 2008/0269149 A1 | 10/2008 | Bowles et al. | |
| 2009/0202490 A1 | 8/2009 | Schaffer et al. | |
| 2010/0166729 A9 | 7/2010 | Madison et al. | |
| 2010/0172871 A1 | 7/2010 | Flannery et al. | |
| 2011/0104120 A1 | 5/2011 | Xiao et al. | |
| 2011/0171262 A1 | 7/2011 | Bakker et al. | |
| 2011/0236353 A1 | 9/2011 | Wilson et al. | |
| 2012/0093772 A1 | 4/2012 | Horsager et al. | |
| 2013/0323302 A1 | 12/2013 | Constable et al. | |
| 2014/0242031 A1 | 8/2014 | Schaffer et al. | |
| 2014/0294771 A1 | 10/2014 | Schaffer et al. | |
| 2014/0364338 A1 | 12/2014 | Schaffer et al. | |
| 2015/0118201 A1 | 4/2015 | Xiao et al. | |
| 2015/0152142 A1 | 6/2015 | Asokan et al. | |
| 2015/0225702 A1 | 8/2015 | Schaffer et al. | |
| 2015/0232953 A1 | 8/2015 | Schaffer et al. | |
| 2015/0315610 A1 | 11/2015 | Nishie et al. | |
| 2016/0017295 A1 | 1/2016 | Schaffer et al. | |
| 2016/0102324 A1 | 4/2016 | Duchateau et al. | |
| 2016/0184394 A1 | 6/2016 | Schaffer et al. | |
| 2017/0096683 A1 | 4/2017 | Scaria et al. | |
| 2019/0255192 A1 | 8/2019 | Kirn et al. | |
| 2019/0300579 A1 | 10/2019 | Dudman et al. | |

FOREIGN PATENT DOCUMENTS

| | | |
|---|---|---|
| CN | 1325451 A | 12/2001 |
| CN | 1826414 A | 8/2006 |
| CN | 1966082 A | 5/2007 |
| CN | 101484005 A | 7/2009 |
| CN | 101532024 A | 9/2009 |
| CN | 103561774 A | 2/2014 |
| CN | 106232618 A | 10/2014 |
| JP | 2008-523813 A | 7/2008 |
| WO | WO 1997/038723 | 10/1997 |
| WO | WO 1999/067393 | 12/1999 |
| WO | WO 2000/028004 | 5/2000 |
| WO | WO 2001/070276 | 9/2001 |
| WO | WO 2002/053703 | 7/2002 |
| WO | WO 2003/018820 | 3/2003 |
| WO | WO 2003/023032 | 3/2003 |
| WO | WO 2003/054197 | 7/2003 |
| WO | WO 2003/093436 | 11/2003 |
| WO | 2004083441 | 9/2004 |
| WO | WO 2004/108922 | 12/2004 |
| WO | WO 2004/112727 | 12/2004 |
| WO | WO 2005/005610 | 1/2005 |
| WO | WO 2005/033321 | 4/2005 |
| WO | WO 2006/066066 | 6/2006 |
| WO | WO 2006/110689 | 10/2006 |
| WO | WO 2007/120542 | 10/2007 |
| WO | WO 2008/131951 | 11/2008 |
| WO | WO 2009/137006 | 11/2009 |
| WO | WO 2009/154452 | 12/2009 |
| WO | WO 2010/093784 | 8/2010 |
| WO | WO 2010/138263 | 12/2010 |
| WO | WO 2011/117258 | 9/2011 |
| WO | WO 2012/145601 | 10/2012 |
| WO | WO 2013/029030 | 2/2013 |
| WO | WO 2013/170078 | 11/2013 |
| WO | WO 2013/173512 | 11/2013 |
| WO | WO 2014/124282 | 8/2014 |
| WO | 2014207190 A1 | 12/2014 |
| WO | WO 2014/194132 | 12/2014 |
| WO | WO 2015/048534 | 4/2015 |
| WO | WO 2015/054653 | 4/2015 |
| WO | 2015121501 | 8/2015 |
| WO | WO 2015/142941 | 9/2015 |
| WO | WO 2015/191693 | 12/2015 |
| WO | 2016134375 | 8/2016 |
| WO | WO 2016/141078 | 9/2016 |
| WO | WO 2016/144892 | 9/2016 |
| WO | WO 2017/023724 | 2/2017 |
| WO | WO 2017/197355 | 11/2017 |
| WO | WO 2019/046069 | 3/2019 |

OTHER PUBLICATIONS

Koerber et al. DNA Shuffling of Adeno-associated Virus Yields Functionally Diverse Viral Progeny. Molecular Therapy, 2008. 16(10): 1703-1709, with Supplement.*

Popa-Wagner, et al.; "Impact of VP1-Specific Protein Sequence Motifs on Adeno-Associated Virus Type 2 Intracellular Trafficking and Nuclear Entry"; Journal of Virology; vol. 86, No. 17, pp. 9163-9174 (Sep. 2012).

Rayaprolu, et al.; "Comparative Analysis of Adeno-Associated Virus Capsid Stability and Dynamics"; Journal of Virology; vol. 87, No. 24, pp. 13150-13160 (Dec. 2013).

Venkatakrishnan, et al.; "Structure and Dynamics of Adeno-Associated Virus Serotype 1 VP1-Unique N-Terminal Domain and Its Role in Capsid Trafficking"; Journal of Virology; vol. 87, No. 9, pp. 4974-4984 (May 2013).

UniProtKB database: B4Y881_9VIRU; "Capsid protein VP1, adeno-associated virus"; 6 pages (Sep. 23, 2008).

Cronin, et al.; "Efficient transduction and optogenetic stimulation of retinal bipolar cells by a synthetic adeno-associated virus capsid and promoter"; EMBO Molecular Medicine; 16 pages (2014).

Khabou, et al.; "Insight Into the Mechanisms of Enhanced Retinal Transduction by the Engineered AAV2 Capsid Variant-7m8"; Biotechnology and Bioengineering; vol. 113, No. 12, pp. 2712-2724 (Dec. 2016).

Ortolano, et al.; "Present and Future of Adeno Associated Virus Based Gene Therapy Approaches"; Recent Patents on Endocrine, Metabolic & Immune Drug Discovery; vol. 6, pp. 47-66 (2012).

Jeune, et al.; "Pre-existing Anti-Adeno-Associated Virus Antibodies as a Challenge in AAV Gene Therapy"; Human Gene Therapy Methods; vol. 24, pp. 59-67 (Apr. 2013).

Kotterman, et al.; "Enhanced selective gene delivery to neural stem cells in vivo by an adeno-associated viral variant"; Development; vol. 142, pp. 1885-1892 (2015).

Miyake, et al.; "Global gene transfer into the CNS across the BBB after neonatal systemic delivery of single-stranded AAV vectors"; Brain Research; vol. 1389, pp. 19-26 (2011).

Shao, et al.; "Gene Transfer to the Gastrointestinal Tract After Peroral Administration of Recombinant Adeno-associated Virus Type 2 Vectors"; Journal of Pediatric Gastroenterology and Nutrition; vol. 43, pp. 168-179 (Aug. 2006).

Tervo, et al.; "A Designer AAV Variant Permits Efficient Retrograde Access to Projection Neurons"; Neuron; vol. 92, pp. 372-382 (2016).

(56) References Cited

OTHER PUBLICATIONS

Willett, et al.; "Immunology of AAV-mediated gene transfer in the eye"; Frontiers in Immunology; vol. 4, No. 261, 8 pages (Aug. 2013).
Yu; "Current Approaches and Future Directions of Gene Therapy in Alzheimer's Disease"; Neurochemical Journal; vol. 5, No. 3, pp. 159-168 (2011).
Zincarelli, et al.; "Analysis of AAV Serotypes 1-9 Mediated Gene Expression and Tropism in Mice After Systemic Injection"; Molecular Therapy; vol. 16, No. 6, pp. 1073-1080 (Jun. 2008).
Jang, et al.; "An Evolved Adena-associated Viral Variant Enhances Gene Delivery and Gene Targeting in Neural Stem Cells"; Molecular Therapy; vol. 19, No. 4, pp. 667-675 (Apr. 2011).
Koerber, et al.; "DNA Shuffling of Adena-associated Virus Yields Functionally Diverse Viral Progeny"; Molecular Therapy; vol. 16, No. 10, pp. 1703-1709 (Oct. 2008).
Adachi, et al.; "A New Recombinant Adeno-Associated Virus (AAV)-Based Random Peptide Display Library System: Infection-Defective AAV1.9-3 As A Novel Detargeted Platform for Vector Evolution"; Gene Therapy and Regulation; vol. 5, No. 1, pp. 31-55 (Oct. 2010).
Akiyama, et al.; "Intraocular Injection of an Aptamer that Binds PDGF-B: A Potential Treatment for Proliferative Retinopathies"; Journal of Cellular Physiology; vol. 207, pp. 407-412 (2006).
Ali, et al.; "Restoration of photoreceptor ultrastructure and function in retinal degeneration slow mice by gene therapy"; Nature Genetics; vol. 25, pp. 306-310 (Jul. 2000).
Allocca, et al.; "Novel adeno-associated virus serotypes efficiently transduce murine photoreceptors"; Journal of Virology; vol. 81, No. 20, pp. 11372-11380 (Oct. 2007).
Asokan, et al., "Reengineering a receptor footprint of adeno-associated virus enables selective and systemic gene transfer to muscle"; Nat Biotechnol; vol. 28, No. 1, pp. 79-82 (Jan. 2010).
Asuri, et al.; "Directed Evolution of Adena-associated Virus for Enhanced Gene Delivery and Gene Targeting in Human Pluripotent Stem Cells"; Molecular Therapy, vol. 20, No. 2, pp. 329-338 (Feb. 1, 2012).
Attached Score Report Result Per SEQ ID No. 17 per US2002/0192823 to Bartlett Published Dec. 19, 2002.
Bichsel, et al.; "Bacterial delivery of nuclear proteins into pluripotent and differentiated cells"; PLoS One; vol. 6, No. 1, pp. 1-9 (Jan. 2011).
Blacklow, et al.; "A Seroepidemiologic Study of Adenovirus-Associated Virus Infection in Infants and Children"; Am J Epidemiol.; vol. 94, No. 4, pp. 359-366 (Oct. 1971).
Boucas, et al.; "Engineering adeno-associated virus serotype 2-based targeting vectors using a new insertion site-position 453-and single point mutations"; J Gene Med.; vol. 11, No. 12, pp. 1103-1113 (Dec. 2009).
Buch, et al., "in Contrast to AAC-Mediated Cntf Expression, AAV-Mediated Gdnf Expression Enhances Gene Replacement Therapy in Rodent Models of Retinal Degeneration"; Molecular Therapy; vol. 14, No. 5, pp. 700-709 (Nov. 2006).
Buning, et al., "Receptor targeting of adeno-associated virus vectors"; Gene Therapy; vol. 10, pp. 1142-1151 (2003).
Chadderton, et al.; "Improved Retinal Function in a Mouse Model of Dominant Retinitis Pigmentosa Following AAV-delivered Gene Therapy"; Molecular Therapy; vol. 17, No. 4, pp. 593-599 (Apr. 2009).
Choi, et al.; "AAV Hybrid Serotypes: Improved Vectors for Gene Delivery."; Current Gene Therapy; vol. 5, No. 3, pp. 299-310 (Jun. 2005).
Dalkara, et al.; "In Vivo-Directed Evolution of a New Adeno-Associated Virus for Therapeutic Outer Retinal Gene Delivery from the Vitreous"; Science Translational Medicine; vol. 5, Issue 187, 11 pages (Jun. 12, 2013).
Dalkara, et al.; "Developing Photoreceptor Targeted AAV Variant by Directed Evolution"; ARVO Annual Meeting Abstract Search and Program Planner; vol. 2011, pp. 4381 (May 2011).
Database Geneseq [Online] Oct. 16, 2008 (Oct. 16, 2008), "Modified Adena-associated virus (hu.44) capsid protein, VP1, hu.44R2.", retrieved from EBI accession No. GSP:AEL63853, Database accession No. AEL63853.
Database Geneseq [Online] Oct. 16, 2008 (Oct. 16, 2008), "Modified Adena-associated virus (hu.44) capsid protein, VP1, hu.44R3.", retrieved from EBI accession No. GSP:AEL63854, Database accession No. AEL63854.
Davidson, et al.; "Recombinant adeno-associated virus type 2, 4, and 5 vectors: transduction of variant cell types and regions in the mammalian central nervous system."; Proc Natl Acad Sci USA.; vol. 97, No. 7, pp. 3428-3432 (Mar. 28, 2000).
Day, et al.; "Advances in AAV Vector Development for Gene Therapy in the Retina"; Adv. Exp. Med. Biol.; vol. 801, pp. 687-693 (2014).
Den Dunnen, et al.; "Mutation nomenclature extensions and suggestions to describe complex mutations: a discussion."; Human Mutation; vol. 15, pp. 7-12 (2000).
Diprimio, et al.; "Surface loop dynamics in adeno-associated virus capsid assembly"; Journal of Virology; vol. 82, No. 11, pp. 5178-5189 (Jun. 2008).
Erles, et al.; "Update on the prevalence of serum antibodies (IgG and IgM) to adeno-associated virus (AAV)."; J Med Virol.; vol. 59, No. 3, pp. 406-411 (Nov. 1999).
Excoffon, et al.; "Directed evolution of adeno-associated virus to an infectious respiratory virus"; Proc Natl Acad Sci USA; vol. 106, No. 10, pp. 3865-3870 (Mar. 10, 2009).
Flotte, et al.; "Gene expression from adeno-associated virus vectors in airway epithelial cells"; Am J Respir Cell Mol Biol.; vol. 7, No. 3, pp. 349-356 (Sep. 1992).
Gen Bank accession No. AAZ79678; rat AAV1 VP3 capsid protein sequence downloaded from NCBI; downloaded on Nov. 3, 2008.
GenBank accession No. ABZ10812; AAV13 capsid protein sequence downloaded from NCBI; downloaded on Nov. 3, 2008.
Girod, et al.; "Genetic capsid modifications allow efficient re-targeting of adeno-associated virus type 2"; Nat. Med.; vol. 5, No. 9, pp. 1052-1056 (Sep. 1999).
Gray, et al.; "Directed Evolution of a Novel Adeno-associated Virus (AAV) Vector That Crosses the Seizure-compromised Blood-Brain Barrier (BBB)"; Molecular Therapy; vol. 18, No. 3, pp. 570-578 (2010).
Gregory-Evans, et al.; "Ex vivo Gene Therapy Using Intravitreal Injection of GDNF-secreting Mouse Embryonic Stem Cells in a Rat Model of Retinal Degeneration"; Molecular Vision; vol. 15, pp. 962-973 (May 13, 2009).
Grieger, et al.; "Separate basic region motifs within the adeno-associated virus capsid proteins are essential for infectivity and assembly"; Journal of Virology; vol. 80, No. 11, pp. 5199-5210 (2006).
Grifman, et al.; "Incorporation of tumor-targeting peptides into recombinant adeno-associated virus capsids"; Molecular Therapy; vol. 3, No. 6, pp. 964-975 (Jun. 2001).
Grimm, et al.; "In Vitro and In Vivo Gene Therapy Vector Evolution via Multispecies Interbreeding and Retargeting of Adeno-Associated Viruses"; Journal of Virology; vol. 82, No. 12, pp. 5887-5911 (Jun. 2008).
Halbert, et al.; "Repeat transduction in the mouse lung by using adeno-associated virus vectors with different serotypes." J. Virol.; vol. 74, No. 3, pp. 1524-1532 (Feb. 2000).
Hellstrom, et al.; "Cellular tropism and transduction properties of seven adeno-associated viral vector serotypes in adult retina after intravitreal injection"; Gene Therapy; vol. 16, pp. 521-532 (2009).
Hirsch, et al.; "Directed Evolution of the AAV Capsid for Human Embryonic Stem Cell Transduction"; Molecular Therapy; vol. 17, Supp. 1, S177-S178 (May 2009).
Huttner, et al. "Genetic Modifications of the Adeno-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002).

(56) References Cited

OTHER PUBLICATIONS

Huttner, et al.; "Genetic modifications of the adeno-associated virus type 2 capsid reduce the affinity and the neutralizing effects of human serum antibodies."; Gene Ther; vol. 10, pp. 2139-2147 (Dec. 2003).

Karp, et al.; "An in vitro model of differentiated human airway epithelia, Methods for establishing primary cultures"; Methods Mol Biol.; vol. 188, pp. 115-137 (2002).

Kern, et al.; "Identification of a heparin-binding motif on adeno-associated virus type 2 capsids"; Journal of Virology; vol. 77, No. 20, pp. 11072-11081 (Oct. 2003).

Khani, et al.; "AAV-Mediated Expression Targeting of Rod and Cone Photoreceptors with a Human Rhodopsin Kinase Promoter"; Investigative Ophthalmology & Visual Science; vol. 48, No. 9, pp. 3954-3961 (Sep. 2007).

Klimczak, et al.; "A Novel Adeno-Associated Viral Variant for Efficient and Selective Intravitreal Transduction of Rat Muller Cells"; PLoS ONE; vol. 4, No. 10, pp. 1-10 (Oct. 2009).

Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 116 pages (2010).

Koerber, et al.; "Engineering of a Novel AAV Vector In a Human Airway Model System for Cystic Fibrosis Gene Therapy"; AIChE Annual Meeting Abstract, 3 pages (Nov. 29, 2008).

Koerber, et al.; "Molecular Evolution of Adeno-associated Virus for Enhanced Glial Gene Delivery", Molecular Therapy; vol. 17, No. 12, pp. 2088-2095 (Dec. 2009).

Kotterman, et al.; "Engineering adeno-associated viruses for clinical gene therapy"; Nat Rev Genet; vol. 15, No. 7, pp. 445-451 (Jul. 1, 2014).

Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).

Lai, et al.; "Long-term evaluation of AAV-mediated sFlt-1 gene therapy for ocular neovascularization in mice and monkeys"; Mol Ther.; vol. 12, No. 4, pp. 659-668 (Oct. 2005).

Li, et al.; "Engineering and Selection of Shuffled AAV Genomes: A New Strategy for Producing Targeted Biological Nanoparticles"; Molecular Therapy; vol. 16, No. 7, pp. 1252-1260 (Jul. 2008).

Li, et al.; "Generation of Novel AAV Variants by Directed Evolution for Improved CFTR Delivery to Human Ciliated Airway Epithelium"; Molecular Therapy; vol. 17, No. 12, pp. 2067-2077 (Dec. 2009).

Limberis, et al.; "Adeno-associated virus serotype 9 vectors transduce murine alveolar and nasal epithelia and can be readministered"; Proc Natl Acad Sci USA; vol. 103, No. 35, pp. 12993-12998 (Aug. 29, 2006).

Loiler, et al.; "Targeting recombinant adeno-associated virus vectors to enhance gene transfer to pancreatic islets and liver"; Gene Ther.; vol. 10, pp. 1551-1558 (2003).

Maguire, et al.; "Directed evolution of adeno-associated virus for glioma cell transduction"; J. Neurooncol.; vol. 96, pp. 337-347 (2010).

Maheshri, et al.; "Directed evolution of adeno-associated virus yields enhanced gene delivery vectors"; Nature Biotechnology; vol. 24, No. 2, pp. 198-204 (Feb. 2006).

McCullum, et al.; "Random Mutagenesis by Error-Prone PCR"; Methods Mol Biol.; vol. 634, pp. 103-109; doi: 10.1007/978-1-60761-652-8_7 (2010).

McGee, et al., "Glial Cell Line Derived Neurotrophic Factor Delays Photoreceptor in a Transgenic Rat Model of Retinitis Pigmentosa"; Molecular Therapy; vol. 4, No. 6, pp. 622-629 (Dec. 2001).

Michelfelder, et al.; "Successful Expansion but Not Complete Restriction of Tropism of Adeno-Associated Virus by In Vivo Biopanning of Random Virus Display Peptide Libraries"; PLoS One; vol. 4, No. 4, pp. 1-13 (Apr. 2009).

Michelfelder, et al.; "Vectors selected from adeno-associated viral display peptide libraries for leukemia cell-targeted cytotoxic gene therapy"; Experimental Hematology; vol. 35, pp. 1766-1776 (2007).

Mitchell, et al.; "AAV's anatomy: Roadmap for optimizing vectors for translational success"; Curr Gene Ther.; vol. 10, No. 5, pp. 319-340 (Oct. 2010).

Moskalenko, et al.; "Epitope mapping of human anti-adeno-associated virus type 2 neutralizing antibodies: implications for gene therapy and virus structure."; J. Virol.; vol. 74, No. 4, pp. 1761-1766 (Feb. 2000).

Muller, et al.; "Random peptide libraries displayed on adeno-associated virus to select for targeted gene therapy vectors"; Nat Biotechnol; vol. 21, No. 9, pp. 1040-1046 (Sep. 2003).

Nguyen, et al.; "Convection-enhanced delivery of AAV-2 combined with heparin increases TK gene transfer in the rat brain."; Neuroreport; vol. 12, No. 9, pp. 1961-1964 (Jul. 3, 2001).

Nicklin, et al.; "Efficient and selective AAV2-mediated gene transfer directed to human vascular endothelial cells"; Mol. Ther.; vol. 4, No. 2, pp. 174-181 (Aug. 2001).

Opie, et al.; "Identification of Amino Acid Residues in the Capsid Proteins of Adeno-Associated Virus Type 2 that Contribute to Heparan Sulfate Proteoglycan Binding"; Journal of Virology; vol. 77, No. 12, pp. 6995-7006 (Jun. 2003).

Paddison, et al.; "Stable suppression of gene expression by RNAi in mammalian cells"; Proc. Nat'l Acad. Sci. USA; vol. 99, No. 3, pp. 1443-1448 (Feb. 5, 2002).

Padron, et al.; "Structure of adeno-associated virus type 4"; Journal of Virology; vol. 79, No. 8, pp. 5047-5058 (Apr. 2005).

Park, et al.; "Intravitreal delivery of AAV8 retinoschisin results in cell type-specific gene expression and retinal rescue in the Rs1-KO mouse"; Gene Therapy; vol. 16, pp. 916-926 (2009).

Pechan, et al.; "Novel anti-VEGF chimeric molecules delivered by AAV vectors for inhibition of retinal neovascularization."; Gene. Ther.; vol. 16, No. 1, pp. 10-16 (Jan. 2009).

Perabo, et al.; "Combinatorial engineering of a gene therapy vector: directed evolution of adeno-associated virus"; The Journal of Gene Medicine; vol. 8, No. 2, pp. 155-162 (Feb. 2006).

Perabo, et al.; "Heparan Sulfate Proteoglycan Binding Properties of Adeno- Associated Virus Retargeting Mutants and Consequences for Their In Vivo Tropism"; Journal of Virology; vol. 80, No. 14, pp. 7265-7269 (Jul. 2006).

Perabo, et al.; "In Vitro Selection of Viral Vectors with Modified Tropism: The Adeno-associated Virus Display"; Molecular Therapy; vol. 8, No. 1, pp. 151-157 (Jul. 2003).

Petrs-Silva, et al.; "High-efficiency transduction of the mouse retina by tyrosine-mutant AAV serotype vectors"; Molecular Therapy; vol. 17, No. 3, pp. 463-471 (Mar. 2009).

Rabinowitz, et al.; "Building a Better Vector: The Manipulation of AAV Virions"; Virology; vol. 278, pp. 301-308 (2000).

Rabinowitz, et al.; "Insertional mutagenesis of AAV2 capsid and the production of recombinant virus."; Virology; vol. 265, No. 2, pp. 274-285 (Dec. 20, 1999).

Ried, et al.; "Adeno-associated virus capsids displaying immuno-globulin-binding domains permit antibody-mediated vector retargeting to specific cell surface receptors"; J. Virol.; vol. 76, No. 9, pp. 4559-4566 (May 2002).

Ryals, et al.; "Quantifying transduction efficiencies of unmodified and tyrosine capsid mutant AAV vectors in vitro using two ocular cell lines"; Mol Vision; vol. 17, pp. 1090-1102 (Apr. 2011).

Santiago-Ortiz, et al.; "AAV Ancestral Reconstruction Library Enables Selection of Broadly Infectious Viral Variants"; Gene. Ther.; vol. 22, No. 12, pp. 934-946 (Dec. 2015).

Schaffer, et al.; "Directed evolution of AAV vector mutants for enhanced gene delivery"; Abstracts of Papers American Chemical Society; vol. 227, Part 1, p. U214 (Mar. 2004).

Score result 33 for Arbetman et al. WO2004112727-A2, Dec. 29, 2004.

Shen, et al.; "Characterization of the relationship of AAV capsid domain swapping to liver transduction efficiency"; Mol Ther.; vol. 15, No. 11, pp. 1955-1962 (Aug. 28, 2007).

Shen, et al.; "Multiple Roles for Sialylated Glycansin Determining the Cardiopulmonary Tropism of Adeno-Associated Virus 4"; Journal of Virology; vol. 87, No. 24, pp. 13206-13213 (Dec. 2013).

(56) References Cited

OTHER PUBLICATIONS

Shi, et al.; "Capsid modifications overcome low heterogeneous expression of heparan sulfate proteoglycan that limits AAV2-mediated gene transfer and therapeutic efficacy in human ovarian carcinoma"; Gynecol. Oncol.; vol. 103, pp. 1054-1062 (2006).
Shi, et al.; "Insertional mutagenesis at positions 520 and 584 of adeno-associated virus type 2 (AAV2) capsid gene and generation of AAV2 vectors with eliminated heparin-binding ability and introduced novel tropism"; Hum. Gene Ther.; vol. 17, pp. 353-361 (Mar. 2006).
Shi, et al.; "RGD inclusion in VP3 provides adeno-associated virus type 2 (AAV2)-based vectors with a heparan sulfate-independent cell entry mechanism"; Mol. Ther.; vol. 7, No. 4, pp. 515-525 (Apr. 2003).
Shi, W. et al.; "Insertional Mutagenesis of the Adeno-Associated Virus Type 2 (AAV2) Capsid Gene and Generation of AAV2 Vectors Targeted to Alternative Cell-Surface Receptors"; Human Gene Therapy; vol. 12, pp. 1697-1711 (Sep. 20, 2001).
Sonntag, et al.; "Adeno-associated virus type 2 capsids with externalized VP1/VP2 trafficking domains are generated prior to passage through the cytoplasm and are maintained until uncoating occurs in the nucleus"; Journal of Virology; vol. 80, No. 22, pp. 11040-11054 (Nov. 2006).
Steinbach, et al.; "Assembly of adeno-associated virus type 2 capsids in vitro" J of Gen Virology; vol. 78, pp. 1453-1462 (1997).
Sullivan, et al.; "Rationally designed AAV2 and AAVrh8R capsids provide improved transduction in the retina and brain"; Gene Therapy; vol. 25, pp. 205-219 (2018).
Sun, et al.; "Immune responses to adeno-associated virus and its recombinant vectors"; Gene Therapy; vol. 10, pp. 964-976 (2003).
Surace, et al.; "Delivery of Adeno-Associated Virus Vectors to the Fetal Retina: Impact of Viral Capsid Proteins on Retinal Neuronal Progenitor Transduction"; Journal of Virology; vol. 77, No. 14, pp. 7957-7962 (Jul. 2003).
Takada, et al.; "Synaptic Pathology in Retinoschisis Knockout (Rs1$^{-/y}$) Mouse Retina and Modification by rAAV-Rs1 Gene Delivery"; Investigative Ophthalmology & Visual Science; vol. 49, No. 8, pp. 3677-3678 (Aug. 2008).
Tal; "Adeno-Associated Virus-Based Vectors in Gene Therapy"; Journal of Biomedical Science; vol. 7, No. 4, pp. 279-291 (Jul. 2000).
Tomar, et al.; "Use of Adeno-Associated Viral Vector for Delivery of Small Interfering RNA"; Oncogene; vol. 22, No. 36, pp. 5712-5715 (Aug. 28, 2003).
Van Vliet, et al.; "Proteolytic mapping of the adeno-associated virus capsid"; Mol Ther.; vol. 14, No. 6, pp. 809-821 (Dec. 2006).
Watanabe, et al.; "Tropisms of AAV for Subretinal Delivery to the Neonatal Mouse Retina and Its Application for In Vivo Rescue of Developmental Photoreceptor Disorders"; PLoS ONE; vol. 8, No. 1, 12 pages (Jan. 15, 2013).
Waterkamp, et al.; "Isolation of targeted AAV2 vectors from novel virus display libraries"; J. Gene. Med.; vol. 8, pp. 1307-1319 (Sep. 6, 2006).
White, et al.; "Genetic Modification of Adeno-Associated Viral Vector Type 2 Capsid Enhances Gene Transfer Efficiency in Polarized Human Airway Epithelial Cells"; Human Gene Therapy; vol. 19, pp. 1407-1414 (Dec. 2008).
White, et al.; "Targeted gene delivery to vascular tissue in vivo by tropism-modified adeno-associated virus vectors"; Circulation; vol. 109, pp. 513-519 (Feb. 3, 2004).
Wickham, et al.; "Increased in vitro and in vivo gene transfer by adenovirus vectors containing chimeric fiber proteins"; Journal of Virology; vol. 71, No. 11, pp. 8221-8229 (Nov. 1997).
Wobus, et al.; "Monoclonal antibodies against the adeno-associated virus type 2 (AAV-2) capsid: epitope mapping and identification of capsid domains involved in AAV-2-cell interaction and neutralization of AAV-2 infection."; J. Virol.; vol. 74, No. 19, pp. 9281-9293 (Oct. 2000).
Work, et al.; "Vascular bed-targeted in vivo gene delivery using tropism-modified adeno-associated viruses"; Mol. Ther.; vol. 13, No. 4, pp. 683-693 (Apr. 2006).
Wu, et al.; "Mutational analysis of the adeno-associated virus type 2 (AAV2) capsid gene and construction of AAV2 vectors with altered tropism"; Journal of Virology; vol. 74, No. 18, pp. 8635-8647 (Sep. 2000).
Wu, et al.; "α2,3 and α2,6 N-linked Sialic Acids Facilitate Efficient Binding and Transduction by Adeno-Associated Virus Types 1 and 6"; Journal of Virology; vol. 80, No. 18, pp. 9093-9103 (Sep. 2006).
Xiao, et al.; "Adenovirus-facilitated nuclear translocation of adeno-associated virus type 2"; Journal of Virology; vol. 76, No. 22, pp. 11505-11517 (Nov. 2002).
Xie, et al.; "The atomic structure of adeno-associated virus (AAV-2), a vector for human gene therapy"; PNAS; vol. 99, No. 16, pp. 10405-10410 (Aug. 6, 2002).
Yang, et al.; "A myocardium tropic adeno-associated virus (AAV) evolved by DNA shuffling and in vivo selection"; PNAS; vol. 106, No. 10, pp. 3946-3951 (Mar. 10, 2009).
Yang, et al.; "Directed Evolution of Adeno-Associated Virus (AAV) as Vector for Muscle Gene Therapy"; Methods in Molecular Biology; vol. 709, pp. 127-139 (2011).
Zabner, et al.; "Adeno-associated virus type 5 (AAV5) but not AAV2 binds to the apical surfaces of airway epithelia and facilitates gene transfer"; J Virol.; No. 74, No. 8, pp. 3852-3858 (Apr. 2000).
Zhao, et al.; "Molecular evolution by staggered extension process (StEP) in vitro recombination"; Nat Biotechnol; vol. 16, No. 3, pp. 258-261 (Mar. 1998).
Zolotukhin, et al.; "Recombinant adeno-associated virus purification using novel methods improves infectious titer and yield"; Gene Therapy; vol. 6, pp. 973-985 (1999).
Kotin, et al., "Geneseq Accession No. BDN88104", computer printout, 2017, 2 pages.
Schaffer, et al., "Geneseq Accession No. BBR00471", computer printout, 2014, 2 pages.

\* cited by examiner

| Parent Percentage Frequency Before AAV Packaging | | | | | | | | |
|---|---|---|---|---|---|---|---|---|
| Parent | Block 1 | Block 2 | Block 3 | Block 4 | Block 5 | Block 6 | Block 7 | Block 8 |
| AAV2 | 14.3 | 15.9 | 13.8 | 9.9 | 13.2 | 11.3 | 12.9 | 10.2 |
| AAV4 | 14.1 | 10 | 28.5 | 25.7 | 19 | 17.1 | 22.7 | 19.4 |
| AAV5 | 10.6 | 9.4 | 12.7 | 18.1 | 16.5 | 23.1 | 20.8 | 21.7 |
| AAV6 | 10.2 | 24.3 | 26.7 | 7.8 | 14.9 | 20.5 | 12.8 | 18.4 |
| AAV8 | 18.4 | 18.6 | 11.3 | 21.5 | 21.3 | 12.8 | 19.1 | 16.2 |
| AAV9 | 32.3 | 21.8 | 7 | 17 | 15.1 | 15.1 | 11.8 | 14 |

| Parent Percentage Frequency After AAV Packaging | | | | | | | | |
|---|---|---|---|---|---|---|---|---|
| Parent | Block 1 | Block 2 | Block 3 | Block 4 | Block 5 | Block 6 | Block 7 | Block 8 |
| AAV2 | 32.4 | 46.9 | 5.4 | 7.2 | 86.1 | 89.9 | 18.7 | 4.4 |
| AAV4 | 4.5 | 0 | 0.2 | 0 | 0.1 | 0 | 1.3 | 0 |
| AAV5 | 0.2 | 0 | 0.2 | 0 | 0 | 0.3 | 0 | 0.1 |
| AAV6 | 60.5 | 21.3 | 24.3 | 3.4 | 3.1 | 4.5 | 17.3 | 3.1 |
| AAV8 | 1 | 32 | 53.1 | 34.1 | 1.9 | 4.9 | 22.3 | 0.7 |
| AAV9 | 1.4 | 28.5 | 16.8 | 55.2 | 8.7 | 0.3 | 40.4 | 91.7 |

| Primer name | Primer sequence (5'-3') | SEQ ID NO |
|---|---|---|
| QC_pBluescript_Fwd | GCTGCAATGATACCGCGAAACCCACGCTC | 13 |
| QC_pBluescript_Rev | GAGCGTGGGTTTCGCGGTATCATTGCAGC | 14 |
| QC_AAV4_Fwd | GCTCCTGGAAAGAAGAGGCCGTTGATTGAATCCCC | 15 |
| QC_AAV4_Rev | GGGGATTCAATCAACGGCCTCTTCTTTCCAGGAGC | 16 |
| QC_AAV5_Fwd | GACCCGGAAACGGACTCGATCGAGGAG | 17 |
| QC_AAV5_Rev | CTCCTCGATCGAGTCCGTTTCCGGGTC | 18 |
| QC_AAV6_Fwd | GTTTAGCCGGGGCTCTCCAGCTGGC | 19 |
| QC_AAV6_Rev | GCCAGCTGGAGAGCCCCGGCTAAAC | 20 |
| QC_AAV8_Fwd | CTCCTGGAAAGAAGAGGCCGGTAGAGCCATCAC | 21 |
| QC_AAV8_Rev | GTGATGGCTCTACCGGCCTCTTCTTTCCAGGAG | 22 |
| BglIIFwd | CAAGCGGCCGCGTAAGCTTAGATCTCTGACGTCGATGGCTGCG | 23 |
| BglIIRev | CGCAGCCATCGACGTCAGAGATCTAAGCTTACGCGGCCGCTTG | 24 |
| Lox66Fwd | GATCTATAACTTCGTATAGCATACATTATACGAACGGTACG | 25 |
| Lox66Rev | CGTACCGTTCGTATAATGTATGCTATACGAAGTTATTTCGA | 26 |
| XhoIFwd | CCGCTTGTTAATCAATAAACCGTTTAATTCGTTTCAGTTGACTCGAGGTCTCTGCGTATTTCTTTCT | 27 |
| XhoIRev | AGAAAGAAATACGCAGAGACCTCGAGTCAACTGAAACGAATTAAACGGTTTATTGATTAACAAGCGG | 28 |
| KpnIFwd | CGTAGATAAGTAGCATGGCGGGTTAATCAGGTACCACAAGGAACCCCTAG | 29 |
| KpnIRev | CTAGGGGTTCCTTGTGGTACCTGATTAACCCGCCATGCTACTTATCTACG | 30 |
| SOELox71Fwd | GTCAGCCTCGAGATAACTTCGTATAATGTATGCTATACGAACGGTACTGTGGTCGTCATTGGCAACTACACCTGTTCG | 31 |
| SOELox71Rev | CGTCACGGTACCTGTGGAATTGTGAGCGCTCACAATTCCACAGCTAGCCTATTTACCGATACCACACGAACAGGTGTAGTTGCCAATGACG | 32 |
| Lox71Fwd | GTCAGCCTCGAGATAACTTCG | 33 |
| Lox71Rev | CGTCACGGTACCTGTGG | 34 |
| Cap_ISF | CATGGAAACTAGATAAGAAAGA | 35 |
| Cap_NSF | GGTACGAAGCTTCGATCAACTACGCAG | 36 |
| Cap_R | AGCTAGCCTATTTACCGATAC | 37 |
| Internal_Cap_ISF | AAGTTCAACTGAAACGAATTA | 38 |
| Internal_Cap_R | CACACGAACAGGTGTAGTT | 39 |

FIG. 3

| Primer name | Primer sequence (5'-3') | SEQ ID NO |
|---|---|---|
| DO_02_(Vector_Backbone)_forward | CACACCAGGTCTCATTGCGCGCTTGGCGTAATCATGG | 50 |
| DO_03_(Vector_Backbone)_reverse | CACACCAGGTCTCATTATAGTGAGTCGTATTACGCGC | 51 |
| DO_04_(AAV2_b1)_forward | CACACCAGGTCTCAATAAGGCGAATTGGGTACCG | 52 |
| DO_05_(AAV2_b1)_reverse | CACACCAGGTCTCAGTTCAAGAACCCTCTTTTCGC | 53 |
| DO_06_(AAV2_b2)_forward | CACACCAGGTCTCAGAACCTCTGGGCCTGGTTGAG | 54 |
| DO_07_(AAV2_b2)_reverse | CACACCAGGTCTCAACCCCAAGGGGTGCTGTAG | 55 |
| DO_08_(AAV2_b3)_forward | CACACCAGGTCTCAGGGTATTTGACTTCAACAGATTCCACTGC | 56 |
| DO_09_(AAV2_b3)_reverse | CACACCAGGTCTCAAAAGACCTGAACCGTGCTGG | 57 |
| DO_10_(AAV2_b4)_forward | CACACCAGGTCTCACTTTACTGACTCGGAGTACCAGC | 58 |
| DO_11_(AAV2_b4)_reverse | CACACCAGGTCTCAGTAGCTGAAGGTAAAGTTGTTTCC | 59 |
| DO_12_(AAV2_b5)_forward | CACACCAGGTCTCACTACACTTTGAGGACGTTCC | 60 |
| DO_13_(AAV2_b5)_reverse | CACACCAGGTCTCAAGTTCCTAGACTGGTCCCGAATG | 61 |
| DO_14_(AAV2_b6)_forward | CACACCAGGTCTCAAACTGGCTTCCTGGACCCTG | 62 |
| DO_15_(AAV2_b6)_reverse | CACACCAGGTCTCAGTTCTGTCCTGCCAGACCATG | 63 |
| DO_16_(AAV2_b7)_forward | CACACCAGGTCTCAAGACGTGTACCTTCAGGGGC | 64 |
| DO_17_(AAV2_b7)_reverse | CACACCAGGTCTCAATGAAGGAAGCAAACTTTGCCG | 65 |
| DO_18_(AAV2_b8)_forward | CACACCAGGTCTCATCATCACACAGTACTCCACGG | 66 |
| DO_19_(AAV2_b8)_reverse | CACACCAGGTCTCAGCAAGCGCAATTAACCTC | 67 |
| DO_20_(AAV4_b1)_reverse | CACACCAGGTCTCAGTTCAAGAACCCTCTTTTGGC | 68 |
| DO_21_(AAV4_b2)_forward | CACACCAGGTCTCAGAACCTCTTGGTCTGGTTGAG | 69 |
| DO_22_(AAV4_b2)_reverse | CACACCAGGTCTCAACCCCAGGGGGTGGAGAAT | 70 |
| DO_23_(AAV4_b3)_forward | CACACCAGGTCTCAGGGTATTTGACTTCAACCGCTTCC | 71 |
| DO_24_(AAV4_b3)_reverse | CACACCAGGTCTCAAAAGATCTGAACCGTGCTGG | 72 |
| DO_25_(AAV4_b4)_forward | CACACCAGGTCTCACTTTGCGGACTCGTCGTACG | 73 |
| DO_26_(AAV4_b4)_reverse | CACACCAGGTCTCAGTAGGTAATTTCAAAGTTGTGCC | 74 |
| DO_27_(AAV4_b5)_forward | CACACCAGGTCTCACTACAGTTTTGAGAAGGTGCCT | 75 |
| DO_28_(AAV4_b5)_reverse | CACACCAGGTCTCAAGTTCTTTTAAAGTTGGAAAAGTTGGT | 76 |
| DO_29_(AAV4_b6)_forward | CACACCAGGTCTCAAACTGGCTGCCCGGGCCTTC | 77 |
| DO_30_(AAV4_b6)_reverse | CACACCAGGTCTCAGTTCTGTTTTGCCAGACCATTC | 78 |
| DO_31_(AAV4_b7)_forward | CACACCAGGTCTCAAGAACATTTACTACCAGGTCCC | 79 |
| DO_32_(AAV4_b7)_reverse | CACACCAGGTCTCAATGAAGGAGTTACCGGAGTAGAG | 80 |

FIG. 3 (Cont.)

| DO_33_(AAV4_b8)_forward | CACACCAGGTCTCATCATTACTCAGTACAGCACTGGC | 81 |
|---|---|---|
| DO_34_(AAV4_b8)_reverse | CACACCAGGTCTCAGCAAGCGCGCAATTAACCCTCACTAAAGG | 82 |
| DO_35_(AAV5_b1)_reverse | CACACCAGGTCTCAGTTGCAGAACCTTTTCTTGGC | 83 |
| DO_36_(AAV5_b2)_forward | CACACCAGGTCTCAGAACCTTTGGCCTGGTTGAA | 84 |
| DO_37_(AAV5_b2)_reverse | CACACCAGGTCTCAACCCCAGGGGGTGCTGTAT | 85 |
| DO_38_(AAV5_b3)_forward | CACACCAGGTCTCAGGGTATTTGACTTTAACCGCTTCC | 86 |
| DO_39_(AAV5_b3)_reverse | CACACCAGGTCTCAAAAGACTTGGACGGTGGAGG | 87 |
| DO_40_(AAV5_b4)_forward | CACACCAGGTCTCACTTTACGGACGACGACTACC | 88 |
| DO_41_(AAV5_b4)_reverse | CACACCAGGTCTCAGTAGGTAAACTCAAAGTTGTTGCC | 89 |
| DO_42_(AAV5_b5)_forward | CACACCAGGTCTCACTACAACTTTGAGGAGGTGCC | 90 |
| DO_43_(AAV5_b5)_reverse | CACACCAGGTCTCAAACTGGTTCCCGGGGCCCAT | 91 |
| DO_44_(AAV5_b6)_forward | CACACCAGGTCTCAGTTCTCTCCATCCACACGC | 92 |
| DO_45_(AAV5_b6)_reverse | CACACCAGGTCTCAAGTTTTGTAGGTGTTGGCGTATCTCC | 93 |
| DO_46_(AAV5_b7)_forward | CACACCAGGTCTCAGACGTGTACCTCCAAGGACC | 94 |
| DO_47_(AAV5_b7)_reverse | CACACCAGGTCTCAATGAAGTGCTGACGGGCAC | 95 |
| DO_48_(AAV5_b8)_forward | CACACCAGGTCTCATCATCACCCAGTACAGCACC | 96 |
| DO_49_(AAV6_b1)_reverse | CACACCAGGTCTCAGTTCGAGAACCCTCTCTTGG | 97 |
| DO_50_(AAV6_b2)_forward | CACACCAGGTCTCAGAACCTTTGGTCTGGTTGAGG | 98 |
| DO_51_(AAV6_b2)_reverse | CACACCAGGTCTCAACCCCAGGGGGTGCTGTAGC | 99 |
| DO_52_(AAV6_b3)_forward | CACACCAGGTCTCAGGGTATTTGATTCAACAGATTCCACTGC | 100 |
| DO_53_(AAV6_b3)_reverse | CACACCAGGTCTCAAAAGACTTGAACCGTGCTGG | 101 |
| DO_54_(AAV6_b4)_forward | CACACCAGGTCTCACTTTTCGGACTCGGAGTACC | 102 |
| DO_55_(AAV6_b4)_reverse | CACACCAGGTCTCAGTAGCTGAAGGTAAAGTTATTGCC | 103 |
| DO_56_(AAV6_b5)_forward | CACACCAGGTCTCACTACACCTCGAGGACGTGC | 104 |
| DO_57_(AAV6_b5)_reverse | CACACCAGGTCTCAAGTTTTGGGCTGAACAGACATGC | 105 |
| DO_58_(AAV6_b6)_forward | CACACCAGGTCTCAAACTGGCTACCTGGACCCTG | 106 |
| DO_59_(AAV6_b6)_reverse | CACACCAGGTCTCAGTCTGTCTTGCCACACCATTC | 107 |
| DO_60_(AAV6_b7)_forward | CACACCAGGTCTCAAGACGTATACCTGCAGGGTCC | 108 |
| DO_61_(AAV6_b7)_reverse | CACACCAGGTCTCAATGAATGAAGCAAACTTTGTAGCC | 109 |
| DO_62_(AAV6_b8)_forward | CACACCAGGTCTCATCATCACCCAGTATTCCACAGG | 110 |
| DO_63_(AAV8_b1)_reverse | CACACCAGGTCTCAGTTCGAGAACCCGCTTCTTGG | 111 |
| DO_64_(AAV8_b2)_forward | CACACCAGGTCTCAGAACCTTCTCGGTCTGGTTGAG | 112 |
| DO_65_(AAV8_b2)_reverse | CACACCAGGTCTCAACCCCAGGGGGTGCTGTAG | 113 |

FIG. 3 (Cont.)

| | | |
|---|---|---|
| DO_66 (AAV8_b3)_forward | CACACCAGGTCTCAGGGTATTTGACTTTAACAGATTCCACTGC | 114 |
| DO_67 (AAV8_b3)_reverse | CACACCAGGTCTCAAAAGACCTGGATGGTGCTGG | 115 |
| DO_68 (AAV8_b4)_forward | CACACCAGGTCTCACTTTACGGACTCGGAGTACC | 116 |
| DO_69 (AAV8_b4)_reverse | CACACCAGGTCTCAGTAGGTAAACTGGAAGTTGTTGC | 117 |
| DO_70 (AAV8_b5)_reverse | CACACCAGGTCTCAAGTTCTTGCCTGATTGGCC | 118 |
| DO_71 (AAV8_b6)_forward | CACACCAGGTCTCAAACTGGCTGCCAGGACCCTG | 119 |
| DO_72 (AAV8_b6)_reverse | CACACCAGGTCTCAGTCTCGGTTCTGCCAGACCATAC | 120 |
| DO_73 (AAV8_b7)_forward | CACACCAGGTCTCAAGACGTGTACCTGCAGGGTCC | 121 |
| DO_74 (AAV8_b7)_reverse | CACACCAGGTCTCAATGAAAGAGTTCAGTTTGACTGG | 122 |
| DO_75 (AAV8_b8)_forward | CACACCAGGTCTCATCATCACGCAATACAGCACCG | 123 |
| DO_76 (AAV9_b1)_reverse | CACACCAGGTCTCAGTTCAAGAAGCCTCTTTTGGC | 124 |
| DO_77 (AAV9_b2)_forward | CACACCAGGTCTCAGAACCTCTTGGTCTGGTTGAGG | 125 |
| DO_78 (AAV9_b3)_reverse | CACACCAGGTCTCAAAAGACCTGGACCGTGCTGG | 126 |
| DO_79 (AAV9_b4)_forward | CACACCAGGTCTCACTTTACGGACTCAGACTATCAGC | 127 |
| DO_80 (AAV9_b4)_reverse | CACACCAGGTCTCAGTAGCTGAACTGGAAGTTGTTACC | 128 |
| DO_81 (AAV9_b5)_forward | CACACCAGGTCTCACTACGAGTTTGAGAACGTACC | 129 |
| DO_82 (AAV9_b5)_reverse | CACACCAGGTCTCAAGTTCTTCCCTGGACAGCC | 130 |
| DO_83 (AAV9_b6)_forward | CACACCAGGTCTCAAACTACATACCTGGACCCAGC | 131 |
| DO_84 (AAV9_b6)_reverse | CACACCAGGTCTCAGTCTCTGTCCTGCCAAACCATACC | 132 |
| DO_85 (AAV9_b7)_forward | CACACCAGGTCTCAAGACGTGTACCTGCAAGGAC | 133 |
| DO_86 (AAV9_b7)_reverse | CACACCAGGTCTCAATGAAAGAGTTCAGTTGTCCTTG | 134 |
| DO_87 (AAV9_b8)_forward | CACACCAGGTCTCATCATCACCCAGTATTCTACTGGC | 135 |

FIG 4

| Block ID Number | Primary Template | Forward Primer | Reverse Primer | Amplicon length (bp) |
|---|---|---|---|---|
| 0 | pBluescript SK+ | DO_02_(Vector_Backbone)_forward | DO_03_(Vector_Backbone)_reverse | 2843 |
| 1 | AAV2 | DO_04_(AAV2_b1)_forward | DO_05_(AAV2_b1)_reverse | 784 |
| 2 | AAV2 | DO_06_(AAV2_b2)_forward | DO_07_(AAV2_b2)_reverse | 491 |
| 3 | AAV2 | DO_08_(AAV2_b3)_forward | DO_09_(AAV2_b3)_reverse | 220 |
| 4 | AAV2 | DO_10_(AAV2_b4)_forward | DO_11_(AAV2_b4)_reverse | 242 |
| 5 | AAV2 | DO_12_(AAV2_b5)_forward | DO_13_(AAV2_b5)_reverse | 222 |
| 6 | AAV2 | DO_14_(AAV2_b6)_forward | DO_15_(AAV2_b6)_reverse | 433 |
| 7 | AAV2 | DO_16_(AAV2_b7)_forward | DO_17_(AAV2_b7)_reverse | 211 |
| 8 | AAV2 | DO_18_(AAV2_b8)_forward | DO_19_(AAV2_b8)_reverse | 298 |
| 9 | AAV4 | DO_04_(AAV2_b1)_forward | DO_20_(AAV4_b1)_reverse | 784 |
| 10 | AAV4 | DO_21_(AAV4_b2)_forward | DO_22_(AAV4_b2)_reverse | 467 |
| 11 | AAV4 | DO_23_(AAV4_b3)_forward | DO_24_(AAV4_b3)_reverse | 220 |
| 12 | AAV4 | DO_25_(AAV4_b4)_forward | DO_26_(AAV4_b4)_reverse | 251 |
| 13 | AAV4 | DO_27_(AAV4_b5)_forward | DO_28_(AAV4_b5)_reverse | 225 |
| 14 | AAV4 | DO_29_(AAV4_b6)_forward | DO_30_(AAV4_b6)_reverse | 445 |
| 15 | AAV4 | DO_31_(AAV4_b7)_forward | DO_32_(AAV4_b7)_reverse | 211 |
| 16 | AAV4 | DO_33_(AAV4_b8)_forward | DO_34_(AAV4_b8)_reverse | 298 |
| 17 | AAV5 | DO_04_(AAV2_b1)_forward | DO_35_(AAV5_b1)_reverse | 787 |
| 18 | AAV5 | DO_36_(AAV5_b2)_forward | DO_37_(AAV5_b2)_reverse | 467 |
| 19 | AAV5 | DO_38_(AAV5_b3)_forward | DO_39_(AAV5_b3)_reverse | 220 |
| 20 | AAV5 | DO_40_(AAV5_b4)_forward | DO_41_(AAV5_b4)_reverse | 248 |
| 21 | AAV5 | DO_42_(AAV5_b5)_forward | DO_43_(AAV5_b5)_reverse | 204 |
| 22 | AAV5 | DO_44_(AAV5_b6)_forward | DO_45_(AAV5_b6)_reverse | 442 |
| 23 | AAV5 | DO_46_(AAV5_b7)_forward | DO_47_(AAV5_b7)_reverse | 208 |
| 24 | AAV5 | DO_48_(AAV5_b8)_forward | DO_19_(AAV2_b8)_reverse | 298 |
| 25 | AAV6 | DO_04_(AAV2_b1)_forward | DO_49_(AAV6_b1)_reverse | 784 |
| 26 | AAV6 | DO_50_(AAV6_b2)_forward | DO_51_(AAV6_b2)_reverse | 494 |
| 27 | AAV6 | DO_52_(AAV6_b3)_forward | DO_53_(AAV6_b3)_reverse | 220 |
| 28 | AAV6 | DO_54_(AAV6_b4)_forward | DO_55_(AAV6_b4)_reverse | 242 |
| 29 | AAV6 | DO_56_(AAV6_b5)_forward | DO_57_(AAV6_b5)_reverse | 222 |
| 30 | AAV6 | DO_58_(AAV6_b6)_forward | DO_59_(AAV6_b6)_reverse | 433 |
| 31 | AAV6 | DO_60_(AAV6_b7)_forward | DO_61_(AAV6_b7)_reverse | 211 |
| 32 | AAV6 | DO_62_(AAV6_b8)_forward | DO_19_(AAV2_b8)_reverse | 298 |
| 33 | AAV8 | DO_04_(AAV2_b1)_forward | DO_63_(AAV8_b1)_reverse | 784 |
| 34 | AAV8 | DO_64_(AAV8_b2)_forward | DO_65_(AAV8_b2)_reverse | 500 |
| 35 | AAV8 | DO_66_(AAV8_b3)_forward | DO_67_(AAV8_b3)_reverse | 220 |
| 36 | AAV8 | DO_68_(AAV8_b4)_forward | DO_69_(AAV8_b4)_reverse | 242 |
| 37 | AAV8 | DO_56_(AAV8_b5)_forward | DO_70_(AAV8_b5)_reverse | 222 |
| 38 | AAV8 | DO_71_(AAV8_b6)_forward | DO_72_(AAV8_b6)_reverse | 433 |
| 39 | AAV8 | DO_73_(AAV8_b7)_forward | DO_74_(AAV8_b7)_reverse | 211 |
| 40 | AAV8 | DO_75_(AAV8_b8)_forward | DO_19_(AAV2_b8)_reverse | 298 |
| 41 | AAV9 | DO_04_(AAV2_b1)_forward | DO_76_(AAV9_b1)_reverse | 787 |
| 42 | AAV9 | DO_77_(AAV9_b2)_forward | DO_51_(AAV6_b2)_reverse | 491 |
| 43 | AAV9 | DO_08_(AAV2_b3)_forward | DO_78_(AAV9_b3)_reverse | 220 |
| 44 | AAV9 | DO_79_(AAV9_b4)_forward | DO_80_(AAV9_b4)_reverse | 242 |
| 45 | AAV9 | DO_81_(AAV9_b5)_forward | DO_82_(AAV9_b5)_reverse | 219 |
| 46 | AAV9 | DO_83_(AAV9_b6)_forward | DO_84_(AAV9_b6)_reverse | 433 |
| 47 | AAV9 | DO_85_(AAV9_b7)_forward | DO_86_(AAV9_b7)_reverse | 211 |
| 48 | AAV9 | DO_87_(AAV9_b8)_forward | DO_34_(AAV4_b8)_reverse | 298 |

FIG 5

| Block Identity | Overhang with Previous Block | Overhang with Next Block |
|---|---|---|
| (Vector_Backbone) | TTGC | ATAA |
| (AAV2_b1) | ATAA | GAAC |
| (AAV2_b2) | GAAC | GGGT |
| (AAV2_b3) | GGGT | CTTT |
| (AAV2_b4) | CTTT | CTAC |
| (AAV2_b5) | CTAC | AACT |
| (AAV2_b6) | AACT | AGAC |
| (AAV2_b7) | AGAC | TCAT |
| (AAV2_b8) | TCAT | TTGC |
| (AAV4_b1) | ATAA | GAAC |
| (AAV4_b2) | GAAC | GGGT |
| (AAV4_b3) | GGGT | CTTT |
| (AAV4_b4) | CTTT | CTAC |
| (AAV4_b5) | CTAC | AACT |
| (AAV4_b6) | AACT | AGAC |
| (AAV4_b7) | AGAC | TCAT |
| (AAV4_b8) | TCAT | TTGC |
| (AAV5_b1) | ATAA | GAAC |
| (AAV5_b2) | GAAC | GGGT |
| (AAV5_b3) | GGGT | CTTT |
| (AAV5_b4) | CTTT | CTAC |
| (AAV5_b5) | CTAC | AACT |
| (AAV5_b6) | AACT | AGAC |
| (AAV5_b7) | AGAC | TCAT |
| (AAV5_b8) | TCAT | TTGC |
| (AAV6_b1) | ATAA | GAAC |
| (AAV6_b2) | GAAC | GGGT |
| (AAV6_b3) | GGGT | CTTT |
| (AAV6_b4) | CTTT | CTAC |
| (AAV6_b5) | CTAC | AACT |
| (AAV6_b6) | AACT | AGAC |
| (AAV6_b7) | AGAC | TCAT |
| (AAV6_b8) | TCAT | TTGC |
| (AAV8_b1) | ATAA | GAAC |
| (AAV8_b2) | GAAC | GGGT |
| (AAV8_b3) | GGGT | CTTT |
| (AAV8_b4) | CTTT | CTAC |
| (AAV8_b5) | CTAC | AACT |
| (AAV8_b6) | AACT | AGAC |
| (AAV8_b7) | AGAC | TCAT |
| (AAV8_b8) | TCAT | TTGC |
| (AAV9_b1) | ATAA | GAAC |
| (AAV9_b2) | GAAC | GGGT |
| (AAV9_b3) | GGGT | CTTT |
| (AAV9_b4) | CTTT | CTAC |
| (AAV9_b5) | CTAC | AACT |
| (AAV9_b6) | AACT | AGAC |
| (AAV9_b7) | AGAC | TCAT |
| (AAV9_b8) | TCAT | TTGC |

| Lane | 1 | 2 | 3 | 4 | 5 | 6 | 7 | 8 | 9 | 10 | 11 |
|---|---|---|---|---|---|---|---|---|---|---|---|
| Sample | 50 bp DNA Ladder (NEB N3236L) | 83 bp stuffer, Cre + | 95 bp stuffer, Cre + | 110 bp stuffer, Cre + | 125 bp stuffer, Cre + | | 83 bp stuffer, recombinase deficient Sure2 | 95 bp stuffer, recombinase deficient Sure2 | 110 bp stuffer, recombinase deficient Sure2 | 125 bp stuffer, recombinase deficient Sure2 | 50 bp DNA Ladder (NEB N3236L) |

FIG. 8

SCH9:

MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEAAKTAPGKKRPVEQSPQEPDSSAGIGKSGAQP
AKKRLNFGQTGDTESVPDPQPIGEPPAAPSGVGSLTMASGGGAPVADNNEGADGVG
SSSGNWHCDSQWLGDRVITTSTRTWALPTYNNHLYKQISNSTSGGSSNDNAYFGYS
TPWGYFDFNRFHCHFSPRDWQRLINNNWGFRPKRLSFKLFNIQVKEVTQNEGTKTIA
NNLTSTIQVFTDSDYQLPYVLGSAHEGCLPPFPADVFMIPQYGYLTLNDGSQAVGRS
SFYCLEYFPSQMLRTGNNFQFSYEFENVPFHSSYAHSQSLDRLMNPLIDQYLYYLSKT
INGSGQNQQTLKFSVAGPSNMAVQGRNWLPGPCYRQQRVSKTSADNNNSEYSWTG
ATKYHLNGRDSLVNPGPAMASHKDDEEKFFPQSGVLIFGKQGSEKTNVDIEKVMITD
EEEIRTTNPVATEQYGSVSTNLQRGNRQAATADVNTQGVLPGMVWQDRDVYLQGPI
WAKIPHTDGNFHPSPLMGGFGMKHPPPQILIKNTPVPADPPTAFNKDKLNSFITQYST
GQVSVEIEWELQKENSKRWNPEIQYTSNYYKSNNVEFAVNTEGVYSEPRPIGTRYLT
RNL (SEQ ID NO:1)

FIG. 9

SCH2:

MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEFQERLQEDTSFGGNLGRAVFQAKKRVLEPLGLVEEAAKTAPGKKRPVEQSPQEPDSSAGIGKSGAQPAKKRLNFGQTGDTESVPDPQPIGEPPAAPSGVGSLTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQRLINNNWGFRPKRLSFKLFNIQVKEVTQNEGTKTIANNLTSTIQVFTDSDYQLPYVLGSAHEGCLPPFPADVFMIPQYGYLTLNDGSQAVGRSSFYCLEYFPSQMLRTGNNFQFSYTFEDVPFHSSYAHSQSLDRLMNPLIDQYLYYLSRTNTPSGTTTQSRLQFSQAGASDIRDQSRNWLPGPCYRQQRVSKTSADNNNSEYSWTGATKYHLNGRDSLVNPGPAMASHKDDEEKFFPQSGVLIFGKQGSEKTNVDIEKVMITDEEEIRTTNPVATEQYGSVSTNLQRGNRQAATADVNTQGVLPGMVWQDRDVYLQGPIWAKIPHTDGNFHPSPLMGGFGMKHPPPQILIKNTPVPADPPTAFNKDKLNSFITQYSTGQVSVEIEWELQKENSKRWNPEIQYTSNYYKSNNVEFAVNTEGVYSEPRPIGTRYLTRNL (SEQ ID NO:2)

FIG. 10

```
        1         10        20        30        40        50
        |         |         |         |         |         |
SCH9   MAADGYLPDWLEDNLSEGIREWWDLKPGAPKPKANQQKQDDGRGLVLPGYKY
       |—AAV6 Block 1——————————————————————————————————————▶

SCH2   MAADGYLPDWLEDNLSEGIREWWDLKPGAPKPKANQQKQDDGRGLVLPGYKY
       |—AAV6 Block 1——————————————————————————————————————▶

AAV2   MAADGYLPDWLEDTLSEGIRQWWKLKPGPPPPKPAERHKDDSRGLVLPGYKY
AAV6   MAADGYLPDWLEDNLSEGIREWWDLKPGAPKPKANQQKQDDGRGLVLPGYKY
AAV8   MAADGYLPDWLEDNLSEGIREWWALKPGAPKPKANQQKQDDGRGLVLPGYKY
AAV9   MAADGYLPDWLEDNLSEGIREWWALKPGAPQPKANQQHQDNARGLVLPGYKY 60        70        80        90
                 |         |         |         |
SCH9   LGPFNGLDKGEPVNAADAAALEHDKAYDQQLKAGDNPYLRYNHADA
       |—AAV6 Block 1————————————————————————————————▶

SCH2   LGPFNGLDKGEPVNAADAAALEHDKAYDQQLKAGDNPYLRYNHADA
       |—AAV6 Block 1————————————————————————————————▶

AAV2   LGPFNGLDKGEPVNEADAAALEHDKAYDRQLDSGDNPYLKYNHADA
AAV6   LGPFNGLDKGEPVNAADAAALEHDKAYDQQLKAGDNPYLRYNHADA
AAV8   LGPFNGLDKGEPVNAADAAALEHDKAYDQQLQAGDNPYLRYNHADA
AAV9   LGPGNGLDKGEPVNAADAAALEHDKAYDQQLKAGDNPYLKYNHADA 100       110       120       130       140       150
        |         |         |         |         |         |
SCH9   EFQERLQEDTSFGGNLGRAVFQAKKRVLEPLGLVEEAAKTAPGKKRPVEQSP
       |—AAV6 Block 1————————————————▶|—AAV9 Block 2—————————▶

SCH2   EFQERLQEDTSFGGNLGRAVFQAKKRVLEPLGLVEEAAKTAPGKKRPVEQSP
       |—AAV6 Block 1————————————————▶|—AAV9 Block 2—————————▶

AAV2   EFQERLKEDTSFGGNLGRAVFQAKKRVLEPLGLVEEPVKTAPGKKRPVEHSP
AAV6   EFQERLQEDTSFGGNLGRAVFQAKKRVLEPFGLVEEGAKTAPGKKRPVEQSP
AAV8   EFQERLQEDTSFGGNLGRAVFQAKKRVLEPLGLVEEGAKTAPGKKRPVEPSP
AAV9   EFQERLKEDTSFGGNLGRAVFQAKKRLLEPLGLVEEAAKTAPGKKRPVEQSP 160       170       180       190
                |         |         |         |
SCH9   Q-EPDSSAGIGKSGAQPAKKRLNFGQTGDTESVPDPQPIGEPPAAP
       |—AAV9 Block 2————————————————————————————————▶

SCH2   Q-EPDSSAGIGKSGAQPAKKRLNFGQTGDTESVPDPQPIGEPPAAP
       |—AAV9 Block 2————————————————————————————————▶

AAV2   V-EPDSSGTGKAGQQPARKRLNFGQTGDADSVPDPQPLGQPPAAP
AAV6   Q-EPDSSGIGKTGQQPAKKRLNFGQTGDSESVPDPQPLGEPPATP
AAV8   QRSPDSSTGIGKKGQQPARKRLNFGQTGDSESVPDPQPLGEPPAAP
AAV9   Q-EPDSSAGIGKSGAQPAKKRLNFGQTGDTESVPDPQPIGEPPAAP
```

FIG. 10 (Cont.)

```
              200         210         220         230         240
                |           |           |           |           |
SCH9   SGVGSLTMASGGGAPVADNNEGADGVGSSSGNWHCDSQWLGDRVITTSTRTW
       |—AAV9 Block 2 ———————————————————————————————————————>

SCH2   SGVGSLTMASGGGAPVADNNEGADGVGSSSGNWHCDSQWLGDRVITTSTRTW
       |—AAV9 Block 2 ———————————————————————————————————————>

AAV2   SGLGTNTMATGSGAPMADNNEGADGVGNSSGNWHCDSTWMGDRVITTSTRTW
AAV6   AAVGPTTMASGGGAPMADNNEGADGVGNASGNWHCDSTWLGDRVITTSTRTW
AAV8   SGVGPNTMAAGGGAPMADNNEGADGVGSSSGNWHCDSTWLGDRVITTSTRTW
AAV9   SGVGSLTMASGGGAPVADNNEGADGVGSSSGNWHCDSQWLGDRVITTSTRTW 250         260         270         280         290
                |           |           |           |           |
SCH9   ALPTYNNHLYKQISNSTSGGSSNDNAYFGYSTPWGYFDFNRFHCHF
       |—AAV9 Block 2 ————————————————————————————>|AAV8 Block 3>

SCH2   ALPTYNNHLYKQISNSTSGGSSNDNAYFGYSTPWGYFDFNRFHCHF
       |—AAV9 Block 2 ————————————————————————————>|AAV8 Block 3>

AAV2   ALPTYNNHLYKQISS--QSGASNDNHYFGYSTPWGYFDFNRFHCHF
AAV6   ALPTYNNHLYKQISSA-STGASNDNHYFGYSTPWGYFDFNRFHCHF
AAV8   ALPTYNNHLYKQISNGTSGGATNDNTYFGYSTPWGYFDFNRFHCHF
AAV9   ALPTYNNHLYKQISNSTSGGSSNDNAYFGYSTPWGYFDFNRFHCHF 300         310         320         330         340
                |           |           |           |           |
SCH9   SPRDWQRLINNNWGFRPKRLSFKLFNIQVKEVTQNEGTKTIANNLTSTIQVF
       |—AAV8 Block 3 ———————————————————————————————————————>

SCH2   SPRDWQRLINNNWGFRPKRLSFKLFNIQVKEVTQNEGTKTIANNLTSTIQVF
       |—AAV8 Block 3 ———————————————————————————————————————>

AAV2   SPRDWQRLINNNWGFRPKRLNFKLFNIQVKEVTQNDGTTTIANNLTSTVQVF
AAV6   SPRDWQRLINNNWGFRPKRLNFKLFNIQVKEVTTNDGVTTIANNLTSTVQVF
AAV8   SPRDWQRLINNNWGFRPKRLSFKLFNIQVKEVTQNEGTKTIANNLTSTIQVF
AAV9   SPRDWQRLINNNWGFRPKRLNFKLFNIQVKEVTDNNGVKTIANNLTSTVQVF 350         360         370         380         390
                |           |           |           |           |
SCH9   TDSDYQLPYVLGSAHEGCLPPFPADVFMIPQYGYLTLNDGSQAVGR
       |—AAV9 Block 4 ———————————————————————————————————————

SCH2   TDSDYQLPYVLGSAHEGCLPPFPADVFMIPQYGYLTLNDGSQAVGR
       |—AAV9 Block 4 ———————————————————————————————————————

AAV2   TDSEYQLPYVLGSAHQGCLPPFPADVFMVPQYGYLTLNNGSQAVGR
AAV6   SDSEYQLPYVLGSAHQGCLPPFPADVFMIPQYGYLTLNNGSQAVGR
AAV8   TDSEYQLPYVLGSAHQGCLPPFPADVFMIPQYGYLTLNNGSQAVGR
AAV9   TDSDYQLPYVLGSAHEGCLPPFPADVFMIPQYGYLTLNDGSQAVGR
```

FIG. 10 (Cont.)

```
             400        410        420        430        440
              |          |          |          |          |
SCH9  SSFYCLEYFPSQMLRTGNNFQFSYEFENVPFHSSYAHSQSLDRLMNPLIDQY
      |—AAV9 Block 4——————————≫|—AAV9 Block 5——————————≫
SCH2  SSFYCLEYFPSQMLRTGNNFQFSYTFEDVPFHSSYAHSQSLDRLMNPLIDQY
      |—AAV9 Block 4——————————≫|—AAV9 Block 5——————————≫
AAV2  SSFYCLEYFPSQMLRTGNNFTFSYTFEDVPFHSSYAHSQSLDRLMNPLIDQY
AAV6  SSFYCLEYFPSQMLRTGNNFTFSYTFEDVPFHSSYAHSQSLDRLMNPLIDQY
AAV8  SSFYCLEYFPSQMLRTGNNFQFTYTFEDVPFHSSYAHSQSLDRLMNPLIDQY
AAV9  SSFYCLEYFPSQMLRTGNNFQFSYEFENVPFHSSYAHSQSLDRLMNPLIDQY 450        460        470        480        490
              |          |          |          |          |
SCH9  LYYLSKTINGSGQNQQT-LKFSVAGPSNMAVQGRNWLPGPCYRQQR
      |—AAV9 Block 5————————————————————≫|AAV2 Block 6≫
SCH2  LYYLSRTNTPSGTTTQSRLQFSQAGASDIRDQSRNWLPGPCYRQQR
      |—AAV9 Block 5————————————————————≫|AAV2 Block 6≫
AAV2  LYYLSRTNTPSGTTTQSRLQFSQAGASDIRDQSRNWLPGPCYRQQR
AAV6  LYYLNRTQNQSGSAQNKDLLFSRGSPAGMSVQPKNWLPGPCYRQQR
AAV8  LYYLSRTQTTGGTANTQTLGFSQGGPNTMANQAKNWLPGPCYRQQR
AAV9  LYYLSKTINGSGQNQQT-LKFSVAGPSNMAVQGRNYIPGPSYRQQR 500        510        520        530        540
              |          |          |          |          |
SCH9  VSKTSADNNNSEYSWTGATKYHLNGRDSLVNPGPAMASHKDDEEKFFPQSGV
      |—AAV2 Block 6——————————————————————————————————≫
SCH2  VSKTSADNNNSEYSWTGATKYHLNGRDSLVNPGPAMASHKDDEEKFFPQSGV
      |—AAV2 Block 6——————————————————————————————————≫
AAV2  VSKTSADNNNSEYSWTGATKYHLNGRDSLVNPGPAMASHKDDEEKFFPQSGV
AAV6  VSKTKTDNNNSNFTWTGASKYNLNGRESIINPGTAMASHKDDKDKFFPMSGV
AAV8  VSTTTGQNNNSNFAWTAGTKYHLNGRNSLANPGIAMATHKDDEERFFPSNGI
AAV9  VSTTVTQNNNSEFAWPGASSWALNGRNSLMNPGPAMASHKEGEDRFFPLSGS 550        560        570        580
              |          |          |          |
SCH9  LIFGKQGSEKTNVDIEKVMITDEEEIRTTNPVATEQYGSVSTNLQR
      |—AAV2 Block 6——————————————————————————≫
SCH2  LIFGKQGSEKTNVDIEKVMITDEEEIRTTNPVATEQYGSVSTNLQR
      |—AAV2 Block 6——————————————————————————≫
AAV2  LIFGKQGSEKTNVDIEKVMITDEEEIRTTNPVATEQYGSVSTNLQR
AAV6  MIFGKESAGASNTALDNVMITDEEEIKATNPVATERFGTVAVNLQS
AAV8  LIFGKQNAARDNADYSDVMLTSEEEIKTTNPVATEEYGIVADNLQQ
AAV9  LIFGKQGTGRDNVDADKVMITNEEEIKTTNPVATESYGQVATNHQS
```

FIG. 10 (Cont.)

```
             590       600       610       620       630       640
              |         |         |         |         |         |
SCH9  GNRQAATADVNTQGVLPGMVWQDRDVYLQGPIWAKIPHTDGNFHPSPLMGGF
      |—AAV2 Block 6——————————→|—AAV9 Block 7————————————→
SCH2  GNRQAATADVNTQGVLPGMVWQDRDVYLQGPIWAKIPHTDGNFHPSPLMGGF
      |—AAV2 Block 6——————————→|—AAV9 Block 7————————————→
AAV2  GNRQAATADVNTQGVLPGMVWQDRDVYLQGPIWAKIPHTDGHFHPSPLMGGF
AAV6  SSTDPATGDVHVMGALPGMVWQDRDVYLQGPIWAKIPHTDGHFHPSPLMGGF
AAV8  QNTAPQIGTVNSQGALPGMVWQNRDVYLQGPIWAKIPHTDGNFHPSPLMGGF
AAV9  AQAQAQTGWVQNQGILPGMVWQDRDVYLQGPIWAKIPHTDGNFHPSPLMGGF 650       660       670       680
              |         |         |         |
SCH9  GMKHPPPQILIKNTPVPADPPTAFNKDKLNSFITQYSTGQVSVEIE
      |—AAV9 Block 7————————————————→|—AAV9 Block 8—→
SCH2  GMKHPPPQILIKNTPVPADPPTAFNKDKLNSFITQYSTGQVSVEIE
      |—AAV9 Block 7————————————————→|—AAV9 Block 8—→
AAV2  GLKHPPPQILIKNTPVPANPSTTFSAAKFASFITQYSTGQVSVEIE
AAV6  GLKHPPPQILIKNTPVPANPPAEFSATKFASFITQYSTGQVSVEIE
AAV8  GLKHPPPQILIKNTPVPADPPTTFNQSKLNSFITQYSTGQVSVEIE
AAV9  GMKHPPPQILIKNTPVPADPPTAFNKDKLNSFITQYSTGQVSVEIE 690       700       710       720       730      738
              |         |         |         |         |        |
SCH9  WELQKENSKRWNPEIQYTSNYYKSNNVEFAVNTEGVYSEPRPIGTRYLTRNL
      |—AAV9 Block 8——————————————————————————————————→
SCH2  WELQKENSKRWNPEIQYTSNYYKSNNVEFAVNTEGVYSEPRPIGTRYLTRNL
      |—AAV9 Block 8——————————————————————————————————→
AAV2  WELQKENSKRWNPEIQYTSNYNKSVNVDFTVDTNGVYSEPRPIGTRYLTRNL
AAV6  WELQKENSKRWNPEVQYTSNYAKSANVDFTVDNNGLYTEPRPIGTRYLTRPL
AAV8  WELQKENSKRWNPEIQYTSNYYKSTSVDFAVNTEGVYSEPRPIGTRYLTRNL
AAV9  WELQKENSKRWNPEIQYTSNYYKSNNVEFAVNTEGVYSEPRPIGTRYLTRNL
```

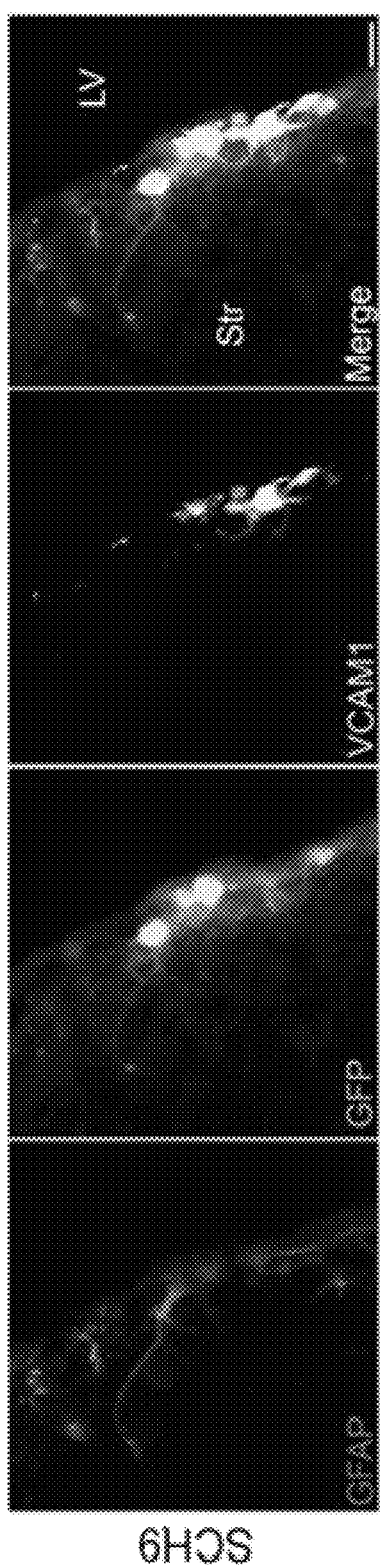
FIG. 13D
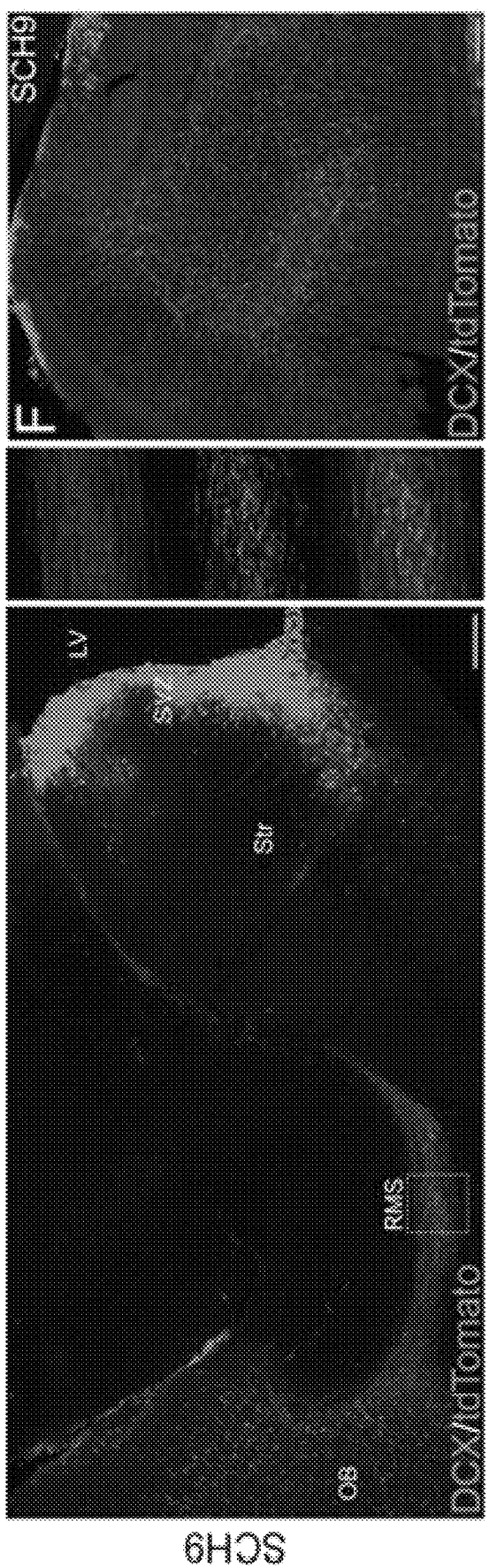
FIG. 13E
FIG. 13F

FIG. 18A

*Streptococcus pyogenes* Cas9

MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDHIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD (SEQ ID NO:40)

FIG. 18B

>nSpCas9 (SpCas9 D10A)
MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYLQNGRDMYVDQE
LDINRLSDYDVDHIVPQSFLKDDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD (SEQ ID NO:41)

FIG. 18C
SpCas9 (H840A)
MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYLQNGRDMYVDQ
ELDINRLSDYDVDA<u>A</u>IVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD (SEQ ID NO:42)

FIG. 18D

SpCas9 (D10A; H840A)
MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSLVSDFRKDFQFYKVREINNYHHAHDAYLN
AVVGTALIKKYPKLESEFVYGDYKVYDVVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD (SEQ ID NO:43)

FIG. 18E enSpCas9 (nCas9 with K848A/K1003A/R1060A mutations

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRYTGWGRLS
RKLINGIRDKQSGKTILDFLKSDGFANRNFMQLIHDDSLTFKEDIQKAQVSGQGDSLHEHIANLAGSPAIKKGILQTVKVDE
LVKVMGRHKPENIVIEMARENQTTQKGQKNSRERMKRIEEGIKELGSQILKEHPVENTQLQNEKLYLYLQNGRDMYVDQE
LDINRLSDYDVDHIVPQSFLADDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPALESEFVYGDYKVYDVRKMIAKSEQEIGKATAKYFFYSNIMNFFKTEITLANGEIRKAPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD (SEQ ID NO:44)

FIG. 18F nSpCas9-HF1

DKKYSIGLAIGTNSVGWAVITDEYKVPSKKFKVLGNTDRHSIKKNLIGALLFDSGETAEATRLKRTARRRYTRRKNRICYLQE
IFSNEMAKVDDSFFHRLEESFLVEEDKKHERHPIFGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARLSKSRRLENLIAQLPGEKKNGLFGNLIALSLGLTPNF
KSNFDLAEDAKLQLSKDTYDDDLDNLLAQIGDQYADLFLAAKNLSDAILLSDILRVNTEITKAPLSASMIKRYDEHHQDLTLL
KALVRQQLPEKYKEIFFDQSKNGYAGYIDGGASQEEFYKFIKPILEKMDGTEELLVKLNREDLLRKQRTFDNGSIPHQIHLGE
LHAILRRQEDFYPFLKDNREKIEKILTFRIPYYVGPLARGNSRFAWMTRKSEETITPWNFEEVVDKGASAQSFIERMTAFDKN
LPNEKVLPKHSLLYEYFTVYNELTKVKYVTEGMRKPAFLSGEQKKAIVDLLFKTNRKVTVKQLKEDYFKKIECFDSVEISGV
EDRFNASLGTYHDLLKIIKDKDFLDNEENEDILEDIVLTLTLFEDREMIEERLKTYAHLFDDKVMKQLKRRRYTGWGALSRK
LINGIRDKQSGKTILDFLKSDGFANRNFMALIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYLQNGRDMYVDQELD
INRLSDYDVDHIVPQSFLKDDSIDNKVLTRSDKNRGKSDNVPSEEVVKKMKNYWRQLLNAKLITQRKFDNLTKAERGGLSE
LDKAGFIKRQLVETRAITKHVAQILDSRMNTKYDENDKLIREVKVITLKSKLVSDFRKDFQFYKVREINNYHHAHDAYLNAV
VGTALIKKYPKLESEFVYGDYKVYDVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDKPIREQAENIIHLFTLTNLGAPAAF
KYFDTTIDRKRYTSTKEVLDATLIHQSITGLYETRIDLSQLGGD (SEQ ID NO:45)

FIG. 19

*Staphylococcus aureus* Cas9

MKRNYILGLDIGITSVGYGIIDYETRDVIDAGVRLFKEANVENNEGRRSKRGARRLKRRRRHRIQRVKKLLFDYNLLTDHSEL SGINPYEARVKGLSQKLSEEEFSAALLHLAKRRGVHNVNEVEEDTGNELSTKEQISRNSKALEEKYVAELQLERLKKDGEV RGSINRFKTSDYVKEAKQLLKVQKAYHQLDQSFIDTYIDLLETRRTYYEGPGEGSPFGWKDIKEWYEMLMGHCTYFPEELR SVKYAYNADLYNALNDLNNLVITRDENEKLEYYEKFQIIENVFKQKKKPTLKQIAKEILVNEEDIKGYRVTSTGKPEFTNLKVY HDIKDITARKEIIENAELLDQIAKILTIYQSSEDIQEELTNLNSELTQEEIEQISNLKGYTGTHNLSLKAINLILDELWHTNDNQIAI FNRLKLVPKKVDLSQQKEIPTTLVDDFILSPVVKRSFIQSIKVINAIIKKYGLPNDIIIELAREKNSKDAQKMINEMQKRNRQTN EREEIIRTTGKENAKYLIEKIKLHDMQEGKCLYSLEAIPLEDLLNNPFNYEVDHIIPRSVSFDNSFNNKVLVKQEENSKKGNR TPFQYLSSSDSKISYETFKKHILNLAKGKGRISKTKKEYLLEERDINRFSVQKDFINRNLVDTRYATRGLMNLLRSYFRVNNL DVKVKSINGGFTSFLRRKWKFKKERNKGYKHHAEDALIIANADFIFKEWKKLDKAKKVMENQMFEEKQAESMPEIETEQEY KEIFITPHQIKHIKDFKDYKYSHRVDKKPNRELINDTLYSTRKDDKGNTLIVNNLNGLYDKDNDKLKKLINKSPEKLLMYHHDP QTYQKLKLIMEQYGDEKNPLYKYYEETGNYLTKYSKKDNGPVIKKIKYYGNKLNAHLDITDDYPNSRNKVVKLSLKPYRFDV YLDNGVYKFVTVKNLDVIKKENYYEVNSKCYEEAKKLKKISNQAEFIASFYNNDLIKINGELYRVIGVNNDLLNRIEVNMIDITY REYLENMNDKRPPRIIKTIASKTQSIKKYSTDILGNLYEVKSKKHPQIIKKG (SEQ ID NO:46)

FIG. 20A

*Francisella tularensis* Cpf1

*Acidaminococcus sp. BV3L6* type V CRISPR-associated protein Cpf1

TQFEGFTNLYQVSKTLRFELIPQGKTLKHIQEQGFIEEDKARNDHYKELKPIIDRIYKTYADQCLQLVQLDWENLSAAIDSYR
KKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMPKCSTQLKAVTAHFQTHTTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMRNSNAATGEDYINSPVRDLNGVCFDSRFQN
PEWPMDADANGAYHIALKGQLLNHLKESKDLKLQNGISNQDWLAYIQELRN (SEQ ID NO:48)

FIG. 20C nCpf1 (AsCpf1 R1225A)

TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMA<u>N</u>SNAATGEDYINSPVRDLNGVCFDSRFQN
PEWPMDADANGAYHIALKGQLLLNHLKESKDLKLQNGISNQDWLAYIQELRN (SEQ ID NO:49)

FIG. 21A

| | | |
|---|---|---|
| AAV1 | ---TFSYTFEEVPFHSSYAHSQSLDRLMNPLIDQYLYYLNRTQ-NQSGSAQNKDLLFSRGS | 467 |
| AAV6 | ---TFSYTFEDVPFHSSYAHSQSLDRLMNPLIDQYLYYLNRTQ-NQSGSAQNKDLLFSRGS | 467 |
| AAV3 | ---FSYTFEDVPFHSSYAHSQSLDRLMNPLIDQYLYYLNRTQGTTSGTTNQSRLLFSQAG | 467 |
| AAV2 | ----FSYTFEDVPFHSSYAHSQSLDRLMNPLIDQYLYYLSRTN-TPSGTTTQSRLQFSQAG | 466 |
| AAV8 | NFQFTYTFEDVPFHSSYAHSQSLDRLMNPLIDQYLYYLSRTQTT-GGTANTQTLGFSQGG | 469 |
| AAV8.1 | NFQFTYTFEDVPFHSSYAHSQSLDRLMNPLIDQYLYYLSRTQTT-GGTANTQTLGFSQGG | 469 |
| AAV8 rh8 | FQFSYTFEDVPFHSSYAHSQSLDRLMNPLIDQYLYYLVRTQTTGTGTQTLAFSQAGPS | 469 |
| AAV10 | NFEFSYTFEDVPFHSSYAHSQSLDRLMNPLIDQYLYYLSRTQST-GGTQGTQQLLFSQAG | 469 |
| AAV7 | -FEFSYSFEDVPFHSSYAHSQSLDRLMNPLIDQYLYYLARTQSNPGGTAGNRELQFYQGG | 469 |
| AAV9 | -FQFSYEFENVPFHSSYAHSQSLDRLMNPLIDQYLYYLSKTI---NGSGQNQQTLKFSVAG | 467 |
| AAV9.1 | -FQFSYEFENVPFHSSYAHSQSLDRLMNPLIDQYLYYLSKTI---NGSGQNQQTLKFSVAG | 467 |
| AAV5 | NFEFTYNFEEVPFHSSFAPSQNLFKLANPLVDQYLYRFVSTN------NTGGVQFNKNL | 453 |

| | | |
|---|---|---|
| AAV1 | PAGMSVQPKNWLPGPCYRQQRVSKTKTDNNNSNFTWTGASKYNLNGRESIINPGTAMASH | 527 |
| AAV6 | PAGMSVQPKNWLPGPCYRQQRVSKTKTDNNNSNFTWTGASKYNLNGRESIINPGTAMASH | 527 |
| AAV3 | PQSMSLQARNWLPGPCYRQQRLSKTANDDNNNSNFPWTAASKYHLNGRDSLVNPGPAMASH | 527 |
| AAV2 | ASDIRDQSRNWLPGPCYRQQRVSKTSADNNNSEYSWTGATKYHLNGRDSLVNPGPAMASH | 526 |
| AAV8 | PNTMANQAKNWLPGPCYRQQRVSTTTGQNNNSNFAWTAGTKYHLNGRNSLANPGIAMATH | 529 |
| AAV8.1 | PNTMANQAKNWLPGPCYRQQRVSTTTGQNNNSNFAWTAGTKYHLNGRNSLANPGIAMATH | 529 |
| AAV8 rh8 | S---MANQARNWVPGPCYRQQRVSTTTNQNNNSNFAWTGAAKFKLNGRDSLMNPGVAMASH | 527 |
| AAV10 | PANMSAQAKNWLPGPCYRQQRVSTTLSQNNNSNFAWTGATKYHLNGRDSLVNPGVAMATH | 529 |
| AAV7 | PSTMAEQAKNWLPGPCFRQQRVSKTLDQNNNSNFSEFAWPGASSWALNGRNSLMNPGPAMASH | 529 |
| AAV9 | PSNMAVQGRNYIPGPSYRQQRVSTTVTQNNNSEFAWPGASSWALNGRNSLMNPGPAMASH | 527 |
| AAV9.1 | PSNMAVQGRNYIPGPSYRQQRVSTTVTQNNNSEFAWPGASSWALNGRNSLMNPGPAMASH | 527 |
| AAV5 | AGRYANTYKNWFPGPMGRTQGWNLGSGVNRASVSAFATTNRMELEGASYQVPPQPNGMTN | 513 |

Figure 21B

```
AAV1     KDDEDKFFPMSGVMIFGK---ESAGASNTALD-NVMITDEEEIKATNPVATERFGTVAVNF  584
AAV6     KDDKDKFFPMSGVMIFGK---ESAGASNTALD-NVMITDEEEIKATNPVATERFGTVAVNL  584
AAV3     KDDEEKFFPMHGNLIFGK---EGTTASNAELD-NVMITDEEEIRTTNPVATEQYGTVANNL  584
AAV2     KDDEEKFFPQSGVLIFGK---QGSEKTNVDIE-KVMITDEEEIRTTNPVATEQYGSVSTNL  583
AAV8     KDDEERFFPSNGILIFGK---QNAARDNADYS-DVMLTSEEEIKTTNPVATEEYGIVADNL  586
AAV8.1   KDDEERFFPSNGILIFGK---QNAARDNADYS-DVMLTSEEEIKTTNPVATEEYGIVADNL  586
AAV8 rh8 KDDDDRFFPSSGVLIFGK---QGAGNDGVDYS-QVLITDEEEIKATNPVATEEYGAVAINN  584
AAV10    KDDEERFFPSSGVLMFGK---QGAGRDNVDYS-SVMLTSEEEIKTTNPVATEQYGVVADNL  586
AAV7     KDDEDRFFPSSGVLIFGK--TGAT-NKTTLE-NVLMTNEEEIRPTNPVATEEYGIVSSNL  585
AAV9     KEGEDRFFPLSGSLIFGK---QGTGRDNVDAD--KVMITNEEEIKTTNPVATESYGQVATNH  584
AAV9.1   KEGEDRFFPLSGSLIFGK---QGTGRDNVDAD--KVMITNEEEIKTTNPVATESYGQVATNH  584
AAV5     NLQGSNTYALENTMIFNSQPANPGTTATYLEGNMLITSESETQPVNRVAYNVGGQMATNN  573
         .:      . ::  *. .             :  **:::* ** :: *  **

AAV1     QSSSTDPATGDVHAMGALPGMVWQDRDVYLQGPIWAKIPHTDGHFHPSPLMGGFGLKNPP  644
AAV6     QSSSTDPATGDVHVMGALPGMVWQDRDVYLQGPIWAKIPHTDGHFHPSPLMGGFGLKHPP  644
AAV3     QSSNTAPTTGTVNHQGALPGMVWQDRDVYLQGPIWAKIPHTDGHFHPSPLMGGFGLKHPP  644
AAV2     QRGNRQAATADVNIQGVLPGMVWQDRDVYLQGPIWAKIPHTDGHFHPSPLMGGFGLKHPP  643
AAV8     QQQNTAPQIGTVNSQGALPGMVWQNRDVYLQGPIWAKIPHTDGNFHPSPLMGGFGLKHPP  646
AAV8.1   QGQRQAAQIGTVNSQGALPGMVWQNRDVYLQGPIWAKIPHTDGNFHPSPLMGGFGLKHPP  646
AAV8 rh8 QAANTQAQTGLVHNQGVIPGMVWQNRDVYLQGPIWAKIPHTDGNFHPSPLMGGFGLKHPP  644
AAV10    QQANTGPIVGNVNSQGALPGMVWQNRDVYLQGPIWAKIPHTDGNFHPSPLMGGFGLKHPP  646
AAV7     QAANTAAQTQVVNNQGALPGMVWQNRDVYLQGPIWAKIPHTDGNFHPSPLMGGFGLKHPP  645
AAV9     QSAQAQAQTGWVQNQGILPGMVWQNRDVYLQGPIWAKIPHTDGNFHPSPLMGGFGMKHPP  644
AAV9.1   QSGQAQAATGWVQNQGILPGMVWQNRDVYLQGPIWAKIPHTDGNFHPSPLMGGFGMKHPP  644
AAV5     QSSTTAPATGTYNLQEIVPGSSVWMERDVYLQGPIWAKIPETGAHFHPSPAMGGFGLKHPP  633
         :    *  ** :  *******::******************** ****:*****
```

Figure 21C

| | | | |
|---|---|---|---|
| AAV1     | PQILIK- | 650 | (SEQ ID NO:139) |
| AAV6     | PQILIK- | 650 | (SEQ ID NO:140) |
| AAV3     | PQIMIK- | 650 | (SEQ ID NO:141) |
| AAV2     | PQILIKN | 650 | (SEQ ID NO:142) |
| AAV8     | PQILIKN | 653 | (SEQ ID NO:143) |
| AAV8.1   | PQILIKN | 653 | (SEQ ID NO:144) |
| AAV8_rh8 | PQILIKN | 651 | (SEQ ID NO:145) |
| AAV10    | PQILIKN | 653 | (SEQ ID NO:146) |
| AAV7     | PQILIKN | 652 | (SEQ ID NO:147) |
| AAV9     | PQILIK- | 650 | (SEQ ID NO:148) |
| AAV9.1   | PQILIK- | 650 | (SEQ ID NO:149) |
| AAV5     | PMMLIKN | 640 | (SEQ ID NO:150) |

* ::.**

ADENO-ASSOCIATED VIRUS CAPSID VARIANTS AND METHODS OF USE THEREOF

CROSS-REFERENCE

This application is a national phase filing under 35 U.S.C. § 371 of PCT/US2018/047561, filed Aug. 22, 2018, which claims the benefit of U.S. Provisional Patent Application No. 62/551,133, filed Aug. 28, 2017, which application are incorporated herein by reference in their entirety.

INTRODUCTION

Adeno-associated virus (AAV) belongs to the Parvoviridae family and *Dependovirus* genus, whose members require co-infection with a helper virus such as adenovirus to promote replication, and AAV establishes a latent infection in the absence of a helper. Virions are composed of a 25 nm icosahedral capsid encompassing a 4.7 kb single-stranded DNA genome with two open reading frames: rep and cap. The non-structural rep gene encodes four regulatory proteins essential for viral replication, whereas cap encodes three structural proteins (VP1-3) that assemble into a 60-mer capsid shell. This viral capsid mediates the ability of AAV vectors to overcome many of the biological barriers of viral transduction—including cell surface receptor binding, endocytosis, intracellular trafficking, and unpackaging in the nucleus.

There is a need in the art for AAV virions with variant capsid proteins that confer increased ability to cross cell barriers and/or that confer increased ability to infect neural stem cells and/or that confer increased ability to infect a neuronal cell.

SUMMARY

The present disclosure provides recombinant adeno-associated virus virions with variant capsid protein, where the recombinant AAV (rAAV) virions exhibit one or more of increased ability to cross neuronal cell barriers, increased infectivity of a neural stem cell, increased infectivity of a neuronal cell, and reduced susceptibility to antibody neutralization, compared to a control AAV, and where the rAAV virions comprise a heterologous nucleic acid. The present disclosure provides methods of delivering a gene product to a neural stem cell or a neuronal cell in an individual. The present disclosure also provides methods of modifying a target nucleic acid present in a neural stem cell or neuronal cell.

BRIEF DESCRIPTION OF THE DRAWINGS

FIG. 1A-1F provide a SCHEMA-guided design of a chimeric adeno-associated virus (AAV) library after applying the Recombination as a Shortest Path Problem (RASPP) method.

FIG. 2 provides the primer sequences used to design constructs and amplify the AAV cap gene.

FIG. 3 provides the primer sequences designed in j5 DNA assembly to amplify each sequence block for combinatorial golden gate assembly of the SCHEMA AAV library.

FIG. 4 provides the polymerase chain reaction (PCR) reactions for combinatorial golden gate cloning of the SCHEMA AAV library.

FIG. 5 provides the primers designed to incorporate silent mutations at block junctures to facilitate combinatorial golden gate cloning into the pBluescript vector backbone.

FIG. 8 provides the amino acid sequence of SCH9 capsid.

FIG. 9 provides the amino acid sequence of SCH2 capsid.

FIG. 10 provides an amino acid alignment of the SCH9 and SCH2 AAV cap amino acid sequences with the parent AAV serotypes. SCH9 amino acid sequence: SEQ ID NO:1; SCH2 amino acid sequence: SEQ ID NO:2; AAV2 capsid amino acid sequence: SEQ ID NO:136; AAV6 capsid amino acid sequence: SEQ ID NO:11; AAV8 capsid amino acid sequence: SEQ ID NO:137; AAV9 capsid amino acid sequence: SEQ ID NO:138.

FIG. 13A-13I depict the effects of SCH9 on the transduction of neural stem cells in the subventricular zone (SVZ).

FIG. 18A-18F provide amino acid sequences of *Streptococcus pyogenes* Cas9 polypeptide and variants.

FIG. 19 provides an amino acid sequence of a *Staphylococcus aureus* Cas9 polypeptide.

FIG. 20A-20C provide amino acid sequences of various Cpf1 polypeptides.

FIGS. 21A-21C provide an alignment of amino acid sequences of AAV capsid protein loop IV (GH loop) regions. Insertion sites are shown in bold and underlining. The amino acid sequences depicted in FIGS. 21A-21C have the following sequence identifiers from top to bottom: SEQ ID NO:139-150.

DEFINITIONS

Figure 1A:
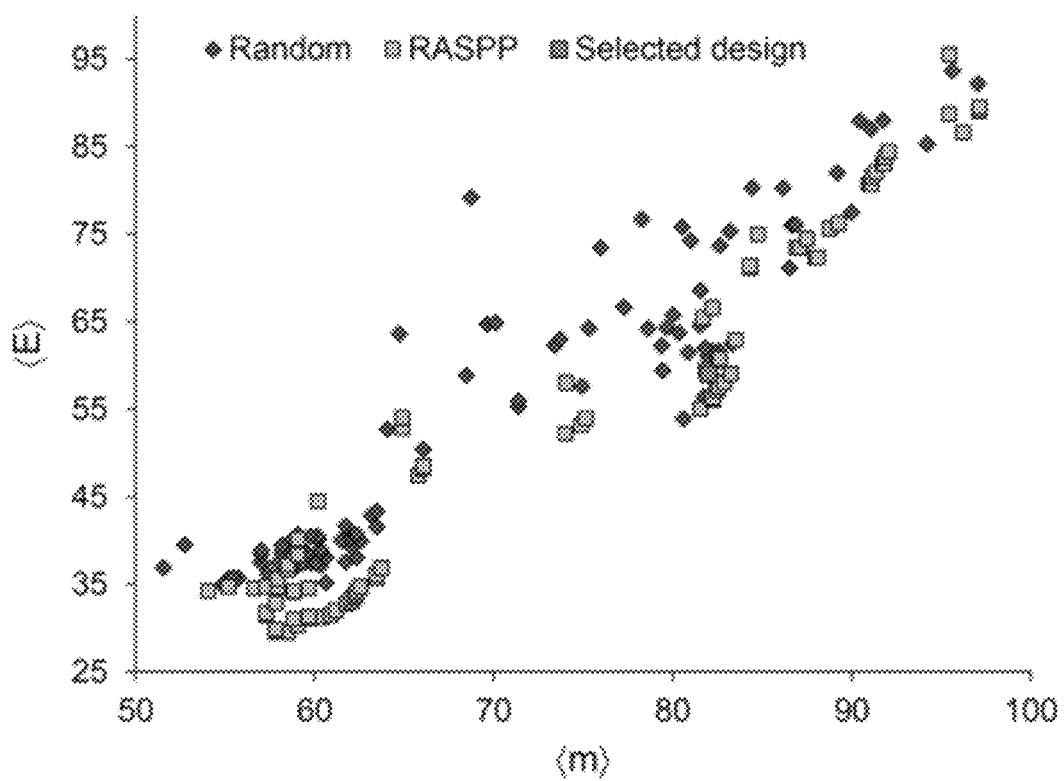

As used herein, the term "neural stem cell" (NSC) refers to an undifferentiated neural cell that can proliferate, self-renew, and differentiate into the main adult neural cells of the brain. NSCs are capable of self-maintenance (self-renewal), meaning that with each cell division, one daughter cell will also be a stem cell. The non-stem cell progeny of NSCs are termed neural progenitor cells. Neural progenitors cells generated from a single multipotent NSC are capable of differentiating into neurons, astrocytes (type I and type II), and oligodendrocytes. Hence, NSCs are "multipotent" because their progeny have multiple neural cell fates. Thus, NSCs can be functionally defined as a cell with the ability to: 1) proliferate, 2) self-renew, and 3) produce functional progeny that can differentiate into the three main cell types found in the central nervous system: neurons, astrocytes and oligodendrocytes. An NSC is generally negative for markers of mature neurons, mature glial cells, mature oligodendrocytes, and mature astrocytes.

As used herein, the terms "neural progenitor cell" or "neural precursor cell" refer to a cell that can generate progeny such as neuronal cells (e.g., neuronal precursors or mature neurons), glial precursors, mature astrocytes, or mature oligodendrocytes. Typically, the cells express some of the phenotypic markers that are characteristic of the neural lineage. A "neuronal progenitor cell" or "neuronal precursor cell" is a cell that can generate progeny that are mature neurons. These cells may or may not also have the capability to generate glial cells.

A "neuronal cell," as used herein, is used interchangeably with "neural cell" and refers to neurons and glia of the central nervous system or peripheral nervous system. The term "neuronal cell" includes cells such as astrocytes, oligodendrocytes, and Schwann cells. The term includes neuronal cells of any brain tissue (e.g., a brain tissue such as cerebral hemisphere, cerebral cortex, subcortex motor cortex, striatum, internal capsule, thalamus, hypothalamus, hippocampus, midbrain, brainstem, and cerebellum). A mature neuron can express one or more markers of a mature neuron, where such markers include, e.g., nestin, NeuroD1, neuron-specific enolase (NSE), neuron-specific nuclear protein (NeuN), neurofilament (NF), 510013, tau, microtubule-associated protein 2 (MAP2), tau, doublecortin (DCX), and the like.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10), avian AAV, bovine AAV, canine AAV, equine AAV, primate AAV, non-primate AAV, and ovine AAV. "Primate AAV" refers to AAV isolated from a primate, "non-primate AAV" refers to AAV isolated from a non-primate mammal, "bovine AAV" refers to AAV isolated from a bovine mammal (e.g., a cow), etc.

An "rAAV vector" as used herein refers to an AAV vector comprising a polynucleotide sequence not of AAV origin (i.e., a polynucleotide heterologous to AAV), typically a sequence of interest for introducing into a target cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome (vg) copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA). Viral infectivity can be expressed as the ratio of infectious viral particles to total viral particles. Methods of determining the ratio of infectious viral particle to total viral particle are known in the art. See, e.g., Grainger et al. (2005) *Mol. Ther.* 11:S337 (describing a TCID50 infectious titer assay); and Zolotukhin et al. (1999) *Gene Ther.* 6:973.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In general, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in some cases will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty:30.0.

A "gene" refers to a polynucleotide containing at least one open reading frame that is capable of encoding a particular protein after being transcribed and translated.

The term "guide RNA", as used herein, refers to an RNA that comprises: i) an "activator" nucleotide sequence that binds to a guide RNA-directed endonuclease (e.g., a class 2 CRISPR/Cas endonuclease such as a type II, type V, or type VI CRISPR/Cas endonuclease) and activates the RNA-directed endonuclease; and ii) a "targeter" nucleotide sequence that comprises a nucleotide sequence that hybridizes with a target nucleic acid. The "activator" nucleotide sequence and the "targeter" nucleotide sequence can be on separate RNA molecules (e.g., a "dual-guide RNA"); or can be on the same RNA molecule (a "single-guide RNA").

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some cases, the length of the duplex of siRNAs is less than 30 nucleotides. In some cases, the duplex can be 29, 28, 27, 26, 25, 24, 23, 22, 21, 20, 19, 18, 17, 16, 15, 14, 13, 12, 11 or 10 nucleotides in length. In some cases, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some cases, the loop is 5, 6, 7, 8, 9, 10, 11, 12 or 13 nucleotides in length. The hairpin structure can also contain 3' or 5' overhang portions. In some cases, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV. As another example, a variant AAV capsid protein that comprises a heterologous peptide inserted into the GH loop of the capsid protein is a variant AAV capsid protein that includes an insertion of a peptide not normally included in a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some cases purified, e.g., from about 80% to about 90% pure, at least about 90% pure, at least about 95% pure, at least about 98% pure, or at least about 99%, or more, pure.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already afflicted (e.g., those with a neurological disorder) as well as those in which prevention is desired (e.g., those with increased susceptibility to a neurological disorder; those suspected of having a neurological disorder; those having one or more risk factors for a neurological disorder, etc.).

The terms "recipient", "individual", "subject", "host", and "patient", are used interchangeably herein and refer to any mammalian subject for whom diagnosis, treatment, or therapy is desired, such as humans. "Mammal" for purposes of treatment refers to any animal classified as a mammal, including humans, domestic and farm animals, and zoo, sports, or pet animals, such as non-human primates, dogs, horses, cats, cows, sheep, goats, pigs, camels, etc. In some cases, the mammal is a human.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The terms "individual," "host," "subject," and "patient" are used interchangeably herein, and refer to a mammal, including, but not limited to, human and non-human primates, including simians and humans; mammalian sport animals (e.g., horses, camels, etc); mammalian farm animals (e.g., sheep, goats, cows, etc.); mammalian pets (dogs, cats, etc.); and rodents (e.g., mice, rats, etc.). In some cases, the individual is a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a neural stem cell" includes a plurality of such cells and reference to "the rAAV" includes reference to one or more rAAVs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides recombinant adeno-associated virus virions with variant capsid protein, where the recombinant AAV (rAAV) virions exhibit one or more of increased ability to cross neuronal cell barriers, increased infectivity of a neural stem cell, increased infectivity of a neuronal cell, and reduced susceptibility to antibody neutralization, compared to a control AAV, and where the rAAV virions comprise a heterologous nucleic acid. The present disclosure provides methods of delivering a gene product to a neural stem cell, a neuronal progenitor cell, or a neuronal cell in an individual. The present disclosure also provides methods of modifying a target nucleic acid present in a neural stem cell or neuronal cell. The present disclosure further provides methods of treating a neural disease.

Recombinant Aav Virions with Variant Capsid Polypeptides

The present disclosure provides an infectious rAAV virion comprising: i) a variant AAV capsid polypeptide of the present disclosure; and ii) a heterologous nucleic acid comprising a nucleotide sequence encoding a heterologous polypeptide (i.e., a non-AAV polypeptide). In some cases, the variant AAV capsid protein comprises at least 5 segments from at least 3 different AAV serotypes, wherein each segment has a length of from about 50 amino acids to about 160 amino acids. The variant capsid protein confers one or more of the following properties: i) increased infectivity of a neural stem cell or neural progenitor cell, compared to the infectivity of the neural stem cell or neural progenitor cell by a control AAV virion comprising a corresponding parental AAV capsid protein or compared to a wild-type AAV virion, or compared to a control AAV virion comprising wild-type AAV capsid; ii) increased infectivity of a neuronal cell, compared to the infectivity of the neuronal cell by a control AAV virion comprising a corresponding parental AAV capsid protein or compared to a wild-type AAV virion, or compared to a control AAV virion comprising wild-type AAV capsid; iii) increased ability to cross a cellular barrier, compared to the ability of a control AAV virion comprising a corresponding parental AAV capsid protein or compared to the ability of a wild-type AAV virion to cross the cellular barrier, or compared to a control AAV virion comprising wild-type AAV capsid; iv) increased resistance to human AAV neutralizing antibodies, compared to the resistance exhibited by a control AAV virion comprising a corresponding parental AAV capsid protein or compared to a wild-type AAV virion, or compared to a control AAV virion comprising wild-type AAV capsid.

A control AAV virion can comprise a parental AAV capsid protein. A control AAV virion can be an AAV virion comprising wild-type AAV capsid, e.g., comprising only wild-type capsid (and not any variant AAV capsid of the present disclosure). For example, a control AAV virion can comprise wild-type AAV2 capsid. As another example, a control AAV virion can comprise wild-type AAV6 capsid. As another example, a control AAV virion can comprise wild-type AAV9 capsid.

Increased Infectivity of a Neural Stem Cell or Neural Progenitor Cell

The present disclosure provides rAAV virions with a variant capsid protein, where rAAV virions exhibit increased infectivity of a neural stem cell (NSC) or a neural progenitor cell compared to the ability of a control, parental AAV not comprising the variant capsid protein, or compared to the ability of wild-type AAV, or compared to a control AAV virion comprising wild-type AAV capsid, to infect the NSC or neural progenitor cell; and where the rAAV virions comprise a heterologous nucleic acid.

In some cases, the NSC is a subventricular zone (SVZ) NSC. The SVZ is located along the ependymal cell layer, which separates the ventricular space from the SVZ. SVZ. NSCs can give rise to transit amplifying progenitors, which divide a few times before becoming neuroblasts. In some cases, the NSC is in the subgranular zone (SGZ) within the dentate gyrus of the hippocampus. Radial glia-like NSCs (RGLs) in the SGZ, at the border between the inner granule cell layer and the hilus, give rise to intermediate progenitor cells (IPCs), which exhibit limited rounds of proliferation before generating neuroblasts. Neural progenitor cells (NPCs) include transit amplifying cells, RGLs, IPCs, and neuroblasts. In some cases, the NSC is from the hippocampus, or is present in the hippocampus. In some cases, the NSC is present in the developing nervous system; e.g., the NSC is present in an embryo.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased infectivity of an NSC, compared to the infectivity of the NSC by an AAV virion comprising the corresponding parental AAV capsid protein, compared to the infectivity of the NSC by an AAV virion not comprising the variant capsid polypeptide, or compared to the infectivity of the NSC by a wild-type AAV virion (comprising a wild-type AAV capsid), or compared to the infectivity of the NSC by a control AAV virion comprising wild-type AAV capsid.

In some cases, a subject rAAV virion exhibits at least 5-fold, at least 10-fold, at least 15-fold, at least 20-fold, at least 25-fold, at least 50-fold, or more than 50-fold, increased infectivity of an NSC, when administered via intracranial, intracerebroventricular, intrathecal, intra-cisterna magna, or intravenous injection, compared to the infectivity of the NSC by an AAV virion comprising the corresponding parental AAV capsid protein, or comprising wild-type AAV capsid, or compared to a control AAV virion comprising wild-type AAV capsid when administered via intracranial, intracerebroventricular, intrathecal, intra-cisterna magna, or intravenous injection.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased infectivity of an NPC, compared to the infectivity of the NPC by an AAV virion comprising the corresponding parental AAV capsid protein, or comprising wild-type AAV capsid, compared to the infectivity of the NPC by an AAV virion not comprising the variant capsid polypeptide, or compared to the infectivity of the NPC by a wild-type AAV virion (comprising a wild-type AAV capsid), or compared to the infectivity of the NPC by a control AAV virion comprising wild-type AAV capsid.

In some cases, a subject rAAV virion exhibits at least 5-fold, at least 10-fold, at least 15-fold, at least 20-fold, at least 25-fold, at least 50-fold, or more than 50-fold, increased infectivity of a neuroblast, compared to the infectivity of the neuroblast by an AAV virion comprising the corresponding parental AAV capsid protein, or comprising wild-type AAV capsid, or compared to a control AAV virion comprising wild-type AAV capsid.

In some cases, a subject rAAV virion exhibits at least 5-fold, at least 10-fold, at least 15-fold, at least 20-fold, at least 25-fold, at least 50-fold, or more than 50-fold, increased infectivity of a neuroblast, when administered via intracranial, intracerebroventricular, intrathecal, intra-cisterna magna, or intravenous injection, compared to the infectivity of the neuroblast by an AAV virion comprising the corresponding parental AAV capsid protein, or comprising wild-type AAV capsid, or compared to a control AAV virion comprising wild-type AAV capsid, when administered via intracranial, intracerebroventicular, intrathecal, intra-cisterna magna, or intravenous injection.

In some cases, a subject rAAV virion exhibits at least 5-fold, at least 10-fold, at least 15-fold, at least 20-fold, at least 25-fold, at least 50-fold, or more than 50-fold, increased infectivity of a transit amplifying cell, compared to the infectivity of the transit amplifying cell by an AAV virion comprising the corresponding parental AAV capsid protein, or comprising wild-type AAV capsid protein, or compared to a control AAV virion comprising wild-type AAV capsid.

In some cases, a subject rAAV virion exhibits at least 5-fold, at least 10-fold, at least 15-fold, at least 20-fold, at least 25-fold, at least 50-fold, or more than 50-fold, increased infectivity of a transit amplifying cell, when administered via intracranial, intracerebroventicular, intrathecal, intra-cisterna magna, or intravenous injection, compared to the infectivity of the transit amplifying cell by an AAV virion comprising the corresponding parental AAV capsid protein, or comprising wild-type AAV capsid protein, or compared to a control AAV virion comprising wild-type AAV capsid when administered via the same route of administration.

Whether a given rAAV virion exhibits increased infectivity of an NSC or a NPC can be determined in vitro or in vivo. For example, whether a given rAAV virion exhibits increased infectivity of an NSC can be determined by contacting the NSC in vitro with the rAAV virion, and detecting expression in the NSC of a heterologous gene product encoded by the rAAV virion. The heterologous gene product can provide a detectable signal, and the level of the detectable signal in the NSC can provide an indication as to whether a given rAAV virion exhibits increased infectivity of an NSC.

In some cases, an rAAV virion of the present disclosure that comprises: a) a variant capsid of the present disclosure comprising at least 5 segments from at least 3 different AAV serotypes, wherein each segment has a length of from about 50 amino acids to about 160 amino acids, as described below; and b) a heterologous nucleotide sequence encoding a heterologous gene product, when administered to an individual, results in a level of the heterologous gene product in a neural stem cell, that is at least 2-fold, at least 5-fold, at least 10-fold, at least 15-fold, at least 20-fold, at least 25-fold, at least 50-fold, or more than 50-fold, greater than the level of the gene product in the neural stem cell that results when a control rAAV virion that comprises: a) a control AAV (e.g., a wild-type AAV capsid); and b) heterologous nucleotide sequence encoding the heterologous gene product is administered to the individual. Administration can be via a number of routes, e.g., via intracranial, intracerebroventicular, intrathecal, intra-cisterna magna, or intravenous injection.

Whether a given rAAV virion exhibits increased infectivity of an NSC can be determined by assessing a therapeutic effect of a therapeutic gene product encoded by the rAAV virion in an NSC. Therapeutic effects can include, e.g., a) an increase in neurogenesis; b) amelioration of a symptom of a neurological disease or disorder; etc. For example, an rAAV virion of the present disclosure that comprises: a) a variant capsid of the present disclosure; and b) a heterologous nucleotide sequence encoding a heterologous therapeutic gene product, when administered to an individual (e.g., via intracranial, intracerebroventicular, intrathecal, intra-cisterna magna, or intravenous injection), results in a therapeutic effect of the therapeutic gene product in a neural stem cell, that is at least 2-fold, at least 5-fold, at least 10-fold, at least 15-fold, at least 20-fold, at least 25-fold, at least 50-fold, or more than 50-fold, greater than the therapeutic effect that results when a control rAAV virion that comprises: a) a control AAV capsid (e.g., a wild-type AAV capsid); and b) heterologous nucleotide sequence encoding the heterologous therapeutic gene product is administered via the same route of administration.

In some cases, a subject rAAV virion exhibits at least 2-fold, at least 5-fold, at least 10-fold, at least 15-fold, at least 20-fold, at least 25-fold, at least 50-fold, or more than 50-fold, increased infectivity of an NSC, when administered via intracranial, intracerebroventicular, intrathecal, intra-cisterna magna, or intravenous injection, compared to the infectivity of the NSC by an AAV virion comprising the corresponding parental AAV capsid protein, or compared to the infectivity of the NSC by a wild-type AAV virion (comprising a wild-type AAV capsid polypeptide), when administered via the same route of administration.

Increased Infectivity of a Neuronal Cell

As noted above, in some cases, a variant capsid polypeptide present in an rAAV virion of the present disclosure confers increased infectivity of a neuronal cell on the rAAV virion, compared to the ability of a control parental AAV not comprising the variant capsid protein, or compared to a wild-type AAV to infect the neuronal cell.

In some cases, a subject rAAV virion exhibits at least 2-fold, at least 5-fold, at least 10-fold, at least 15-fold, at least 20-fold, at least 25-fold, at least 50-fold, or more than 50-fold, increased infectivity of a neuronal cell, compared to the infectivity of the neuronal cell by an AAV virion comprising the corresponding parental AAV capsid protein, or compared to the infectivity of the neuronal cell by an AAV virion comprising wild-type AAV capsid polypeptide.

In some cases, a subject rAAV virion exhibits at least 2-fold, at least 5-fold, at least 10-fold, at least 15-fold, at least 20-fold, at least 25-fold, at least 50-fold, or more than 50-fold, increased infectivity of a neuronal cell, when administered via intracranial, intracerebroventicular, intrathecal, intra-cisterna magna, or intravenous injection, compared to the infectivity of the neuronal cell by an AAV virion comprising the corresponding parental AAV capsid protein, or compared to the infectivity of the neuronal cell by wild-type AAV, or compared to a control AAV virion comprising wild-type AAV capsid when administered via the same route of administration.

In some cases, a subject rAAV virion exhibits at least 2-fold, at least 5-fold, at least 10-fold, at least 15-fold, at least 20-fold, at least 25-fold, at least 50-fold, or more than 50-fold, increased infectivity of a neuronal cell of the cerebral hemisphere, cerebral cortex, subcortex motor cortex, striatum, internal capsule, thalamus, hypothalamus, hippocampus, midbrain, brainstem, or the cerebellum, compared to the infectivity of the neuronal cell of the same tissue by an AAV virion comprising the corresponding parental AAV capsid protein, or compared to the infectivity of the neuronal cell by an AAV virion comprising wild-type AAV capsid polypeptide.

As one example, in some cases, a subject rAAV virion exhibits at least 5-fold, at least 10-fold, at least 15-fold, at least 20-fold, at least 25-fold, at least 50-fold, or more than 50-fold, increased infectivity of a Purkinje cell, compared to the infectivity of the Purkinje cell by an AAV virion comprising the corresponding parental AAV capsid protein, or comprising wild-type AAV capsid protein.

As one example, in some cases, a subject rAAV virion exhibits at least 5-fold, at least 10-fold, at least 15-fold, at least 20-fold, at least 25-fold, at least 50-fold, or more than 50-fold, increased infectivity of a Purkinje cell, when administered via intracranial, intracerebroventicular, intrathecal, intra-cisterna magna, or intravenous injection, compared to the infectivity of the Purkinje cell by an AAV virion comprising the corresponding parental AAV capsid protein, or comprising wild-type AAV capsid protein, when administered via the same route of administration.

As one example, in some cases, a subject rAAV virion exhibits at least 5-fold, at least 10-fold, at least 15-fold, at least 20-fold, at least 25-fold, at least 50-fold, or more than 50-fold, increased infectivity of a GABAergic cell, compared to the infectivity of the GABAergic cell by an AAV virion comprising the corresponding parental AAV capsid protein, or comprising wild-type AAV capsid protein.

As one example, in some cases, a subject rAAV virion exhibits at least 5-fold, at least 10-fold, at least 15-fold, at least 20-fold, at least 25-fold, at least 50-fold, or more than 50-fold, increased infectivity of a GABAergic cell, when administered via intracranial, intracerebroventicular, intrathecal, intra-cisterna magna, or intravenous injection, compared to the infectivity of the GABAergic cell by an AAV virion comprising the corresponding parental AAV capsid protein, or comprising wild-type AAV capsid protein, when administered via the same route of administration.

In some cases, a subject rAAV virion exhibits at least 5-fold, at least 10-fold, at least 15-fold, at least 20-fold, at least 25-fold, at least 50-fold, or more than 50-fold, increased infectivity of a glial cell, compared to the infectivity of the glial cell by an AAV virion comprising the corresponding parental AAV capsid protein, or comprising wild-type AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of a glial cell, when administered via intracranial, intracerebroventicular, intrathecal, intra-cisterna magna, or intravenous injection, compared to the infectivity of the glial cell by an AAV virion comprising the corresponding parental AAV capsid protein, or comprising wild-type AAV capsid protein, when administered via the same route of administration.

In some cases, a subject rAAV virion exhibits at least 5-fold, at least 10-fold, at least 15-fold, at least 20-fold, at least 25-fold, at least 50-fold, or more than 50-fold, increased infectivity of an astrocyte, compared to the infectivity of the astrocyte by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of an astrocyte, when administered via intracranial, intracerebroventicular, intrathecal, intra-cisterna magna, or intravenous injection, compared to the infectivity of the astrocyte by an AAV virion comprising the corresponding parental AAV capsid protein, when administered via intracranial, intracerebroventicular, intrathecal, intra-cisterna magna, or intravenous injection.

Whether a given rAAV virion exhibits increased infectivity of a neuronal cell can be determined in vitro or in vivo. For example, whether a given rAAV virion exhibits increased infectivity of a neuronal cell can be determined by contacting the neuronal cell in vitro with the rAAV virion, and detecting expression in the neuronal cell of a heterologous gene product encoded by the rAAV virion. The heterologous gene product can provide a detectable signal, and the level of the detectable signal in the neuronal cell can provide an indication as to whether a given rAAV virion exhibits increased infectivity of a neuronal cell.

Whether a given rAAV virion exhibits increased infectivity of a neuronal cell can be determined by detecting expression in a neuronal cell of a heterologous gene product encoded by the rAAV virion, following administration of the rAAV virion to an individual. Whether a given rAAV virion exhibits increased infectivity of a neuronal cell can be determined by detecting expression in a neuronal cell of a heterologous gene product encoded by the rAAV virion, following intracranial, intracerebroventicular, intrathecal, intra-cisterna magna, or intravenous administration of the rAAV virion. For example, an rAAV virion of the present disclosure that comprises: a) a variant capsid of the present disclosure comprising at least 5 segments from at least 3 different AAV serotypes, wherein each segment has a length of from about 50 amino acids to about 160 amino acids, as described above; and b) a heterologous nucleotide sequence encoding a heterologous gene product, when administered, results in a level of the heterologous gene product in a neuronal cell, that is at least 2-fold, at least 5-fold, at least 10-fold, at least 15-fold, at least 20-fold, at least 25-fold, at least 50-fold, or more than 50-fold, greater than the level of the gene product in the neuronal cell that results when a control rAAV virion that comprises: a) a control AAV capsid or a wild-type AAV capsid; and b) heterologous nucleotide sequence encoding the heterologous gene product is administered via intracranial, intracerebroventicular, intrathecal, intra-cisterna magna, or intravenous injection.

Whether a given rAAV virion exhibits increased infectivity of a neuronal cell can be determined by assessing a therapeutic effect of a therapeutic gene product encoded by the rAAV virion in a neuronal cell. Therapeutic effects can include, e.g., a) an increase in neuronal cell function; b) amelioration of a symptom of a neurological disease or disorder; etc. For example, an rAAV virion of the present disclosure that comprises: a) a variant capsid of the present disclosure comprising a peptide insert or a peptide replacement, as described above; and b) a heterologous nucleotide sequence encoding a heterologous therapeutic gene product, when administered via intracranial, intracerebroventicular, intrathecal, intra-cisterna magna, or intravenous injection, results in a therapeutic effect of the therapeutic gene product in a neuronal cell, that is at least 2-fold, at least 5-fold, at least 10-fold, at least 15-fold, at least 20-fold, at least 25-fold, at least 50-fold, or more than 50-fold, greater than the therapeutic effect in the neuronal cell that results when a control rAAV virion that comprises: a) a control AAV capsid that does not comprises the peptide insert or the peptide replacement; and b) heterologous nucleotide sequence encoding the heterologous therapeutic gene product is administered via the same route of administration.

Crossing a Cellular Barrier

The present disclosure provides recombinant adeno-associated virus virions with variant capsid protein, where the rAAV virions exhibit increased ability to cross a cell barrier, i.e., a physiological barrier. For example, a cell barrier can comprise a layer of cells between a first compartment that does not include a neural stem cell and a second compartment that does include a neural stem cell. Such barriers include, e.g., the ependymal cell layer lining the lateral ventricles, the hypocellular layer, the astrocyte cell bodies layer, the blood-brain barrier, and the transition zone layer. Thus, the present disclosure provides an rAAV virion with a variant capsid protein, where the rAAV virion exhibits at least 2-fold, at least 5-fold, at least 10-fold, at least 15-fold, at least 20-fold, at least 25-fold, at least 50-fold, or more than 50-fold, increased ability to cross one or more of the ependymal cell layer, the hypocellular layer, the astrocyte cell bodies layer, and the transition zone layer, compared to the ability of a control AAV not comprising the variant capsid protein, or compared to the ability of a control AAV comprising wild-type AAV capsid protein, to cross the layer; and where the rAAV virions comprise a heterologous nucleic acid comprising a nucleotide sequence encoding a heterologous gene product.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased ability to cross the ependymal cell layer lining the lateral ventricles, compared to the ability of a control rAAV virion comprising the corresponding parental AAV capsid, or comprising wild-type AAV capsid protein, to cross the ependymal cell layer.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased ability to cross the blood-brain barrier, compared to the ability of a control rAAV virion comprising the corresponding parental AAV capsid, or comprising wild-type AAV capsid protein, to cross the blood-brain barrier.

In some cases, a subject rAAV virion exhibits at least 2-fold, at least 5-fold, at least 10-fold, at least 15-fold, at least 20-fold, at least 25-fold, at least 50-fold, or more than 50-fold, increased ability to cross the ependymal cell layer, when administered via intracranial, intracerebroventicular, intrathecal, intra-cisterna magna, or intravenous injection, compared to the ability to cross the ependymal cell layer by an AAV virion comprising the corresponding parental AAV capsid protein, or comprising wild-type AAV capsid protein, when administered via the same route of administration.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased ability to cross the hypocellular layer, compared to the ability of a control rAAV virion comprising the corresponding parental AAV capsid, or comprising wild-type AAV capsid protein, to cross the hypocellular cell layer.

In some cases, a subject rAAV virion exhibits at least 2-fold, at least 5-fold, at least 10-fold, at least 15-fold, at least 20-fold, at least 25-fold, at least 50-fold, or more than 50-fold, increased ability to cross the hypocellular layer, when administered via intracranial, intracerebroventicular, intrathecal, intra-cisterna magna, or intravenous injection, compared to the ability to cross the hypocellular layer by an AAV virion comprising the corresponding parental AAV capsid protein, when administered via the same route of administration.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased ability to cross the astrocyte cell bodies layer, compared to the ability of a control rAAV virion comprising the corresponding parental AAV capsid, or comprising wild-type AAV capsid protein, to cross the astrocytes cell bodies layer.

In some cases, a subject rAAV virion exhibits at least 2-fold, at least 5-fold, at least 10-fold, at least 15-fold, at least 20-fold, at least 25-fold, at least 50-fold, or more than 50-fold, increased ability to cross the astrocyte cell bodies layer, when administered via intracranial, intracerebroventicular, intrathecal, intra-cisterna magna, or intravenous injection, compared to the ability to cross the astrocyte cell bodies layer by an AAV virion comprising the corresponding parental AAV capsid protein, or comprising wild-type AAV capsid protein, when administered via the same route of administration.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased ability to cross the transition zone layer, compared to the ability of a control rAAV virion comprising the corresponding parental AAV capsid, or comprising wild-type AAV capsid protein, to cross the transition zone layer.

In some cases, a subject rAAV virion exhibits at least 2-fold, at least 5-fold, at least 10-fold, at least 15-fold, at least 20-fold, at least 25-fold, at least 50-fold, or more than 50-fold, increased ability to cross the transition zone layer, when administered via intracranial, intracerebroventicular, intrathecal, intra-cisterna magna, or intravenous injection, compared to the ability to cross the transition zone layer by an AAV virion comprising the corresponding parental AAV capsid protein, or comprising wild-type AAV capsid protein, when administered via the same route of administration.

In some cases, an rAAV virion of the present disclosure exhibits at least 2-fold, at least 5-fold, at least 10-fold, at least 15-fold, at least 20-fold, at least 25-fold, at least 50-fold, or more than 50-fold, increased ability to cross the brain parenchyma, compared to the ability of a control rAAV virion comprising the corresponding parental AAV capsid, or comprising wild-type AAV capsid protein, to cross the brain parenchyma.

In some cases, a subject rAAV virion exhibits at least 2-fold, at least 5-fold, at least 10-fold, at least 15-fold, at least 20-fold, at least 25-fold, at least 50-fold, or more than 50-fold, increased ability to cross the brain parenchyma, when administered via intracranial, intracerebroventicular, intrathecal, intra-cisterna magna, or intravenous injection, compared to the ability to cross the brain parenchyma by an AAV virion comprising the corresponding parental AAV capsid protein, or comprising wild-type AAV capsid protein, when administered via the same route of administration.

In some cases, a subject rAAV virion, when injected via intracranial, intracerebroventicular, intrathecal, intra-cisterna magna, or intravenous administration, exhibits at least 2-fold, at least 5-fold, at least 10-fold, at least 15-fold, at least 20-fold, at least 25-fold, at least 50-fold, or more than 50-fold, increased localization past the ependymal layer, compared to the extent of localization past the ependymal layer by a control AAV virion comprising the corresponding parental AAV capsid protein, or comprising wild-type AAV capsid protein, when injected via the same route of administration.

For example, in some cases, a subject rAAV virion, when injected via intracranial, intracerebroventicular, intrathecal, intra-cisterna magna, or intravenous administration, exhibits at least 2-fold, at least 5-fold, at least 10-fold, at least 15-fold, at least 20-fold, at least 25-fold, at least 50-fold, or more than 50-fold, increased localization to the hypocellular layer, compared to the extent of localization to the hypocellular layer by a control AAV virion comprising the corresponding parental AAV capsid protein, or comprising wild-type AAV capsid protein, when injected via the same route of administration.

As another example, in some cases, a subject rAAV virion, when injected by a via intracranial, intracerebroventicular, intrathecal, intra-cisterna magna, or intravenous administration, exhibits at least 5-fold, at least 10-fold, at least 15-fold, at least 20-fold, at least 25-fold, at least 50-fold, or more than 50-fold, increased localization to the astrocyte cell bodies layer, compared to the extent of localization to the astrocyte cell bodies layer by a control AAV virion comprising the corresponding parental AAV capsid protein, or comprising wild-type AAV capsid protein, when injected via the same route of administration.

As another example, in some cases, a subject rAAV virion, when injected via intracranial, intracerebroventicular, intrathecal, intra-cisterna magna, or intravenous administration, exhibits at least 2-fold, at least 5-fold, at least 10-fold, at least 15-fold, at least 20-fold, at least 25-fold, at least 50-fold, or more than 50-fold, increased localization to the transition zone layer, compared to the extent of localization to the transition zone layer by a control AAV virion comprising the corresponding parental AAV capsid protein, or comprising wild-type AAV capsid protein, when injected via the same route of administration.

As another example, in some cases, a subject rAAV virion, when injected via intracranial, intracerebroventicu-lar, intrathecal, intra-cisterna magna, or intravenous administration, exhibits at least 2-fold, at least 5-fold, at least 10-fold, at least 15-fold, at least 20-fold, at least 25-fold, at least 50-fold, or more than 50-fold, increased localization to the brain parenchyma, compared to the extent of localization to the brain parenchyma by a control AAV virion comprising the corresponding parental AAV capsid protein, or comprising wild-type AAV capsid protein, when injected via the same route of administration.

Decreased Susceptibility to Neutralization by Neutralizing Antibodies

As noted above, in some cases, an rAAV virion of the present disclosure exhibits decreased binding to neutralizing antibodies, compared to the binding of the neutralizing antibodies to AAV comprising wild-type AAV capsid.

Decreased binding to neutralizing antibodies is advantageous. Neutralizing antibodies bind to wild-type capsid proteins. Binding of neutralizing antibodies to wild-type capsid proteins may have several effects, including limiting the residence time of an rAAV virions that comprises wild-type capsid proteins in the viral particle, preventing the virus from binding to the cell surface, aggregating the virus, induction of structural alterations in the capsid, and prevention of viral disassembly and uncoating (a step necessary to release the DNA). An rAAV particle that has decreased binding to neutralizing antibodies thus has increased capacity to infect cells, and increased residence time in the body of an individual administered with the rAAV virion. Thus, the effective duration of delivery of gene product is increased.

In some case, an rAAV virion of the present disclosure exhibits increased resistance to neutralizing antibodies compared to wild-type AAV ("wt AAV") or AAV comprising a wild-type capsid protein. In some cases, an rAAV virion of the present disclosure has from about 1.5-fold to about 10-fold 10,000-fold greater resistance to neutralizing antibodies than wt AAV; e.g., in some cases, an rAAV virion of the present disclosure has from about 1.5-fold to about 2-fold, from about 2-fold to about 2.-5 fold, from about 2.5-fold to about 3-fold, from about 3-fold to about 4-fold, from about 4-fold to about 5-fold, from about 5-fold to about 6-fold, from about 6-fold to about 7-fold, from about 7-fold to about 8-fold, from about 8-fold to about 9-fold, or from about 9-fold to about 10-fold, greater resistance to neutralizing antibodies than wt AAV. In some cases, an rAAV virion of the present disclosure has from about 10-fold to about 10,000-fold greater resistance to neutralizing antibodies than wt AAV, e.g., an rAAV virion of the present disclosure has from about 10-fold to about 25-fold, from about 25-fold to about 50-fold, from about 50-fold to about 75-fold, from about 75-fold to about 100-fold, from about 100-fold to about 150-fold, from about 150-fold to about 200-fold, from about 200-fold to about 250-fold, from about 250-fold to about 300-fold, at least about 350-fold, at least about 400-fold, from about 400-fold to about 450-fold, from about 450-fold to about 500-fold, from about 500-fold to about 550-fold, from about 550-fold to about 600-fold, from about 600-fold to about 700-fold, from about 700-fold to about 800-fold, from about 800-fold to about 900-fold, from about 900-fold to about 1000-fold, from about 1,000-fold to about 2,000-fold, from about 2,000-fold to about 3,000-fold, from about 3,000-fold to about 4,000-fold, from about 4,000-fold to about 5,000-fold, from about 5,000-fold to about 6,000-fold, from about 6,000-fold to about 7,000-fold, from about 7,000-fold to about 8,000-fold, from about 8,000-fold to about 9,000-fold, or from about 9,000-fold to about 10,000-fold greater resistance to neutralizing antibodies than a wild-type AAV or an AAV comprising a wild-type capsid protein.

In some cases, an rAAV virion of the present disclosure exhibits decreased binding to a neutralizing antibody that binds a wild-type AAV capsid protein. For example, in some cases, an rAAV virion of the present disclosure exhibits from about 10-fold to about 10,000-fold reduced binding to a neutralizing antibody that binds a wild-type AAV capsid protein. For example, in some cases, an rAAV virion of the present disclosure exhibits from about 10-fold to about 25-fold, from about 25-fold to about 50-fold, from about 50-fold to about 75-fold, from about 75-fold to about 100-fold, from about 100-fold to about 150-fold, from about 150-fold to about 200-fold, from about 200-fold to about 250-fold, from about 250-fold to about 300-fold, at least about 350-fold, at least about 400-fold, from about 400-fold to about 450-fold, from about 450-fold to about 500-fold, from about 500-fold to about 550-fold, from about 550-fold to about 600-fold, from about 600-fold to about 700-fold, from about 700-fold to about 800-fold, from about 800-fold to about 900-fold, from about 900-fold to about 1000-fold, from about 1,000-fold to about 2,000-fold, from about 2,000-fold to about 3,000-fold, from about 3,000-fold to about 4,000-fold, from about 4,000-fold to about 5,000-fold, from about 5,000-fold to about 6,000-fold, from about 6,000-fold to about 7,000-fold, from about 7,000-fold to about 8,000-fold, from about 8,000-fold to about 9,000-fold, or from about 9,000-fold to about 10,000-fold reduced binding (e.g., reduced affinity) to a neutralizing antibody that binds a wild-type capsid AAV protein, compared to the binding affinity of the antibody to wild-type AAV capsid protein.

In some cases, an anti-AAV neutralizing antibody binds to an rAAV virion of the present disclosure with an affinity of less than about $10^{-7}$M, less than about $5\times10^{-6}$M, less than about $10^{-6}$M, less than about $5\times10^{-5}$M, less than about $10^{-5}$M, less than about $10^{-4}$M, or lower.

In some cases, an rAAV virion of the present disclosure exhibits increased in vivo residence time compared to a wild-type AAV. For example, in some cases, an rAAV virion of the present disclosure exhibits a residence time that is at least about 10%, at least about 25%, at least about 50%, at least about 100%, at least about 3-fold, at least about 5-fold, at least about 10-fold, at least about 25-fold, at least about 50-fold, at least about 100-fold, or more, longer than the residence time of a wild-type AAV.

Whether a given rAAV of the present disclosure exhibits reduced binding to a neutralizing antibody can be determined using any of a variety of standard binding assays used to determine affinity.

Selective Infectivity

In some cases, an rAAV virion of the present disclosure selectively infects a neuronal cell, e.g., an rAAV virion of the present disclosure infects a neural cell with 10-fold, 15-fold, 20-fold, 25-fold, 50-fold, or more than 50-fold, specificity than a non-neuronal cell.

In some cases, an rAAV virion of the present disclosure selectively infects a neural stem cell, e.g., a subject rAAV virion infects a neural stem cell with 10-fold, 15-fold, 20-fold, 25-fold, 50-fold, or more than 50-fold, specificity than a non-neural stem cell, e.g., a mesenchymal stem cell, a hematopoietic stem cell, etc.

Variant Capsid Polypeptides

As noted above, an rAAV virion of the present disclosure comprises a variant AAV capsid protein. In some cases, a variant AAV capsid protein present in an rAAV virion of the present disclosure comprises at least 5 segments from at least 3 different AAV serotypes, and each segment has a length of from about 50 amino acids to about 160 amino acids.

A variant AAV capsid protein of the present disclosure comprises segments from at least 3 different AAV serotypes. For example, in some cases, a variant AAV capsid protein variant AAV capsid protein of the present disclosure comprises a first segment having a length of from about 50 amino acids to about 160 amino acids from amino acids 1-160 of a first AAV serotype; a second segment having a length of from about 50 amino acids to about 160 amino acids from amino acids 51-320 of a second AAV serotype; a third segment having a length of from about 50 amino acids to about 160 amino acids from amino acids 101-480 of a third AAV serotype; a fourth segment having a length of from about 50 amino acids to about 160 amino acids from amino acids 151-640 of the second AAV serotype; and a fifth segment having a length of from about 50 amino acids to about 160 amino acids from amino acid 201 to the C-terminus of the second AAV serotype. In some cases, the first AAV serotype is AAV6, the second AAV serotype is AAV9, and the third AAV serotype is AAV8.

In some cases, a variant AAV capsid protein of the present disclosure comprises a first segment having a length of from about 50 amino acids to about 160 amino acids from amino acids 1-160 of a first AAV serotype; a second segment having a length of from about 50 amino acids to about 160 amino acids from amino acids 51-320 of a second AAV serotype; a third segment having a length of from about 50 amino acids to about 160 amino acids from amino acids 101-480 of a third AAV serotype; a fourth segment having a length of from about 50 amino acids to about 160 amino acids from amino acids 151-640 of the second AAV serotype; and a fifth segment having a length of from about 50 amino acids to about 160 amino acids from amino acid 201 to the C-terminus of a fourth AAV serotype. In some cases the first AAV serotype is AAV6, the second AAV serotype is AAV9, the third AAV serotype is AAV8, and the fourth AAV serotype is AAV2.

In some cases, a variant AAV capsid protein of the present disclosure comprises: i) a first segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 1-160 of the AAV6 capsid amino acid sequence depicted in FIG. 10; ii) a second segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 1-160 of the AAV9 capsid amino acid sequence depicted in FIG. 10; iii) a third segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 101-480 of the AAV8 capsid amino acid sequence depicted in FIG. 10; iv) a fourth segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 151-640 of the AAV9 capsid amino acid sequence depicted in FIG. 10; v) a fifth segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 201 to the C-terminus of the AAV9 capsid amino acid sequence depicted in FIG. 10.

In some cases, a variant AAV capsid protein of the present disclosure comprises: i) a first segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 1-160 of the AAV6 capsid amino acid sequence depicted in FIG. 10; ii) a second segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 1-160 of the AAV9 capsid amino acid sequence depicted in FIG. 10; iii) a third segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 101-480 of the AAV8 capsid amino acid sequence depicted in FIG. 10; iv) a fourth segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 151-640 of the AAV9 capsid amino acid sequence depicted in FIG. 10; v) a fifth segment having a length of from about 50 amino acids to about 160 amino acids and comprising an amino acid sequence having at least 85%, at least 90%, at least 95%, at least 98%, at least 99%, or 100%, to a stretch of contiguous amino acids of amino acids 201 to the C-terminus of the AAV2 capsid amino acid sequence depicted in FIG. 10.

In some cases, a variant AAV capsid protein of the present disclosure comprises a first segment having a length of from about 50 amino acids to about 160 amino acids from amino acids 1-160 of a first AAV serotype, a second segment having a length of from about 50 amino acids to about 160 amino acids of a second AAV serotype, a third segment having a length of from about 50 amino acids to about 160 amino acids of a third AAV serotype, a fourth segment having a length of from about 50 amino acids to about 160 amino acids from the second AAV serotype, a fifth segment having a length of from about 50 amino acids to about 160 amino acids from the second AAV serotype, a sixth segment having a length of from about 50 amino acids to about 160 amino acids from a fourth AAV serotype, a seventh segment having a length of from about 50 amino acids to about 160 amino acids from the second AAV serotype, and an eighth segment having a length of from about 50 amino acids to about 160 amino acids from the second AAV serotype. In some cases, the first AAV serotype is AAV6, the second AAV serotype is AAV9, the third AAV serotype is AAV8, and the fourth AAV serotype is AAV2.

In some cases, a variant AAV capsid protein of the present disclosure comprises an amino acid sequence having at least 85%, at least 90%, at least 95%, at least 98%, at least 99%, or 100%, to the SCH9 amino acid sequence depicted in FIG. 10. In some cases, the variant capsid protein comprises the amino acid sequence of the SCH9 amino acid sequence depicted in FIG. 10.

In some cases, a variant AAV capsid protein of the present disclosure comprises a first segment having a length of from about 50 amino acids to about 160 amino acids from a first AAV serotype, a second segment having a length of from about 50 amino acids to about 160 amino acids from a second AAV serotype, a third segment having a length of from about 50 amino acids to about 160 amino acids from a third AAV serotype, a fourth segment having a length of from about 50 amino acids to about 160 amino acids from the second AAV serotype, a fifth segment having a length of from about 50 amino acids to about 160 amino acids from a fourth AAV serotype, a sixth segment having a length of from about 50 amino acids to about 160 amino acids from the fourth AAV serotype, a seventh segment having a length of from about 50 amino acids to about 160 amino acids from the second AAV serotype, and an eighth segment having a length of from about 50 amino acids to about 160 amino acids from the second AAV serotype. In some cases, the first serotype is AAV6, the second AAV serotype is AAV9, the third AAV serotype is AAV8, and the fourth AAV serotype is AAV2.

In some cases, a variant AAV capsid protein of the present disclosure comprises an amino acid sequence having at least 85%, at least 90%, at least 95%, at least 98%, at least 99%, or 100%, to the SCH2 amino acid sequence depicted in FIG. 10. In some cases, the variant capsid protein comprises the amino acid sequence of the SCH2 amino acid sequence depicted in FIG. 10.

In some cases, a variant AAV capsid protein of the present disclosure comprises an amino acid sequence having at least 85%, at least 90%, at least 95%, at least 98%, at least 99%, or 100%, to the SCH9 amino acid sequence depicted in FIG. 8. In some cases, a variant AAV capsid protein of the present disclosure comprises an amino acid sequence having at least 85%, at least 90%, at least 95%, at least 98%, at least 99%, or 100%, to the SCH2 amino acid sequence depicted in FIG. 9.

Additional Variations

In some cases, a variant capsid polypeptide of the present disclosure comprises one or more additional mutations (e.g., amino acid substitution; insertion of one or more amino acids; deletion of one or more amino acids).

For example, in some cases, a variant capsid polypeptide of the present disclosure comprises an insertion of from about 5 amino acids to about 20 amino acids (e.g., from 5 amino acids to 7 amino acids, from 7 amino acids to 10 amino acids, from 10 amino acids to 15 amino acids, or from 15 amino acids to 20 amino acids) in the capsid protein GH loop relative to a corresponding parental AAV capsid protein. The insertion site can be in the GH loop, or loop IV, of the AAV capsid protein, e.g., in a solvent-accessible portion of the GH loop, or loop IV, of the AAV capsid protein. For the GH loop/loop IV of AAV capsid, see, e.g., van Vliet et al. (2006) Mol. Ther. 14:809; Padron et al. (2005) J. Virol. 79:5047; and Shen et al. (2007) Mol. Ther. 15:1955.

In some cases, a heterologous peptide of from about 5 amino acids to about 20 amino acids (e.g., from 5 to 7, from 7 to 10, from 10 to 12, from 12 to 15, or from 15 to 20 amino acids) in length is inserted in an insertion site in the GH loop or loop IV of the capsid protein relative to a corresponding parental AAV capsid protein. For example, the insertion site can be within amino acids 411-650 of an AAV capsid protein, as depicted in FIG. 21A-21C, or a corresponding region of a variant AAV capsid protein of the present disclosure. Those skilled in the art, given the amino acid sequences depicted in FIG. 21A-21C, can readily determine a suitable insertion site in variant capsid of the present disclosure. For example, the insertion site can be between amino acids 587 and 588 of AAV2, or between amino acids 588 and 589 of AAV2, or the corresponding positions of the capsid subunit of another AAV serotype, or the corresponding positions of the capsid subunit of a variant AAV capsid of the present disclosure. It should be noted that the insertion site 587/588 is based on an AAV2 capsid protein. A heterologous peptide of 5 amino acids to about 20 amino acids (e.g., from 5 to 7, from 7 to 10, from 10 to 12, from 12 to 15, or from 15 to 20 amino acids) in length can be inserted in a corresponding site in an AAV serotype other than AAV2 (e.g., AAV8, AAV9, etc.), or the corresponding positions of the capsid subunit of a variant AAV capsid of the present disclosure. Those skilled in the art would know, based on a comparison of the amino acid sequences of capsid proteins of various AAV serotypes, where an insertion site "corresponding to amino acids 587-588 of AAV2" would be in a capsid protein of any given AAV serotype, or the corresponding positions of the capsid subunit of a variant AAV capsid of the present disclosure. See, e.g., GenBank Accession No. NP_049542 for AAV1; GenBank Accession No. NP_044927 for AAV4; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9; GenBank Accession No. AAT46337 for AAV10; and GenBank Accession No. AAO88208 for AAVrh10. See, e.g., Santiago-Ortiz et al. (2015) Gene Ther. 22:934 for ancestral AAV capsid.

In some cases, a variant capsid polypeptide of the present disclosure comprises an insertion comprising an amino acid sequence selected from LGETTRP (SEQ ID NO:3), NETITRP (SEQ ID NO:4), KAGQANN (SEQ ID NO:5), KDPKTTN (SEQ ID NO:6), KDTDTTR (SEQ ID NO:7), RAGGSVG (SEQ ID NO:8), AVDTTKF (SEQ ID NO:9), and STGKVPN (SEQ ID NO:10).

In some cases, a variant capsid polypeptide of the present disclosure comprises an insertion comprising an amino acid sequence selected from LALIQDSMRA (SEQ ID NO:151); LANQEHVKNA (SEQ ID NO:152); TGVMRSTNSGLN (SEQ ID NO:153); TGEVDLAGGGLS (SEQ ID NO:154); TSPYSGSSDGLS (SEQ ID NO:155); TGGHDSSLDGLS (SEQ ID NO:156); TGDGGTTMNGLS (SEQ ID NO:157); TGGHGSAPDGLS (SEQ ID NO:158); TGMHVTMMAGLN (SEQ ID NO:159); TGASYLDNSGLS (SEQ ID NO:160); TVVSTQAGIGLS (SEQ ID NO:161); TGVMHSQASGLS (SEQ ID NO:162); TGDGSPAAPGLS (SEQ ID NO:163); TGSDMAHGTGLS (SEQ ID NO:164); TGLDATRDHGLSPVTGT (SEQ ID NO:165); TGSDGTRDHGLSPVTWT (SEQ ID NO:166); NGAVADYTRGLSPATGT (SEQ ID NO:167); TGGDPTRGTGLSPVTGA (SEQ ID NO:168); LQKNARPASTESVNFQ (SEQ ID NO:169); LQRGVRIPSVLEVNGQ (SEQ ID NO:170); LQRGNRPVTTADVNTQ (SEQ ID NO:171); and LQKADRQPGVVVVNCQ (SEQ ID NO:172). In some cases, the peptide insert is TGVMRSTNSGLN (SEQ ID NO:153). In some cases, the peptide insert is TGEVDLAGGGLS (SEQ ID NO:154). In some cases, the peptide insert is TSPYSGSSDGLS (SEQ ID NO:155). In some cases, the peptide insert is TGGHDSSLDGLS (SEQ ID NO:156). In some cases, the peptide insert is TGDGGTTMNGLS (SEQ ID NO:157). In some cases, the peptide insert is TGGHGSAPDGLS (SEQ ID NO:158). In some cases, the peptide insert is TGMHVTMMAGLN (SEQ ID NO:159). In some cases, the peptide insert is TGASYLDNSGLS (SEQ ID NO:160). In some cases, the peptide insert is TVVSTQAGIGLS (SEQ ID NO:161). In some cases, the peptide insert is TGVMHSQASGLS (SEQ ID NO:162). In some cases, the peptide insert is TGDGSPAAPGLS (SEQ ID NO:163). In some cases, the peptide insert is TGSDMAHGTGLS (SEQ ID NO:164). In some cases, the peptide insert is TGSDGTRDHGLSPVTWT (SEQ ID NO:166). In some cases, the peptide insert is NGAVADYTRGLSPATGT (SEQ ID NO:167). In some cases, the peptide insert is TGGDPTRGTGLSPVTGA (SEQ ID NO:168). In some cases, the peptide insert is LQKNARPASTESVNFQ (SEQ ID NO:169). In some cases, the peptide insert is LQRGVRIPSVLEVNGQ (SEQ ID NO:170). In some cases, the peptide insert is LQRGNRPVTTADVNTQ (SEQ ID NO:171). In some cases, the peptide insert is LQKADRQPGVVVVNCQ (SEQ ID NO:172).

In some cases, the insertion site is between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

As another example, in some cases, a variant capsid polypeptide of the present disclosure comprises an amino acid substitution compared to a parental AAV capsid protein. The amino acid substitution(s) can be located in a solvent accessible site in the capsid, e.g., a solvent-accessible loop. For example, the amino acid substitution(s) can be located in a GH loop in the AAV capsid protein. In some cases, the variant capsid protein comprises an amino acid substitution at amino acid 451 and/or 532, compared to the amino acid sequence of AAV6 capsid (SEQ ID NO:11), or the corresponding amino acid in a serotype other than AAV6. In some cases, the variant capsid protein comprises an amino acid substitution at amino acid 319 and/or 451 and/or 532 and/or 642, compared to the amino acid sequence of AAV6 capsid (SEQ ID NO:11), or the corresponding amino acid in a serotype other than AAV6. In some cases, the variant capsid protein comprises one or more of the following substitutions compared to the amino acid sequence of AAV6 capsid (SEQ ID NO:11): I319V, N451D, D532N, and H642N.

Heterologous Gene Products

As noted above, an rAAV virion of the present disclosure comprises a heterologous nucleic acid comprising a nucleotide sequence encoding one or more gene products (one or more heterologous gene products). In some cases, the gene product is a polypeptide. In some cases, the gene product is an RNA. In some cases, an rAAV virion of the present disclosure comprises a heterologous nucleotide sequence encoding both a heterologous nucleic acid gene product and a heterologous polypeptide gene product. Where the gene product is an RNA, in some cases, the RNA gene product encodes a polypeptide. Where the gene product is an RNA, in some cases, the RNA gene product does not encode a polypeptide. In some cases, an rAAV virion of the present disclosure comprises a single heterologous nucleic acid comprising a nucleotide sequence encoding a single heterologous gene product. In some cases, an rAAV virion of the present disclosure comprises a single heterologous nucleic acid comprising a nucleotide sequence encoding two heterologous gene products. Where the single heterologous nucleic acid encodes two heterologous gene products, in some cases, nucleotide sequences encoding the two heterologous gene products are operably linked to the same promoter. Where the single heterologous nucleic acid encodes two heterologous gene products, in some cases, nucleotide sequences encoding the two heterologous gene products are operably linked to two different promoters. In some cases, an rAAV virion of the present disclosure comprises a single heterologous nucleic acid comprising a nucleotide sequence encoding three heterologous gene products. Where the single heterologous nucleic acid encodes three heterologous gene products, in some cases, nucleotide sequences encoding the three heterologous gene products are operably linked to the same promoter. Where the single heterologous nucleic acid encodes three heterologous gene products, in some cases, nucleotide sequences encoding the three heterologous gene products are operably linked to two or three different promoters. In some cases, an rAAV virion of the present disclosure comprises two heterologous nucleic acids, each comprising a nucleotide sequence encoding a heterologous gene product.

In some cases, the gene product is a polypeptide-encoding RNA. In some cases, the gene product is an interfering RNA. In some cases, the gene product is a microRNA (miRNA). In some cases, the gene product is an aptamer. In some cases, the gene product is a polypeptide. In some cases, the gene product is a therapeutic polypeptide, e.g., a polypeptide that provides clinical benefit. In some cases, the gene product is a site-specific nuclease that provide for site-specific knock-down of gene function. In some cases, the gene product is an RNA-guided endonuclease that provides for modification of a target nucleic acid. In some cases, the gene products are: i) an RNA-guided endonuclease that provides for modification of a target nucleic acid; and ii) a guide RNA that comprises a first segment that binds to a target sequence in a target nucleic acid and a second segment that binds to the RNA-guided endonuclease. In some cases, the gene products are: i) an RNA-guided endonuclease that provides for modification of a target nucleic acid; ii) a first guide RNA that comprises a first segment that binds to a first target sequence in a target nucleic acid and a second segment that binds to the RNA-guided endonuclease; and iii) a first guide RNA that comprises a first segment that binds to a second target sequence in the target nucleic acid and a second segment that binds to the RNA-guided endonuclease.

Nucleic Acid Gene Products

Where the gene product is an interfering RNA (RNAi), suitable RNAi include RNAi that decrease the level of an apoptotic or angiogenic factor in a cell. For example, an RNAi can be an shRNA or siRNA that reduces the level of a gene product that induces or promotes apoptosis in a cell. Genes whose gene products induce or promote apoptosis are referred to herein as "pro-apoptotic genes" and the products of those genes (mRNA; protein) are referred to as "pro-apoptotic gene products." Pro-apoptotic gene products include, e.g., Bax, Bid, Bak, and Bad gene products. See, e.g., U.S. Pat. No. 7,846,730.

As one example, in some cases, an interfering RNA specifically reduces the level of an RNA and/or a polypeptide product of a defective allele. For example, in some cases, an RNAi specifically reduces the level of an RNA encoding Huntingtin and/or specifically reduces the level of a Huntingtin polypeptide.

As another example, in some cases, an miRNA specifically reduces the level of an RNA and/or a polypeptide product of a defective allele.

As another example, in some cases, an RNAi specifically reduces the level of an RNA encoding superoxide dismutase-1 (SOD1) RNA and/or specifically reduces the level of a SOD1 polypeptide, e.g., where the SOD1 RNA and polypeptide are encoded by a defective allele.

As another example, in some cases, an RNAi specifically reduces the level of an RNA encoding survival of motor neuron-1 (SMN1) RNA and/or specifically reduces the level of a SMN1 polypeptide, e.g., where the SMN1 RNA and polypeptide are encoded by a defective allele.

Interfering RNAs could also be against an angiogenic product, for example vascular endothelial growth factor (VEGF) (e.g., Cand5; see, e.g., U.S. Patent Publication No. 2011/0143400; U.S. Patent Publication No. 2008/0188437; and Reich et al. (2003) Mol. Vis. 9:210); VEGF receptor-1 (VEGFR1) (e.g., Sirna-027; see, e.g., Kaiser et al. (2010) Am. J. Ophthalmol. 150:33; and Shen et al. (2006) Gene Ther. 13:225); or VEGF receptor-2 (VEGFR2) (Kou et al. (2005) Biochem. 44:15064). See also, U.S. Pat. Nos. 6,649,596, 6,399,586, 5,661,135, 5,639,872, and 5,639,736; and 7,947,659 and 7,919,473.

Where the gene product is an aptamer, exemplary aptamers of interest include an aptamer against VEGF. See, e.g., Ng et al. (2006) Nat. Rev. Drug Discovery 5:123; and Lee et al. (2005) Proc. Natl. Acad. Sci. USA 102:18902. For example, a VEGF aptamer can comprise the nucleotide sequence 5'-cgcaaucagugaaugcuuauacauccg-3' (SEQ ID NO:12). Also suitable for use is a platelet-derived growth factor (PDGF)-specific aptamer, e.g., E10030; see, e.g., Ni and Hui (2009) Ophthalmologica 223:401; and Akiyama et al. (2006) J. Cell Physiol. 207:407).

Polypeptide Gene Products

Where the gene product is a polypeptide, in some cases, the polypeptide is a polypeptide that enhances function of a neural stem cell, a neural progenitor cell, or a neuronal cell.

In some cases, the gene product is a polypeptide that induces differentiation of a neural stem cell, e.g., induces the neural stem cell to differentiate into a neuron, a glial cell, an astrocyte, or an oligodendrocyte. Non-limiting examples of polypeptides that induce differentiation of a neural stem cell include achaete-scute family basic helix-loop-helix transcription factor 1 (MASH1; Deng et al. (2010) Biochem. Biophys. Res. Commun. 392:548), paired like homeobox 2a (PHOX2A), neurogenin 1 (NGN1), paired box 6 (PAX6), sex determining region Y-box1 (SOX1), neurogenic differentiation 1 (NeuroD1), NeuroD-related factor (NDRF), oligodendrocyte transcription factor 2 (Olig2). See, e.g., Ohtsuka et al. (1998) Cell Tissue Res. 293:23; and Bond et al (2015) Cell Stem Cell 17:385.

Exemplary polypeptides include neuroprotective polypeptides (e.g., glial cell derived neurotrophic factor (GDNF), ciliary neurotrophic factor (CNTF), neurotrophin-4 (NT4), nerve growth factor (NGF), and neurturin (NTN)); an aromatic L-amino acid decarboxylase; a glutamic acid decarboxylase; a tripeptidyl peptidase; an aspartoacylase; anti-angiogenic polypeptides (e.g., a soluble VEGF receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) Mol. Ther. 12:659); an Fc fusion protein comprising a soluble Flt polypeptide (see, e.g., Pechan et al. (2009) Gene Ther. 16:10); ciliary neurotrophic factors; pituitary adenylate cyclase-activating polypeptides; tissue inhibitor of metalloproteinases-3 (TIMP-3); a transcription factor, e.g., neurogenic differentiation 1 (Neuro D1), oligodendrocyte transcription factor 1 (Olig1), oligodendrocyte transcription factor 2 (Olig2), Achaete-Scute Family BHLH Transcription Factor 1 (ASCii), DNA-protein inhibitor ID-1 (Id1), DNA-protein inhibitor ID-2 (Id2), neurogenin, signal transducer and activator of transcription 3, NK2 Transcription Factor-Like Protein B; and the like. Suitable polypeptides include, but are not limited to, glial derived neurotrophic factor (GDNF); fibroblast growth factor; fibroblast growth factor 2; neurturin (NTN); ciliary neurotrophic factor (CNTF); nerve growth factor (NGF); neurotrophin-4 (NT4); brain derived neurotrophic factor (BDNF); epidermal growth factor; X-linked inhibitor of apoptosis; and Sonic hedgehog.

Site-Specific Endonucleases

In some cases, a gene product of interest is a site-specific endonuclease that provides for site-specific knock-down of gene function, e.g., where the endonuclease knocks out an allele associated with a neural disease. For example, where a dominant allele encodes a defective copy of a gene that, when wild-type, is a neural structural protein and/or provides for normal neural function, a site-specific endonuclease can be targeted to the defective allele and knock out the defective allele. In some cases, a site-specific endonuclease is an RNA-guided endonuclease.

A site-specific nuclease can also be used to stimulate homologous recombination with a donor DNA that encodes a functional copy of the protein encoded by the defective allele. Thus, e.g., a subject rAAV virion can be used to deliver a site-specific endonuclease that knocks out a defective allele, and can be used to deliver a functional copy of the defective allele, resulting in repair of the defective allele, thereby providing for production of a functional neural protein. In some cases, a subject rAAV virion comprises a heterologous nucleic acid comprising a nucleotide sequence that encodes a site-specific endonuclease; and a heterologous nucleotide sequence that encodes a functional copy of a defective allele, where the functional copy encodes a functional neural protein.

Examples of genes that can include mutations that are associated with or give rise to neurological diseases and disorders include, but are not limited to, hypoxanthine guanine phosphoriboxyltransferase (HPRT1), neurofibromatosis type II (NF2), ATP1A3 (encoding the α3 subunit of Na$^+$/K$^+$-ATPase), DYNC1H1 (encoding the heavy chain of cytoplasmic dynein-1), HTT (encoding huntingtin), SOD1, SMN1, ATX3 (encoding spinocerebellar ataxia-3), FXN/X25 (encoding frataxin), DMPK (encoding dystrophia myotonica protein kinase), ATXN2 (encoding ataxin-2), atrophin-1, NR4A2 (encoding nuclear receptor subfamily 4, Group A, member 2 protein), PINK1 (encoding PTEN induced putative kinase 1), LRRK2 (encoding leucine-rich repeat kinase 2), MeCP2 (encoding methyl-CpG-binding protein-2), and the like.

Site-specific endonucleases that are suitable for use include, e.g., zinc finger nucleases (ZFNs); meganucleases; and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073. Suitable site-specific endonucleases include engineered meganuclease re-engineered homing endonucleases. Suitable endonucleases include an I-TevI nuclease. Suitable meganucleases include I-ScelI (see, e.g., Bellaiche et al. (1999) Genetics 152:1037); and I-CreI (see, e.g., Heath et al. (1997) Nature Structural Biology 4:468).

RNA-Guided Endonucleases

In some cases, the gene product is an RNA-guided endonuclease. In some cases, the gene product is an RNA comprising a nucleotide sequence encoding an RNA-guided endonuclease. In some cases, the gene product is a guide RNA, e.g., a single-guide RNA. In some cases, the gene products are: 1) a guide RNA; and 2) an RNA-guided endonuclease. The guide RNA can comprise: a) a protein-binding region that binds to the RNA-guided endonuclease; and b) a region that binds to a target nucleic acid. An RNA-guided endonuclease is also referred to herein as a "genome editing nuclease."

Examples of RNA-guided endonucleases are CRISPR/Cas endonucleases (e.g., class 2 CRISPR/Cas endonucleases such as a type II, type V, or type VI CRISPR/Cas endonucleases). A suitable genome editing nuclease is a CRISPR/Cas endonuclease (e.g., a class 2 CRISPR/Cas endonuclease such as a type II, type V, or type VI CRISPR/Cas endonuclease). In some cases, a suitable RNA-guided endonuclease is a class 2 CRISPR/Cas endonuclease. In some cases, a suitable RNA-guided endonuclease is a class 2 type II CRISPR/Cas endonuclease (e.g., a Cas9 protein). In some cases, a genome targeting composition includes a class 2 type V CRISPR/Cas endonuclease (e.g., a Cpf1 protein, a C2c1 protein, or a C2c3 protein). In some cases, a suitable RNA-guided endonuclease is a class 2 type VI CRISPR/Cas endonuclease (e.g., a C2c2 protein; also referred to as a "Cas13a" protein). Also suitable for use is a CasX protein. Also suitable for use is a CasY protein.

In some cases, the genome-editing endonuclease is a Type II CRISPR/Cas endonuclease. In some cases, the genome-editing endonuclease is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 18A. In some cases, the Cas9 polypeptide used in a composition or method of the present disclosure is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 19.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 18A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 19A, where amino acids N497, R661, Q695, and Q926 are substituted, e.g., with alanine. A suitable Cas9 polypeptide comprises the amino acid sequence set forth in any one of FIG. 18A-18F.

In some cases, a suitable Cas9 polypeptide exhibits altered PAM specificity. See, e.g., Kleinstiver et al. (2015) *Nature* 523:481.

Figure 20A:
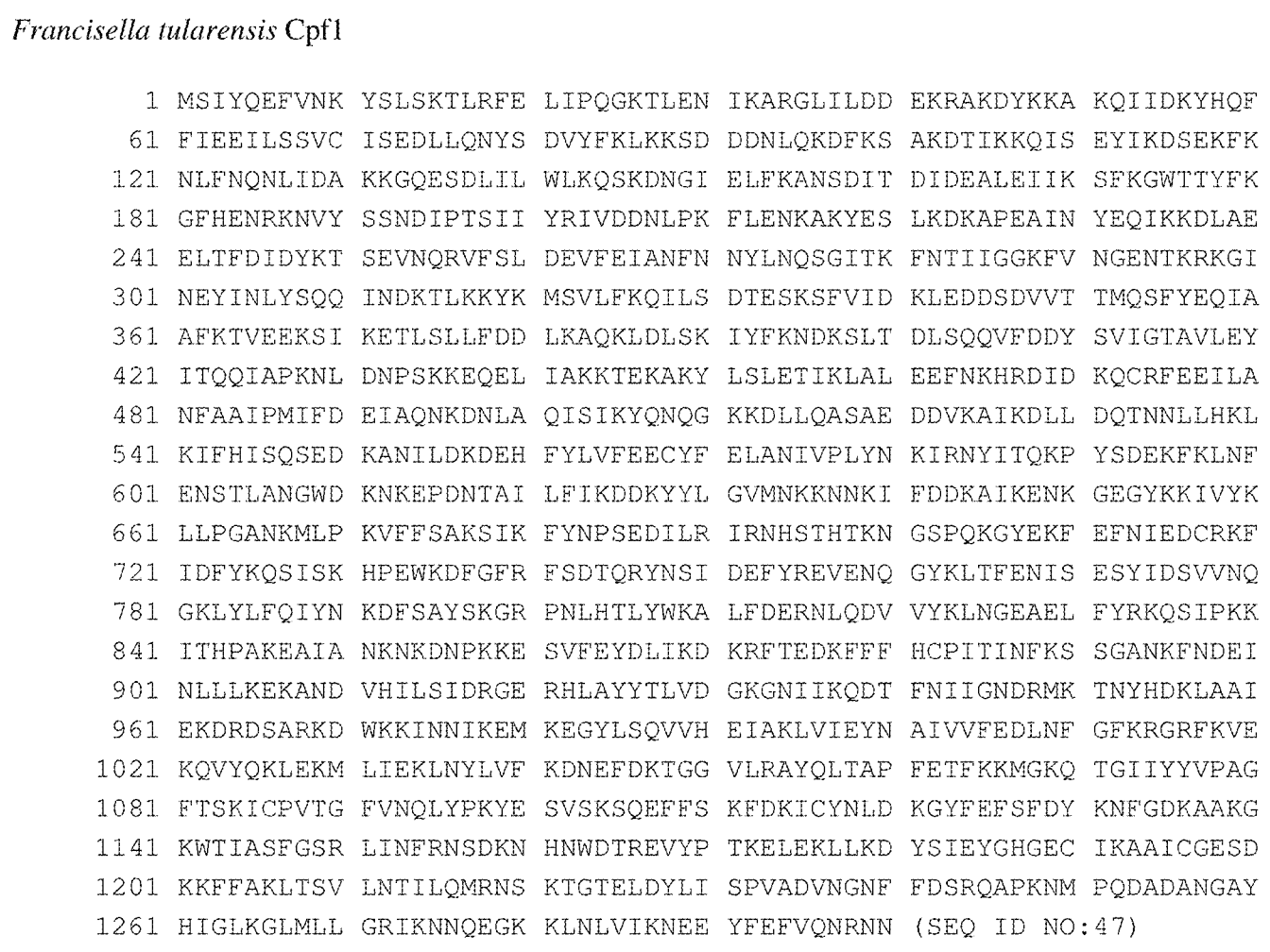

In some cases, the genome-editing endonuclease is a type V CRISPR/Cas endonuclease. In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 20.

In some cases, the genome-editing endonuclease is a CasX or a CasY polypeptide. CasX and CasY polypeptides are described in Burstein et al. (2017) *Nature* 542:237.

RNA-Guided Endonucleases

An RNA-guided endonuclease is also referred to herein as a "genome editing nuclease." Examples of suitable genome editing nucleases are CRISPR/Cas endonucleases (e.g., class 2 CRISPR/Cas endonucleases such as a type II, type V, or type VI CRISPR/Cas endonucleases). A suitable genome editing nuclease is a CRISPR/Cas endonuclease (e.g., a class 2 CRISPR/Cas endonuclease such as a type II, type V, or type VI CRISPR/Cas endonuclease). In some cases, a suitable genome editing nuclease is a class 2 CRISPR/Cas endonuclease. In some cases, a suitable genome editing nuclease a class 2 type II CRISPR/Cas endonuclease (e.g., a Cas9 protein). In some cases, a suitable genome editing nuclease a class 2 type V CRISPR/Cas endonuclease (e.g., a Cpf1 protein, a C2c1 protein, or a C2c3 protein). In some cases, a suitable genome editing nuclease is a class 2 type VI CRISPR/Cas endonuclease (e.g., a C2c2 protein; also referred to as a "Cas13a" protein). Also suitable for use is a CasX protein. Also suitable for use is a CasY protein.

In some cases, a genome editing nuclease is a fusion protein that is fused to a heterologous polypeptide (also referred to as a "fusion partner"). In some cases, a genome editing nuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

In some cases, the genome-editing endonuclease is a Type II CRISPR/Case endonuclease. In some cases, the genome-editing endonuclease is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 18A. In some cases, the Cas9 polypeptide used in a composition or method of the present disclosure is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 19.

In some cases, a suitable Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 18A, but with K848A, K1003A, and R1060A substitutions. Slaymaker et al. (2016) Science 351: 84-88. In some cases, a suitable Cas9 polypeptide comprises the amino acid sequence depicted in FIG. 18E. A suitable Cas9 polypeptide comprises an amino acid sequence depicted in any one of FIG. 18A-18F.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 18A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 18A, where amino acids N497, R661, Q695, and Q926 are substituted, e.g., with alanine. In some cases, a suitable Cas9 polypeptide comprises the amino acid sequence depicted in FIG. 18F.

In some cases, a suitable Cas9 polypeptide exhibits altered PAM specificity. See, e.g., Kleinstiver et al. (2015) Nature 523:481.

In some cases, the genome-editing endonuclease is a type V CRISPR/Cas endonuclease.

In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 20A. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 20B. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 20C.

Enzymatically Inactive RNA-Guided Endonucleases

Also suitable for use is an RNA-guided endonuclease with reduced enzymatic activity. Such an RNA-guided endonuclease is referred to as a "dead" RNA-guided endonuclease; for example, a Cas9 polypeptide that comprises certain amino acid substitutions such that it exhibits substantially no endonuclease activity, but such that it still binds to a target nucleic acid when complexed with a guide RNA, is referred to as a "dead" Cas9 or "dCas9." In some cases, a "dead" Cas9 protein has a reduced ability to cleave both the complementary and the non-complementary strands of a double stranded target nucleic acid. For example, a "nuclease defective" Cas9 lacks a functioning RuvC domain (i.e., does not cleave the non-complementary strand of a double stranded target DNA) and lacks a functioning HNH domain (i.e., does not cleave the complementary strand of a double stranded target DNA). As a non-limiting example, in some cases, the nuclease defective Cas9 protein harbors mutations at amino acid positions corresponding to residues D10 and H840 (e.g., D10A and H840A) of SEQ ID NO:40 (or the corresponding residues of a homolog of Cas9) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "nuclease defective Cas9", "dead Cas9" or simply "dCas9." Other residues can be mutated to achieve the above effects (i.e. inactivate one or the other nuclease portions). As non-limiting examples, residues D10, G12, G17, E762, H840, N854, N863, H982, H983, A984, D986, and/or A987 of Streptococcus pyogenes Cas9 (or the corresponding amino acids of a Cas9 homolog) can be altered (i.e., substituted). In some cases, two or more of D10, E762, H840, N854, N863, and D986 of Streptococcus pyogenes Cas9 (or the corresponding amino acids of a Cas9 homolog) are substituted. In some cases, D10 and N863 of Streptococcus pyogenes Cas9 (or the corresponding amino acids of a Cas9 homolog) are substituted with Ala. Also, mutations other than alanine substitutions are suitable.

In some cases, the genome-editing endonuclease is an RNA-guided endonuclease (and it corresponding guide RNA) known as Cas9-synergistic activation mediator (Cas9-SAM). The RNA-guided endonuclease (e.g., Cas9) of the Cas9-SAM system is a "dead" Cas9 fused to a transcriptional activation domain (wherein suitable transcriptional activation domains include, e.g., VP64, p65, MyoD1, HSF1, RTA, and SETT/9) or a transcriptional repressor domain (where suitable transcriptional repressor domains include, e.g., a KRAB domain, a NuE domain, an NcoR domain, a SID domain, and a SID4X domain) The guide RNA of the Cas9-SAM system comprises a loop that binds an adapter protein fused to a transcriptional activator domain (e.g., VP64, p65, MyoD1, HSF1, RTA, or SETT/9) or a transcriptional repressor domain (e.g., a KRAB domain, a NuE domain, an NcoR domain, a SID domain, or a SID4X domain) For example, in some cases, the guide RNA is a single-guide RNA comprising an MS2 RNA aptamer inserted into one or two loops of the sgRNA; the dCas9 is a fusion polypeptide comprising dCas9 fused to VP64; and the adaptor/functional protein is a fusion polypeptide comprising: i) MS2; ii) p65; and iii) HSF1. See, e.g., U.S. Patent Publication No. 2016/0355797.

Also suitable for use is a chimeric polypeptide comprising: a) a dead RNA-guided endonuclease; and b) a heterologous fusion polypeptide. Examples of suitable heterologous fusion polypeptides include a polypeptide having, e.g., methylase activity, demethylase activity, transcription activation activity, transcription repression activity, transcription release factor activity, histone modification activity, RNA cleavage activity, DNA cleavage activity, DNA integration activity, or nucleic acid binding activity.

Guide RNA

A nucleic acid that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Where the gene product is an RNA-guided endonuclease, or is both an RNA-guided endonuclease and a guide RNA, the gene product can modify a target nucleic acid. In some cases, e.g., where a target nucleic acid comprises a deleterious mutation in a defective allele (e.g., a deleterious mutation in a neural cell target nucleic acid), the RNA-guided endonuclease/guide RNA complex, together with a donor nucleic acid comprising a nucleotide sequence that corrects the deleterious mutation (e.g., a donor nucleic acid comprising a nucleotide sequence that encodes a functional copy of the protein encoded by the defective allele), can be used to correct the deleterious mutation, e.g., via homology-directed repair (HDR).

In some cases, the gene products are an RNA-guided endonuclease and 2 separate sgRNAs, where the 2 separate sgRNAs provide for deletion of a target nucleic acid via non-homologous end joining (NHEJ).

In some cases, the gene products are: i) an RNA-guided endonuclease; and ii) one guide RNA. In some cases, the guide RNA is a single-molecule (or "single guide") guide RNA (an "sgRNA"). In some cases, the guide RNA is a dual-molecule (or "dual-guide") guide RNA ("dgRNA").

In some cases, the gene products are: i) an RNA-guided endonuclease; and ii) 2 separate sgRNAs, where the 2 separate sgRNAs provide for deletion of a target nucleic acid via non-homologous end joining (NHEJ). In some cases, the guide RNAs are sgRNAs. In some cases, the guide RNAs are dgRNAs.

In some cases, the gene products are: i) a Cpf1 polypeptide; and ii) a guide RNA precursor; in these cases, the precursor can be cleaved by the Cpf1 polypeptide to generate 2 or more guide RNAs.

The present disclosure provides a method of modifying a target nucleic acid in a neuronal cell in an individual, where the target nucleic acid comprises a deleterious mutation, the method comprising administering to the individual an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a sgRNA that comprises a nucleotide sequence that is complementary to the target nucleic acid; and iii) a nucleotide sequence encoding a donor DNA template that comprises a nucleotide sequence that corrects the deleterious mutation. Administration of the rAAV virion results in correction of the deleterious mutation in the target nucleic acid by HDR.

The present disclosure provides a method of modifying a target nucleic acid in a neuronal cell in an individual, where the target nucleic acid comprises a deleterious mutation, the method comprising administering to the individual an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a first sgRNA that comprises a nucleotide sequence that is complementary to a first sequence in the target nucleic acid; and iii) a nucleotide sequence encoding a second sgRNA that comprises a nucleotide sequence that is complementary to a second sequence in the target nucleic acid. Administration of the rAAV virion results in excision of the deleterious mutation in the target nucleic acid by NHEJ.

The present disclosure provides a method of modifying a target nucleic acid in a neural stem cell in an individual, where the target nucleic acid comprises a deleterious mutation, the method comprising administering to the individual an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a sgRNA that comprises a nucleotide sequence that is complementary to the target nucleic acid; and iii) a nucleotide sequence encoding a donor DNA template that comprises a nucleotide sequence that corrects the deleterious mutation. Administration of the rAAV virion results in correction of the deleterious mutation in the target nucleic acid by HDR.

The present disclosure provides a method of modifying a target nucleic acid in a neural stem cell in an individual, where the target nucleic acid comprises a deleterious mutation, the method comprising administering to the individual an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a first sgRNA that comprises a nucleotide sequence that is complementary to a first sequence in the target nucleic acid; and iii) a nucleotide sequence encoding a second sgRNA that comprises a nucleotide sequence that is complementary to a second sequence in the target nucleic acid. Administration of the rAAV virion results in excision of the deleterious mutation in the target nucleic acid by NHEJ.

Pharmaceutical Compositions

The present disclosure provides a pharmaceutical composition comprising: a) a subject rAAV virion, as described above; and b) a pharmaceutically acceptable carrier, diluent, excipient, or buffer. In some cases, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H.C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

Methods

Methods of Delivering a Gene Product

The present disclosure provides a method of delivering a gene product to a neuronal cell in an individual, the method comprising administering to the individual a subject rAAV virion as described above. The gene product can be a polypeptide or an interfering RNA (e.g., an shRNA, an siRNA, and the like), an aptamer, or a site-specific endonuclease (e.g., an RNA-guided endonuclease), as described above. Delivering a gene product to a neuronal cell can provide for treatment of a neural disease.

The present disclosure provides a method modifying a target nucleic acid in a neuronal cell, the method comprising contacting the neuronal cell with: 1) an rAAV virion of the present disclosure, wherein the rAAV virion comprises a heterologous nucleic acid comprising a nucleotide sequence encoding an RNA-guided endonuclease that binds a guide RNA; and 2) the guide RNA. The present disclosure provides a method modifying a target nucleic acid in a neuronal cell, the method comprising contacting the neuronal cell with an rAAV virion of the present disclosure, wherein the rAAV virion comprises a heterologous nucleic acid comprising a nucleotide sequence encoding: i) an RNA-guided endonuclease that binds a guide RNA; and ii) the guide RNA. In some cases, the method comprises contacting the neuronal cell with a donor DNA template. In some cases, the RNA-guided endonuclease is a Cas9 polypeptide. In some cases, the guide RNA is a single-guide RNA.

The present disclosure provides a method of delivering a gene product to an NSC cell in an individual, the method comprising administering to the individual a subject rAAV virion as described above. The gene product can be a polypeptide or an interfering RNA (e.g., an shRNA, an siRNA, and the like), an aptamer, or a site-specific endonuclease (e.g., an RNA-guided endonuclease), as described above. Delivering a gene product to an NSC can provide for treatment of a neural disease.

The present disclosure provides a method modifying a target nucleic acid in an NSC, the method comprising contacting the neural stem cell with: 1) an rAAV virion of the present disclosure, wherein the rAAV virion comprises a heterologous nucleic acid comprising a nucleotide sequence encoding an RNA-guided endonuclease that binds a guide RNA; and 2) the guide RNA. The present disclosure provides a method modifying a target nucleic acid in an NSC, the method comprising contacting the NSC with an rAAV virion of the present disclosure, wherein the rAAV virion comprises a heterologous nucleic acid comprising a nucleotide sequence encoding: i) an RNA-guided endonuclease that binds a guide RNA; and ii) the guide RNA. In some cases, the method comprises contacting the NSC with a donor DNA template. In some cases, the RNA-guided endonuclease is a Cas9 polypeptide. In some cases, the guide RNA is a single-guide RNA.

The present disclosure provides a method of treating a neural disease (e.g., a neural disease), the method comprising administering to an individual in need thereof an effective amount of a subject rAAV virion as described above. A subject rAAV virion can be administered via intracranial injection, or by any other convenient mode or route of administration. Other convenient modes or routes of administration include, e.g., intracerebroventicular, intrathecal, intra-cisterna magna, or intravenous etc.

A "therapeutically effective amount" will fall in a relatively broad range that can be determined through experimentation and/or clinical trials. For example, for in vivo injection, i.e., injection directly into the brain, a therapeutically effective dose will be on the order of from about $10^6$ to about $10^{15}$ of the rAAV virions, e.g., from about $10^8$ to $10^{12}$ rAAV virions. For in vitro transduction, an effective amount of rAAV virions to be delivered to cells will be on the order of from about $10^8$ to about $10^{13}$ of the rAAV virions. Other effective dosages can be readily established by one of ordinary skill in the art through routine trials establishing dose response curves.

In some cases, more than one administration (e.g., two, three, four or more administrations) may be employed to achieve the desired level of gene expression. In some cases, the more than one administration is administered at various intervals, e.g., daily, weekly, twice monthly, monthly, every 3 months, every 6 months, yearly, etc. In some cases, multiple administrations are administered over a period of time of from 1 month to 2 months, from 2 months to 4 months, from 4 months to 8 months, from 8 months to 12 months, from 1 year to 2 years, from 2 years to 5 years, or more than 5 years.

Methods of Treating a Neurological Disease or Disorder

Neurological diseases that can be treated using a subject method include neurological diseases and disorders of the central nervous system (CNS), and neurological diseases and disorders of the peripheral nervous system (PNS).

Neurological diseases and disorders include, but are not limited to, diffuse axonal injury, perinatal hypoxic-ischemic injury, traumatic brain injury, stroke, ischemic infarction, embolism, and hypertensive hemorrhage; exposure to CNS toxins, infections of the central nervous system, such as bacterial meningitis; metabolic diseases such as those involving hypoxic-ischemic encephalopathy, peripheral neuropathy, and glycogen storage diseases; or from chronic neural injury or neurodegenerative disease, including but not limited to multiple sclerosis, Lewy Body dementia, Alzheimer's disease, Parkinson's disease, and Huntington's disease.

Neurological diseases and disorders include, but are not limited to, Parkinson's disease, Alzheimer's disease, Huntington's disease, Amyotrophic lateral sclerosis, Friedreich's ataxia, Lewy body disease, spinal muscular atrophy, multiple system atrophy, dementia, schizophrenia, paralysis, multiple sclerosis, spinal cord injuries, brain injuries, cranial nerve disorders, peripheral sensory neuropathies, epilepsy, prion disorders, Creutzfeldt-Jakob disease, Alper's disease, cerebellar/spinocerebellar degeneration, Batten disease, corticobasal degeneration, Bell's palsy, Guillain-Barre Syndrome, Pick's disease, Rett syndrome, frontotemporal dementia, and autism.

Neurological diseases and disorders of the PNS include, e.g., diabetic neuropathy; polyneuropathies; chronic inflammatory demyelinating polyneuropathy (CIPD); and the like.

The present disclosure provides methods of treating a neural disorder. In some cases, the methods comprise administering an rAAV virion of the present disclosure, or a composition comprising an rAAV virion of the present disclosure, to the brain of an individual in need thereof.

One of ordinary skill in the art can readily determine an effective amount of an rAAV virion by testing for an effect on one or more parameters, such as a symptom associated with a neurological disease or disorder. In some cases, administering an effective amount of an rAAV virion of the present disclosure results in a decrease in the rate of loss of brain function, anatomical integrity, or brain health, e.g. a 2-fold, 3-fold, 4-fold, or 5-fold or more decrease in the rate of loss and hence progression of disease, e.g. a 10-fold decrease or more in the rate of loss and hence progression of disease. In some cases, administering an effective amount of an rAAV virion of the present disclosure results in a gain in brain function, an improvement in brain anatomy or health, and/or a stabilization in brain function, e.g. a 2-fold, 3-fold, 4-fold or 5-fold improvement or more in brain function, brain anatomy or health, e.g. a 10-fold improvement or more in brain function, brain anatomy or health, and/or stability of the brain.

Nucleic Acids and Host Cells

The present disclosure provides an isolated nucleic acid comprising a nucleotide sequence that encodes a subject variant adeno-associated virus (AAV) capsid protein as described above.

A subject recombinant AAV vector can be used to generate a subject recombinant AAV virion, as described above.

Thus, the present disclosure provides a recombinant AAV vector that, when introduced into a suitable cell, can provide for production of a subject recombinant AAV virion.

The present disclosure further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some cases, a subject host cell is stably genetically modified with a subject nucleic acid. In other cases, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like. Non-limiting examples of suitable host cells include, e.g., HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. A subject host cell can also be made using a baculovirus to infect insect cells such as Sf9 cells, which produce AAV (see, e.g., U.S. Pat. No. 7,271,002; U.S. patent application Ser. No. 12/297,958).

In some cases, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other cases, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-65 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A recombinant adeno-associated virus (rAAV) virion comprising: a) a variant AAV capsid protein, wherein the variant AAV capsid protein comprises at least 5 segments from at least 3 different AAV serotypes, wherein each segment has a length of from about 50 amino acids to about 160 amino acids, and wherein the variant capsid protein confers one or more of the following properties: i) increased infectivity of a neural stem cell compared to the infectivity of the neural stem cell by a control AAV virion comprising the corresponding parental AAV capsid protein, or comprising wild-type AAV capsid; ii) increased infectivity of a neuron compared to the infectivity of the neuron by a control AAV virion comprising the corresponding parental AAV capsid protein, or comprising wild-type AAV capsid; and iii) increased resistance to human AAV neutralizing antibodies compared to the resistance exhibited by the control AAV virion comprising the corresponding parental AAV capsid protein, or comprising wild-type AAV capsid; and b) a heterologous nucleic acid comprising a nucleotide sequence encoding a heterologous gene product.

Aspect 2. The rAAV virion of aspect 1, wherein the variant AAV capsid protein comprises, in order from N-terminus to C-terminus: a first segment having a length of from about 50 amino acids to about 160 amino acids from amino acids 1-160 of a first AAV serotype; a second segment having a length of from about 50 amino acids to about 160 amino acids from amino acids 51-320 of a second AAV serotype; a third segment having a length of from about 50 amino acids to about 160 amino acids from amino acids 101-480 of a third AAV serotype; a fourth segment having a length of from about 50 amino acids to about 160 amino acids from amino acids 151-640 of the second AAV serotype; and a fifth segment having a length of from about 50 amino acids to about 160 amino acids from amino acid 201 to the C-terminus of the second AAV serotype.

Aspect 3. The rAAV virion of aspect 2, wherein the first AAV serotype is AAV6.

Aspect 4. The rAAV virion of aspect 2, wherein the second AAV serotype is AAV9.

Aspect 5. The rAAV virion of aspect 2, wherein the third AAV serotype is AAV8.

Aspect 6. The rAAV virion of aspect 1, wherein the variant AAV capsid protein comprises, in order from N-terminus to C-terminus: a first segment having a length of from about 50 amino acids to about 160 amino acids from amino acids 1-160 of a first AAV serotype; a second segment having a length of from about 50 amino acids to about 160 amino acids from amino acids 51-320 of a second AAV serotype; a third segment having a length of from about 50 amino acids to about 160 amino acids from amino acids 101-480 of a third AAV serotype; a fourth segment having a length of from about 50 amino acids to about 160 amino acids from amino acids 151-640 of the second AAV serotype; and a fifth segment having a length of from about 50 amino acids to about 160 amino acids from amino acid 201 to the C-terminus of a fourth AAV serotype.

Aspect 7. The rAAV virion of aspect 6, wherein the first AAV serotype is AAV6.

Aspect 8. The rAAV virion of aspect 6, wherein the second AAV serotype is AAV9.

Aspect 9. The rAAV virion of aspect 6, wherein the third AAV serotype is AAV8.

Aspect 10. The rAAV virion of aspect 6, wherein the fourth AAV serotype is AAV2.

Aspect 11. The rAAV virion of aspect 1, wherein the variant AAV capsid protein comprises, in order from N-terminus to C-terminus: a first segment having a length of from about 50 amino acids to about 160 amino acids from amino acids 1-160 of a first AAV serotype; a second segment having a length of from about 50 amino acids to about 160 amino acids of a second AAV serotype; a third segment having a length of from about 50 amino acids to about 160 amino acids of a third AAV serotype; a fourth segment having a length of from about 50 amino acids to about 160 amino acids from the second AAV serotype; a fifth segment having a length of from about 50 amino acids to about 160 amino acids from the second AAV serotype; a sixth segment having a length of from about 50 amino acids to about 160 amino acids from a fourth AAV serotype; a seventh segment having a length of from about 50 amino acids to about 160 amino acids from the second AAV serotype; and an eighth segment having a length of from about 50 amino acids to about 160 amino acids from the second AAV serotype.

Aspect 12. The rAAV virion of aspect 11, wherein the first AAV serotype is AAV6.

Aspect 13. The rAAV virion of aspect 11, wherein the second AAV serotype is AAV9.

Aspect 14. The rAAV virion of aspect 11, wherein the third AAV serotype is AAV8.

Aspect 15. The rAAV virion of aspect 11, wherein the fourth AAV serotype is AAV2.

Aspect 16. The rAAV virion of aspect 1, wherein the variant AAV capsid protein comprises, in order from N-terminus to C-terminus: a first segment having a length of from about 50 amino acids to about 160 amino acids from a first AAV serotype; a second segment having a length of from about 50 amino acids to about 160 amino acids from a second AAV serotype; a third segment having a length of from about 50 amino acids to about 160 amino acids from a third AAV serotype; a fourth segment having a length of from about 50 amino acids to about 160 amino acids from the second AAV serotype; a fifth segment having a length of from about 50 amino acids to about 160 amino acids from a fourth AAV serotype; a sixth segment having a length of from about 50 amino acids to about 160 amino acids from the fourth AAV serotype; a seventh segment having a length of from about 50 amino acids to about 160 amino acids from the second AAV serotype; and an eighth segment having a length of from about 50 amino acids to about 160 amino acids from the second AAV serotype.

Aspect 17. The rAAV virion of aspect 16, wherein the first AAV serotype is AAV6.

Aspect 18. The rAAV virion of aspect 16, wherein the second AAV serotype is AAV9.

Aspect 19. The rAAV virion of aspect 16, wherein the third AAV serotype is AAV8.

Aspect 20. The rAAV virion of aspect 16, wherein the fourth AAV serotype is AAV2.

Aspect 21. The rAAV virion of aspect 1, wherein the rAAV virion exhibits at least 5-fold increased infectivity of a neural stem cell compared to the infectivity of the neural stem cell by the control AAV virion comprising the corresponding parental AAV capsid protein, or comprising wild-type AAV capsid.

Aspect 22. The rAAV virion of aspect 21, wherein the control AAV virion is AAV9.

Aspect 23. The rAAV virion of aspect 21, wherein the control AAV virion is AAV2.

Aspect 24. The rAAV virion of aspect 1, wherein the rAAV virion exhibits at least 10-fold increased infectivity of a neural stem cell compared to the infectivity of the neural stem cell by the control AAV virion comprising the corresponding parental AAV capsid protein, or comprising wild-type AAV capsid.

Aspect 25. The rAAV virion of aspect 24, wherein the control AAV virion is AAV9.

Aspect 26. The rAAV virion of aspect 24, wherein the control AAV virion is AAV2.

Aspect 27. The rAAV virion of aspect 1, wherein the variant AAV capsid protein comprises an amino acid sequence having at least about 90% amino acid sequence identity to the amino acid sequence set forth in SEQ ID NO:1 (and depicted in FIG. 8).

Aspect 28. The rAAV virion of aspect 1, wherein the variant AAV capsid protein comprises an amino acid sequence having at least about 95% amino acid sequence identity to the amino acid sequence set forth in SEQ ID NO:1 (and depicted in FIG. 8).

Aspect 29. The rAAV virion of aspect 1, wherein the variant AAV capsid protein comprises the amino acid sequence set forth in SEQ ID NO:1 (and depicted in FIG. 8).

Aspect 30. The rAAV virion of aspect 1, wherein the variant AAV capsid protein comprises an amino acid sequence having at least about 90% amino acid sequence identity to the amino acid sequence set forth in SEQ ID NO:2 (and depicted in FIG. 9).

Aspect 31. The rAAV virion of aspect 1, wherein the variant AAV capsid protein comprises an amino acid sequence having at least about 95% amino acid sequence identity to the amino acid sequence set forth in SEQ ID NO:2 (and depicted in FIG. 9).

Aspect 32. The rAAV virion of aspect 1, wherein the variant AAV capsid protein comprises the amino acid sequence set forth in SEQ ID NO:2 (and depicted in FIG. 9).

Aspect 33. The rAAV virion of aspect 1, wherein the variant AAV capsid protein exhibits increased resistance to human AAV neutralizing antibodies compared to the resistance exhibited by the control AAV virion comprising the corresponding parental AAV capsid protein, or comprising wild-type AAV capsid.

Aspect 34. The rAAV virion of aspect 34, wherein the control AAV virion is AAV9.

Aspect 35. The rAAV virion of aspect 34, wherein the control AAV virion is AAV2.

Aspect 36. The rAAV virion of aspect 1, wherein the variant AAV capsid protein exhibits at least about 1.5-fold greater resistance to human AAV neutralizing antibodies compared to the resistance exhibited by the control AAV virion comprising the corresponding parental AAV capsid protein, or comprising wild-type AAV capsid.

Aspect 37. The rAAV virion of aspect 1, wherein the variant AAV capsid protein exhibits at least about 3-fold greater resistance to human AAV neutralizing antibodies compared to the resistance exhibited by the control AAV virion comprising the corresponding parental AAV capsid protein, or comprising wild-type AAV capsid.

Aspect 38. The rAAV virion of aspect 1, wherein the variant AAV capsid protein exhibits at least about 5-fold greater resistance to human AAV neutralizing antibodies compared to the resistance exhibited by the control AAV virion comprising the corresponding parental AAV capsid protein, or comprising wild-type AAV capsid.

Aspect 39. The rAAV virion of aspect 1, wherein the variant AAV capsid protein exhibits at least about 10-fold greater resistance to human AAV neutralizing antibodies compared to the resistance exhibited by the control AAV virion comprising the corresponding parental AAV capsid protein, or comprising wild-type AAV capsid.

Aspect 40. The rAAV virion of aspect 1, wherein the neural stem cell is from the subventricular zone.

Aspect 41. The rAAV virion of aspect 1, wherein the Purkinje cell is from the cerebellum.

Aspect 42. The rAAV virion of any one of aspects 1-41, wherein the gene product is an interfering RNA or an aptamer.

Aspect 43. The rAAV virion of any one of aspects 1-41, wherein the gene product is a polypeptide.

Aspect 44. The rAAV virion of aspect 43, wherein the polypeptide is a neuroprotective polypeptide, an anti-angiogenic polypeptide, a polypeptide that induces differentiation of a neural stem cell, or a polypeptide that enhances function of a neural stem cell.

Aspect 45. The rAAV virion of aspect 43, wherein the polypeptide is cerebrolysin, laminin-IKVAV, cripto, pituitary adenylate cyclase-activating polypeptide, nerve growth factor, brain derived neurotrophic factor, glial derived neurotrophic factor, fibroblast growth factor 2, neurturin, ciliary neurotrophic factor, epidermal growth factor, X-linked inhibitor of apoptosis, or Sonic hedgehog.

Aspect 46. The rAAV virion of aspect 43, wherein the polypeptide is a genome-editing enzyme.

Aspect 47. The rAAV virion of aspect 46, wherein the genome-editing enzyme is a Cas9 polypeptide, a zinc finger nuclease, a TALEN, or an enzymatically inactive type II CRISPR/Cas polypeptide.

Aspect 48. The rAAV virion of aspect 47, wherein the polypeptide is an RNA-guided endonuclease selected from a type II CRISPR/Cas polypeptide, a type V CRISPR/Cas polypeptide, and a type VI CRISPR/Cas polypeptide.

Aspect 49. The rAAV virion of any one of aspects 1-41, wherein the gene product is an RNA-guided endonuclease and a guide RNA.

Aspect 50. A pharmaceutical composition comprising: a) a recombinant adeno-associated virus virion of any one of aspects 1-49; and b) a pharmaceutically acceptable excipient.

Aspect 51. A method of delivering a gene product to a neural stem cell in an individual, the method comprising administering to the individual a recombinant adeno-associated virus (rAAV) virion according any one of aspects 1-49 or the composition of aspect 50.

Aspect 52. The method of aspect 51, wherein said administering is by intracranial, intracerebroventicular, intrathecal, intra-cisterna magna, or intravenous injection.

Aspect 53. The method of aspect 51, wherein the gene product is a short interfering RNA or an aptamer.

Aspect 54. The method of aspect 51, wherein the gene product is a polypeptide.

Aspect 55. The method of aspect 43, wherein the polypeptide is a neuroprotective polypeptide, an anti-angiogenic polypeptide, or a polypeptide that enhances function of a neural stem cell.

Aspect 56. The rAAV virion of aspect 44, wherein the polypeptide is cerebrolysin, laminin-IKVAV, cripto, pituitary adenylate cyclase-activating polypeptide, nerve growth factor, brain derived neurotrophic factor, glial derived neurotrophic factor, fibroblast growth factor 2, neurturin, ciliary neurotrophic factor, epidermal growth factor, X-linked inhibitor of apoptosis, aromatic L-amino acid decarboxylase, glutamic acid decarboxylase, tripeptidyl peptidase, aspartoacyclase, or Sonic hedgehog.

Aspect 57. The method of aspect 54, wherein the polypeptide is a genome-editing enzyme.

Aspect 58. The method of aspect 57, wherein the genome-editing enzyme is a Cas9 polypeptide, a zinc finger nuclease, a TALEN, or an enzymatically inactive type II CRISPR/Cas polypeptide.

Aspect 59. The method of aspect 57, wherein the polypeptide is an RNA-guided endonuclease selected from a type II CRISPR/Cas polypeptide, a type V CRISPR/Cas polypeptide, and a type VI CRISPR/Cas polypeptide.

Aspect 60. The method of aspect 51, wherein the gene product is an RNA-guided endonuclease and a guide RNA.

Aspect 61. A method of treating a neurological disorder, the method comprising administering to an individual in need thereof an effective amount of a recombinant adeno-associated virus (rAAV) virion according to any one of aspects 1-49 or the composition of aspect 50.

Aspect 62. The method of aspect 62, wherein the neurological disorder is spinocerebellar ataxia, Huntington's disease, Parkinson's disease, Alzheimer's disease, a lysosomal storage disorder, Friedreich's ataxia, glioblastoma, Rett syndrome, frontotemporal dementia, or epilepsy.

Aspect 63. An isolated nucleic acid comprising a nucleotide sequence that encodes a variant adeno-associated virus (AAV) capsid protein, wherein the variant AAV capsid protein comprises at least 5 segments from at least 3 different AAV serotypes, wherein each segment has a length of from about 50 amino acids to about 160 amino acids, and wherein the variant capsid protein confers one or more of the following properties: i) increased infectivity of a neural stem cell compared to the infectivity of the neural stem cell by a control AAV virion comprising the corresponding parental AAV capsid protein, or comprising wild-type AAV capsid; ii) increased infectivity of a neuron compared to the infectivity of the neuron by a control AAV virion comprising the corresponding parental AAV capsid protein, or comprising wild-type AAV capsid; and iii) increased resistance to human AAV neutralizing antibodies compared to the resistance exhibited by the control AAV virion comprising the corresponding parental AAV capsid protein, or comprising wild-type AAV capsid.

Aspect 64. An isolated, genetically modified host cell comprising the nucleic acid of aspect 63.

Aspect 65. A variant adeno-associated virus (AAV) capsid protein, wherein the variant AAV capsid protein comprises at least 5 segments from at least 3 different AAV serotypes, wherein each segment has a length of from about 50 amino acids to about 160 amino acids, and wherein the variant capsid protein confers one or more of the following properties: i) increased infectivity of a neural stem cell compared to the infectivity of the neural stem cell by a control AAV virion comprising the corresponding parental AAV capsid protein, or comprising wild-type AAV capsid; ii) increased infectivity of a neuron compared to the infectivity of the neuron by a control AAV virion comprising the corresponding parental AAV capsid protein, or comprising wild-type AAV capsid; and iii) increased resistance to human AAV neutralizing antibodies compared to the resistance exhibited by the control AAV virion comprising the corresponding parental AAV capsid protein, or comprising wild-type AAV capsid.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: SCHEMA-Guided Design of a Chimeric AAV Library

Materials and Methods

The following materials and methods generally apply to the results presented in the Examples described herein except where noted otherwise.

SCHEMA Library Design

A library of chimeric AAVs was designed using the SCHEMA scoring function and the RASPP algorithm, see, e.g., Voigt et al. (2002) *Nature Struct. Mol. Biol.* 6; and Endelman et al. (2004) PEDS 17—that represented multiple phylogenetic clades, see, e.g., Gao et al. (2004) *J. Virol.* 78, had diverse receptor binding properties, see, e.g., Asokan et al. (2012) *Mol. Ther.* 20, and enjoyed some success in the clinic, see, e.g., Kotterman et al. (2015) *Annu. Rev. Biomed. Eng.* 17. The amino acid sequences of AAV2, 4, 5, 6, 8, and 9 were aligned using MUSCLE, see, e.g., Edgar et al. (2004) *Nucleic Acids Res.* 32, to generate the parent sequence alignment. SCHEMA was modified to consider both intra- and inter-subunit amino acid contacts in the multimeric AAV capsid, wherein a pair of residues is contacting if they contained nonhydrogen atoms within 4.5 angstroms. The crystal structures used for AAV2 (1LP3), AAV4 (2G8G), AAV5 (3NTT), AAV6 (3OAH), AAV8 (2QA0), and AAV9 (3UX1) to calculate contacting residue positions. The final contact map contained residue pairs that were contacting in at least 50% of these six parent structures. To achieve high library diversity, a library containing six crossovers should be designed within the crystallized region of the capsid and a seventh in the uncrystallized VP1 region (amino acids 1-216) at position 128 based on a previous example of successful recombination at that location. See, e.g., Excoffon et al. (2009) *Proc. Natl. Acad. Sci. U.S.A.* 106. A library containing eight capsid protein blocks from six parent serotypes yields a theoretical library diversity of over 1.6 million ($6^8$) chimeric variants. A chimeric capsid's SCHEMA disruption <E> was the number of contacts that contain new amino acid combinations that were not present in any of the parent sequences. A chimeric capsid's <m> was the number of mutations from the closest parent sequence.

FIGS. 1A-1F. The RASPP algorithm was used to design libraries that balanced the average structural disruption (E) and average sequence diversity (m). The SCHEMA scoring function was additionally modified to search for crossover locations that were amenable to combinatorial golden gate assembly for library construction, which required four nucleotide stretches that were conserved across all AAV parent sequences. In order to increase the number of possible crossovers sites and thereby probe a larger sequence space in silico, four nucleotide stretches were included that could be silently mutated during library assembly to be identical in all parent sequences. For the library design, a minimum allowed sequence block length of 20 amino acids and maximum length of 250 amino acids were considered. The final library was chosen based on its low (E), its uniform block size, and recombination of key capsid structural features.

SCHEMA Library Construction

FIG. 2. In order to facilitate combinatorial golden gate cloning with the type IIs restriction enzyme BsaI, all BsaI recognition sites found in pBluescript SK (+), AAV2, 4, 5, 6, 8, and 9 were silently mutated by QuikChange site-directed mutagenesis. FIGS. 3 & 4. The 48 DNA sequences corresponding to each shuffled block were PCR amplified from the parent cap genes using PCR primers designed in j5, a DNA assembly design automation software. See, e.g., Hillson et al. (2012) *ACS Synth. Biol.* 1. FIG. 5. Primers were designed to incorporate silent mutations at block junctures to facilitate golden gate cloning into the pBluescript vector backbone. The golden gate reaction was transformed into electrocompetent DH10B *E. coli* to achieve a library size greater than the theoretical diversity of $6^8$ clones. The library was then subcloned from pBluescript to the AAV packaging plasmid pSub2FloxCap using the restriction enzymes HindIII and NotI.

The SCHEMA library, before and after packaging, was analyzed using Illumina sequencing. A 2.5-kb fragment containing the AAV cap gene was cut out of the pSub2FloxCap vector using the HindIII and NotI sites and gel extracted. These gel-extracted inserts were used as inputs to the Nextera XT DNA Sample Prep Kit (Illumina). Each sample was barcoded using a different index primer. The resulting libraries were quantified using a high-sensitivity Bioanalyzer chip (Agilent), a Qubit Assay Kit (Invitrogen), and finally quantitative PCR (Kapa Biosystems). The average sequence fragment was ~1,400 bp. The two libraries were pooled in equimolar proportions and sequenced using a MiSeq, version 3, 2×300 run with a 5% PhiX control spike-in. Sequencing reads were mapped to all AAV parents using Bowtie2, see, e.g., Langmead et al. (2009) *Genome Biol.* 10, and the specific sequence blocks present were determined considering the read position and sequence identity to the parents.

Design of AAV Constructs for Cre-Dependent Selections

PCR primers used for construct design and amplification of cap are presented in FIG. 2. pSub2RepKO and pRepHelper were used. pSub2RepKO, a rep knockout in the AAV packaging plasmid pSub2, see, e.g., Maheshri et al. (2006) *Nature Biotechnol.* 24, was generated by digestion with SgraI and BamHI, Klenow reaction, and blunt-end ligation. pRepHelper, used to supply Rep in trans during AAV packaging, was created by sequential digestion of pAAV2/rh10 with PmeI and BsmI, Klenow reaction, and blunt-end ligation. To insert the lox66 site 5' of cap, a unique BglII site was introduced into pSub2RepKO by site-directed mutagenesis using the primers BglIIFwd and BglIIRev. Oligonucleotides Lox66Fwd and Lox66Rev were annealed and ligated into the BglII and HindIII sites of pSub2RepKO to form pSub2Lox66. To insert the lox71 site 3' of cap, unique XhoI and KpnI sites were introduced into pSub2Lox66 by site-directed mutagenesis with the primers XhoIFwd/XhoIRev and KpnIFwd/KpnIRev respectively. Oligonucleotides SOELox71Fwd and SOELox71Rev were assembled by splice overlap extension and amplified with Lox71Fwd and Lox71Rev. The resulting fragment and pSub2Lox66 were digested with XhoI and KpnI and ligated to create pSub2Flox. pSub2Flox and the AAV cap libraries used in this selection were digested with HindIII and NotI and ligated to generate pSub2FloxCap libraries for viral packaging.

AAV Vector Production

HEK293T cells were obtained from the American Type Culture Collection (Manassas, Va.) and cultured in Dulbecco's Modified Eagle's medium (DMEM, Gibco) with 10% fetal bovine serum (Invitrogen) and 1% penicillin/streptomycin (Invitrogen) at 37° C. and 5% $CO_2$. AAV libraries or self-complementary recombinant AAV vectors driving expression of green fluorescent protein (GFP) or Cre recombinase under the control of a cytomegalovirus early enhancer/chicken beta actin (CAG) promoter were packaged in HEK293T cells as previously described in Koerber et al. (2008) Mol. Ther. 16, and Maheshri et al. (2006) Nature Biotechnol. 24. Briefly, AAV vectors were produced by triple transient transfection, purified by iodixanol density centrifugation, and buffer exchanged into phosphate buffered saline (PBS) by Amicon filtration. DNase-resistant viral genomic titers were measured by quantitative real time PCR using a Biorad iCycler (Bio-Rad, Hercules, Calif.).

In Vivo Selections and Characterization of SCHEMA AAV Variants

Seven-week-old GFAP-Cre 73.12 (Jackson Laboratory Stock 012886), C57BL/6J (Jackson Laboratory Stock 000664), or Ai9 tdTomato mice (Jackson Laboratory Stock 007909) were anesthetized with isoflurane and placed in a stereotaxic apparatus. An incision was made to expose the skull and a hole was drilled for injection. For library selections, five microliters of an equimolar mixture of AAV libraries (1×1010 viral genomes/µl) was stereotaxically injected into the right lateral ventricle of GFAP-Cre mice (n=3) at the coordinates 0.05 mm posterior and 1.0 mm lateral to the bregma at a depth of 2.5 mm using a Hamilton syringe as previously described 100. Injection coordinates were selected using a mouse brain atlas (Franklin and Paxinos, 2007) and adjusted after test injections with 0.1% FastGreen dye (Sigma). Injection accuracy throughout the study was confirmed by reporter expression in the choroid plexus and surrounding the contralateral ventricle. Mice were sacrificed three weeks after injection and brain tissue was harvested. The hemisphere contralateral to the injection site was homogenized on dry ice using a mortar and pestle. Homogenized tissue was digested in Hirt lysis buffer with proteinase K (New England Biolabs) and RNase A (ThermoFisher) at 55° C. for 3 hours and extrachromosomal DNA was isolated using the Hirt method as previously described in Arad et al. (1998) BioTechniques 24. The PCR primers Cap_ISF and Cap_R were used to amplify inverted cap, while primers Cap_NSF and Cap_R specifically amplify non-inverted cap. The primers Internal_Cap_ISF and Internal_Cap_R may be used for nested PCR if amplification of inverted cap is challenging. After three rounds of selection, capsid sequences were determined by Sanger sequencing (UC Berkeley DNA Sequencing Facility) and dominant variants were digested with HindIII and NotI and ligated into pXX2Not for recombinant AAV packaging.

To characterize SCH9 and AAV9 in vivo, five microliters of self-complementary recombinant vector ($1 \times 10^{10}$ viral genomes/µl) expressing GFP or Cre was stereotaxically injected into the right lateral ventricle of C57BL/6 or Ai9 tdTomato mice respectively at the coordinates 0.05 mm posterior and 1.0 mm lateral to the bregma at a depth of 2.5 mm using a Hamilton syringe. Ai9 mice received injections of 50 mg/kg BrdU (Sigma-Aldrich) for three consecutive days prior to injection of single-stranded SCH9 CAG-Cre. For injections of the deep cerebellar nuclei, four microliters of recombinant AAV vector ($2 \times 10^9$ viral genomes/µl) expressing GFP was stereotaxically injected into the right hemisphere with coordinates 6.0 mm posterior and 2.0 mm lateral to the bregma at a depth of 2.2 mm from the cerebellar surface using a Hamilton syringe. Animal procedures were approved by the UC Berkeley Laboratory Animal Care and Use Committee and conducted in accordance with NIH guidelines for animal care.

Immunohistochemistry

Mice were anesthetized by intraperitoneal injection of 100 mg/kg ketamine and 10 mg/kg xylazine and were transcardially perfused with 0.9% saline followed by 4% paraformaldehyde. Brains were post-fixed overnight in 4% paraformaldehyde at 4° C., washed in PBS, and stored in 30% sucrose until they sank. Serial coronal or sagittal sections were cut at 40 inn thickness on a Series 8000 sliding microtome (Bright) and stored in cryoprotectant at −20° C. until use. Free-floating sections were washed three times in PBS, incubated with blocking solution (10% donkey serum and 1% Triton X-100 in PBS) for 2 hours at room temperature, and stained with primary antibodies in blocking solution for 72 hours at 4° C. The following primary antibodies were used in this study: mouse anti-Calbindin (1:2000; Abcam, ab82812), rabbit anti-GFP (1:1000; Life Technologies, A-11122), goat anti-GFAP (1:750; Abcam, ab53554), guinea pig anti-DCX (1:1000, EMD Millipore, AB2253), rat anti-VCAM1 (1:50; EMD Millipore, MAB2627), chicken anti-GFAP (1:750; Abcam, ab4674), rat anti-BrdU (1:750; Abcam, ab6326), and rabbit anti-tdTomato (1:750, Rockland, 600-401-379). After three washes in PBS, sections were incubated with secondary antibodies for 2 hours at room temperature and stained with DAPI (Thermo Fisher) for ten minutes. Stained sections were washed three times in PBS and mounted onto slides using VectaShield HardSet Antifade Mounting Medium (Vector Laboratories).

Imaging and Analysis

Images were acquired using a Zeiss Axio Scan.Z1 or a confocal Zeiss LSM 880 NLO

AxioExaminer (UC Berkeley Molecular Imaging Center). All image analyses were conducted on original images acquired with equivalent settings. Data were presented as mean±SEM and statistical significance was established by two-tailed Student's t-test.

The SVZ is composed of multiple cell types including ependymal cells, adult NSCs (B cells), transit amplifying cells (type C cells), neuroblasts (type A cells), and mature astrocytes. See, e.g., Lim et al. (2016) Cold Spring Harb. Perspect. Biol. 8. To evaluate the efficiency of NSC transduction in the SVZ, the molecular markers that were selectively expressed within NSCs were first assessed. Although most markers are expressed in multiple cell types in the SVZ, reflecting the continuum of gene expression during lineage progression, vascular cell adhesion molecule 1 (VCAM1) specifically localizes to the endfeet of NSCs that contact the ventricle. See, e.g., Kokovay et al. (2012) Cell Stem Cell 11.

To determine transduction volume in the SVZ, the surface area of GFP expression in the SVZ was quantified from thresholded images using CellProfiler, see, e.g., Carpenter et al. (2006) Genome Biol. 7, in six coronal sections spanning the SVZ from the anterior horn of the lateral ventricle to the anterior commissure with three mice per group. The total surface area was multiplied by the section thickness (40 µm) and the distance between sections to obtain the transduction volume. The same thresholded images were used for quantification of integrated intensity of GFP expression using CellProfiler.

To quantify the percentage of tdTomato positive neuroblasts in the rostral migratory stream the cell segmentation capabilities of CellProfiler were applied to threshold, segment, and score doublecortin and tdTomato positive cell bodies in the rostral migratory stream. Measurements were taken from two to five sagittal tissue sections containing the rostral migratory stream in each animal, with four to five mice in each group. To evaluate transduction of adult neural stem cells, the identities of all BrdU positive cells in the subventricular zone were scored by colocalization with tdTomato and GFAP or DCX. Counts were performed on confocal images of every fifth sagittal section spanning the SVZ in five mice with four to five sections per animal.

To calculate the percentage of calbindin stained area that is tdTomato positive, a CellProfiler pipeline was employed to generate a thresholded mask of the calbindin stain. This mask was applied to the thresholded tdTomato image and the tdTomato positive area was dividing by the total calbindin area. The integrated intensity of thresholded tdTomato within the calbindin mask was also recorded. Measurements were taken from four to seven 40 µm sagittal tissue sections spanning the cerebellum, with four to five mice in each group.

In Vitro Characterization of SCHEMA AAV Variants

Unless otherwise noted all cell lines were cultured in DMEM (Gibco) supplemented with 10% fetal bovine serum (Invitrogen) and 1% penicillin/streptomycin (Invitrogen) at 37° C. and 5% $CO_2$. The heparin affinity of SCH9, SCH2, and wild-type AAV2 were determined as previously described in Jang et al. (2011) Mol. Ther. 19. A 1 ml HiTrap heparin column (GE Healthcare Sciences) was equilibrated with 150 mM NaCl and 50 mM Tris at pH 7.5. $1 \times 10^{11}$ purified viral genomic particles were loaded onto the column and eluted by 50 mM stepwise increases in NaCl up to a final concentration of 950 mM, followed by a 1M NaCl wash. A fraction of each elution was used to infect HEK293T cells, and the percentage of GFP positive cells was quantified 48 hours after infection using a Guava EasyCyte 6HT flow cytometer (EMD/Millipore) (UC Berkeley Stem Cell Center, Berkeley, Calif.).

AAV utilization of galactose and heparan sulfate proteoglycans for cell transduction was characterized as previously described in Shen et al. (2013) J. Biol. Chem. 288. CHO-Lec2 cells presenting terminal galactose residues on their surface were obtained from the tissue culture facility at the University of California, Berkeley and cultured in MEM α nucleosides (Gibco) supplemented with 10% fetal bovine serum (Invitrogen) and 1% penicillin/streptomycin (Invitrogen) at 37° C. and 5% $CO_2$. One day after seeding, cells were incubated at 4° C. for 30 minutes followed by a complete media change into MEM with or without 100 µg/mL Erythrina cristagalli lectin (ECL) (Vector Labs). Self-complementary rAAV CAG-GFP virions were treated with soluble heparin (500 µg/mL) in PBS or mock-treated for 1 hour and then used to infect cells at a genomic MOI of 12,000 (n=3). After a 1 hour incubation with virus, Lec2 cells were washed three times in cold PBS to remove unbound AAV, and the percentage of GFP-expressing cells was quantified 72 hours after infection by flow cytometry.

To analyze antibody evasion properties, SCH9, AAV2, AAV6, AAV8, and AAV9 were incubated at 37° C. for 1 hour with serial dilutions of heat inactivated IVIG (Gammagard) and then used to infect HEK293T cells at a genomic MOI of 8,000 (n=3) as previously described in Santiago-Ortiz et al. (2015) Gene Ther. 22. The percentage of GFP-expressing cells was quantified 48 hours after infection by flow cytometry. Neutralizing antibody titers were recorded as the first IVIG concentration at which a 50% or greater reduction in GFP expression was observed.

To study dependence on AAVR, wild type HeLa or AAVRKO cells (Clone KIAA0319L) were infected at a genomic MOI of 20,000 (n=6) with SCH9, SCH2, or AAV2 carrying self-complementary CAG-GFP. The percentage of GFP-expressing cells was quantified 72 hours after infection by flow cytometry.

Results

Figure 1B:
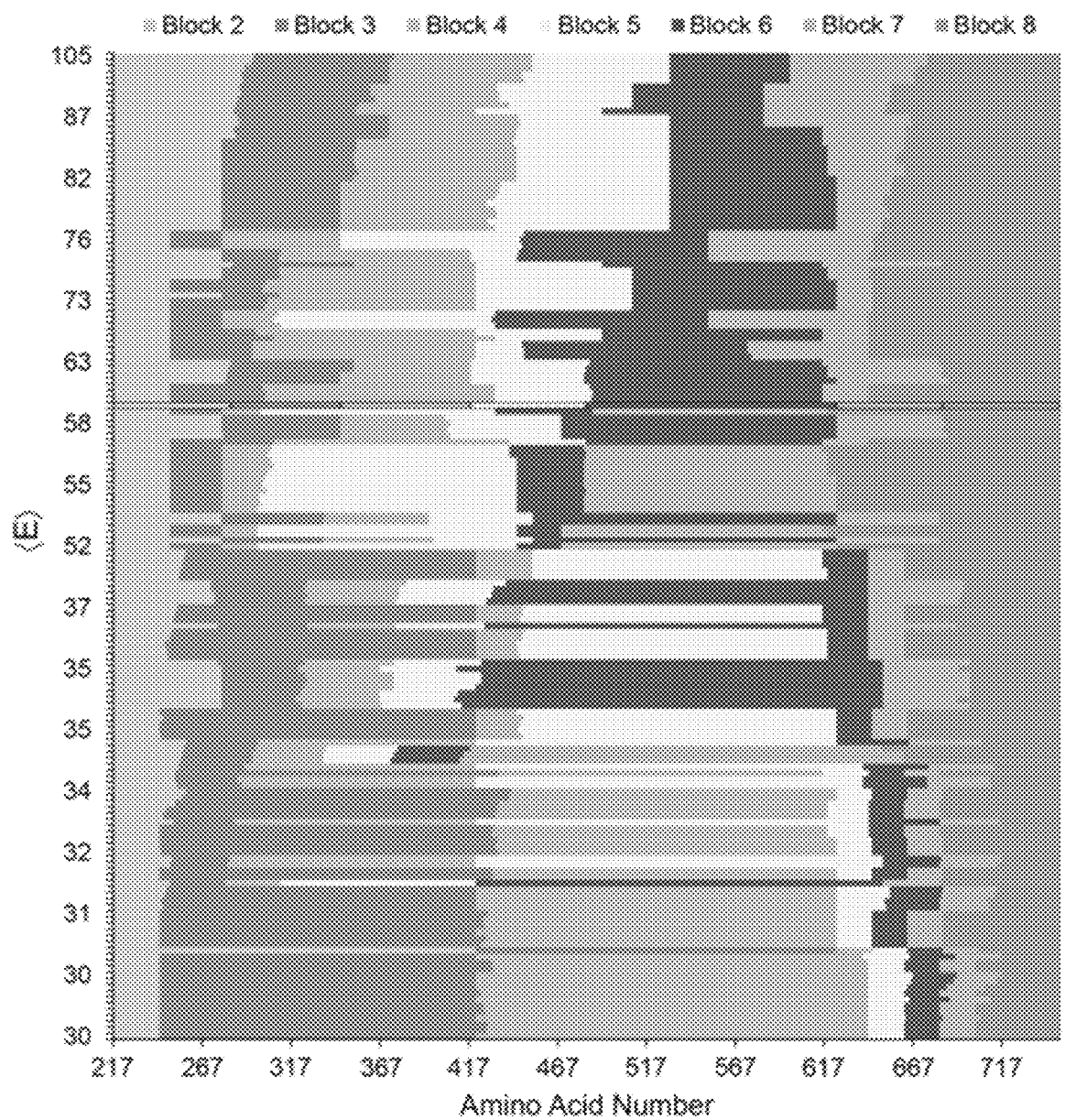
Figure 1C:
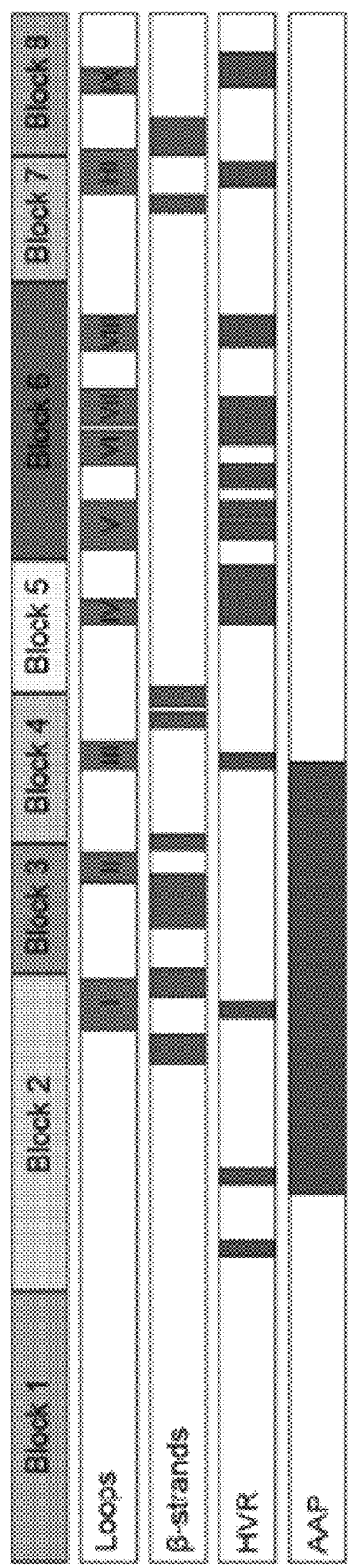
Figure 1D:
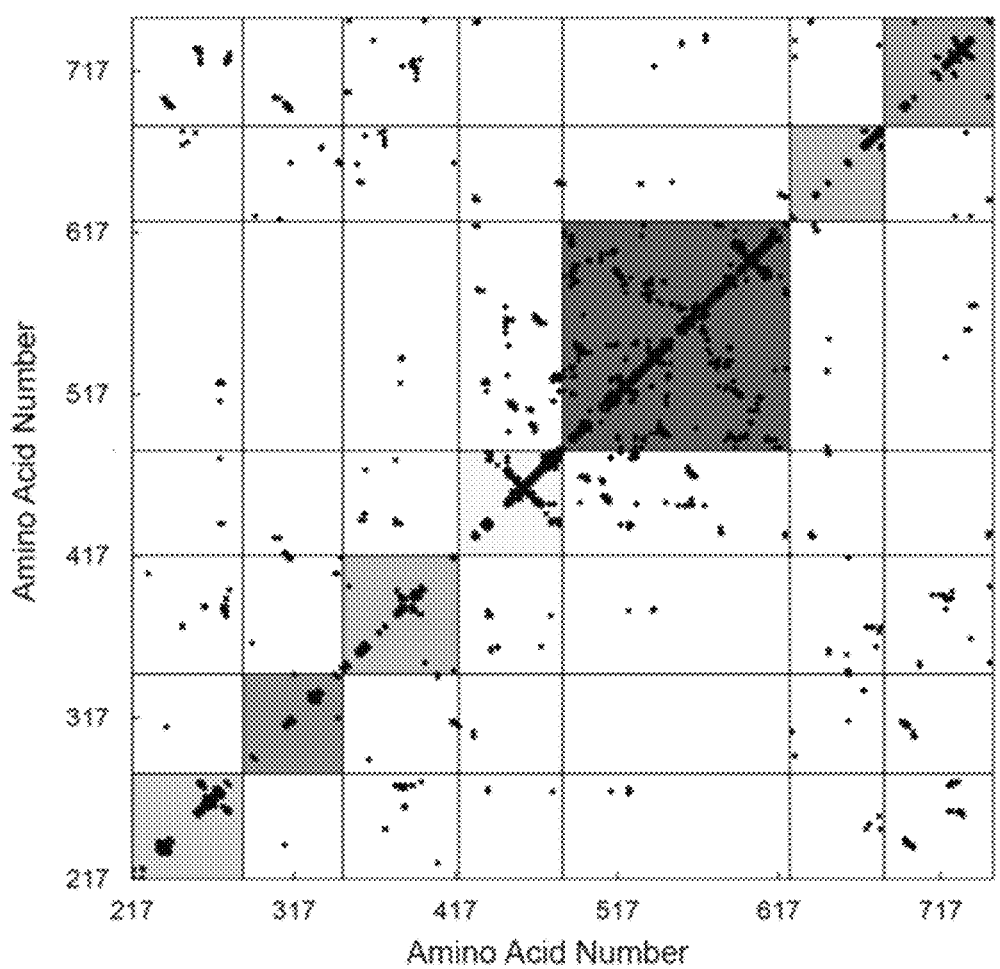
Figure 1E:
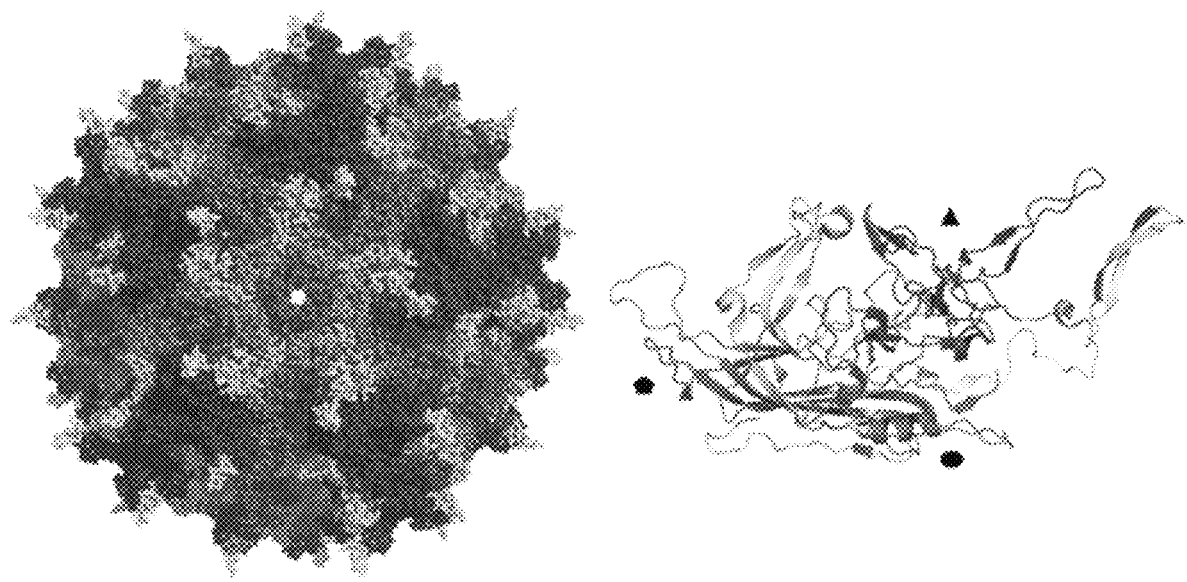

A chimeric AAV library was designed that recombined six natural serotypes—AAV2, 4, 5, 6, 8, and 9. FIGS. 1A-1F. After specifying the design parameters, the RASPP method (Recombination as a Shortest Path Problem), see, e.g., Endelman et al. (2004) PEDS 17, was applied to rapidly identify 160 of the least disruptive library designs (sets of seven crossover positions) over a range of mutation levels. For each of these designs, the average library disruption score (E) and number of amino acid mutations introduced (m) relative to the closest parent serotype were calculated (FIG. 1A), and the crossover locations of all RASPP designs were presented in FIG. 1B. A final design with an average disruption score (E) of 59 and average number of mutations (m) of 82 per subunit in the crystallized region of the capsid (FIG. 1A-C) was chosen for several reasons. First, this design was in a cluster of RASPP libraries (FIG. 1A) that represented a relative minimum in (E) at high mutation levels. Second, the selected design shuffled key capsid structural features, which included surface exposed loops and hypervariable regions that represented the most divergent regions in the evolution of natural AAV serotypes (FIG. 1C). Recombination within these contact rich regions resulted in greater disruption, but was also more likely to generate AAV chimeras with new and interesting functions. For example, significantly lower disruption scores could be achieved by combining blocks five and six, but doing so would generate capsids with surface exposed loop regions derived from a single parent sequence. Finally, this set of crossover positions was selected since it provided a relatively even distribution of block sizes. RASPP was programmed to consider a range of permissible block sizes from 20-250 amino acids. The majority of the lowest (E) designs contained two long blocks (>175 amino acids for blocks 3 and 4) followed by a series of short blocks (<30 amino acids for blocks 5-7) (FIG. 1B). In contrast, the chosen set of crossover positions (FIG. 1C) offered a more even distribution of block sizes, ensuring shuffling throughout the capsid as opposed to confining crossovers within a few regions that were of limited diversity in the parent sequences.

The selected library design was assembled by combinatorial golden gate cloning, see, e.g., Engler et al. (2013) Methods Mol. Biol. 1073, cloned in electrocompetent E. coli to yield over $5 \times 10^6$ transformants, and packaged into AAV virions. The frequency of parent serotypes at each block position was analyzed by deep sequencing before and after viral packaging (FIG. 1F). Each parent serotype sequence was well represented and distributed at each block location prior to viral packaging, but packaging presumably imposed a significant selective pressure for stable capsids and thereby resulted in dramatic changes in library composition. For example, the frequency of AAV4 and AAV5 decreased by an average of 348 and 372-fold respectively across the packaged library, likely due to the low average amino acid sequence identity (AAV4: 60%, AAV5: 65%) of these serotypes with the other AAV parents used for library assembly. Changes in library composition upon packaging were also reflected in the decrease in the average disruption score <E> per crystallized subunit from 59 to 4 and in the average number of mutations <m> from 82 to 28. In agreement with prior applications of SCHEMA as described in Meyer et al. (2006) PEDS 19, and Otey et al. (2004) Chem. & Biol. 11, lower <E> chimeras were thus heavily enriched in the library. There was a preference for AAV2 at blocks five and six and AAV9 at block eight. These trends could be used in the future to guide rational capsid engineering.

Example 2: A Cre-Dependent Selection Strategy for AAV Directed Evolution

To specifically target NSCs, an in vivo Cre-dependent directed evolution and selection strategy was designed to drive positive selection of AAV variants that infected NSCs in the SVZ. A conceptually analogous but distinct Cre-dependent system was reported during the course of this study. See Deverman et al. (2016) *Nature Biotechnol.* 34.

Figure 6A:
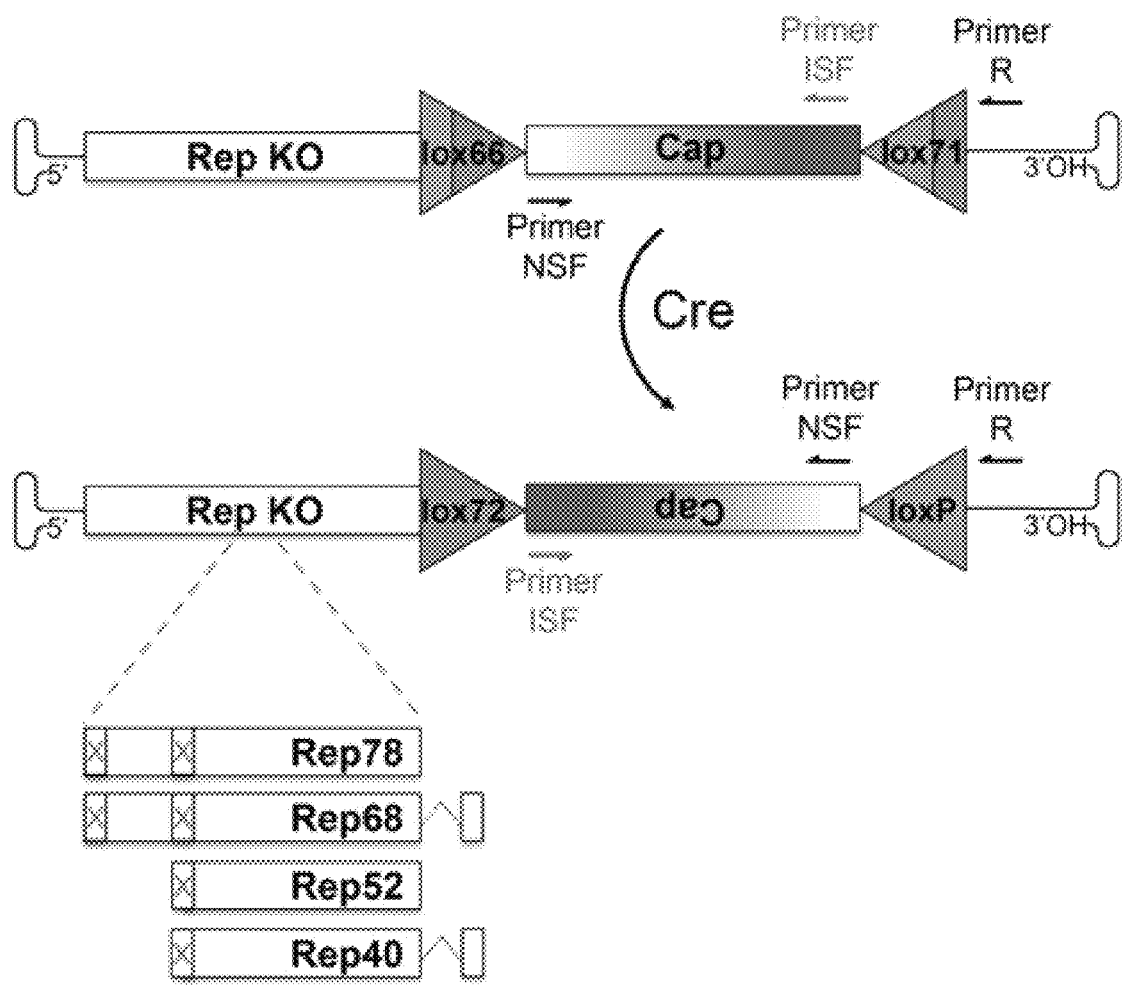
FIG. 6A-6D provide a depiction of a Cre-dependent selection strategy for AAV directed evolution.
Figure 6B:
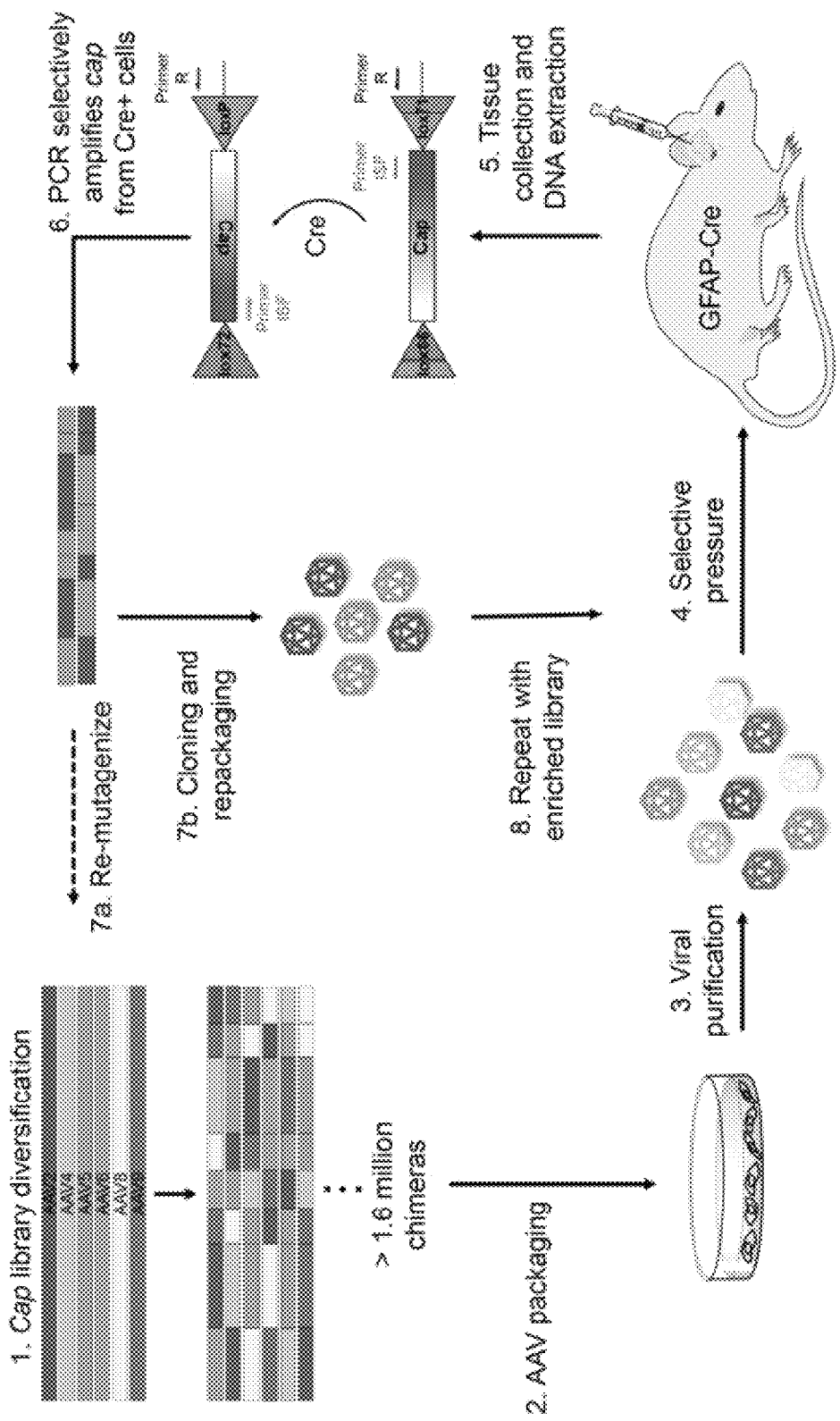
Figure 6C:
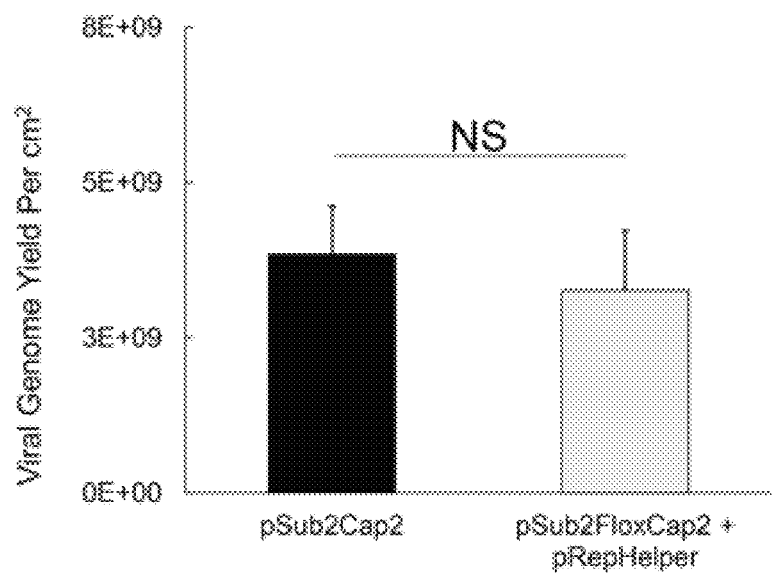
Figure 6D:
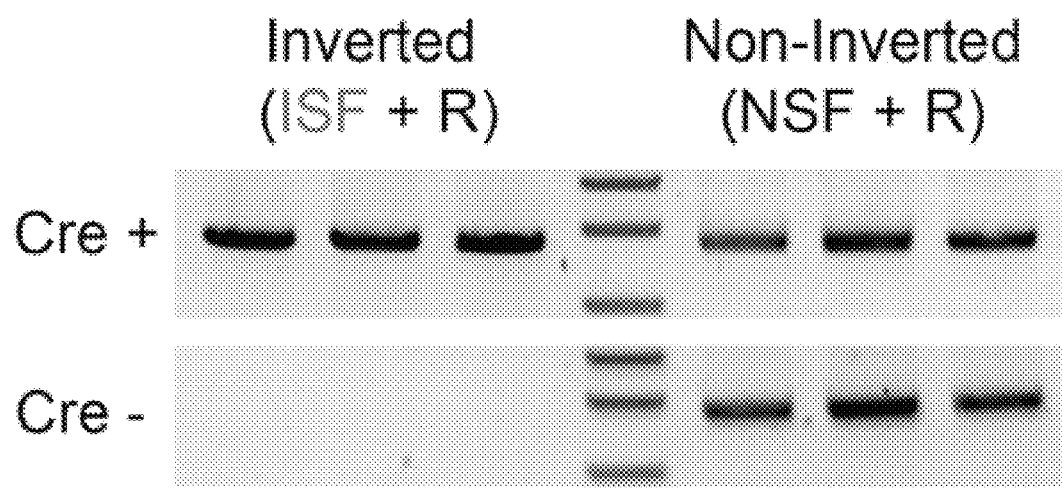
Figure 7:
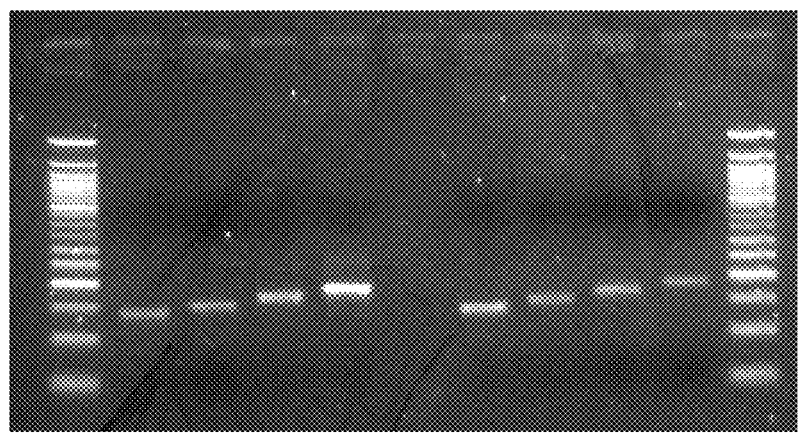
FIG. 7 depicts the levels of recombination during bacterial plasmid propagation in Sure2 recombinase deficient *E. coli*.

Over 300 transgenic mice that drove Cre expression under the control of a cell-type-specific promoter were developed. See, e.g., Heffner et al. (2012) Nature Commun. 3. FIGS. 6A-6D. The cell-type-specificity of Cre expression was developed to mediate selective recovery of the AAV cap gene by flanking the cap gene with a pair of loxP sites. AAV infection of a Cre-expressing cell followed by second strand AAV genome synthesis led to the inversion of the floxed cap, and PCR primers that served as a forward and reverse pair only in the inverted gene template were used to selectively recover the Cre-inverted cap genes from the brain tissue (FIGS. 6A, B). Mutant loxP sites lox66 and lox71 40 were utilized to drive the equilibrium of Cre recombination towards unidirectional inversion. The loxP sites were initially inserted in the 3' UTR of cap, where they flanked short stuffer sequences containing the target sequence for the reverse primer used for Cre-dependent recovery. Recombination occurred at low levels during bacterial plasmid propagation, even in Sure2 recombinase deficient *E. coli* as depicted in FIG. 7. To prevent this undesired recovery of inverted cap during in vivo selections, the loxP sites were repositioned to flank cap such that artefactual inversion during bacterial propagation of the vector plasmid library would result in an inverted cap sequence that does not encode viral proteins and thus would not subsequently package in 293 cells, a provision not included in an alternate design. See, e.g., Deverman et al. (2016) *Nature Biotechnol.* 34. Note that insertion of loxP sites flanking the cap gene altered the reading frame of the rep gene. The translation initiation codons of rep were thus removed, the viral promoter that drove cap expression was maintained (FIG. 6A), and rep was instead supplied in trans for viral packaging by transient transfection of a separate rep-encoding helper. These modifications to the viral packaging plasmids resulted in a high AAV viral genomic yield as quantified by qPCR (FIG. 6C).

Adult NSCs in the SVZ express glial markers including glial-fibrillary acidic protein (GFAP), see, e.g., Doetsch et al. (1999) *Cell* 97, glutamate aspartate transporter (GLAST), see, e.g., Platel et al. (2009) *Glia* 57, and brain lipid-binding protein (BLBP), see, e.g., Giachino et al. (2014) *Stem Cells* 32. To select for adult NSC transduction, the GFAP-Cre 73.12 mouse line was utilized in which Cre recombinase expression was controlled by the mouse GFAP promoter. Cre expression was observed in adult GFAP-expressing neural stem cells and mature astrocytes. See, e.g., Garcia et al. (2004) *Nature Neurosci.* 7. Although Cre was expressed in astrocytes in addition to neural stem cells, the intracerebroventricular (ICV) route of administration resulted in preferential transduction of the SVZ where the neural stem cells resided, and GFAP served as an important marker of NSC identity. See, e.g., Doetsch et al. (1999) *Cell* 97. To validate Cre-dependent recovery of cap, AAV libraries containing floxed cap genes (pSub2FloxCap) were delivered to GFAP-Cre 73.12 or C57BL/6J control mice through an intracerebroventricular injection. Inverted cap could only be amplified from brain tissue of mice expressing Cre, while non-inverted cap was present in both groups (FIG. 6D). For Cre recombination to occur, the AAV genome must be in double-stranded form, as required for expression of a therapeutic transgene. It was therefore likely that the non-inverted pool of cap genes amplified from the GFAP-Cre 73.12 mice represented capsids that failed to infect GFAP positive cells, were defective in some aspect of the viral life cycle (e.g. capsid uncoating, endosomal escape), or did not complete second strand synthesis. The Cre-dependent selection strategy thus exclusively recovered capsid variants that complete all steps necessary for robust transgene expression in the target cell type.

Example 3: In Vivo Library Selections Converge on a Dominant SCHEMA AAV Variant

After validating Cre-dependent recovery of cap, in vivo selections were initiated using an equimolar mixture of six AAV libraries, each containing $10^6$ to $10^7$ unique variants: (i) the new SCHEMA AAV, (ii) error-prone AAV9, (iii) ancestral AAV, see, e.g., Santiago-Ortiz et al. (2015) *Gene Ther.* 22, (iv) shuffled AAV generated by DNase I digestion and reassembly of AAV1, 2, 4, 5, 6, 8, and 9, see, e.g., Koerber et al. (2008) *Mol. Ther.* 16, (v) error-prone AAV2, see, e.g., Koerber et al. (2006) *Nature Protoc.* 1, and (vi) AAV2 7mer peptide insertion at amino acid 588, see, e.g., Muller et al. (2003) *Nature Biotechnol.* 21. Libraries iii-vi have previously yielded highly infectious clones in our directed evolution selections and provided evolutionary competition for the SCHEMA library. See, e.g., Dalkara et al. (2013) *Sci. Transl. Med.* 5; Tervo et al. (2016) *Neuron*; Steines et al. (2016) *JCI Insight* 1; Koerber et al. (2008) Mol. Ther. 16; and Santiago-Ortiz et al. (2015) *Gene Ther.* 22. The libraries were combined and injected via intracerebroventricular administration into the right lateral ventricle of adult GFAP-Cre mice (n=3) to transduce NSCs throughout the entire SVZ in both hemispheres. In contrast, direct SVZ injection is more disruptive to the local tissue and could require multiple injections to cover the same tissue volume.

Figure 11A:
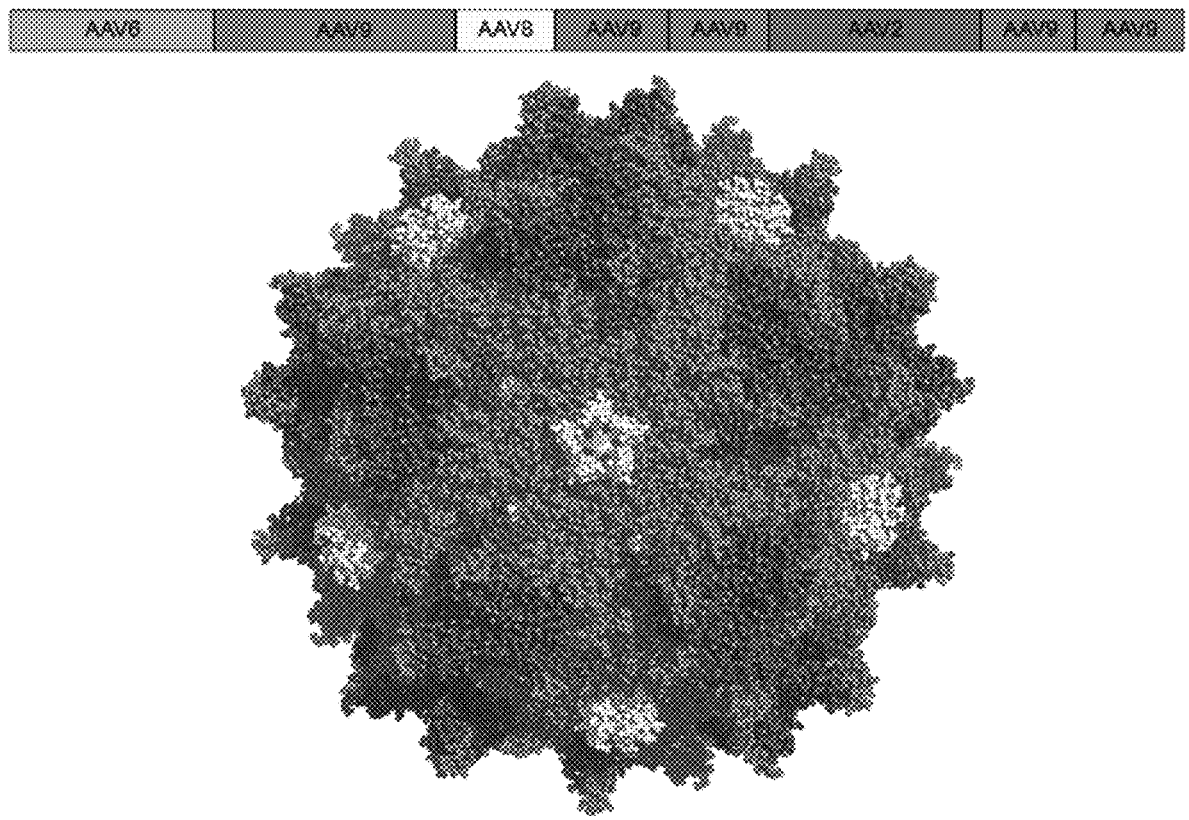
FIG. 11A-11B provide three-dimensional models of the SCH9 capsid.
Figure 11B:
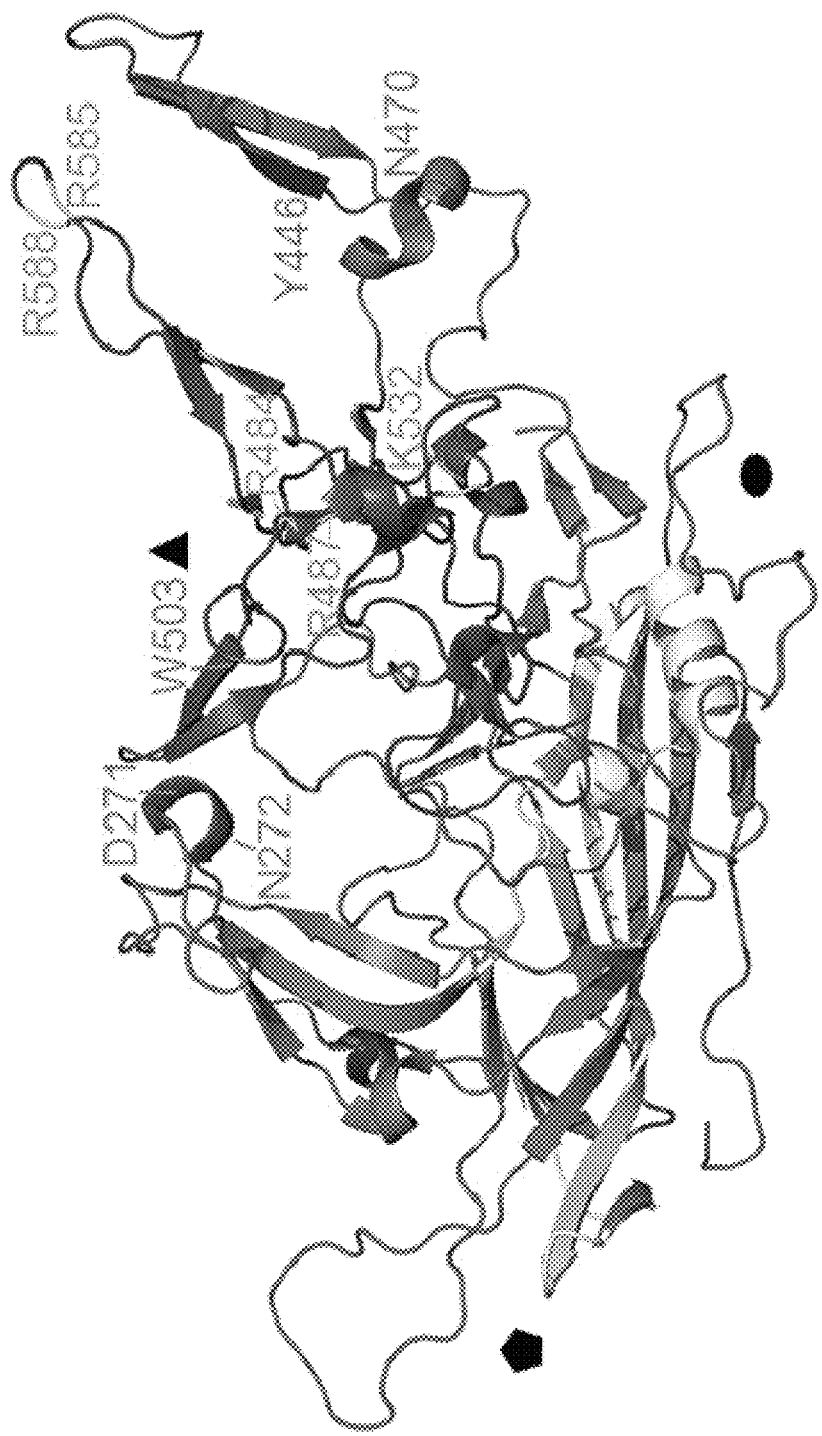

Three weeks after injection the contralateral brain hemisphere was harvested, genomic DNA was extracted, and Cre-recombined AAV cap variants were recovered from GFAP expressing cells by PCR. The contralateral hemisphere was harvested to ensure that cap variants were not recovered from transduction associated with the injection tract through the cortex superior to the lateral ventricle. After three rounds of in vivo selection, Sanger sequencing analysis of 24 clones revealed convergence on two variants originating from the SCHEMA library. SCH9 (chimera 6, 9, 8, 9, 9, 2, 9, 9; (E) 9, (m) 49) represented 54% of the clones recovered, while SCH2 (chimera 6, 9, 8, 9, 2, 2, 9, 9; (E) 4, (m) 37) represented 33%. The remaining clones were derived from the AAV2 7mer insertion (8%) and ancestral libraries (4%). SCH9 differs from the closest parent, AAV9, by 58 total mutations (92% amino acid identity). Forty-nine of these ((m)) are in the crystallized region of the capsid, and 9 are in the uncrystallized region. An amino acid alignment of sequences of SCH9, SCH2, and multiple parent AAV serotypes are presented in FIGS. 8, 9, and 10, respectively. The two SCHEMA variants differed only at block five, resulting in a difference of 18 amino acids. FIGS. 11A-11B. A model of the three-dimensional structure of SCH9 depicted AAV9 at loop VR-IV on the capsid surface, AAV2 at loops V-VIII, and AAV8 at the fivefold pore structure.

Based on these intriguing features, and its dominance of the selected pool, the in vivo characterization of SCH9.

Figure 12:
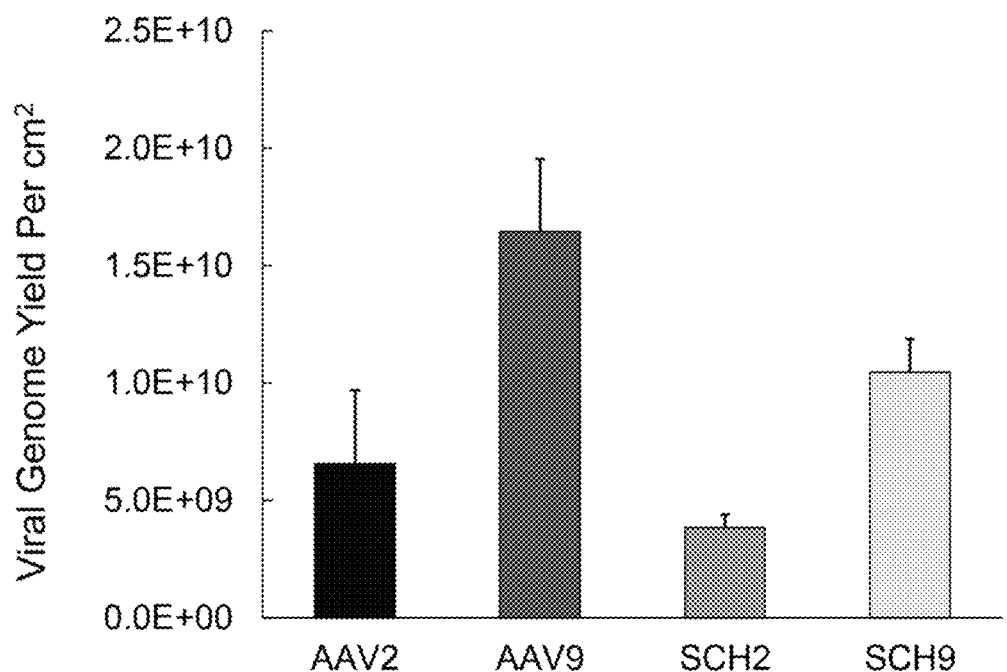
FIG. 12 depicts the viral genomic yield of recombinant self-complementary AAV vectors.

Example 4: SCH9 Efficiently Transduces Adult Neural Stem Cells in the SVZ of Adult Mice To assess the transduction profile of SCH9 in the SVZ, rAAV carrying a self-complementary CAG-GFP cassette was successfully packaged (recombinant AAV packaging yields are reported in FIG. 12) and delivered to the right lateral ventricle of adult C57BL/6J mice. SCH9 was benchmarked against AAV9 due to its broad use in the CNS and capacity to transduce the brain parenchyma from the cerebrospinal fluid (CSF) after intrathecal injection. See, e.g., Samaranch et al. (2012) Hum. Gene Ther. 23; and Schuster et al. (2014) Front. Neuroanat. 8. Moreover, of the natural serotypes, AAV9 is the most closely related sequence to SCH9.

Figure 13A:
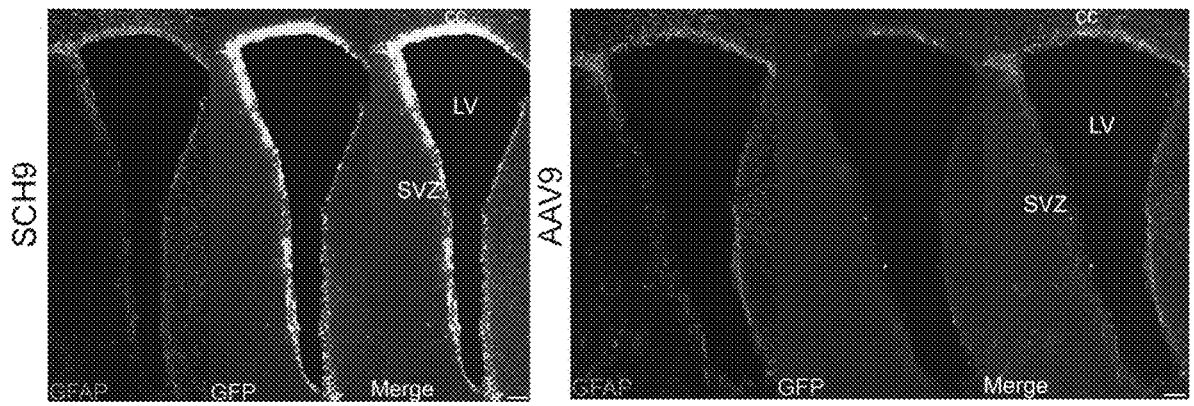
Figure 13B:
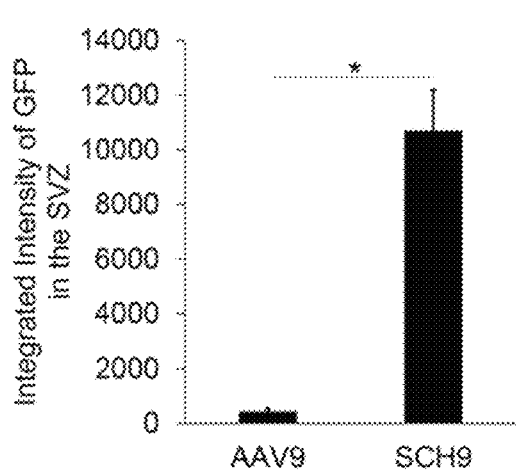
Figure 13C:
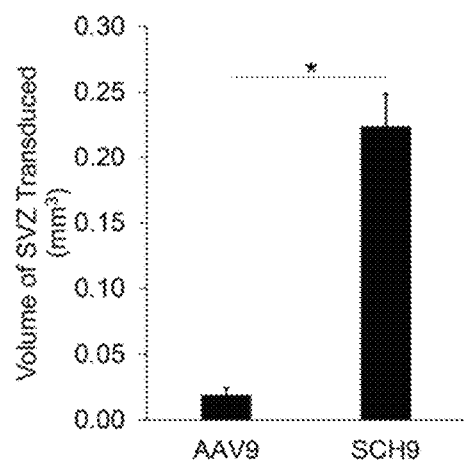
Figure 13G:
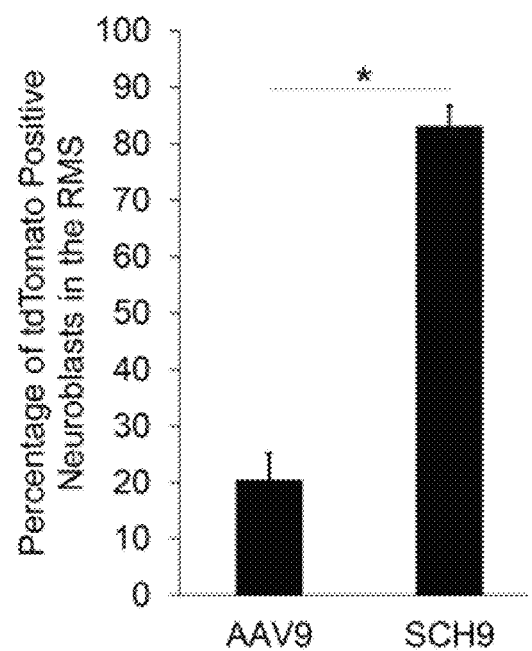

FIGS. 13A-13I. Transduction of the contralateral hemisphere was analyzed four weeks after injection, and GFP expression was primarily associated with the region surrounding the ventricle, with greatest intensity in the subventricular zone (FIG. 13A). Transduction efficiency was evaluated by both the intensity of GFP expression and the total volume of the SVZ that was positive for GFP. The integrated GFP fluorescence intensity for SCH9 was 24-fold higher, and GFP was expressed in a 12-fold greater SVZ transduction volume, compared to AAV9 (FIGS. 13B, C). As an initial characterization, GFP/GFAP/VCAM1 positive adult neural stem cells were transduced by SCH9 in the subventricular zone (FIG. 13D).

Recombinant AAV genomes were maintained episomally and were progressively lost during the cell divisions characteristic of adult neurogenesis in the SVZ. Specifically, lineage progression from a neural stem cell to an olfactory bulb interneuron involved over seven cell divisions. See, e.g., Ponti et al. (2013) Cell Cycle 12. As a result of the accompanying AAV genome dilution, at late time points after injection the majority of cells that continue to express transgene were slowly dividing NSCs or post-mitotic cells. Moreover, prior studies using integrating retroviral vectors indicated that the time required for neuroblasts to traverse the rostral migratory stream to the olfactory bulb was nine days, and that all transit amplifying cells and neuroblasts present in the SVZ at the time of injection differentiated and/or migrated to the olfactory bulb and established dendrites by 30 days post-injection. See, e.g., Petreanu et al. (2002) J. Neurosci. 22; and Lois et al. (1994) Science 264. These results indicated that neuroblasts present in the rostral migratory stream at late time points after injection were derived from NSCs, a conclusion that was previously used to establish lentiviral or non-viral transduction of NSCs in the SVZ. See, e.g., Consiglio et al. (2004) Proc. Natl. Acad. Sci. U.S.A. 101; and Barnabe-Heider et al. (2008) Nature Methods 5. A similar lineage analysis strategy was designed to determine the number of migrating neuroblasts expressing tdTomato 30 days post-injection as an indication of NSC transduction. Recombinant SCH9 or AAV9 encoding Cre recombinase was injected into the right lateral ventricle of adult Ai9 floxed STOP tdTomato mice, see, e.g., Madisen et al. (2010) Nature Neurosci. 13, within which Cre activity resulted in tdTomato expression in transduced cells and their progeny. The majority (injected right hemisphere 83.2±3.6%, left hemisphere 50.3±4.4%) of neuroblasts were positive for tdTomato in the rostral migratory stream 30 days post-injection of SCH9 expressing Cre (FIGS. 13E, G), exceeding AAV9 transduction by over 4-fold. Furthermore, large numbers of tdTomato positive neuroblasts were observed migrating radially in the olfactory bulb and adopting the morphology of granule cell neurons (FIG. 13F).

Figure 13H:
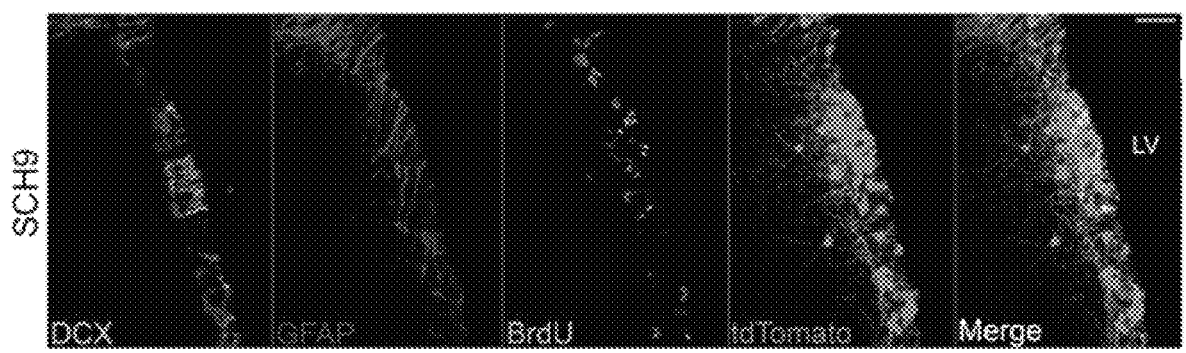
Figure 13I:
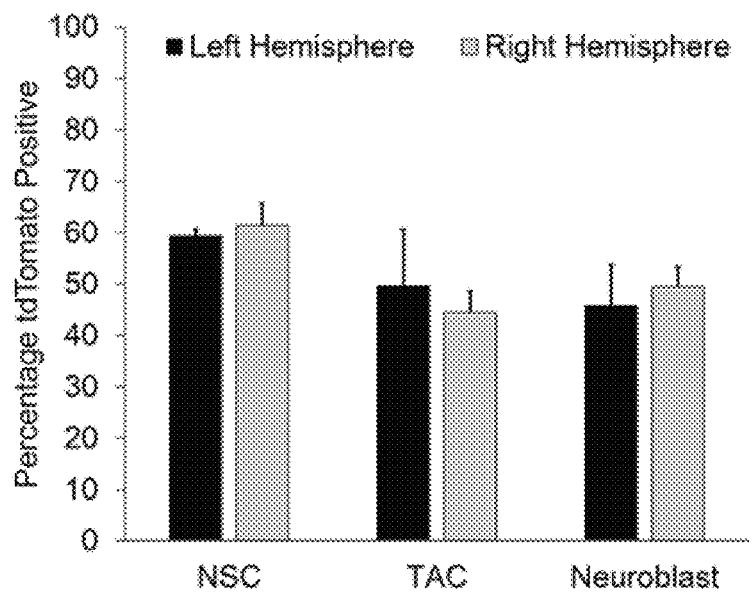

To further characterize NSC transduction, the thymidine analog BrdU (5-bromo-2'-deoxyuridine) was administered to label dividing cells in the SVZ prior to injection of single-stranded SCH9 CAG-Cre. After a wash-out period of two weeks, colocalization of tdTomato expression with BrdU incorporation into GFAP$^+$NSCs was analyzed (FIG. 13H). The percentage of adult NSCs (GFAP+, BrdU+, doublecortin−), transit amplifying cells (GFAP− BrdU+, doublecortin−), and neuroblasts (GFAP− BrdU+, doublecortin+) expressing tdTomato in the SVZ were quantified (FIG. 13I). Approximately 60% of NSCs were transduced in both hemispheres, supporting the efficacy of SCH9 for gene delivery to NSCs using both single-stranded and self-complementary formats.

Example 5: SCH9 Also Displays Tropism for Purkinje Cells in the Cerebellum

Figure 14A:
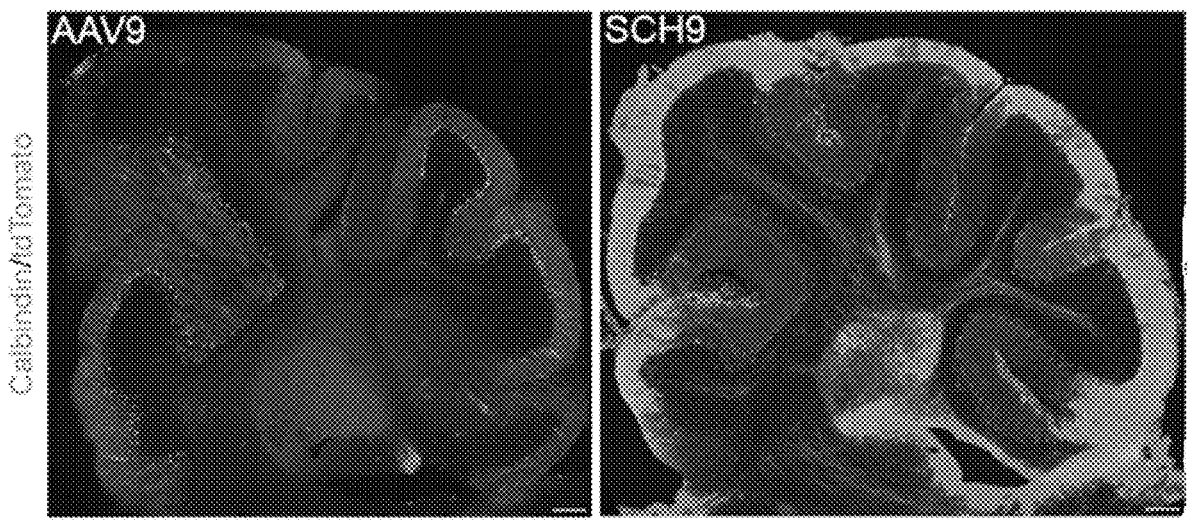
FIG. 14A-14C depict marker expression of SCH9 transduction in Purkinje cells of the cerebellum.
Figure 14B:
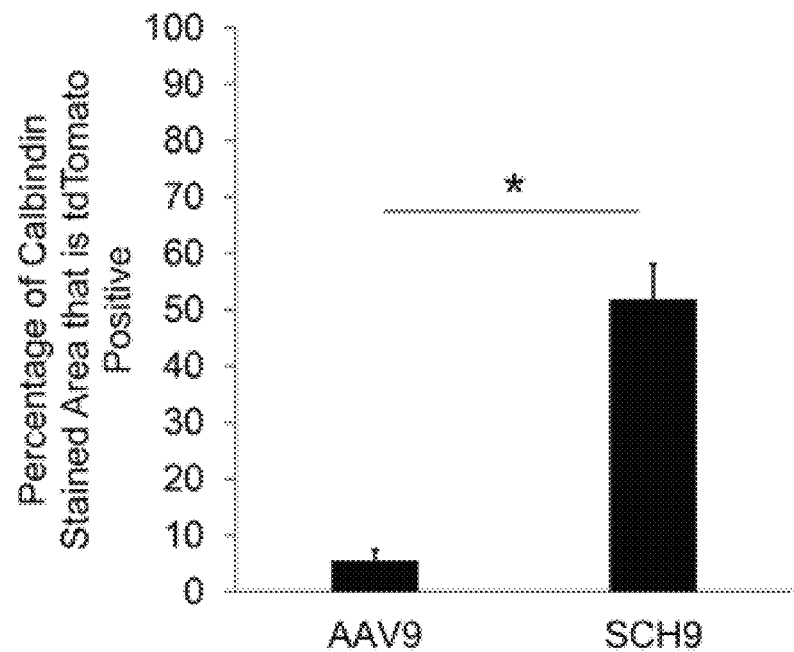
Figure 14C:
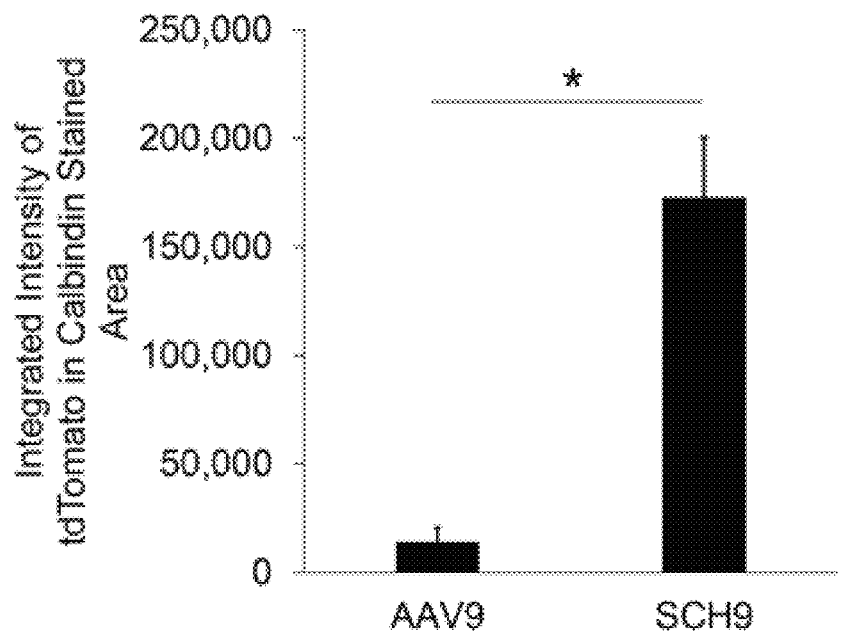

Capsid mutations that enhance infection of the target cell type can simultaneously improve transduction in other regions of the brain. FIGS. 14A-14C. Although SCH9 transduction following intracerebroventricular injection was primarily associated with the SVZ, increased reporter expression was also observed in Purkinje cells of the cerebellum, a region of the brain directly accessible to vector circulating in the cerebrospinal fluid (FIG. 14A). Purkinje cells are a key target of gene therapies for neurodegenerative diseases including spinocerebellar ataxias. See, e.g., On et al. (2012) J. Cell Biol. 197. Delivery of SCH9-Cre activated tdTomato reporter expression that was 12.2-fold more intense and covered 9.3-fold greater calbindin positive area than AAV9-Cre (FIGS. 14B, C) as quantified by CellProfiler.

Figure 15:
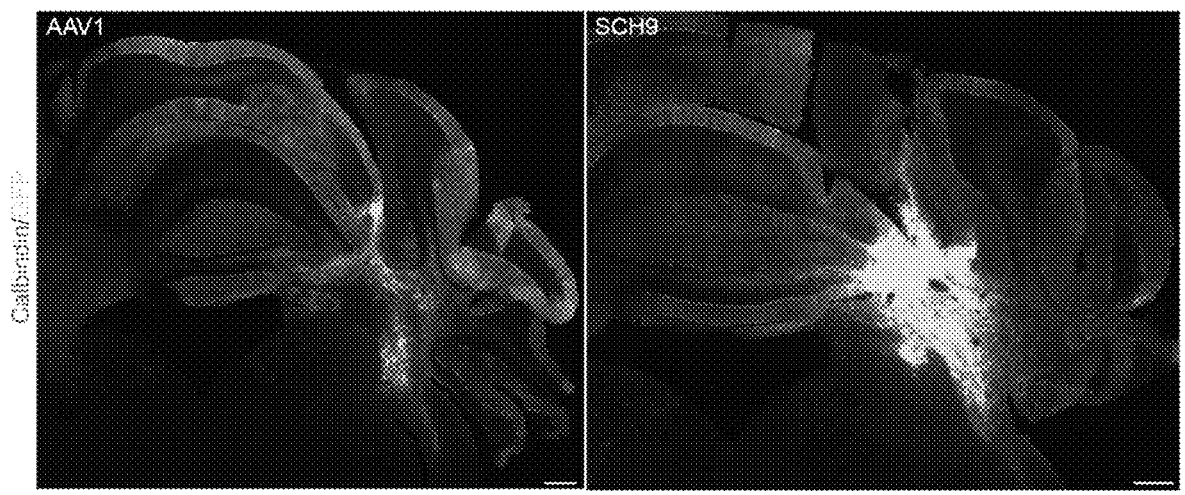
FIG. 15 depicts GFP expression in the cerebellum three weeks after unilateral injection of recombinant AAV1 or SCH9 in the deep cerebellar nuclei.

The success of SCH9 in transducing Purkinje cells from the cerebrospinal fluid suggested its potential as a gene delivery vector for the cerebellum. Cerebellar gene therapies have employed rAAV delivery to the deep cerebellar nuclei, a major hub in cerebellar circuitry that receives inhibitory inputs from Purkinje cells. See, e.g., Keiser et al. (2015) Brain: J. Neurol. 138; and Dodge et al. (2008) Mol. Ther. 16. By harnessing this circuitry, a single injection of rAAV into the deep cerebellar nuclei could transduce Purkinje cells throughout the cerebellar cortex through retrograde transport of the vector. FIG. 15. Transduction patterns of SCH9 with AAV1, the most commonly used serotype for gene delivery to the cerebellum, were compared after unilateral injection into the deep cerebellar nuclei of the right hemisphere. Both vectors supported strong transduction of Purkinje cells throughout the cerebellum in the ipsilateral hemisphere, indicating that SCH9 can be transported in the retrograde direction.

Example 6: SCH9 can Utilize Both Heparan Sulfate Proteoglycans and Galactose for Cell Transduction Given the promising infectious properties of SCH9, its chimeric nature was next examined to determine whether it may have conferred a selective advantage to SCH9 by modulating the receptor binding capabilities of its multiple parent serotypes. Block six of SCH9 contained the heparin binding pocket of the AAV2 capsid. See, e.g., Kern et al. (2003) J. Virol. 77. In addition, blocks two and five contained the galactose binding residues D271, N272, N470, and Y446 of AAV9, while block six conserved residue W503. See, e.g., Bell et al. (2012) *J. Virol.* 86. In contrast, SCH2 lacked two of the key galactose binding residues due to substitution of AAV2 for AAV9 at block five.

Figure 16A:
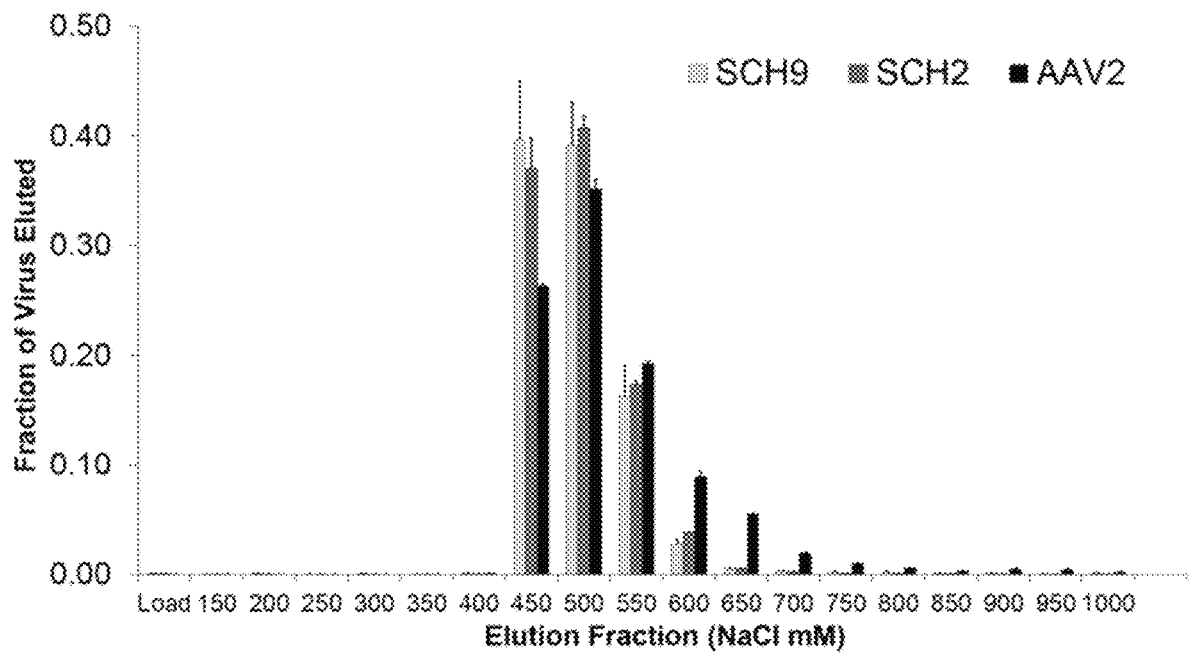
FIG. 16A-16C depict the characterization of SCH9 glycan binding and resistance to neutralizing antibodies.
Figure 16B:
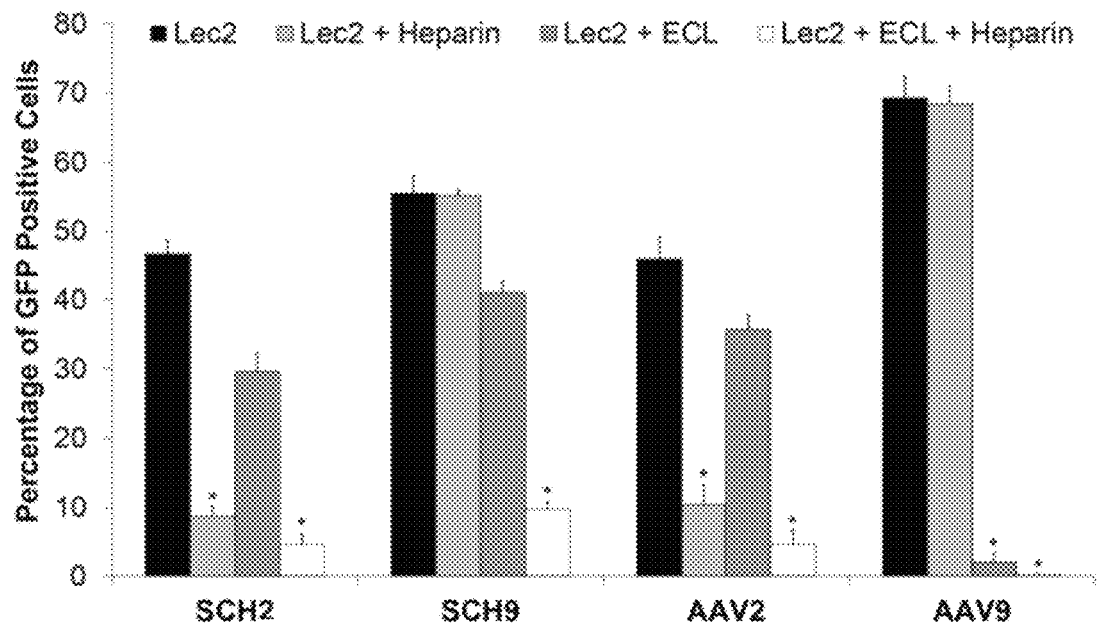
Figure 16C:
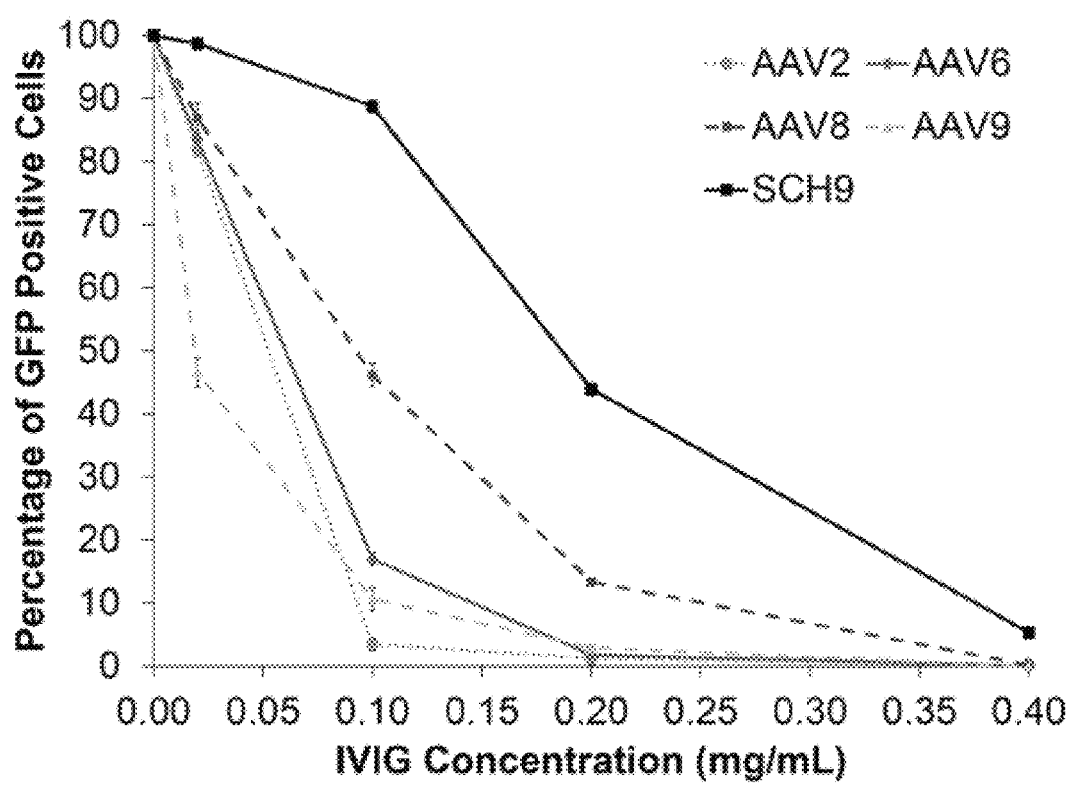
Figure 17:
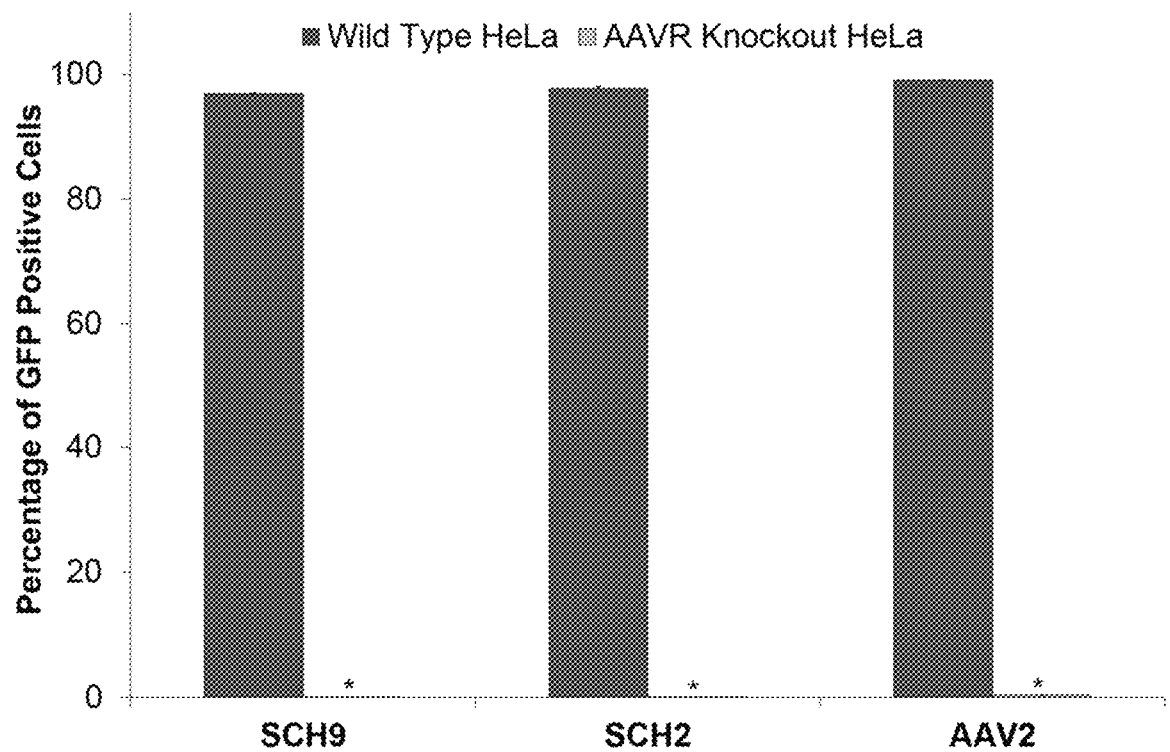
FIG. 17 depicts the infectivity of SCH2 and SCH9, compared with AAV2, a control that is known to utilize AAVR.

FIG. 16A-16C. Chromatography was first employed to demonstrate that the heparin affinity of both SCHEMA variants was comparable to AAV2, indicating that the chimeric sequence context outside of the heparin pocket did not significantly influence binding affinity (FIG. 16A). The potential for dual utilization of heparan sulfate proteoglycans (HSPG) and galactose was next evaluated by infecting CHO-Lec2 cells that express terminal galactose residues and HSPG on the cell surface. As previously described in Shen et al. (2013) *J. Biol. Chem.* 288, addition of *Erythrina cristagalli* lectin (ECL) blocked terminal galactose, whereas virus incubation with soluble heparin competitively inhibited AAV serotypes that utilized HSPG for cell entry. As expected, the AAV2 and AAV9 control vectors utilized HSPG and galactose, respectively. Interestingly, SCH2 was solely dependent on HSPG, while SCH9 was able to use both HSPG and galactose, and actually required that both be blocked to prevent cell transduction (FIG. 16B). After characterizing the different glycan binding properties of SCH2 and SCH9, both variants were examined to determine whether they retained utilization of AAVR, a newly described protein receptor that was critical for AAV infection in natural AAV serotypes. See, e.g., Pillay et al. (2016) *Nature* 530. FIG. 17. SCH2, SCH9, and the AAV2 control were all clearly dependent on AAVR.

Finally, since DNA shuffling had been shown to disrupt neutralizing antibody epitopes, see, e.g., Maheshri et al. (2006) *Nature Biotechnol.* 24, and Grimm et al. (2008) *J. Virol.* 82, the resistance of SCH9 to human intravenous immunoglobulin (IVIG), a polyclonal mixture of antibodies against natural AAV serotypes, was quantified. The antibody titer required to neutralize SCH9 was two to ten-fold higher as presented herein in Table 1, than the parent sequences from which it was derived (FIG. 16C). Notably, the greatest fold improvement was relative to AAV9, the most closely related parent sequence.

TABLE 1

Neutralizing IVIG titers of SCH9 and the parent serotypes from which they were derived. The neutralizing titers represent the first IVIG concentration at which 50% or greater reduction in GFP expression were observed.

| Variant | Neutralizing IVIG Concentration (mg/mL) | SCH9 Fold Improvement |
|---|---|---|
| SCH9 | 0.20 | N/A |
| AAV2 | 0.10 | 2 |
| AAV6 | 0.10 | 2 |
| AAV8 | 0.10 | 2 |
| AAV9 | 0.02 | 10 |

REFERENCES

Abel, T. W. et al. GFAP-Cre-mediated activation of oncogenic K-ras results in expansion of the subventricular zone and infiltrating glioma. Molecular cancer research: MCR 7, 645-653, doi:10.1158/1541-7786.MCR-08-0477 (2009).

Agrawal, S. & Schaffer, D. V. In situ stem cell therapy: novel targets, familiar challenges. Trends in biotechnology 23, 78-83, doi:10.1016/j.tibtech.2004.12.004 (2005).

Albert, H., Dale, E. C., Lee, E. & Ow, D. W. Site-specific integration of DNA into wild-type and mutant lox sites placed in the plant genome. The Plant journal: for cell and molecular biology 7, 649-659 (1995).

Arad, U. Modified Hirt procedure for rapid purification of extrachromosomal DNA from mammalian cells. BioTechniques 24, 760-762 (1998).

Asokan, A., Schaffer, D. V. & Samulski, R. J. The AAV vector toolkit: poised at the clinical crossroads. Molecular therapy: the journal of the American Society of Gene Therapy 20, 699-708, doi:10.1038/mt.2011.287 (2012).

Barnabe-Heider, F. et al. Genetic manipulation of adult mouse neurogenic niches by in vivo electroporation. Nature methods 5, 189-196, doi:10.1038/nmeth.1174 (2008).

Bell, C. L., Gurda, B. L., Van Vliet, K., Agbandje-McKenna, M. & Wilson, J. M. Identification of the galactose binding domain of the adeno-associated virus serotype 9 capsid. Journal of virology 86, 7326-7333, doi:10.1128/JVI.00448-12 (2012).

Bockstael, O. et al. Rapid transgene expression in multiple precursor cell types of adult rat subventricular zone mediated by adeno-associated type 1 vectors. Human gene therapy 23, 742-753, doi:10.1089/hum.2011.216 (2012).

Burda, J. E. & Sofroniew, M. V. Reactive gliosis and the multicellular response to CNS damage and disease. Neuron 81, 229-248, doi:10.1016/j.neuron.2013.12.034 (2014).

Carpenter, A. E. et al. CellProfiler: image analysis software for identifying and quantifying cell phenotypes. Genome biology 7, R100, doi:10.1186/gb-2006-7-10-r100 (2006).

Chaparro-Riggers, J. F. et al. Revealing biases inherent in recombination protocols. BMC biotechnology 7, 77, doi: 10.1186/1472-6750-7-77 (2007).

Cho, S. W. et al. Analysis of off-target effects of CRISPR/Cas-derived RNA-guided endonucleases and nickases. Genome research 24, 132-141, doi:10.1101/gr.162339.113 (2014).

Consiglio, A. et al. Robust in vivo gene transfer into adult mammalian neural stem cells by lentiviral vectors. Proceedings of the National Academy of Sciences of the United States of America 101, 14835-14840, doi:10.1073/pnas.0404180101 (2004).

Crameri, A., Raillard, S. A., Bermudez, E. & Stemmer, W. P. DNA shuffling of a family of genes from diverse species accelerates directed evolution. Nature 391, 288-291, doi:10.1038/34663 (1998).

Curtis, M. A. et al. Increased cell proliferation and neurogenesis in the adult human Huntington's disease brain. Proceedings of the National Academy of Sciences of the United States of America 100, 9023-9027, doi:10.1073/pnas.1532244100 (2003).

Dalkara, D. et al. In vivo-directed evolution of a new adeno-associated virus for therapeutic outer retinal gene delivery from the vitreous. Science translational medicine 5, 189ra176, doi:10.1126/scitranslmed.3005708 (2013).

Deverman, B. E. et al. Cre-dependent selection yields AAV variants for widespread gene transfer to the adult brain. Nature biotechnology 34, 204-209, doi:10.1038/nbt.3440 (2016).

Dodge, J. C. et al. Delivery of AAV-IGF-1 to the CNS extends survival in ALS mice through modification of aberrant glial cell activity. Molecular therapy: the journal of the American Society of Gene Therapy 16, 1056-1064, doi:10.1038/mt.2008.60 (2008).

Doetsch, F., Caille, I., Lim, D. A., Garcia-Verdugo, J. M. & Alvarez-Buylla, A. Subventricular zone astrocytes are neural stem cells in the adult mammalian brain. Cell 97, 703-716 (1999).

Dymecki, S. M., Ray, R. S. & Kim, J C. Mapping cell fate and function using recombinase-based intersectional strategies. Methods in enzymology 477, 183-213, doi: 10.1016/50076-6879(10)77011-7 (2010).

Earley, L. F. et al. Adeno-associated Virus (AAV) Assembly-Activating Protein Is Not an Essential Requirement for Capsid Assembly of AAV Serotypes 4, 5, and 11. Journal of virology 91, doi:10.1128/JVI.01980-16 (2017).

Edgar, R. C. MUSCLE: multiple sequence alignment with high accuracy and high throughput. Nucleic acids research 32, 1792-1797, doi:10.1093/nar/gkh340 (2004).

Endelman, J. B., Silberg, J. J., Wang, Z. G. & Arnold, F. H. Site-directed protein recombination as a shortest-path problem. Protein engineering, design & selection: PEDS 17, 589-594, doi:10.1093/protein/gzh067 (2004).

Engler, C. & Marillonnet, S. Combinatorial DNA assembly using Golden Gate cloning. Methods in molecular biology 1073, 141-156, doi:10.1007/978-1-62703-625-2_12 (2013).

Ernst, A. et al. Neurogenesis in the striatum of the adult human brain. Cell 156, 1072-1083, doi:10.1016/j.cell.2014.01.044 (2014).

Evers, P. et al. Irradiation of the potential cancer stem cell niches in the adult brain improves progression-free survival of patients with malignant glioma. BMC cancer 10, 384, doi:10.1186/1471-2407-10-384 (2010).

Excoffon, K. J. et al. Directed evolution of adeno-associated virus to an infectious respiratory virus. Proceedings of the National Academy of Sciences of the United States of America 106, 3865-3870, doi:10.1073/pnas.0813365106 (2009).

Falk, A. et al. Gene delivery to adult neural stem cells. Experimental cell research 279, 34-39 (2002).

Gage, F. H. Mammalian neural stem cells. Science 287, 1433-1438 (2000).

Gao, G. et al. Clades of Adeno-associated viruses are widely disseminated in human tissues. Journal of virology 78, 6381-6388, doi:10.1128/JVI.78.12.6381-6388.2004 (2004).

Garcia, A. D., Doan, N. B., Imura, T., Bush, T. G. & Sofroniew, M. V. GFAP-expressing progenitors are the principal source of constitutive neurogenesis in adult mouse forebrain. Nature neuroscience 7, 1233-1241, doi: 10.1038/nn1340 (2004).

Gascon, E., Vutskits, L. & Kiss, J. Z. The role of PSA-NCAM in adult neurogenesis. Advances in experimental medicine and biology 663, 127-136, doi:10.1007/978-1-4419-1170-4_8 (2010).

Giachino, C. et al. Molecular diversity subdivides the adult forebrain neural stem cell population. Stem cells 32, 70-84, doi:10.1002/stem.1520 (2014).

Grimm, D. et al. In vitro and in vivo gene therapy vector evolution via multispecies interbreeding and retargeting of adeno-associated viruses. Journal of virology 82, 5887-5911, doi:10.1128/JVI.00254-08 (2008).

Heffner, C. S. et al. Supporting conditional mouse mutagenesis with a comprehensive cre characterization resource. Nature communications 3, 1218, doi:10.1038/ncomms2186 (2012).

Heidenreich, M. & Zhang, F. Applications of CRISPR-Cas systems in neuroscience. Nature reviews. Neuroscience 17, 36-44, doi:10.1038/nrn.2015.2 (2016).

Heintz, N. Gene expression nervous system atlas (GENSAT). Nature neuroscience 7, 483, doi:10.1038/nn0504-483 (2004).

Heinzelman, P. et al. Efficient screening of fungal cellobiohydrolase class I enzymes for thermostabilizing sequence blocks by SCHEMA structure-guided recombination. Protein engineering, design & selection: PEDS 23, 871-880, doi:10.1093/protein/gzq063 (2010).

Heinzelman, P., Romero, P. A. & Arnold, F. H. Efficient sampling of SCHEMA chimera families to identify useful sequence elements. Methods in enzymology 523, 351-368, doi:10.1016/B978-0-12-394292-0.00016-3 (2013).

Hennen, E. & Faissner, A. LewisX: a neural stem cell specific glycan? The international journal of biochemistry & cell biology 44, 830-833, doi:10.1016/j.biocel.2012.02.019 (2012).

Hillson, N. J., Rosengarten, R. D. & Keasling, J. D. j5 DNA assembly design automation software. ACS synthetic biology 1, 14-21, doi:10.1021/sb2000116 (2012).

Ho, M. L., Adler, B. A., Torre, M. L., Silberg, J. J. & Suh, J. SCHEMA computational design of virus capsid chimeras: calibrating how genome packaging, protection, and transduction correlate with calculated structural disruption. ACS synthetic biology 2, 724-733, doi:10.1021/sb400076r (2013).

Jang, J. H. et al. An evolved adeno-associated viral variant enhances gene delivery and gene targeting in neural stem cells. Molecular therapy: the journal of the American Society of Gene Therapy 19, 667-675, doi:10.1038/mt.2010.287 (2011).

Jang, J.-H. et al. An evolved adeno-associated viral variant enhances gene delivery and gene targeting in neural stem cells. Molecular Therapy 19, 667-675 (2011).

Keiser, M. S., Kordower, J. H., Gonzalez-Alegre, P. & Davidson, B. L. Broad distribution of ataxin 1 silencing in rhesus cerebella for spinocerebellar ataxia type 1 therapy. Brain: a journal of neurology 138, 3555-3566, doi: 10.1093/brain/awv292 (2015).

Kern, A. et al. Identification of a heparin-binding motif on adeno-associated virus type 2 capsids. Journal of virology 77, 11072-11081 (2003).

Klimczak, R. R., Koerber, J. T., Dalkara, D., Flannery, J. G. & Schaffer, D. V. A novel adeno-associated viral variant for efficient and selective intravitreal transduction of rat Muller cells. PloS one 4, e7467, doi:10.1371/journal.pone.0007467 (2009).

Koerber, J. T. et al. Molecular evolution of adeno-associated virus for enhanced glial gene delivery. Molecular therapy: the journal of the American Society of Gene Therapy 17, 2088-2095, doi:10.1038/mt.2009.184 (2009).

Koerber, J. T., Jang, J. H. & Schaffer, D. V. DNA shuffling of adeno-associated virus yields functionally diverse viral progeny. Molecular therapy: the journal of the American Society of Gene Therapy 16, 1703-1709, doi:10.1038/mt.2008.167 (2008).

Koerber, J. T., Maheshri, N., Kaspar, B. K. & Schaffer, D. V. Construction of diverse adeno-associated viral libraries for directed evolution of enhanced gene delivery vehicles. Nature protocols 1, 701-706, doi:10.1038/nprot.2006.93 (2006).

Kokovay, E. et al. VCAM1 is essential to maintain the structure of the SVZ niche and acts as an environmental sensor to regulate SVZ lineage progression. Cell stem cell 11, 220-230, doi:10.1016/j.stem.2012.06.016 (2012).

Kotterman, M. A., Chalberg, T. W. & Schaffer, D. V. Viral Vectors for Gene Therapy: Translational and Clinical Outlook. Annual review of biomedical engineering 17, 63-89, doi:10.1146/annurev-bioeng-071813-104938 (2015).

Kotterman, M. A., Vazin, T. & Schaffer, D. V. Enhanced selective gene delivery to neural stem cells in vivo by an adeno-associated viral variant. Development 142, 1885-1892, doi:10.1242/dev.115253 (2015).

Lai, K., Kaspar, B. K., Gage, F. H. & Schaffer, D. V. Sonic hedgehog regulates adult neural progenitor proliferation in vitro and in vivo. Nature neuroscience 6, 21-27, doi: 10.1038/nn983 (2003).

Lanctot, P. M., Gage, F. H. & Varki, A. P. The glycans of stem cells. Current opinion in chemical biology 11, 373-380, doi:10.1016/j.cbpa.2007.05.032 (2007).

Langmead, B., Trapnell, C., Pop, M. & Salzberg, S. L. Ultrafast and memory-efficient alignment of short DNA sequences to the human genome. Genome biology 10, R25, doi:10.1186/gb-2009-10-3-r25 (2009).

Lee, Y., Messing, A., Su, M. & Brenner, M. GFAP promoter elements required for region-specific and astrocyte-specific expression. Glia 56, 481-493, doi:10.1002/glia.20622 (2008).

Lemkine, G. F. et al. Preferential transfection of adult mouse neural stem cells and their immediate progeny in vivo with polyethylenimine Molecular and cellular neurosciences 19, 165-174, doi:10.1006/mcne.2001.1084 (2002).

Lim, D. A. & Alvarez-Buylla, A. The Adult Ventricular-Subventricular Zone (V-SVZ) and Olfactory Bulb (OB) Neurogenesis. Cold Spring Harbor perspectives in biology 8, doi:10.1101/cshperspect.a018820 (2016).

Liu, G., Martins, I. H., Chiorini, J. A. & Davidson, B. L. Adeno-associated virus type 4 (AAV4) targets ependyma and astrocytes in the subventricular zone and RMS. Gene therapy 12, 1503-1508, doi:10.1038/sj.gt.3302554 (2005).

Liu, Y. et al. Identification of small-molecule modulators of mouse SVZ progenitor cell proliferation and differentiation through high-throughput screening. Journal of biomolecular screening 14, 319-329, doi:10.1177/1087057109332596 (2009).

Liu, Y. W. et al. Doublecortin expression in the normal and epileptic adult human brain. The European journal of neuroscience 28, 2254-2265, doi:10.1111/j.1460-9568.2008.06518.x (2008).

Lois, C. & Alvarez-Buylla, A. Long-distance neuronal migration in the adult mammalian brain. Science 264, 1145-1148 (1994).

Macas, J., Nern, C., Plate, K. H. & Momma, S. Increased generation of neuronal progenitors after ischemic injury in the aged adult human forebrain. The Journal of neuroscience: the official journal of the Society for Neuroscience 26, 13114-13119, doi:10.1523/JNEUROSCI.4667-06.2006 (2006).

Madisen, L. et al. A robust and high-throughput Cre reporting and characterization system for the whole mouse brain. Nature neuroscience 13, 133-140, doi:10.1038/nn.2467 (2010).

Maheshri, N., Koerber, J. T., Kaspar, B. K. & Schaffer, D. V. Directed evolution of adeno-associated virus yields enhanced gene delivery vectors. Nature biotechnology 24, 198-204, doi:10.1038/nbt1182 (2006).

McCluskey, L., Campbell, S., Anthony, D. & Allan, S. M. Inflammatory responses in the rat brain in response to different methods of intra-cerebral administration. Journal of neuroimmunology 194, 27-33, doi: 10.1016/j.jneuroim.2007.11.009 (2008).

Menzella, H. G. et al. Combinatorial polyketide biosynthesis by de novo design and rearrangement of modular polyketide synthase genes. Nature biotechnology 23, 1171-1176, doi:10.1038/nbt1128 (2005).

Meyer, M. M., Hochrein, L. & Arnold, F. H. Structure-guided SCHEMA recombination of distantly related beta-lactamases. Protein engineering, design & selection: PEDS 19, 563-570, doi:10.1093/protein/gzl045 (2006).

Moore, J. C. & Arnold, F. H. Directed evolution of a para-nitrobenzyl esterase for aqueous-organic solvents. Nature biotechnology 14, 458-467, doi:10.1038/nbt0496-458 (1996).

Muller, O. J. et al. Random peptide libraries displayed on adeno-associated virus to select for targeted gene therapy vectors. Nature biotechnology 21, 1040-1046, doi: 10.1038/nbt856 (2003).

Murlidharan, G., Corriher, T., Ghashghaei, H. T. & Asokan, A. Unique glycan signatures regulate adeno-associated virus tropism in the developing brain. Journal of virology 89, 3976-3987, doi:10.1128/JVI.02951-14 (2015).

Nierode, G. J. et al. High-Throughput Toxicity and Phenotypic Screening of 3D Human Neural Progenitor Cell Cultures on a Microarray Chip Platform. Stem cell reports 7, 970-982, doi:10.1016/j.stemcr.2016.10.001 (2016).

Ojala, D. S., Amara, D. P. & Schaffer, D. V. Adeno-associated virus vectors and neurological gene therapy. The Neuroscientist: a review journal bringing neurobiology, neurology and psychiatry 21, 84-98, doi:10.1177/1073858414521870 (2015).

Orelle, C. et al. Protein synthesis by ribosomes with tethered subunits. Nature 524, 119-124, doi:10.1038/nature14862 (2015).

On, H. T. Cell biology of spinocerebellar ataxia. The Journal of cell biology 197, 167-177, doi:10.1083/jcb.201105092 (2012).

Otey, C. R. et al. Functional evolution and structural conservation in chimeric cytochromes p450: calibrating a structure-guided approach. Chemistry & biology 11, 309-318, doi:10.1016/j.chembiol.2004.02.018 (2004).

Otey, C. R. et al. Structure-guided recombination creates an artificial family of cytochromes P450. PLoS biology 4, e112, doi:10.1371/journal.pbio.0040112 (2006).

Passini, M. A., Lee, E. B., Heuer, G. G. & Wolfe, J. H. Distribution of a lysosomal enzyme in the adult brain by axonal transport and by cells of the rostral migratory stream. The Journal of neuroscience: the official journal of the Society for Neuroscience 22, 6437-6446, doi: 20026665 (2002).

Petreanu, L. & Alvarez-Buylla, A. Maturation and death of adult-born olfactory bulb granule neurons: role of olfaction. The Journal of neuroscience: the official journal of the Society for Neuroscience 22, 6106-6113, doi: 20026588 (2002).

Piccirillo, S. G. et al. Contributions to drug resistance in glioblastoma derived from malignant cells in the subependymal zone. Cancer research 75, 194-202, doi: 10.1158/0008-5472.CAN-13-3131 (2015).

Pierce, E. A. & Bennett, J. The Status of RPE65 Gene Therapy Trials: Safety and Efficacy. Cold Spring Harbor perspectives in medicine 5, a017285, doi:10.1101/cshperspect.a017285 (2015).

Pillay, S. et al. An essential receptor for adeno-associated virus infection. Nature 530, 108-112, doi:10.1038/nature16465 (2016).

Platel, J. C., Gordon, V., Heintz, T. & Bordey, A. GFAP-GFP neural progenitors are antigenically homogeneous and anchored in their enclosed mosaic niche. Glia 57, 66-78, doi:10.1002/glia.20735 (2009).

Ponti, G., Obernier, K. & Alvarez-Buylla, A. Lineage progression from stem cells to new neurons in the adult brain ventricular-subventricular zone. Cell cycle 12, 1649-1650, doi:10.4161/cc.24984 (2013).

Rogelius, N., Ericson, C. & Lundberg, C. In vivo labeling of neuroblasts in the subventricular zone of rats. Journal of neuroscience methods 142, 285-293, doi:10.1016/j.jneumeth.2004.09.008 (2005).

Romero, P. A. et al. SCHEMA-designed variants of human Arginase I and II reveal sequence elements important to stability and catalysis. ACS synthetic biology 1, 221-228, doi:10.1021/sb300014t (2012).

Samaranch, L. et al. Adeno-associated virus serotype 9 transduction in the central nervous system of nonhuman primates. Human gene therapy 23, 382-389, doi:10.1089/hum.2011.200 (2012).

Sanai, N. et al. Corridors of migrating neurons in the human brain and their decline during infancy. Nature 478, 382-386, doi:10.1038/nature10487 (2011).

Sanai, N. et al. Unique astrocyte ribbon in adult human brain contains neural stem cells but lacks chain migration. Nature 427, 740-744, doi:10.1038/nature02301 (2004).

Santiago-Ortiz, J. et al. AAV ancestral reconstruction library enables selection of broadly infectious viral variants. Gene therapy 22, 934-946, doi:10.1038/gt.2015.74 (2015).

Santiago-Ortiz, J. L. & Schaffer, D. V. Adeno-associated virus (AAV) vectors in cancer gene therapy. Journal of controlled release: official journal of the Controlled Release Society 240, 287-301, doi:10.1016/jjconrel.2016.01.001 (2016).

Saxena, A. et al. Trehalose-enhanced isolation of neuronal sub-types from adult mouse brain. BioTechniques 52, 381-385, doi:10.2144/0000113878 (2012).

Schuster, D. J. et al. Biodistribution of adeno-associated virus serotype 9 (AAV9) vector after intrathecal and intravenous delivery in mouse. Frontiers in neuroanatomy 8, 42, doi:10.3389/fnana.2014.00042 (2014).

Shen, S. et al. Engraftment of a galactose receptor footprint onto adeno-associated viral capsids improves transduction efficiency. The Journal of biological chemistry 288, 28814-28823, doi:10.1074/jbc.M113.482380 (2013).

Sonntag, F. et al. The assembly-activating protein promotes capsid assembly of different adeno-associated virus serotypes. Journal of virology 85, 12686-12697, doi:10.1128/JVI.05359-11 (2011).

Spencer, H. T., Riley, B. E. & Doering, C. B. State of the art: gene therapy of haemophilia. Haemophilia: the official journal of the World Federation of Hemophilia 22 Suppl 5, 66-71, doi:10.1111/hae.13011 (2016).

Steines, B. et al. CFTR gene transfer with AAV improves early cystic fibrosis pig phenotypes. JCI insight 1, e88728, doi:10.1172/jci.insight.88728 (2016).

Tang, J. C. et al. Cell type-specific manipulation with GFP-dependent Cre recombinase. Nature neuroscience 18, 1334-1341, doi:10.1038/nn.4081 (2015).

Tervo, D. G. et al. A Designer AAV Variant Permits Efficient Retrograde Access to Projection Neurons. Neuron, doi:10.1016/j.neuron.2016.09.021 (2016).

Voigt, C. A., Martinez, C., Wang, Z. G., Mayo, S. L. & Arnold, F. H. Protein building blocks preserved by recombination. Nature structural and molecular biology 9, 553-558, doi:10.1038/nsb805 (2002).

Yagi, H., Saito, T., Yanagisawa, M., Yu, R. K. & Kato, K. Lewis X-carrying N-glycans regulate the proliferation of mouse embryonic neural stem cells via the Notch signaling pathway. The Journal of biological chemistry 287, 24356-24364, doi:10.1074/jbc.M112.365643 (2012).

Yoon, S. O. et al. Adenovirus-mediated gene delivery into neuronal precursors of the adult mouse brain. Proceedings of the National Academy of Sciences of the United States of America 93, 11974-11979 (1996).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant adeno-associated virus (rAAV) virion comprising:
   a) a variant AAV capsid protein, wherein the variant AAV capsid protein comprises an amino acid sequence having at least 95% sequence identity to the amino acid sequence of SEQ ID NO:1, and wherein the variant capsid protein confers increased infectivity of a neural stem cell, compared to the infectivity of the neural stem cell by a control AAV virion comprising a wild-type AAV capsid protein; and
   b) a heterologous nucleic acid comprising a nucleotide sequence encoding a heterologous gene product.

2. The rAAV virion of claim 1, wherein the rAAV virion exhibits at least 5-fold increased infectivity of a neural stem cell compared to the infectivity of the neural stem cell by the control AAV virion comprising a wild-type AAV capsid protein.

3. The rAAV virion of claim 1, wherein the variant AAV capsid protein exhibits increased resistance to human AAV neutralizing antibodies compared to the resistance exhibited by a control AAV virion comprising a wild-type AAV capsid protein.

4. The rAAV virion of claim 1, wherein the gene product is an interfering RNA or an aptamer.

5. The rAAV virion of claim 1, wherein the gene product is a polypeptide.

6. The rAAV virion of claim 5, wherein the polypeptide is a neuroprotective polypeptide, an anti-angiogenic polypeptide, a polypeptide that induces differentiation of a neural stem cell, or a polypeptide that enhances function of a neural stem cell.

7. The rAAV virion of claim 5, wherein the polypeptide is cerebrolysin, laminin-IKVAV, cripto, pituitary adenylate cyclase-activating polypeptide, nerve growth factor, brain derived neurotrophic factor, glial derived neurotrophic factor, fibroblast growth factor 2, neurturin, ciliary neurotrophic factor, epidermal growth factor, X-linked inhibitor of apoptosis, aromatic L-amino acid decarboxylase, glutamic acid decarboxylase, tripeptidyl peptidase, aspartoacylase, or Sonic hedgehog.

8. A pharmaceutical composition comprising:
   a) a recombinant adeno-associated virus virion of claim 1; and
   b) a pharmaceutically acceptable excipient.

9. A method of delivering a gene product to a neural stem cell in an individual, the method comprising administering to the individual a recombinant adeno-associated virus (rAAV) virion according to claim 1.

10. The rAAV virion of claim 1, wherein the amino acid sequence has at least 98% amino acid sequence identity to the amino acid sequence of SEQ ID NO:1.

11. The rAAV virion of claim 1, wherein the amino acid sequence has at least 99% amino acid sequence identity to the amino acid sequence of SEQ ID NO:1.

12. The rAAV virion of claim 1, wherein the amino acid sequence has the amino acid sequence of SEQ ID NO:1.

13. An isolated nucleic acid comprising a nucleotide sequence that encodes a variant adeno-associated virus (AAV) capsid protein comprising an amino acid sequence having at least 95% sequence identity to the amino acid sequence of SEQ ID NO:1, and wherein the variant capsid protein confers increased infectivity of a neural stem cell compared to the infectivity of the neural stem cell by a control AAV virion comprising a wild-type AAV capsid.

14. An isolated, genetically modified host cell comprising the nucleic acid of claim 13.

15. The isolated nucleic acid of claim 13, wherein the amino acid sequence has at least 98% amino acid sequence identity to the amino acid sequence of SEQ ID NO:1.

16. The isolated nucleic acid of claim 13, wherein the amino acid sequence has at least 99% amino acid sequence identity to the amino acid sequence of SEQ ID NO:1.

17. The isolated nucleic acid of claim 13, wherein the amino acid sequence has the amino acid sequence of SEQ ID NO:1.

18. A variant adeno-associated virus (AAV) capsid protein, wherein the variant AAV capsid protein comprises an amino acid sequence having at least 95% sequence identity to the amino acid sequence of SEQ ID NO:1, and wherein the variant capsid protein confers increased infectivity of a neural stem cell compared to the infectivity of the neural stem cell by a control AAV virion comprising a wild-type AAV capsid.

* * * * *

SEQUENCE LISTING

<160> NUMBER OF SEQ ID NOS: 172

<210> SEQ ID NO 1
<211> LENGTH: 736
<212> TYPE: PRT
<213> ORGANISM: Adeno-associated virus

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala

```
                85                  90                  95
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Trp Leu Pro
465                 470                 475                 480

Gly Pro Cys Tyr Arg Gln Gln Arg Val Ser Lys Thr Ser Ala Asp Asn
                485                 490                 495

Asn Asn Ser Glu Tyr Ser Trp Thr Gly Ala Thr Lys Tyr His Leu Asn
            500                 505                 510
```

```
Gly Arg Asp Ser Leu Val Asn Pro Gly Pro Ala Met Ala Ser His Lys
            515                 520                 525

Asp Asp Glu Glu Lys Phe Phe Pro Gln Ser Gly Val Leu Ile Phe Gly
530                 535                 540

Lys Gln Gly Ser Glu Lys Thr Asn Val Asp Ile Glu Lys Val Met Ile
545                 550                 555                 560

Thr Asp Glu Glu Glu Ile Arg Thr Thr Asn Pro Val Ala Thr Glu Gln
                565                 570                 575

Tyr Gly Ser Val Ser Thr Asn Leu Gln Arg Gly Asn Arg Gln Ala Ala
            580                 585                 590

Thr Ala Asp Val Asn Thr Gln Gly Val Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 737
<212> TYPE: PRT
<213> ORGANISM: Adeno-associated virus

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
```

```
        145                 150                 155                 160
Lys Ser Gly Ala Gln Pro Ala Lys Lys Arg Leu Asn Phe Gly Gln Thr
                    165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Ser Phe Lys Leu Phe Asn Ile
305                 310                 315                 320
Gln Val Lys Glu Val Thr Gln Asn Glu Gly Thr Lys Thr Ile Ala Asn
                325                 330                 335
Asn Leu Thr Ser Thr Ile Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Arg Thr Asn Thr Pro Ser Gly Thr Thr Thr Gln Ser Arg Leu Gln Phe
    450                 455                 460
Ser Gln Ala Gly Ala Ser Asp Ile Arg Asp Gln Ser Arg Asn Trp Leu
465                 470                 475                 480
Pro Gly Pro Cys Tyr Arg Gln Gln Arg Val Ser Lys Thr Ser Ala Asp
                485                 490                 495
Asn Asn Asn Ser Glu Tyr Ser Trp Thr Gly Ala Thr Lys Tyr His Leu
                500                 505                 510
Asn Gly Arg Asp Ser Leu Val Asn Pro Gly Pro Ala Met Ala Ser His
                515                 520                 525
Lys Asp Asp Glu Glu Lys Phe Phe Pro Gln Ser Gly Val Leu Ile Phe
    530                 535                 540
Gly Lys Gln Gly Ser Glu Lys Thr Asn Val Asp Ile Glu Lys Val Met
545                 550                 555                 560
Ile Thr Asp Glu Glu Glu Ile Arg Thr Thr Asn Pro Val Ala Thr Glu
                565                 570                 575
```

```
Gln Tyr Gly Ser Val Ser Thr Asn Leu Gln Arg Gly Asn Arg Gln Ala
                580                 585                 590

Ala Thr Ala Asp Val Asn Thr Gln Gly Val Leu Pro Gly Met Val Trp
            595                 600                 605

Gln Asp Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Met Lys His Pro Pro Gln Ile Leu Ile Lys Asn Thr Pro Val Pro
            645                 650                 655

Ala Asp Pro Pro Thr Ala Phe Asn Lys Asp Lys Leu Asn Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
        690                 695                 700

Asn Tyr Tyr Lys Ser Asn Asn Val Glu Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 3
<211> LENGTH: 7
<212> TYPE: PRT
<213> ORGANISM: Artificial sequence
<220> FEATURE:
<223> OTHER INFORMATION: Synthetic sequence

<400> SEQUENCE: 3

Leu Gly Glu Thr Thr Arg Pro
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic sequence

<400> SEQUENCE: 4

Asn Glu Thr Ile Thr Arg Pro
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic sequence

<400> SEQUENCE: 5

Lys Ala Gly Gln Ala Asn Asn
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic sequence
```

-continued

```
<400> SEQUENCE: 6

Lys Asp Pro Lys Thr Thr Asn
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic sequence

<400> SEQUENCE: 7

Lys Asp Thr Asp Thr Thr Arg
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic sequence

<400> SEQUENCE: 8

Arg Ala Gly Gly Ser Val Gly
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic sequence

<400> SEQUENCE: 9

Ala Val Asp Thr Thr Lys Phe
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic sequence

<400> SEQUENCE: 10

Ser Thr Gly Lys Val Pro Asn
1               5

<210> SEQ ID NO 11
<211> LENGTH: 736
<212> TYPE: PRT
<213> ORGANISM: Adeno-associated virus

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
```

-continued

```
                65                  70                  75                  80
        Gln Gln Leu Lys Ala Gly Asp Asn Pro Tyr Leu Arg Tyr Asn His Ala
                         85                  90                  95

Asp Ala Glu Phe Gln Glu Arg Leu Gln Glu Asp Thr Ser Phe Gly Gly
                        100                 105                 110

Asn Leu Gly Arg Ala Val Phe Gln Ala Lys Lys Arg Val Leu Glu Pro
                        115                 120                 125

Phe Gly Leu Val Glu Gly Ala Lys Thr Ala Pro Gly Lys Lys Arg
                        130                 135                 140

Pro Val Glu Gln Ser Pro Gln Glu Pro Asp Ser Ser Gly Ile Gly
        145                 150                 155                 160

Lys Thr Gly Gln Gln Pro Ala Lys Lys Arg Leu Asn Phe Gly Gln Thr
                        165                 170                 175

Gly Asp Ser Glu Ser Val Pro Asp Pro Gln Pro Leu Gly Glu Pro Pro
                        180                 185                 190

Ala Thr Pro Ala Ala Val Gly Pro Thr Thr Met Ala Ser Gly Gly Gly
                        195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
        225                 230                 235                 240

Thr Thr Ser Thr Arg Thr Trp Ala Leu Pro Thr Tyr Asn Asn His Leu
                        245                 250                 255

Tyr Lys Gln Ile Ser Ser Ala Ser Thr Gly Ala Ser Asn Asp Asn His
                        260                 265                 270

Tyr Phe Gly Tyr Ser Thr Pro Trp Gly Tyr Phe Asp Phe Asn Arg Phe
                        275                 280                 285

His Cys His Phe Ser Pro Arg Asp Trp Gln Arg Leu Ile Asn Asn Asn
                        290                 295                 300

Trp Gly Phe Arg Pro Lys Arg Leu Asn Phe Lys Leu Phe Asn Ile Gln
        305                 310                 315                 320

Val Lys Glu Val Thr Thr Asn Asp Gly Val Thr Thr Ile Ala Asn Asn
                        325                 330                 335

Leu Thr Ser Thr Val Gln Val Phe Ser Asp Ser Glu Tyr Gln Leu Pro
                        340                 345                 350

Tyr Val Leu Gly Ser Ala His Gln Gly Cys Leu Pro Pro Phe Pro Ala
                        355                 360                 365

Asp Val Phe Met Ile Pro Gln Tyr Gly Tyr Leu Thr Leu Asn Asn Gly
                        370                 375                 380

Ser Gln Ala Val Gly Arg Ser Ser Phe Tyr Cys Leu Glu Tyr Phe Pro
        385                 390                 395                 400

Ser Gln Met Leu Arg Thr Gly Asn Asn Phe Thr Phe Ser Tyr Thr Phe
                        405                 410                 415

Glu Asp Val Pro Phe His Ser Ser Tyr Ala His Ser Gln Ser Leu Asp
                        420                 425                 430

Arg Leu Met Asn Pro Leu Ile Asp Gln Tyr Leu Tyr Tyr Leu Asn Arg
                        435                 440                 445

Thr Gln Asn Gln Ser Gly Ser Ala Gln Asn Lys Asp Leu Leu Phe Ser
                        450                 455                 460

Arg Gly Ser Pro Ala Gly Met Ser Val Gln Pro Lys Asn Trp Leu Pro
        465                 470                 475                 480

Gly Pro Cys Tyr Arg Gln Gln Arg Val Ser Lys Thr Lys Thr Asp Asn
                        485                 490                 495
```

```
Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
                580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 12
<211> LENGTH: 20
<212> TYPE: DNA
<213> ORGANISM: Artificial sequence
<220> FEATURE:
<223> OTHER INFORMATION: Synthetic sequence

<400> SEQUENCE: 12
cgcaacagga agcaacaccg                                          20

<210> SEQ ID NO 13
<211> LENGTH: 29
<212> TYPE: DNA
<213> ORGANISM: Artificial sequence
<220> FEATURE:
<223> OTHER INFORMATION: Synthetic sequence

<400> SEQUENCE: 13
gctgcaatga taccgcgaaa cccacgctc                                29

<210> SEQ ID NO 14
<211> LENGTH: 29
<212> TYPE: DNA
<213> ORGANISM: Artificial sequence
<220> FEATURE:
<223> OTHER INFORMATION: Synthetic sequence

<400> SEQUENCE: 14

```
gagcgtgggt tcgcggtat cattgcagc                                 29

<210> SEQ ID NO 15
<211> LENGTH: 35
<212> TYPE: DNA
<213> ORGANISM: Artificial sequence
<220> FEATURE:
<223> OTHER INFORMATION: Synthetic sequence

<400> SEQUENCE: 15
gctcctggaa agaagaggcc gttgattgaa tcccc                         35

<210> SEQ ID NO 16
<211> LENGTH: 35
<212> TYPE: DNA
<213> ORGANISM: Artificial sequence
<220> FEATURE:
<223> OTHER INFORMATION: Synthetic sequence

<400> SEQUENCE: 16
ggggattcaa tcaacggcct cttctttcca ggagc                         35

<210> SEQ ID NO 17
<211> LENGTH: 27
<212> TYPE: DNA
<213> ORGANISM: Artificial sequence
<220> FEATURE:
<223> OTHER INFORMATION: Synthetic sequence

<400> SEQUENCE: 17
gacccggaaa cggactcgat cgaggag                                  27

<210> SEQ ID NO 18
<211> LENGTH: 27
<212> TYPE: DNA
<213> ORGANISM: Artificial sequence
<220> FEATURE:
<223> OTHER INFORMATION: Synthetic sequence

<400> SEQUENCE: 18
ctcctcgatc gagtccgttt ccgggtc                                  27

<210> SEQ ID NO 19
<211> LENGTH: 25
<212> TYPE: DNA
<213> ORGANISM: Artificial sequence
<220> FEATURE:
<223> OTHER INFORMATION: Synthetic sequence

<400> SEQUENCE: 19
gtttagccgg ggctctccag ctggc                                    25

<210> SEQ ID NO 20
<211> LENGTH: 25
<212> TYPE: DNA
<213> ORGANISM: Artificial sequence
<220> FEATURE:
<223> OTHER INFORMATION: Synthetic sequence

<400> SEQUENCE: 20
gccagctgga gagccccggc taaac                                    25

<210> SEQ ID NO 21
<211> LENGTH: 33
<212> TYPE: DNA
```

```
<213> ORGANISM: Artificial sequence
<220> FEATURE:
<223> OTHER INFORMATION: Synthetic sequence

<400> SEQUENCE: 21
ctcctggaaa gaagaggccg gtagagccat cac                                    33

<210> SEQ ID NO 22
<211> LENGTH: 33
<212> TYPE: DNA
<213> ORGANISM: Artificial sequence
<220> FEATURE:
<223> OTHER INFORMATION: Synthetic sequence

<400> SEQUENCE: 22
gtgatggctc taccggcctc ttctttccag gag                                    33

<210> SEQ ID NO 23
<211> LENGTH: 43
<212> TYPE: DNA
<213> ORGANISM: Artificial sequence
<220> FEATURE:
<223> OTHER INFORMATION: Synthetic sequence

<400> SEQUENCE: 23
caagcggccg cgtaagctta gatctctgac gtcgatggct gcg                         43

<210> SEQ ID NO 24
<211> LENGTH: 43
<212> TYPE: DNA
<213> ORGANISM: Artificial sequence
<220> FEATURE:
<223> OTHER INFORMATION: Synthetic sequence

<400> SEQUENCE: 24
cgcagccatc gacgtcagag atctaagctt acgcggccgc ttg                         43

<210> SEQ ID NO 25
<211> LENGTH: 41
<212> TYPE: DNA
<213> ORGANISM: Artificial sequence
<220> FEATURE:
<223> OTHER INFORMATION: Synthetic sequence

<400> SEQUENCE: 25
gatctataac ttcgtatagc atacattata cgaacggtac g                           41

<210> SEQ ID NO 26
<211> LENGTH: 41
<212> TYPE: DNA
<213> ORGANISM: Artificial sequence
<220> FEATURE:
<223> OTHER INFORMATION: Synthetic sequence

<400> SEQUENCE: 26
cgtaccgttc gtataatgta tgctatacga agttatttcg a                           41

<210> SEQ ID NO 27
<211> LENGTH: 67
<212> TYPE: DNA
<213> ORGANISM: Artificial sequence
<220> FEATURE:
<223> OTHER INFORMATION: Synthetic sequence

<400> SEQUENCE: 27
ccgcttgtta atcaataaac cgtttaattc gtttcagttg actcgaggtc tctgcgtatt       60
```

```
tctttct                                                              67

<210> SEQ ID NO 28
<211> LENGTH: 67
<212> TYPE: DNA
<213> ORGANISM: Artificial sequence
<220> FEATURE:
<223> OTHER INFORMATION: Synthetic sequence

<400> SEQUENCE: 28
agaaagaaat acgcagagac ctcgagtcaa ctgaaacgaa ttaaacggtt tattgattaa    60
caagcgg                                                              67

<210> SEQ ID NO 29
<211> LENGTH: 50
<212> TYPE: DNA
<213> ORGANISM: Artificial sequence
<220> FEATURE:
<223> OTHER INFORMATION: Synthetic sequence

<400> SEQUENCE: 29
cgtagataag tagcatggcg ggttaatcag gtaccacaag gaacccctag               50

<210> SEQ ID NO 30
<211> LENGTH: 50
<212> TYPE: DNA
<213> ORGANISM: Artificial sequence
<220> FEATURE:
<223> OTHER INFORMATION: Synthetic sequence

<400> SEQUENCE: 30
ctaggggttc cttgtggtac ctgattaacc cgccatgcta cttatctacg               50

<210> SEQ ID NO 31
<211> LENGTH: 78
<212> TYPE: DNA
<213> ORGANISM: Artificial sequence
<220> FEATURE:
<223> OTHER INFORMATION: Synthetic sequence

<400> SEQUENCE: 31
gtcagcctcg agataacttc gtataatgta tgctatacga acggtactgt ggtcgtcatt    60
ggcaactaca cctgttcg                                                  78

<210> SEQ ID NO 32
<211> LENGTH: 91
<212> TYPE: DNA
<213> ORGANISM: Artificial sequence
<220> FEATURE:
<223> OTHER INFORMATION: Synthetic sequence

<400> SEQUENCE: 32
cgtcacggta cctgtggaat tgtgagcgct cacaattcca cagctagcct atttaccgat    60
accacacgaa caggtgtagt tgccaatgac g                                   91

<210> SEQ ID NO 33
<211> LENGTH: 21
<212> TYPE: DNA
<213> ORGANISM: Artificial sequence
<220> FEATURE:
<223> OTHER INFORMATION: Synthetic sequence

<400> SEQUENCE: 33
```

```
gtcagcctcg agataacttc g                                          21

<210> SEQ ID NO 34
<211> LENGTH: 17
<212> TYPE: DNA
<213> ORGANISM: Artificial sequence
<220> FEATURE:
<223> OTHER INFORMATION: Synthetic sequence

<400> SEQUENCE: 34
cgtcacggta cctgtgg                                               17

<210> SEQ ID NO 35
<211> LENGTH: 22
<212> TYPE: DNA
<213> ORGANISM: Artificial sequence
<220> FEATURE:
<223> OTHER INFORMATION: Synthetic sequence

<400> SEQUENCE: 35
catggaaact agataagaaa ga                                         22

<210> SEQ ID NO 36
<211> LENGTH: 27
<212> TYPE: DNA
<213> ORGANISM: Artificial sequence
<220> FEATURE:
<223> OTHER INFORMATION: Synthetic sequence

<400> SEQUENCE: 36
ggtacgaagc ttcgatcaac tacgcag                                    27

<210> SEQ ID NO 37
<211> LENGTH: 21
<212> TYPE: DNA
<213> ORGANISM: Artificial sequence
<220> FEATURE:
<223> OTHER INFORMATION: Synthetic sequence

<400> SEQUENCE: 37
agctagccta tttaccgata c                                          21

<210> SEQ ID NO 38
<211> LENGTH: 21
<212> TYPE: DNA
<213> ORGANISM: Artificial sequence
<220> FEATURE:
<223> OTHER INFORMATION: Synthetic sequence

<400> SEQUENCE: 38
aagttcaact gaaacgaatt a                                          21

<210> SEQ ID NO 39
<211> LENGTH: 19
<212> TYPE: DNA
<213> ORGANISM: Artificial sequence
<220> FEATURE:
<223> OTHER INFORMATION: Synthetic sequence

<400> SEQUENCE: 39
cacacgaaca ggtgtagtt                                             19

<210> SEQ ID NO 40
<211> LENGTH: 1368
<212> TYPE: PRT
<213> ORGANISM: Streptococcus pyogenes
```

<400> SEQUENCE: 40

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu

```
                    405                 410                 415
        Gly Glu Leu His Ala Ile Leu Arg Arg Gln Glu Asp Phe Tyr Pro Phe
                        420                 425                 430

Leu Lys Asp Asn Arg Glu Lys Ile Glu Lys Ile Leu Thr Phe Arg Ile
                        435                 440                 445

Pro Tyr Tyr Val Gly Pro Leu Ala Arg Gly Asn Ser Arg Phe Ala Trp
                        450                 455                 460

Met Thr Arg Lys Ser Glu Glu Thr Ile Thr Pro Trp Asn Phe Glu Glu
        465                 470                 475                 480

Val Val Asp Lys Gly Ala Ser Ala Gln Ser Phe Ile Glu Arg Met Thr
                        485                 490                 495

Asn Phe Asp Lys Asn Leu Pro Asn Glu Lys Val Leu Pro Lys His Ser
                        500                 505                 510

Leu Leu Tyr Glu Tyr Phe Thr Val Tyr Asn Glu Leu Thr Lys Val Lys
                        515                 520                 525

Tyr Val Thr Glu Gly Met Arg Lys Pro Ala Phe Leu Ser Gly Glu Gln
                        530                 535                 540

Lys Lys Ala Ile Val Asp Leu Leu Phe Lys Thr Asn Arg Lys Val Thr
        545                 550                 555                 560

Val Lys Gln Leu Lys Glu Asp Tyr Phe Lys Lys Ile Glu Cys Phe Asp
                        565                 570                 575

Ser Val Glu Ile Ser Gly Val Glu Asp Arg Phe Asn Ala Ser Leu Gly
                        580                 585                 590

Thr Tyr His Asp Leu Leu Lys Ile Ile Lys Asp Lys Asp Phe Leu Asp
                        595                 600                 605

Asn Glu Glu Asn Glu Asp Ile Leu Glu Asp Ile Val Leu Thr Leu Thr
                        610                 615                 620

Leu Phe Glu Asp Arg Glu Met Ile Glu Glu Arg Leu Lys Thr Tyr Ala
        625                 630                 635                 640

His Leu Phe Asp Asp Lys Val Met Lys Gln Leu Lys Arg Arg Arg Tyr
                        645                 650                 655

Thr Gly Trp Gly Arg Leu Ser Arg Lys Leu Ile Asn Gly Ile Arg Asp
                        660                 665                 670

Lys Gln Ser Gly Lys Thr Ile Leu Asp Phe Leu Lys Ser Asp Gly Phe
                        675                 680                 685

Ala Asn Arg Asn Phe Met Gln Leu Ile His Asp Asp Ser Leu Thr Phe
                        690                 695                 700

Lys Glu Asp Ile Gln Lys Ala Gln Val Ser Gly Gln Gly Asp Ser Leu
        705                 710                 715                 720

His Glu His Ile Ala Asn Leu Ala Gly Ser Pro Ala Ile Lys Lys Gly
                        725                 730                 735

Ile Leu Gln Thr Val Lys Val Val Asp Glu Leu Val Lys Val Met Gly
                        740                 745                 750

Arg His Lys Pro Glu Asn Ile Val Ile Glu Met Ala Arg Glu Asn Gln
                        755                 760                 765

Thr Thr Gln Lys Gly Gln Lys Asn Ser Arg Glu Arg Met Lys Arg Ile
                        770                 775                 780

Glu Glu Gly Ile Lys Glu Leu Gly Ser Gln Ile Leu Lys Glu His Pro
        785                 790                 795                 800

Val Glu Asn Thr Gln Leu Gln Asn Glu Lys Leu Tyr Leu Tyr Tyr Leu
                        805                 810                 815

Gln Asn Gly Arg Asp Met Tyr Val Asp Gln Glu Leu Asp Ile Asn Arg
                        820                 825                 830
```

```
Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230
```

```
Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 41
<211> LENGTH: 1368
<212> TYPE: PRT
<213> ORGANISM: Artificial sequence
<220> FEATURE:
<223> OTHER INFORMATION: Synthetic sequence

<400> SEQUENCE: 41

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
```

-continued

```
                645                 650                 655
Thr Gly Trp Gly Arg Leu Ser Arg Lys Leu Ile Asn Gly Ile Arg Asp
                    660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065
```

```
Thr Gly Glu Ile Val Trp Asp Lys Gly Arg Asp Phe Ala Thr Val
    1070            1075                1080

Arg Lys Val Leu Ser Met Pro Gln Val Asn Ile Val Lys Lys Thr
    1085            1090                1095

Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365
```

<210> SEQ ID NO 42
<211> LENGTH: 1368
<212> TYPE: PRT
<213> ORGANISM: Artificial sequence
<220> FEATURE:
<223> OTHER INFORMATION: Synthetic sequence

<400> SEQUENCE: 42

```
Met Asp Lys Lys Tyr Ser Ile Gly Leu Asp Ile Gly Thr Asn Ser
1               5                   10                  15

Gly Trp Ala Val Ile Thr Asp Glu Tyr Lys Val Pro Ser Lys Phe
            20                  25                  30

Lys Val Leu Gly Asn Thr Asp Arg His Ser Ile Lys Lys Asn Leu Ile
            35                  40                  45
```

```
Gly Ala Leu Leu Phe Asp Ser Gly Glu Thr Ala Glu Ala Thr Arg Leu
     50                  55                  60

Lys Arg Thr Ala Arg Arg Tyr Thr Arg Lys Asn Arg Ile Cys
 65              70                  75                  80

Tyr Leu Gln Glu Ile Phe Ser Asn Glu Met Ala Lys Val Asp Asp Ser
                     85                  90                  95

Phe Phe His Arg Leu Glu Glu Ser Phe Leu Val Glu Glu Asp Lys Lys
             100                 105                 110

His Glu Arg His Pro Ile Phe Gly Asn Ile Val Asp Glu Val Ala Tyr
             115                 120                 125

His Glu Lys Tyr Pro Thr Ile Tyr His Leu Arg Lys Lys Leu Val Asp
             130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
             165                 170                 175

Asp Asn Ser Asp Val Asp Lys Leu Phe Ile Gln Leu Val Gln Thr Tyr
             180                 185                 190

Asn Gln Leu Phe Glu Glu Asn Pro Ile Asn Ala Ser Gly Val Asp Ala
             195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
             245                 250                 255

Asp Leu Ala Glu Asp Ala Lys Leu Gln Leu Ser Lys Asp Thr Tyr Asp
             260                 265                 270

Asp Asp Leu Asp Asn Leu Leu Ala Gln Ile Gly Asp Gln Tyr Ala Asp
             275                 280                 285

Leu Phe Leu Ala Ala Lys Asn Leu Ser Asp Ala Ile Leu Leu Ser Asp
             290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
             325                 330                 335

Ala Leu Val Arg Gln Gln Leu Pro Glu Lys Tyr Lys Glu Ile Phe Phe
             340                 345                 350

Asp Gln Ser Lys Asn Gly Tyr Ala Gly Tyr Ile Asp Gly Gly Ala Ser
             355                 360                 365

Gln Glu Glu Phe Tyr Lys Phe Ile Lys Pro Ile Leu Glu Lys Met Asp
             370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
             405                 410                 415

Gly Glu Leu His Ala Ile Leu Arg Arg Gln Glu Asp Phe Tyr Pro Phe
             420                 425                 430

Leu Lys Asp Asn Arg Glu Lys Ile Glu Lys Ile Leu Thr Phe Arg Ile
             435                 440                 445

Pro Tyr Tyr Val Gly Pro Leu Ala Arg Gly Asn Ser Arg Phe Ala Trp
450                 455                 460
```

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys

```
                885             890             895
Phe Asp Asn Leu Thr Lys Ala Glu Arg Gly Gly Leu Ser Glu Leu Asp
                900             905             910

Lys Ala Gly Phe Ile Lys Arg Gln Leu Val Glu Thr Arg Gln Ile Thr
                915             920             925

Lys His Val Ala Gln Ile Leu Asp Ser Arg Met Asn Thr Lys Tyr Asp
                930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
                965             970             975

Glu Ile Asn Asn Tyr His His Ala His Asp Ala Tyr Leu Asn Ala Val
                980             985             990

Val Gly Thr Ala Leu Ile Lys Lys Tyr Pro Lys Leu Glu Ser Glu Phe
                995             1000            1005

Val Tyr Gly Asp Tyr Lys Val Tyr Asp Val Arg Lys Met Ile Ala
        1010            1015            1020

Lys Ser Glu Gln Glu Ile Gly Lys Ala Thr Ala Lys Tyr Phe Phe
        1025            1030            1035

Tyr Ser Asn Ile Met Asn Phe Phe Lys Thr Glu Ile Thr Leu Ala
        1040            1045            1050

Asn Gly Glu Ile Arg Lys Arg Pro Leu Ile Glu Thr Asn Gly Glu
        1055            1060            1065

Thr Gly Glu Ile Val Trp Asp Lys Gly Arg Asp Phe Ala Thr Val
        1070            1075            1080

Arg Lys Val Leu Ser Met Pro Gln Val Asn Ile Val Lys Lys Thr
        1085            1090            1095

Glu Val Gln Thr Gly Gly Phe Ser Lys Glu Ser Ile Leu Pro Lys
        1100            1105            1110

Arg Asn Ser Asp Lys Leu Ile Ala Arg Lys Lys Asp Trp Asp Pro
        1115            1120            1125

Lys Lys Tyr Gly Gly Phe Asp Ser Pro Thr Val Ala Tyr Ser Val
        1130            1135            1140

Leu Val Val Ala Lys Val Glu Lys Gly Lys Ser Lys Lys Leu Lys
        1145            1150            1155

Ser Val Lys Glu Leu Leu Gly Ile Thr Ile Met Glu Arg Ser Ser
        1160            1165            1170

Phe Glu Lys Asn Pro Ile Asp Phe Leu Glu Ala Lys Gly Tyr Lys
        1175            1180            1185

Glu Val Lys Lys Asp Leu Ile Ile Lys Leu Pro Lys Tyr Ser Leu
        1190            1195            1200

Phe Glu Leu Glu Asn Gly Arg Lys Arg Met Leu Ala Ser Ala Gly
        1205            1210            1215

Glu Leu Gln Lys Gly Asn Glu Leu Ala Leu Pro Ser Lys Tyr Val
        1220            1225            1230

Asn Phe Leu Tyr Leu Ala Ser His Tyr Glu Lys Leu Lys Gly Ser
        1235            1240            1245

Pro Glu Asp Asn Glu Gln Lys Gln Leu Phe Val Glu Gln His Lys
        1250            1255            1260

His Tyr Leu Asp Glu Ile Ile Glu Gln Ile Ser Glu Phe Ser Lys
        1265            1270            1275

Arg Val Ile Leu Ala Asp Ala Asn Leu Asp Lys Val Leu Ser Ala
        1280            1285            1290
```

-continued

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 43
<211> LENGTH: 1368
<212> TYPE: PRT
<213> ORGANISM: Artificial sequence
<220> FEATURE:
<223> OTHER INFORMATION: Synthetic sequence

<400> SEQUENCE: 43

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

```
Leu Phe Leu Ala Ala Lys Asn Leu Ser Asp Ala Ile Leu Leu Ser Asp
        290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
```

-continued

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro

```
                1115                1120                1125

Lys Lys Tyr Gly Gly Phe Asp Ser Pro Thr Val Ala Tyr Ser Val
            1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys
            1250                1255                1260

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
            1295                1300                1305

Ile Ile His Leu Phe Thr Leu Thr Asn Leu Gly Ala Pro Ala Ala
            1310                1315                1320

Phe Lys Tyr Phe Asp Thr Thr Ile Asp Arg Lys Arg Tyr Thr Ser
            1325                1330                1335

Thr Lys Glu Val Leu Asp Ala Thr Leu Ile His Gln Ser Ile Thr
            1340                1345                1350

Gly Leu Tyr Glu Thr Arg Ile Asp Leu Ser Gln Leu Gly Gly Asp
            1355                1360                1365

<210> SEQ ID NO 44
<211> LENGTH: 1368
<212> TYPE: PRT
<213> ORGANISM: Artificial sequence
<220> FEATURE:
<223> OTHER INFORMATION: Synthetic sequence

<400> SEQUENCE: 44

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
```

-continued

```
                100                 105                 110
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525
```

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Ala
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940
```

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Ala Leu Glu Ser Glu Phe
        995                 1000                1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Ala Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
```

-continued

```
            1340                1345                1350
Gly Leu Tyr Glu Thr Arg Ile Asp Leu Ser Gln Leu Gly Gly Asp
        1355                1360                1365

<210> SEQ ID NO 45
<211> LENGTH: 1367
<212> TYPE: PRT
<213> ORGANISM: Artificial sequence
<220> FEATURE:
<223> OTHER INFORMATION: Synthetic sequence

<400> SEQUENCE: 45

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
```

```
            340             345             350
Gln Ser Lys Asn Gly Tyr Ala Gly Tyr Ile Asp Gly Gly Ala Ser Gln
            355                 360             365

Glu Glu Phe Tyr Lys Phe Ile Lys Pro Ile Leu Glu Lys Met Asp Gly
    370                 375             380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
            405                 410             415

Glu Leu His Ala Ile Leu Arg Arg Gln Glu Asp Phe Tyr Pro Phe Leu
            420             425             430

Lys Asp Asn Arg Glu Lys Ile Glu Lys Ile Leu Thr Phe Arg Ile Pro
            435             440             445

Tyr Tyr Val Gly Pro Leu Ala Arg Gly Asn Ser Arg Phe Ala Trp Met
            450             455             460

Thr Arg Lys Ser Glu Glu Thr Ile Thr Pro Trp Asn Phe Glu Glu Val
465             470             475             480

Val Asp Lys Gly Ala Ser Ala Gln Ser Phe Ile Glu Arg Met Thr Ala
                485             490             495

Phe Asp Lys Asn Leu Pro Asn Glu Lys Val Leu Pro Lys His Ser Leu
            500             505             510

Leu Tyr Glu Tyr Phe Thr Val Tyr Asn Glu Leu Thr Lys Val Lys Tyr
            515             520             525

Val Thr Glu Gly Met Arg Lys Pro Ala Phe Leu Ser Gly Glu Gln Lys
            530             535             540

Lys Ala Ile Val Asp Leu Leu Phe Lys Thr Asn Arg Lys Val Thr Val
545             550             555             560

Lys Gln Leu Lys Glu Asp Tyr Phe Lys Lys Ile Glu Cys Phe Asp Ser
                565             570             575

Val Glu Ile Ser Gly Val Glu Asp Arg Phe Asn Ala Ser Leu Gly Thr
                580             585             590

Tyr His Asp Leu Leu Lys Ile Ile Lys Asp Lys Asp Phe Leu Asp Asn
            595             600             605

Glu Glu Asn Glu Asp Ile Leu Glu Asp Ile Val Leu Thr Leu Thr Leu
    610             615             620

Phe Glu Asp Arg Glu Met Ile Glu Glu Arg Leu Lys Thr Tyr Ala His
625             630             635             640

Leu Phe Asp Asp Lys Val Met Lys Gln Leu Lys Arg Arg Arg Tyr Thr
            645             650             655

Gly Trp Gly Ala Leu Ser Arg Lys Leu Ile Asn Gly Ile Arg Asp Lys
            660             665             670

Gln Ser Gly Lys Thr Ile Leu Asp Phe Leu Lys Ser Asp Gly Phe Ala
            675             680             685

Asn Arg Asn Phe Met Ala Leu Ile His Asp Asp Ser Leu Thr Phe Lys
            690             695             700

Glu Asp Ile Gln Lys Ala Gln Val Ser Gly Gln Gly Asp Ser Leu His
705             710             715             720

Glu His Ile Ala Asn Leu Ala Gly Ser Pro Ala Ile Lys Lys Gly Ile
                725             730             735

Leu Gln Thr Val Lys Val Val Asp Glu Leu Val Lys Val Met Gly Arg
            740             745             750

His Lys Pro Glu Asn Ile Val Ile Glu Met Ala Arg Glu Asn Gln Thr
            755             760             765
```

-continued

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Lys Asp
                835                 840                 845

Asp Ser Ile Asp Asn Lys Val Leu Thr Arg Ser Asp Lys Asn Arg Gly
                850                 855                 860

Lys Ser Asp Asn Val Pro Ser Glu Glu Val Val Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Ala Ile Thr Lys
                915                 920                 925

His Val Ala Gln Ile Leu Asp Ser Arg Met Asn Thr Lys Tyr Asp Glu
930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
                995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

-continued

```
Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 46
<211> LENGTH: 1053
<212> TYPE: PRT
<213> ORGANISM: Staphylococcus aureus

<400> SEQUENCE: 46

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175
```

```
Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Glu Thr Arg
            195                 200                 205

Arg Thr Tyr Tyr Glu Gly Pro Gly Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
            530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590
```

```
Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
```

```
                   1010                1015                1020

Thr Gln  Ser Ile Lys Lys Tyr  Ser Thr Asp Ile Leu  Gly Asn Leu
         1025                1030                1035

Tyr Glu  Val Lys Ser Lys Lys  His Pro Gln Ile Ile  Lys Lys Gly
         1040                1045                1050

<210> SEQ ID NO 47
<211> LENGTH: 1300
<212> TYPE: PRT
<213> ORGANISM: Francisella tularensis

<400> SEQUENCE: 47

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
                100                 105                 110

Ile Lys Asp Ser Glu Lys Phe Lys Asn Leu Phe Asn Gln Asn Leu Ile
            115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
                180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335
```

-continued

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Tyr Ser Val Ile Gly Thr Ala
                405                 410                 415

Val Leu Glu Tyr Ile Thr Gln Ile Ala Pro Lys Asn Leu Asp Asn
        420                 425                 430

Pro Ser Lys Lys Glu Gln Leu Ile Ala Lys Thr Glu Lys Ala
        435                 440                 445

Lys Tyr Leu Ser Leu Glu Thr Ile Lys Leu Ala Leu Glu Glu Phe Asn
        450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn

```
              755                 760                 765
Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170
```

```
Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 48
<211> LENGTH: 1306
<212> TYPE: PRT
<213> ORGANISM: Acidaminococcus

<400> SEQUENCE: 48

Thr Gln Phe Glu Gly Phe Thr Asn Leu Tyr Gln Val Ser Lys Thr Leu
1               5                   10                  15

Arg Phe Glu Leu Ile Pro Gln Gly Lys Thr Leu Lys His Ile Gln Glu
            20                  25                  30

Gln Gly Phe Ile Glu Glu Asp Lys Ala Arg Asn Asp His Tyr Lys Glu
        35                  40                  45

Leu Lys Pro Ile Ile Asp Arg Ile Tyr Lys Thr Tyr Ala Asp Gln Cys
    50                  55                  60

Leu Gln Leu Val Gln Leu Asp Trp Glu Asn Leu Ser Ala Ala Ile Asp
65                  70                  75                  80

Ser Tyr Arg Lys Glu Lys Thr Glu Glu Thr Arg Asn Ala Leu Ile Glu
                85                  90                  95

Glu Gln Ala Thr Tyr Arg Asn Ala Ile His Asp Tyr Phe Ile Gly Arg
            100                 105                 110

Thr Asp Asn Leu Thr Asp Ala Ile Asn Lys Arg His Ala Glu Ile Tyr
        115                 120                 125

Lys Gly Leu Phe Lys Ala Glu Leu Phe Asn Gly Lys Val Leu Lys Gln
    130                 135                 140

Leu Gly Thr Val Thr Thr Thr Glu His Glu Asn Ala Leu Leu Arg Ser
145                 150                 155                 160

Phe Asp Lys Phe Thr Thr Tyr Phe Ser Gly Phe Tyr Glu Asn Arg Lys
                165                 170                 175

Asn Val Phe Ser Ala Glu Asp Ile Ser Thr Ala Ile Pro His Arg Ile
            180                 185                 190

Val Gln Asp Asn Phe Pro Lys Phe Lys Glu Asn Cys His Ile Phe Thr
        195                 200                 205

Arg Leu Ile Thr Ala Val Pro Ser Leu Arg Glu His Phe Glu Asn Val
    210                 215                 220

Lys Lys Ala Ile Gly Ile Phe Val Ser Thr Ser Ile Glu Glu Val Phe
```

-continued

```
          225                 230                 235                 240

Ser Phe Pro Phe Tyr Asn Gln Leu Leu Thr Gln Thr Gln Ile Asp Leu
                245                 250                 255

Tyr Asn Gln Leu Leu Gly Gly Ile Ser Arg Glu Ala Gly Thr Glu Lys
                260                 265                 270

Ile Lys Gly Leu Asn Glu Val Leu Asn Leu Ala Ile Gln Lys Asn Asp
                275                 280                 285

Glu Thr Ala His Ile Ile Ala Ser Leu Pro His Arg Phe Ile Pro Leu
    290                 295                 300

Phe Lys Gln Ile Leu Ser Asp Arg Asn Thr Leu Ser Phe Ile Leu Glu
305                 310                 315                 320

Glu Phe Lys Ser Asp Glu Val Ile Gln Ser Phe Cys Lys Tyr Lys
                325                 330                 335

Thr Leu Leu Arg Asn Glu Asn Val Leu Glu Thr Ala Glu Ala Leu Phe
                340                 345                 350

Asn Glu Leu Asn Ser Ile Asp Leu Thr His Ile Phe Ile Ser His Lys
                355                 360                 365

Lys Leu Glu Thr Ile Ser Ser Ala Leu Cys Asp His Trp Asp Thr Leu
    370                 375                 380

Arg Asn Ala Leu Tyr Glu Arg Arg Ile Ser Glu Leu Thr Gly Lys Ile
385                 390                 395                 400

Thr Lys Ser Ala Lys Glu Lys Val Gln Arg Ser Leu Lys His Glu Asp
                405                 410                 415

Ile Asn Leu Gln Glu Ile Ile Ser Ala Ala Gly Lys Glu Leu Ser Glu
                420                 425                 430

Ala Phe Lys Gln Lys Thr Ser Glu Ile Leu Ser His Ala His Ala Ala
                435                 440                 445

Leu Asp Gln Pro Leu Pro Thr Thr Leu Lys Lys Gln Glu Glu Lys Glu
    450                 455                 460

Ile Leu Lys Ser Gln Leu Asp Ser Leu Leu Gly Leu Tyr His Leu Leu
465                 470                 475                 480

Asp Trp Phe Ala Val Asp Glu Ser Asn Glu Val Asp Pro Glu Phe Ser
                485                 490                 495

Ala Arg Leu Thr Gly Ile Lys Leu Glu Met Glu Pro Ser Leu Ser Phe
                500                 505                 510

Tyr Asn Lys Ala Arg Asn Tyr Ala Thr Lys Lys Pro Tyr Ser Val Glu
                515                 520                 525

Lys Phe Lys Leu Asn Phe Gln Met Pro Thr Leu Ala Ser Gly Trp Asp
    530                 535                 540

Val Asn Lys Glu Lys Asn Asn Gly Ala Ile Leu Phe Val Lys Asn Gly
545                 550                 555                 560

Leu Tyr Tyr Leu Gly Ile Met Pro Lys Gln Lys Gly Arg Tyr Lys Ala
                565                 570                 575

Leu Ser Phe Glu Pro Thr Glu Lys Thr Ser Glu Gly Phe Asp Lys Met
                580                 585                 590

Tyr Tyr Asp Tyr Phe Pro Asp Ala Ala Lys Met Ile Pro Lys Cys Ser
                595                 600                 605

Thr Gln Leu Lys Ala Val Thr Ala His Phe Gln Thr His Thr Thr Pro
    610                 615                 620

Ile Leu Leu Ser Asn Asn Phe Ile Glu Pro Leu Glu Ile Thr Lys Glu
625                 630                 635                 640

Ile Tyr Asp Leu Asn Asn Pro Glu Lys Glu Pro Lys Lys Phe Gln Thr
                645                 650                 655
```

```
Ala Tyr Ala Lys Lys Thr Gly Asp Gln Lys Gly Tyr Arg Glu Ala Leu
            660                 665                 670

Cys Lys Trp Ile Asp Phe Thr Arg Asp Phe Leu Ser Lys Tyr Thr Lys
            675                 680                 685

Thr Thr Ser Ile Asp Leu Ser Ser Leu Arg Pro Ser Ser Gln Tyr Lys
690                 695                 700

Asp Leu Gly Glu Tyr Tyr Ala Glu Leu Asn Pro Leu Leu Tyr His Ile
705                 710                 715                 720

Ser Phe Gln Arg Ile Ala Glu Lys Glu Ile Met Asp Ala Val Glu Thr
            725                 730                 735

Gly Lys Leu Tyr Leu Phe Gln Ile Tyr Asn Lys Asp Phe Ala Lys Gly
            740                 745                 750

His His Gly Lys Pro Asn Leu His Thr Leu Tyr Trp Thr Gly Leu Phe
            755                 760                 765

Ser Pro Glu Asn Leu Ala Lys Thr Ser Ile Lys Leu Asn Gly Gln Ala
770                 775                 780

Glu Leu Phe Tyr Arg Pro Lys Ser Arg Met Lys Arg Met Ala His Arg
785                 790                 795                 800

Leu Gly Glu Lys Met Leu Asn Lys Lys Leu Lys Asp Gln Lys Thr Pro
            805                 810                 815

Ile Pro Asp Thr Leu Tyr Gln Glu Leu Tyr Asp Tyr Val Asn His Arg
            820                 825                 830

Leu Ser His Asp Leu Ser Asp Glu Ala Arg Ala Leu Leu Pro Asn Val
835                 840                 845

Ile Thr Lys Glu Val Ser His Glu Ile Ile Lys Asp Arg Arg Phe Thr
            850                 855                 860

Ser Asp Lys Phe Phe Phe His Val Pro Ile Thr Leu Asn Tyr Gln Ala
865                 870                 875                 880

Ala Asn Ser Pro Ser Lys Phe Asn Gln Arg Val Asn Ala Tyr Leu Lys
            885                 890                 895

Glu His Pro Glu Thr Pro Ile Ile Gly Ile Asp Arg Gly Glu Arg Asn
            900                 905                 910

Leu Ile Tyr Ile Thr Val Ile Asp Ser Thr Gly Lys Ile Leu Glu Gln
            915                 920                 925

Arg Ser Leu Asn Thr Ile Gln Gln Phe Asp Tyr Gln Lys Lys Leu Asp
930                 935                 940

Asn Arg Glu Lys Glu Arg Val Ala Ala Arg Gln Ala Trp Ser Val Val
945                 950                 955                 960

Gly Thr Ile Lys Asp Leu Lys Gln Gly Tyr Leu Ser Gln Val Ile His
            965                 970                 975

Glu Ile Val Asp Leu Met Ile His Tyr Gln Ala Val Val Val Leu Glu
            980                 985                 990

Asn Leu Asn Phe Gly Phe Lys Ser Lys Arg Thr Gly Ile Ala Glu Lys
            995                 1000                1005

Ala Val Tyr Gln Gln Phe Glu Lys Met Leu Ile Asp Lys Leu Asn
    1010                1015                1020

Cys Leu Val Leu Lys Asp Tyr Pro Ala Glu Lys Val Gly Gly Val
    1025                1030                1035

Leu Asn Pro Tyr Gln Leu Thr Asp Gln Phe Thr Ser Phe Ala Lys
    1040                1045                1050

Met Gly Thr Gln Ser Gly Phe Leu Phe Tyr Val Pro Ala Pro Tyr
    1055                1060                1065
```

Thr Ser Lys Ile Asp Pro Leu Thr Gly Phe Val Asp Pro Phe Val
1070                1075                1080

Trp Lys Thr Ile Lys Asn His Glu Ser Arg Lys His Phe Leu Glu
    1085                1090                1095

Gly Phe Asp Phe Leu His Tyr Asp Val Lys Thr Gly Asp Phe Ile
1100                1105                1110

Leu His Phe Lys Met Asn Arg Asn Leu Ser Phe Gln Arg Gly Leu
    1115                1120                1125

Pro Gly Phe Met Pro Ala Trp Asp Ile Val Phe Glu Lys Asn Glu
1130                1135                1140

Thr Gln Phe Asp Ala Lys Gly Thr Pro Phe Ile Ala Gly Lys Arg
    1145                1150                1155

Ile Val Pro Val Ile Glu Asn His Arg Phe Thr Gly Arg Tyr Arg
1160                1165                1170

Asp Leu Tyr Pro Ala Asn Glu Leu Ile Ala Leu Leu Glu Glu Lys
    1175                1180                1185

Gly Ile Val Phe Arg Asp Gly Ser Asn Ile Leu Pro Lys Leu Leu
1190                1195                1200

Glu Asn Asp Asp Ser His Ala Ile Asp Thr Met Val Ala Leu Ile
    1205                1210                1215

Arg Ser Val Leu Gln Met Arg Asn Ser Asn Ala Ala Thr Gly Glu
1220                1225                1230

Asp Tyr Ile Asn Ser Pro Val Arg Asp Leu Asn Gly Val Cys Phe
    1235                1240                1245

Asp Ser Arg Phe Gln Asn Pro Glu Trp Pro Met Asp Ala Asp Ala
1250                1255                1260

Asn Gly Ala Tyr His Ile Ala Leu Lys Gly Gln Leu Leu Leu Asn
    1265                1270                1275

His Leu Lys Glu Ser Lys Asp Leu Lys Leu Gln Asn Gly Ile Ser
1280                1285                1290

Asn Gln Asp Trp Leu Ala Tyr Ile Gln Glu Leu Arg Asn
    1295                1300                1305

<210> SEQ ID NO 49
<211> LENGTH: 1306
<212> TYPE: PRT
<213> ORGANISM: Artificial sequence
<220> FEATURE:
<223> OTHER INFORMATION: Synthetic sequence

<400> SEQUENCE: 49

Thr Gln Phe Glu Gly Phe Thr Asn Leu Tyr Gln Val Ser Lys Thr Leu
1               5                   10                  15

Arg Phe Glu Leu Ile Pro Gln Gly Lys Thr Leu Lys His Ile Gln Glu
            20                  25                  30

Gln Gly Phe Ile Glu Glu Asp Lys Ala Arg Asn Asp His Tyr Lys Glu
        35                  40                  45

Leu Lys Pro Ile Ile Asp Arg Ile Tyr Lys Thr Tyr Ala Asp Gln Cys
50                  55                  60

Leu Gln Leu Val Gln Leu Asp Trp Glu Asn Leu Ser Ala Ala Ile Asp
65                  70                  75                  80

Ser Tyr Arg Lys Glu Lys Thr Glu Glu Thr Arg Asn Ala Leu Ile Glu
                85                  90                  95

Glu Gln Ala Thr Tyr Arg Asn Ala Ile His Asp Tyr Phe Ile Gly Arg
            100                 105                 110

-continued

```
Thr Asp Asn Leu Thr Asp Ala Ile Asn Lys Arg His Ala Glu Ile Tyr
            115                 120                 125

Lys Gly Leu Phe Lys Ala Glu Leu Phe Asn Gly Lys Val Leu Lys Gln
130                 135                 140

Leu Gly Thr Val Thr Thr Glu His Glu Asn Ala Leu Leu Arg Ser
145                 150                 155                 160

Phe Asp Lys Phe Thr Thr Tyr Phe Ser Gly Phe Tyr Glu Asn Arg Lys
                165                 170                 175

Asn Val Phe Ser Ala Glu Asp Ile Ser Thr Ala Ile Pro His Arg Ile
            180                 185                 190

Val Gln Asp Asn Phe Pro Lys Phe Lys Glu Asn Cys His Ile Phe Thr
        195                 200                 205

Arg Leu Ile Thr Ala Val Pro Ser Leu Arg Glu His Phe Glu Asn Val
    210                 215                 220

Lys Lys Ala Ile Gly Ile Phe Val Ser Thr Ser Ile Glu Glu Val Phe
225                 230                 235                 240

Ser Phe Pro Phe Tyr Asn Gln Leu Leu Thr Gln Thr Gln Ile Asp Leu
                245                 250                 255

Tyr Asn Gln Leu Leu Gly Gly Ile Ser Arg Glu Ala Gly Thr Glu Lys
            260                 265                 270

Ile Lys Gly Leu Asn Glu Val Leu Asn Leu Ala Ile Gln Lys Asn Asp
        275                 280                 285

Glu Thr Ala His Ile Ile Ala Ser Leu Pro His Arg Phe Ile Pro Leu
    290                 295                 300

Phe Lys Gln Ile Leu Ser Asp Arg Asn Thr Leu Ser Phe Ile Leu Glu
305                 310                 315                 320

Glu Phe Lys Ser Asp Glu Glu Val Ile Gln Ser Phe Cys Lys Tyr Lys
                325                 330                 335

Thr Leu Leu Arg Asn Glu Asn Val Leu Glu Thr Ala Glu Ala Leu Phe
            340                 345                 350

Asn Glu Leu Asn Ser Ile Asp Leu Thr His Ile Phe Ile Ser His Lys
        355                 360                 365

Lys Leu Glu Thr Ile Ser Ser Ala Leu Cys Asp His Trp Asp Thr Leu
    370                 375                 380

Arg Asn Ala Leu Tyr Glu Arg Arg Ile Ser Glu Leu Thr Gly Lys Ile
385                 390                 395                 400

Thr Lys Ser Ala Lys Glu Lys Val Gln Arg Ser Leu Lys His Glu Asp
                405                 410                 415

Ile Asn Leu Gln Glu Ile Ser Ala Ala Gly Lys Glu Leu Ser Glu
            420                 425                 430

Ala Phe Lys Gln Lys Thr Ser Glu Ile Leu Ser His Ala His Ala Ala
        435                 440                 445

Leu Asp Gln Pro Leu Pro Thr Thr Leu Lys Lys Gln Glu Glu Lys Glu
    450                 455                 460

Ile Leu Lys Ser Gln Leu Asp Ser Leu Leu Gly Leu Tyr His Leu Leu
465                 470                 475                 480

Asp Trp Phe Ala Val Asp Glu Ser Asn Glu Val Asp Pro Glu Phe Ser
                485                 490                 495

Ala Arg Leu Thr Gly Ile Lys Leu Glu Met Glu Pro Ser Leu Ser Phe
            500                 505                 510

Tyr Asn Lys Ala Arg Asn Tyr Ala Thr Lys Lys Pro Tyr Ser Val Glu
        515                 520                 525

Lys Phe Lys Leu Asn Phe Gln Met Pro Thr Leu Ala Ser Gly Trp Asp
```

```
                530               535               540
Val Asn Lys Glu Lys Asn Asn Gly Ala Ile Leu Phe Val Lys Asn Gly
545                 550               555               560

Leu Tyr Tyr Leu Gly Ile Met Pro Lys Gln Lys Gly Arg Tyr Lys Ala
                565               570               575

Leu Ser Phe Glu Pro Thr Glu Lys Thr Ser Glu Gly Phe Asp Lys Met
                580               585               590

Tyr Tyr Asp Tyr Phe Pro Asp Ala Ala Lys Met Ile Pro Lys Cys Ser
                595               600               605

Thr Gln Leu Lys Ala Val Thr Ala His Phe Gln Thr His Thr Thr Pro
        610               615               620

Ile Leu Leu Ser Asn Asn Phe Ile Glu Pro Leu Glu Ile Thr Lys Glu
625               630               635               640

Ile Tyr Asp Leu Asn Asn Pro Glu Lys Glu Pro Lys Lys Phe Gln Thr
                645               650               655

Ala Tyr Ala Lys Lys Thr Gly Asp Gln Lys Gly Tyr Arg Glu Ala Leu
                660               665               670

Cys Lys Trp Ile Asp Phe Thr Arg Asp Phe Leu Ser Lys Tyr Thr Lys
                675               680               685

Thr Thr Ser Ile Asp Leu Ser Ser Leu Arg Pro Ser Ser Gln Tyr Lys
        690               695               700

Asp Leu Gly Glu Tyr Tyr Ala Glu Leu Asn Pro Leu Leu Tyr His Ile
705               710               715               720

Ser Phe Gln Arg Ile Ala Glu Lys Glu Ile Met Asp Ala Val Glu Thr
                725               730               735

Gly Lys Leu Tyr Leu Phe Gln Ile Tyr Asn Lys Asp Phe Ala Lys Gly
                740               745               750

His His Gly Lys Pro Asn Leu His Thr Leu Tyr Trp Thr Gly Leu Phe
                755               760               765

Ser Pro Glu Asn Leu Ala Lys Thr Ser Ile Lys Leu Asn Gly Gln Ala
        770               775               780

Glu Leu Phe Tyr Arg Pro Lys Ser Arg Met Lys Arg Met Ala His Arg
785               790               795               800

Leu Gly Glu Lys Met Leu Asn Lys Lys Leu Lys Asp Gln Lys Thr Pro
                805               810               815

Ile Pro Asp Thr Leu Tyr Gln Glu Leu Tyr Asp Tyr Val Asn His Arg
                820               825               830

Leu Ser His Asp Leu Ser Asp Glu Ala Arg Ala Leu Leu Pro Asn Val
        835               840               845

Ile Thr Lys Glu Val Ser His Glu Ile Ile Lys Asp Arg Arg Phe Thr
850               855               860

Ser Asp Lys Phe Phe Phe His Val Pro Ile Thr Leu Asn Tyr Gln Ala
865               870               875               880

Ala Asn Ser Pro Ser Lys Phe Asn Gln Arg Val Asn Ala Tyr Leu Lys
                885               890               895

Glu His Pro Glu Thr Pro Ile Ile Gly Ile Asp Arg Gly Glu Arg Asn
                900               905               910

Leu Ile Tyr Ile Thr Val Ile Asp Ser Thr Gly Lys Ile Leu Glu Gln
                915               920               925

Arg Ser Leu Asn Thr Ile Gln Gln Phe Asp Tyr Gln Lys Lys Leu Asp
        930               935               940

Asn Arg Glu Lys Glu Arg Val Ala Ala Arg Gln Ala Trp Ser Val Val
945               950               955               960
```

-continued

Gly Thr Ile Lys Asp Leu Lys Gln Gly Tyr Leu Ser Gln Val Ile His
            965                 970                 975
Glu Ile Val Asp Leu Met Ile His Tyr Gln Ala Val Val Leu Glu
        980                 985                 990
Asn Leu Asn Phe Gly Phe Lys Ser Lys Arg Thr Gly Ile Ala Glu Lys
    995                 1000                1005
Ala Val Tyr Gln Gln Phe Glu Lys Met Leu Ile Asp Lys Leu Asn
    1010                1015                1020
Cys Leu Val Leu Lys Asp Tyr Pro Ala Glu Lys Val Gly Gly Val
    1025                1030                1035
Leu Asn Pro Tyr Gln Leu Thr Asp Gln Phe Thr Ser Phe Ala Lys
    1040                1045                1050
Met Gly Thr Gln Ser Gly Phe Leu Phe Tyr Val Pro Ala Pro Tyr
    1055                1060                1065
Thr Ser Lys Ile Asp Pro Leu Thr Gly Phe Val Asp Pro Phe Val
    1070                1075                1080
Trp Lys Thr Ile Lys Asn His Glu Ser Arg Lys His Phe Leu Glu
    1085                1090                1095
Gly Phe Asp Phe Leu His Tyr Asp Val Lys Thr Gly Asp Phe Ile
    1100                1105                1110
Leu His Phe Lys Met Asn Arg Asn Leu Ser Phe Gln Arg Gly Leu
    1115                1120                1125
Pro Gly Phe Met Pro Ala Trp Asp Ile Val Phe Glu Lys Asn Glu
    1130                1135                1140
Thr Gln Phe Asp Ala Lys Gly Thr Pro Phe Ile Ala Gly Lys Arg
    1145                1150                1155
Ile Val Pro Val Ile Glu Asn His Arg Phe Thr Gly Arg Tyr Arg
    1160                1165                1170
Asp Leu Tyr Pro Ala Asn Glu Leu Ile Ala Leu Leu Glu Glu Lys
    1175                1180                1185
Gly Ile Val Phe Arg Asp Gly Ser Asn Ile Leu Pro Lys Leu Leu
    1190                1195                1200
Glu Asn Asp Asp Ser His Ala Ile Asp Thr Met Val Ala Leu Ile
    1205                1210                1215
Arg Ser Val Leu Gln Met Ala Asn Ser Asn Ala Ala Thr Gly Glu
    1220                1225                1230
Asp Tyr Ile Asn Ser Pro Val Arg Asp Leu Asn Gly Val Cys Phe
    1235                1240                1245
Asp Ser Arg Phe Gln Asn Pro Glu Trp Pro Met Asp Ala Asp Ala
    1250                1255                1260
Asn Gly Ala Tyr His Ile Ala Leu Lys Gly Gln Leu Leu Leu Asn
    1265                1270                1275
His Leu Lys Glu Ser Lys Asp Leu Lys Leu Gln Asn Gly Ile Ser
    1280                1285                1290
Asn Gln Asp Trp Leu Ala Tyr Ile Gln Glu Leu Arg Asn
    1295                1300                1305

<210> SEQ ID NO 50
<211> LENGTH: 37
<212> TYPE: DNA
<213> ORGANISM: Artificial sequence
<220> FEATURE:
<223> OTHER INFORMATION: Synthetic sequence

<400> SEQUENCE: 50
cacaccaggt ctcattgcgc gcttggcgta atcatgg                                    37

<210> SEQ ID NO 51
<211> LENGTH: 37
<212> TYPE: DNA
<213> ORGANISM: Artificial sequence
<220> FEATURE:
<223> OTHER INFORMATION: Synthetic sequence

<400> SEQUENCE: 51
cacaccaggt ctcattatag tgagtcgtat tacgcgc                                    37

<210> SEQ ID NO 52
<211> LENGTH: 34
<212> TYPE: DNA
<213> ORGANISM: Artificial sequence
<220> FEATURE:
<223> OTHER INFORMATION: Synthetic sequence

<400> SEQUENCE: 52
cacaccaggt ctcaataagg cgaattgggt accg                                       34

<210> SEQ ID NO 53
<211> LENGTH: 36
<212> TYPE: DNA
<213> ORGANISM: Artificial sequence
<220> FEATURE:
<223> OTHER INFORMATION: Synthetic sequence

<400> SEQUENCE: 53
cacaccaggt ctcagttcaa gaaccctctt tttcgc                                     36

<210> SEQ ID NO 54
<211> LENGTH: 35
<212> TYPE: DNA
<213> ORGANISM: Artificial sequence
<220> FEATURE:
<223> OTHER INFORMATION: Synthetic sequence

<400> SEQUENCE: 54
cacaccaggt ctcagaacct ctgggcctgg ttgag                                      35

<210> SEQ ID NO 55
<211> LENGTH: 34
<212> TYPE: DNA
<213> ORGANISM: Artificial sequence
<220> FEATURE:
<223> OTHER INFORMATION: Synthetic sequence

<400> SEQUENCE: 55
cacaccaggt ctcaacsccc aagggtgct gtag                                        34

<210> SEQ ID NO 56
<211> LENGTH: 44
<212> TYPE: DNA
<213> ORGANISM: Artificial sequence
<220> FEATURE:
<223> OTHER INFORMATION: Synthetic sequence

<400> SEQUENCE: 56
cacaccaggt ctcagggtat tttgacttca acagattcca ctgc                            44

<210> SEQ ID NO 57
<211> LENGTH: 34
<212> TYPE: DNA

```
<213> ORGANISM: Artificial sequence
<220> FEATURE:
<223> OTHER INFORMATION: Synthetic sequence

<400> SEQUENCE: 57
cacaccaggt ctcaaaagac ctgaaccgtg ctgg                              34

<210> SEQ ID NO 58
<211> LENGTH: 37
<212> TYPE: DNA
<213> ORGANISM: Artificial sequence
<220> FEATURE:
<223> OTHER INFORMATION: Synthetic sequence

<400> SEQUENCE: 58
cacaccaggt ctcactttac tgactcggag taccagc                           37

<210> SEQ ID NO 59
<211> LENGTH: 38
<212> TYPE: DNA
<213> ORGANISM: Artificial sequence
<220> FEATURE:
<223> OTHER INFORMATION: Synthetic sequence

<400> SEQUENCE: 59
cacaccaggt ctcagtagct gaaggtaaag ttgtttcc                          38

<210> SEQ ID NO 60
<211> LENGTH: 35
<212> TYPE: DNA
<213> ORGANISM: Artificial sequence
<220> FEATURE:
<223> OTHER INFORMATION: Synthetic sequence

<400> SEQUENCE: 60
cacaccaggt ctcactacac ttttgaggac gttcc                             35

<210> SEQ ID NO 61
<211> LENGTH: 37
<212> TYPE: DNA
<213> ORGANISM: Artificial sequence
<220> FEATURE:
<223> OTHER INFORMATION: Synthetic sequence

<400> SEQUENCE: 61
cacaccaggt ctcaagttcc tagactggtc ccgaatg                           37

<210> SEQ ID NO 62
<211> LENGTH: 34
<212> TYPE: DNA
<213> ORGANISM: Artificial sequence
<220> FEATURE:
<223> OTHER INFORMATION: Synthetic sequence

<400> SEQUENCE: 62
cacaccaggt ctcaaactgg cttcctggac cctg                              34

<210> SEQ ID NO 63
<211> LENGTH: 36
<212> TYPE: DNA
<213> ORGANISM: Artificial sequence
<220> FEATURE:
<223> OTHER INFORMATION: Synthetic sequence

<400> SEQUENCE: 63
cacaccaggt ctcagtctct gtcctgccag accatg                            36
```

<210> SEQ ID NO 64
<211> LENGTH: 34
<212> TYPE: DNA
<213> ORGANISM: Artificial sequence
<220> FEATURE:
<223> OTHER INFORMATION: Synthetic sequence

<400> SEQUENCE: 64
cacaccaggt ctcaagacgt gtaccttcag gggc                          34

<210> SEQ ID NO 65
<211> LENGTH: 36
<212> TYPE: DNA
<213> ORGANISM: Artificial sequence
<220> FEATURE:
<223> OTHER INFORMATION: Synthetic sequence

<400> SEQUENCE: 65
cacaccaggt ctcaatgaag gaagcaaact ttgccg                        36

<210> SEQ ID NO 66
<211> LENGTH: 35
<212> TYPE: DNA
<213> ORGANISM: Artificial sequence
<220> FEATURE:
<223> OTHER INFORMATION: Synthetic sequence

<400> SEQUENCE: 66
cacaccaggt ctcatcatca cacagtactc cacgg                         35

<210> SEQ ID NO 67
<211> LENGTH: 35
<212> TYPE: DNA
<213> ORGANISM: Artificial sequence
<220> FEATURE:
<223> OTHER INFORMATION: Synthetic sequence

<400> SEQUENCE: 67
cacaccaggt ctcagcaagc gcgcaattaa ccctc                         35

<210> SEQ ID NO 68
<211> LENGTH: 36
<212> TYPE: DNA
<213> ORGANISM: Artificial sequence
<220> FEATURE:
<223> OTHER INFORMATION: Synthetic sequence

<400> SEQUENCE: 68
cacaccaggt ctcagttcaa gaaccctctt tttggc                        36

<210> SEQ ID NO 69
<211> LENGTH: 35
<212> TYPE: DNA
<213> ORGANISM: Artificial sequence
<220> FEATURE:
<223> OTHER INFORMATION: Synthetic sequence

<400> SEQUENCE: 69
cacaccaggt ctcagaacct cttggtctgg ttgag                         35

<210> SEQ ID NO 70
<211> LENGTH: 34
<212> TYPE: DNA
<213> ORGANISM: Artificial sequence
<220> FEATURE:

<223> OTHER INFORMATION: Synthetic sequence

<400> SEQUENCE: 70
cacaccaggt ctcaaccccc aggggtgga gaat            34

<210> SEQ ID NO 71
<211> LENGTH: 39
<212> TYPE: DNA
<213> ORGANISM: Artificial sequence
<220> FEATURE:
<223> OTHER INFORMATION: Synthetic sequence

<400> SEQUENCE: 71
cacaccaggt ctcagggtat tttgacttca accgcttcc       39

<210> SEQ ID NO 72
<211> LENGTH: 34
<212> TYPE: DNA
<213> ORGANISM: Artificial sequence
<220> FEATURE:
<223> OTHER INFORMATION: Synthetic sequence

<400> SEQUENCE: 72
cacaccaggt ctcaaaagat ctgaaccgtg ctgg            34

<210> SEQ ID NO 73
<211> LENGTH: 34
<212> TYPE: DNA
<213> ORGANISM: Artificial sequence
<220> FEATURE:
<223> OTHER INFORMATION: Synthetic sequence

<400> SEQUENCE: 73
cacaccaggt ctcactttgc ggactcgtcg tacg            34

<210> SEQ ID NO 74
<211> LENGTH: 38
<212> TYPE: DNA
<213> ORGANISM: Artificial sequence
<220> FEATURE:
<223> OTHER INFORMATION: Synthetic sequence

<400> SEQUENCE: 74
cacaccaggt ctcagtaggt aatttcaaag ttgttgcc        38

<210> SEQ ID NO 75
<211> LENGTH: 35
<212> TYPE: DNA
<213> ORGANISM: Artificial sequence
<220> FEATURE:
<223> OTHER INFORMATION: Synthetic sequence

<400> SEQUENCE: 75
cacaccaggt ctcactacag trtgagaagg tgcct           35

<210> SEQ ID NO 76
<211> LENGTH: 42
<212> TYPE: DNA
<213> ORGANISM: Artificial sequence
<220> FEATURE:
<223> OTHER INFORMATION: Synthetic sequence

<400> SEQUENCE: 76
cacaccaggt ctcaagttct ttttaaagtt ggaaaagttg gt   42

```
<210> SEQ ID NO 77
<211> LENGTH: 34
<212> TYPE: DNA
<213> ORGANISM: Artificial sequence
<220> FEATURE:
<223> OTHER INFORMATION: Synthetic sequence

<400> SEQUENCE: 77
cacaccaggt ctcaaactgg ctgcccgggc cttc                          34

<210> SEQ ID NO 78
<211> LENGTH: 37
<212> TYPE: DNA
<213> ORGANISM: Artificial sequence
<220> FEATURE:
<223> OTHER INFORMATION: Synthetic sequence

<400> SEQUENCE: 78
cacaccaggt ctcagtctct gttttgccag accattc                       37

<210> SEQ ID NO 79
<211> LENGTH: 36
<212> TYPE: DNA
<213> ORGANISM: Artificial sequence
<220> FEATURE:
<223> OTHER INFORMATION: Synthetic sequence

<400> SEQUENCE: 79
cacaccaggt ctcaagacat ttactaccag ggtccc                        36

<210> SEQ ID NO 80
<211> LENGTH: 37
<212> TYPE: DNA
<213> ORGANISM: Artificial sequence
<220> FEATURE:
<223> OTHER INFORMATION: Synthetic sequence

<400> SEQUENCE: 80
cacaccaggt ctcaatgaag gagttaccgg agtagag                       37

<210> SEQ ID NO 81
<211> LENGTH: 37
<212> TYPE: DNA
<213> ORGANISM: Artificial sequence
<220> FEATURE:
<223> OTHER INFORMATION: Synthetic sequence

<400> SEQUENCE: 81
cacaccaggt ctcatcatta ctcagtacag cactggc                       37

<210> SEQ ID NO 82
<211> LENGTH: 43
<212> TYPE: DNA
<213> ORGANISM: Artificial sequence
<220> FEATURE:
<223> OTHER INFORMATION: Synthetic sequence

<400> SEQUENCE: 82
cacaccaggt ctcagcaagc gcgcaattaa ccctcactaa agg                43

<210> SEQ ID NO 83
<211> LENGTH: 36
<212> TYPE: DNA
<213> ORGANISM: Artificial sequence
<220> FEATURE:
<223> OTHER INFORMATION: Synthetic sequence
```

<400> SEQUENCE: 83
cacaccaggt ctcagttcga gaaccctttt cttggc    36

<210> SEQ ID NO 84
<211> LENGTH: 35
<212> TYPE: DNA
<213> ORGANISM: Artificial sequence
<220> FEATURE:
<223> OTHER INFORMATION: Synthetic sequence

<400> SEQUENCE: 84
cacaccaggt ctcagaacct tttggcctgg ttgaa    35

<210> SEQ ID NO 85
<211> LENGTH: 34
<212> TYPE: DNA
<213> ORGANISM: Artificial sequence
<220> FEATURE:
<223> OTHER INFORMATION: Synthetic sequence

<400> SEQUENCE: 85
cacaccaggt ctcaaccccc aggggtgct gtat    34

<210> SEQ ID NO 86
<211> LENGTH: 39
<212> TYPE: DNA
<213> ORGANISM: Artificial sequence
<220> FEATURE:
<223> OTHER INFORMATION: Synthetic sequence

<400> SEQUENCE: 86
cacaccaggt ctcagggtat tttgacttta accgcttcc    39

<210> SEQ ID NO 87
<211> LENGTH: 34
<212> TYPE: DNA
<213> ORGANISM: Artificial sequence
<220> FEATURE:
<223> OTHER INFORMATION: Synthetic sequence

<400> SEQUENCE: 87
cacaccaggt ctcaaaagac ttggacggtg gagg    34

<210> SEQ ID NO 88
<211> LENGTH: 34
<212> TYPE: DNA
<213> ORGANISM: Artificial sequence
<220> FEATURE:
<223> OTHER INFORMATION: Synthetic sequence

<400> SEQUENCE: 88
cacaccaggt ctcactttac ggacgacgac tacc    34

<210> SEQ ID NO 89
<211> LENGTH: 38
<212> TYPE: DNA
<213> ORGANISM: Artificial sequence
<220> FEATURE:
<223> OTHER INFORMATION: Synthetic sequence

<400> SEQUENCE: 89
cacaccaggt ctcagtaggt aaactcaaag ttgttgcc    38

<210> SEQ ID NO 90
<211> LENGTH: 35

```
<212> TYPE: DNA
<213> ORGANISM: Artificial sequence
<220> FEATURE:
<223> OTHER INFORMATION: Synthetic sequence

<400> SEQUENCE: 90
cacaccaggt ctcactacaa ctttgaggag gtgcc                           35

<210> SEQ ID NO 91
<211> LENGTH: 41
<212> TYPE: DNA
<213> ORGANISM: Artificial sequence
<220> FEATURE:
<223> OTHER INFORMATION: Synthetic sequence

<400> SEQUENCE: 91
cacaccaggt ctcaagtttt tgtaggtgtt ggcgtatctc c                    41

<210> SEQ ID NO 92
<211> LENGTH: 34
<212> TYPE: DNA
<213> ORGANISM: Artificial sequence
<220> FEATURE:
<223> OTHER INFORMATION: Synthetic sequence

<400> SEQUENCE: 92
cacaccaggt ctcaaactgg ttcccggggc ccat                            34

<210> SEQ ID NO 93
<211> LENGTH: 34
<212> TYPE: DNA
<213> ORGANISM: Artificial sequence
<220> FEATURE:
<223> OTHER INFORMATION: Synthetic sequence

<400> SEQUENCE: 93
cacaccaggt ctcagtctct ctccatccac acgc                            34

<210> SEQ ID NO 94
<211> LENGTH: 35
<212> TYPE: DNA
<213> ORGANISM: Artificial sequence
<220> FEATURE:
<223> OTHER INFORMATION: Synthetic sequence

<400> SEQUENCE: 94
cacaccaggt ctcaagacgt gtacctccaa ggacc                           35

<210> SEQ ID NO 95
<211> LENGTH: 34
<212> TYPE: DNA
<213> ORGANISM: Artificial sequence
<220> FEATURE:
<223> OTHER INFORMATION: Synthetic sequence

<400> SEQUENCE: 95
cacaccaggt ctcaatgaag ctgctgacgg gcac                            34

<210> SEQ ID NO 96
<211> LENGTH: 34
<212> TYPE: DNA
<213> ORGANISM: Artificial sequence
<220> FEATURE:
<223> OTHER INFORMATION: Synthetic sequence

<400> SEQUENCE: 96
```

```
cacaccaggt ctcatcatca cccagtacag cacc                              34
```

<210> SEQ ID NO 97
<211> LENGTH: 35
<212> TYPE: DNA
<213> ORGANISM: Artificial sequence
<220> FEATURE:
<223> OTHER INFORMATION: Synthetic sequence

<400> SEQUENCE: 97

```
cacaccaggt ctcagttcga gaaccctctt cttgg                             35
```

<210> SEQ ID NO 98
<211> LENGTH: 36
<212> TYPE: DNA
<213> ORGANISM: Artificial sequence
<220> FEATURE:
<223> OTHER INFORMATION: Synthetic sequence

<400> SEQUENCE: 98

```
cacaccaggt ctcagaacct tttggtctgg ttgagg                            36
```

<210> SEQ ID NO 99
<211> LENGTH: 35
<212> TYPE: DNA
<213> ORGANISM: Artificial sequence
<220> FEATURE:
<223> OTHER INFORMATION: Synthetic sequence

<400> SEQUENCE: 99

```
cacaccaggt ctcaaccccc aggggtgct gtagc                              35
```

<210> SEQ ID NO 100
<211> LENGTH: 44
<212> TYPE: DNA
<213> ORGANISM: Artificial sequence
<220> FEATURE:
<223> OTHER INFORMATION: Synthetic sequence

<400> SEQUENCE: 100

```
cacaccaggc ctcagggtat tttgatttca acagattcca ctgc                   44
```

<210> SEQ ID NO 101
<211> LENGTH: 34
<212> TYPE: DNA
<213> ORGANISM: Artificial sequence
<220> FEATURE:
<223> OTHER INFORMATION: Synthetic sequence

<400> SEQUENCE: 101

```
cacaccaggt ctcaaaagac ttgaaccgtg ctgg                              34
```

<210> SEQ ID NO 102
<211> LENGTH: 34
<212> TYPE: DNA
<213> ORGANISM: Artificial sequence
<220> FEATURE:
<223> OTHER INFORMATION: Synthetic sequence

<400> SEQUENCE: 102

```
cacaccaggt ctcactttc ggactcggag tacc                               34
```

<210> SEQ ID NO 103
<211> LENGTH: 38
<212> TYPE: DNA
<213> ORGANISM: Artificial sequence -continued

```
<220> FEATURE:
<223> OTHER INFORMATION: Synthetic sequence

<400> SEQUENCE: 103
cacaccaggt ctcagtagct gaaggtaaag ttattgcc                              38

<210> SEQ ID NO 104
<211> LENGTH: 34
<212> TYPE: DNA
<213> ORGANISM: Artificial sequence
<220> FEATURE:
<223> OTHER INFORMATION: Synthetic sequence

<400> SEQUENCE: 104
cacaccaggt ctcactacac cttcgaggac gtgc                                  34

<210> SEQ ID NO 105
<211> LENGTH: 38
<212> TYPE: DNA
<213> ORGANISM: Artificial sequence
<220> FEATURE:
<223> OTHER INFORMATION: Synthetic sequence

<400> SEQUENCE: 105
cacaccaggt ctcaagtttt tgggctgaac agacatgc                              38

<210> SEQ ID NO 106
<211> LENGTH: 34
<212> TYPE: DNA
<213> ORGANISM: Artificial sequence
<220> FEATURE:
<223> OTHER INFORMATION: Synthetic sequence

<400> SEQUENCE: 106
cacaccaggt ctcaaactgg ctacctggac cctg                                  34

<210> SEQ ID NO 107
<211> LENGTH: 37
<212> TYPE: DNA
<213> ORGANISM: Artificial sequence
<220> FEATURE:
<223> OTHER INFORMATION: Synthetic sequence

<400> SEQUENCE: 107
cacaccaggt ctcagtctct gtcttgccac accattc                               37

<210> SEQ ID NO 108
<211> LENGTH: 35
<212> TYPE: DNA
<213> ORGANISM: Artificial sequence
<220> FEATURE:
<223> OTHER INFORMATION: Synthetic sequence

<400> SEQUENCE: 108
cacaccaggt ctcaagacgt atacctgcag ggtcc                                 35

<210> SEQ ID NO 109
<211> LENGTH: 38
<212> TYPE: DNA
<213> ORGANISM: Artificial sequence
<220> FEATURE:
<223> OTHER INFORMATION: Synthetic sequence

<400> SEQUENCE: 109
cacaccaggt ctcaatgaat gaagcaaact ttgtagcc                              38
```

<210> SEQ ID NO 110
<211> LENGTH: 36
<212> TYPE: DNA
<213> ORGANISM: Artificial sequence
<220> FEATURE:
<223> OTHER INFORMATION: Synthetic sequence

<400> SEQUENCE: 110
cacaccaggt ctcatcatca cccagtattc cacagg          36

<210> SEQ ID NO 111
<211> LENGTH: 35
<212> TYPE: DNA
<213> ORGANISM: Artificial sequence
<220> FEATURE:
<223> OTHER INFORMATION: Synthetic sequence

<400> SEQUENCE: 111
cacaccaggt ctcagttcga gaacccgctt cttgg           35

<210> SEQ ID NO 112
<211> LENGTH: 35
<212> TYPE: DNA
<213> ORGANISM: Artificial sequence
<220> FEATURE:
<223> OTHER INFORMATION: Synthetic sequence

<400> SEQUENCE: 112
cacaccaggt ctcagaacct ctcggtctgg ttgag           35

<210> SEQ ID NO 113
<211> LENGTH: 34
<212> TYPE: DNA
<213> ORGANISM: Artificial sequence
<220> FEATURE:
<223> OTHER INFORMATION: Synthetic sequence

<400> SEQUENCE: 113
cacaccaggt ctcaaccccc aggggtgct gtag             34

<210> SEQ ID NO 114
<211> LENGTH: 44
<212> TYPE: DNA
<213> ORGANISM: Artificial sequence
<220> FEATURE:
<223> OTHER INFORMATION: Synthetic sequence

<400> SEQUENCE: 114
cacaccaggt ctcagggtat tttgacttta acagattcca ctgc          44

<210> SEQ ID NO 115
<211> LENGTH: 34
<212> TYPE: DNA
<213> ORGANISM: Artificial sequence
<220> FEATURE:
<223> OTHER INFORMATION: Synthetic sequence

<400> SEQUENCE: 115
cacaccaggt ctcaaaagac ctggatggtg ctgg             34

<210> SEQ ID NO 116
<211> LENGTH: 34
<212> TYPE: DNA
<213> ORGANISM: Artificial sequence
<220> FEATURE:
<223> OTHER INFORMATION: Synthetic sequence

<400> SEQUENCE: 116
cacaccaggt ctcactttac ggactcggag tacc                        34

<210> SEQ ID NO 117
<211> LENGTH: 37
<212> TYPE: DNA
<213> ORGANISM: Artificial sequence
<220> FEATURE:
<223> OTHER INFORMATION: Synthetic sequence

<400> SEQUENCE: 117
cacaccaggt ctcagtaggt aaactggaag ttgttgc                     37

<210> SEQ ID NO 118
<211> LENGTH: 34
<212> TYPE: DNA
<213> ORGANISM: Artificial sequence
<220> FEATURE:
<223> OTHER INFORMATION: Synthetic sequence

<400> SEQUENCE: 118
cacaccaggt ctcaagttct ttgcctgatt ggcc                        34

<210> SEQ ID NO 119
<211> LENGTH: 34
<212> TYPE: DNA
<213> ORGANISM: Artificial sequence
<220> FEATURE:
<223> OTHER INFORMATION: Synthetic sequence

<400> SEQUENCE: 119
cacaccaggt ctcaaactgg ctgccaggac cctg                        34

<210> SEQ ID NO 120
<211> LENGTH: 37
<212> TYPE: DNA
<213> ORGANISM: Artificial sequence
<220> FEATURE:
<223> OTHER INFORMATION: Synthetic sequence

<400> SEQUENCE: 120
cacaccaggt ctcagtctcg gttctgccag accatac                     37

<210> SEQ ID NO 121
<211> LENGTH: 35
<212> TYPE: DNA
<213> ORGANISM: Artificial sequence
<220> FEATURE:
<223> OTHER INFORMATION: Synthetic sequence

<400> SEQUENCE: 121
cacaccaggt ctcaagacgt gtacctgcag ggtcc                       35

<210> SEQ ID NO 122
<211> LENGTH: 38
<212> TYPE: DNA
<213> ORGANISM: Artificial sequence
<220> FEATURE:
<223> OTHER INFORMATION: Synthetic sequence

<400> SEQUENCE: 122
cacaccaggt ctcaatgaaa gagttcagct ttgactgg                    38

<210> SEQ ID NO 123

```
<211> LENGTH: 35
<212> TYPE: DNA
<213> ORGANISM: Artificial sequence
<220> FEATURE:
<223> OTHER INFORMATION: Synthetic sequence

<400> SEQUENCE: 123
cacaccaggt ctcatcatca cgcaatacag caccg                               35

<210> SEQ ID NO 124
<211> LENGTH: 36
<212> TYPE: DNA
<213> ORGANISM: Artificial sequence
<220> FEATURE:
<223> OTHER INFORMATION: Synthetic sequence

<400> SEQUENCE: 124
cacaccaggt ctcagttcaa gaagcctctt tttggc                              36

<210> SEQ ID NO 125
<211> LENGTH: 36
<212> TYPE: DNA
<213> ORGANISM: Artificial sequence
<220> FEATURE:
<223> OTHER INFORMATION: Synthetic sequence

<400> SEQUENCE: 125
cacaccaggt ctcagaacct cttggtctgg ttgagg                              36

<210> SEQ ID NO 126
<211> LENGTH: 34
<212> TYPE: DNA
<213> ORGANISM: Artificial sequence
<220> FEATURE:
<223> OTHER INFORMATION: Synthetic sequence

<400> SEQUENCE: 126
cacaccaggt ctcaaaagac ctggaccgtg ctgg                                34

<210> SEQ ID NO 127
<211> LENGTH: 37
<212> TYPE: DNA
<213> ORGANISM: Artificial sequence
<220> FEATURE:
<223> OTHER INFORMATION: Synthetic sequence

<400> SEQUENCE: 127
cacaccaggt ctcactttac ggactcagac tatcagc                             37

<210> SEQ ID NO 128
<211> LENGTH: 38
<212> TYPE: DNA
<213> ORGANISM: Artificial sequence
<220> FEATURE:
<223> OTHER INFORMATION: Synthetic sequence

<400> SEQUENCE: 128
cacaccaggt ctcagtagct gaactggaag ttgttacc                            38

<210> SEQ ID NO 129
<211> LENGTH: 35
<212> TYPE: DNA
<213> ORGANISM: Artificial sequence
<220> FEATURE:
<223> OTHER INFORMATION: Synthetic sequence

<400> SEQUENCE: 129
```
cacaccaggt ctcactacga gtttgagaac gtacc					35

<210> SEQ ID NO 130
<211> LENGTH: 34
<212> TYPE: DNA
<213> ORGANISM: Artificial sequence
<220> FEATURE:
<223> OTHER INFORMATION: Synthetic sequence

<400> SEQUENCE: 130
cacaccaggt ctcaagtttc ttccctggac agcc					34

<210> SEQ ID NO 131
<211> LENGTH: 35
<212> TYPE: DNA
<213> ORGANISM: Artificial sequence
<220> FEATURE:
<223> OTHER INFORMATION: Synthetic sequence

<400> SEQUENCE: 131
cacaccaggt ctcaaactac atacctggac ccagc					35

<210> SEQ ID NO 132
<211> LENGTH: 38
<212> TYPE: DNA
<213> ORGANISM: Artificial sequence
<220> FEATURE:
<223> OTHER INFORMATION: Synthetic sequence

<400> SEQUENCE: 132
cacaccaggt ctcagtctct gtcctgccaa accatacc				38

<210> SEQ ID NO 133
<211> LENGTH: 34
<212> TYPE: DNA
<213> ORGANISM: Artificial sequence
<220> FEATURE:
<223> OTHER INFORMATION: Synthetic sequence

<400> SEQUENCE: 133
cacaccaggt ctcaagacgt gtacctgcaa ggac					34

<210> SEQ ID NO 134
<211> LENGTH: 38
<212> TYPE: DNA
<213> ORGANISM: Artificial sequence
<220> FEATURE:
<223> OTHER INFORMATION: Synthetic sequence

<400> SEQUENCE: 134
cacaccaggt ctcaatgaaa gagttcagct tgtccttg				38

<210> SEQ ID NO 135
<211> LENGTH: 37
<212> TYPE: DNA
<213> ORGANISM: Artificial sequence
<220> FEATURE:
<223> OTHER INFORMATION: Synthetic sequence

<400> SEQUENCE: 135
cacaccaggt ctcatcatca cccagtattc tactggc				37

<210> SEQ ID NO 136
<211> LENGTH: 735
<212> TYPE: PRT

<213> ORGANISM: Adeno-associated virus

<400> SEQUENCE: 136

```
Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
```

```
Gln Met Leu Arg Thr Gly Asn Asn Phe Thr Phe Ser Tyr Thr Phe Glu
            405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
            485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
            530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
            565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
            645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
            690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
            725                 730                 735

<210> SEQ ID NO 137
<211> LENGTH: 738
<212> TYPE: PRT
<213> ORGANISM: Adeno-associated virus

<400> SEQUENCE: 137

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
```

```
Gly Tyr Lys Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
 65              70                  75                  80

Gln Gln Leu Gln Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460
```

```
Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 138
<211> LENGTH: 736
<212> TYPE: PRT
<213> ORGANISM: Adeno-associated virus

<400> SEQUENCE: 138

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95
```

```
Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
```

```
              515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
            610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
            690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 139
<211> LENGTH: 240
<212> TYPE: PRT
<213> ORGANISM: Adeno-associated virus

<400> SEQUENCE: 139

Thr Phe Ser Tyr Thr Phe Glu Glu Val Pro Phe His Ser Ser Tyr Ala
1               5                   10                  15
His Ser Gln Ser Leu Asp Arg Leu Met Asn Pro Leu Ile Asp Gln Tyr
            20                  25                  30
Leu Tyr Tyr Leu Asn Arg Thr Gln Asn Gln Ser Gly Ser Ala Gln Asn
        35                  40                  45
Lys Asp Leu Leu Phe Ser Arg Gly Ser Pro Ala Gly Met Ser Val Gln
50                  55                  60
Pro Lys Asn Trp Leu Pro Gly Pro Cys Tyr Arg Gln Gln Arg Val Ser
65                  70                  75                  80
Lys Thr Lys Thr Asp Asn Asn Asn Ser Asn Phe Thr Trp Thr Gly Ala
                85                  90                  95
Ser Lys Tyr Asn Leu Asn Gly Arg Glu Ser Ile Ile Asn Pro Gly Thr
            100                 105                 110
Ala Met Ala Ser His Lys Asp Asp Glu Asp Lys Phe Phe Pro Met Ser
        115                 120                 125
Gly Val Met Ile Phe Gly Lys Glu Ser Ala Gly Ala Ser Asn Thr Ala
    130                 135                 140
Leu Asp Asn Val Met Ile Thr Asp Glu Glu Glu Ile Lys Ala Thr Asn
145                 150                 155                 160
```

```
Pro Val Ala Thr Glu Arg Phe Gly Thr Val Ala Val Asn Phe Gln Ser
            165                 170                 175

Ser Ser Thr Asp Pro Ala Thr Gly Asp Val His Ala Met Gly Ala Leu
            180                 185                 190

Pro Gly Met Val Trp Gln Asp Arg Asp Val Tyr Leu Gln Gly Pro Ile
            195                 200                 205

Trp Ala Lys Ile Pro His Thr Asp Gly His Phe His Pro Ser Pro Leu
            210                 215                 220

Met Gly Gly Phe Gly Leu Lys Asn Pro Pro Gln Ile Leu Ile Lys
225                 230                 235                 240

<210> SEQ ID NO 140
<211> LENGTH: 240
<212> TYPE: PRT
<213> ORGANISM: Adeno-associated virus

<400> SEQUENCE: 140

Thr Phe Ser Tyr Thr Phe Glu Asp Val Pro Phe His Ser Ser Tyr Ala
1               5                   10                  15

His Ser Gln Ser Leu Asp Arg Leu Met Asn Pro Leu Ile Asp Gln Tyr
            20                  25                  30

Leu Tyr Tyr Leu Asn Arg Thr Gln Asn Gln Ser Gly Ser Ala Gln Asn
        35                  40                  45

Lys Asp Leu Leu Phe Ser Arg Gly Ser Pro Ala Gly Met Ser Val Gln
50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
            85                  90                  95

Ser Lys Tyr Asn Leu Asn Gly Arg Glu Ser Ile Ile Asn Pro Gly Thr
        100                 105                 110

Ala Met Ala Ser His Lys Asp Asp Lys Asp Lys Phe Phe Pro Met Ser
    115                 120                 125

Gly Val Met Ile Phe Gly Lys Glu Ser Ala Gly Ala Ser Asn Thr Ala
130                 135                 140

Leu Asp Asn Val Met Ile Thr Asp Glu Glu Glu Ile Lys Ala Thr Asn
145                 150                 155                 160

Pro Val Ala Thr Glu Arg Phe Gly Thr Val Ala Val Asn Leu Gln Ser
            165                 170                 175

Ser Ser Thr Asp Pro Ala Thr Gly Asp Val His Val Met Gly Ala Leu
            180                 185                 190

Pro Gly Met Val Trp Gln Asp Arg Asp Val Tyr Leu Gln Gly Pro Ile
            195                 200                 205

Trp Ala Lys Ile Pro His Thr Asp Gly His Phe His Pro Ser Pro Leu
            210                 215                 220

Met Gly Gly Phe Gly Leu Lys His Pro Pro Gln Ile Leu Ile Lys
225                 230                 235                 240

<210> SEQ ID NO 141
<211> LENGTH: 240
<212> TYPE: PRT
<213> ORGANISM: Adeno-associated virus

<400> SEQUENCE: 141

Phe Ser Tyr Thr Phe Glu Asp Val Pro Phe His Ser Ser Tyr Ala His
1               5                   10                  15
```

-continued

```
Ser Gln Ser Leu Asp Arg Leu Met Asn Pro Leu Ile Asp Gln Tyr Leu
            20                  25                  30

Tyr Tyr Leu Asn Arg Thr Gln Gly Thr Thr Ser Gly Thr Thr Asn Gln
        35                  40                  45

Ser Arg Leu Leu Phe Ser Gln Ala Gly Pro Gln Ser Met Ser Leu Gln
50                  55                  60

Ala Arg Asn Trp Leu Pro Gly Pro Cys Tyr Arg Gln Gln Arg Leu Ser
65                  70                  75                  80

Lys Thr Ala Asn Asp Asn Asn Asn Ser Asn Phe Pro Trp Thr Ala Ala
                85                  90                  95

Ser Lys Tyr His Leu Asn Gly Arg Asp Ser Leu Val Asn Pro Gly Pro
            100                 105                 110

Ala Met Ala Ser His Lys Asp Asp Glu Glu Lys Phe Phe Pro Met His
        115                 120                 125

Gly Asn Leu Ile Phe Gly Lys Glu Gly Thr Thr Ala Ser Asn Ala Glu
130                 135                 140

Leu Asp Asn Val Met Ile Thr Asp Glu Glu Ile Arg Thr Thr Asn
145                 150                 155                 160

Pro Val Ala Thr Glu Gln Tyr Gly Thr Val Ala Asn Asn Leu Gln Ser
                165                 170                 175

Ser Asn Thr Ala Pro Thr Thr Gly Thr Val Asn His Gln Gly Ala Leu
            180                 185                 190

Pro Gly Met Val Trp Gln Asp Arg Asp Val Tyr Leu Gln Gly Pro Ile
        195                 200                 205

Trp Ala Lys Ile Pro His Thr Asp Gly His Phe His Pro Ser Pro Leu
210                 215                 220

Met Gly Gly Phe Gly Leu Lys His Pro Pro Pro Gln Ile Met Ile Lys
225                 230                 235                 240

<210> SEQ ID NO 142
<211> LENGTH: 240
<212> TYPE: PRT
<213> ORGANISM: Adeno-associated virus

<400> SEQUENCE: 142

Phe Ser Tyr Thr Phe Glu Asp Val Pro Phe His Ser Ser Tyr Ala His
1               5                   10                  15

Ser Gln Ser Leu Asp Arg Leu Met Asn Pro Leu Ile Asp Gln Tyr Leu
            20                  25                  30

Tyr Tyr Leu Ser Arg Thr Asn Thr Pro Ser Gly Thr Thr Thr Gln Ser
        35                  40                  45

Arg Leu Gln Phe Ser Gln Ala Gly Ala Ser Asp Ile Arg Asp Gln Ser
50                  55                  60

Arg Asn Trp Leu Pro Gly Pro Cys Tyr Arg Gln Gln Arg Val Ser Lys
65                  70                  75                  80

Thr Ser Ala Asp Asn Asn Asn Ser Glu Tyr Ser Trp Thr Gly Ala Thr
                85                  90                  95

Lys Tyr His Leu Asn Gly Arg Asp Ser Leu Val Asn Pro Gly Pro Ala
            100                 105                 110

Met Ala Ser His Lys Asp Asp Glu Glu Lys Phe Phe Pro Gln Ser Gly
        115                 120                 125

Val Leu Ile Phe Gly Lys Gln Gly Ser Glu Lys Thr Asn Val Asp Ile
130                 135                 140

Glu Lys Val Met Ile Thr Asp Glu Glu Glu Ile Arg Thr Thr Asn Pro
145                 150                 155                 160
```

```
Val Ala Thr Glu Gln Tyr Gly Ser Val Ser Thr Asn Leu Gln Arg Gly
            165                 170                 175

Asn Arg Gln Ala Ala Thr Ala Asp Val Asn Thr Gln Gly Val Leu Pro
        180                 185                 190

Gly Met Val Trp Gln Asp Arg Asp Val Tyr Leu Gln Gly Pro Ile Trp
        195                 200                 205

Ala Lys Ile Pro His Thr Asp Gly His Phe His Pro Ser Pro Leu Met
        210                 215                 220

Gly Gly Phe Gly Leu Lys His Pro Pro Gln Ile Leu Ile Lys Asn
225                 230                 235                 240

<210> SEQ ID NO 143
<211> LENGTH: 243
<212> TYPE: PRT
<213> ORGANISM: Adeno-associated virus

<400> SEQUENCE: 143

Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Thr Thr Gly Gly Thr Ala
        35                  40                  45

Asn Thr Gln Thr Leu Gly Phe Ser Gln Gly Gly Pro Asn Thr Met Ala
    50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

Ser Asn Gly Ile Leu Ile Phe Gly Lys Gln Asn Ala Ala Arg Asp Asn
    130                 135                 140

Ala Asp Tyr Ser Asp Val Met Leu Thr Ser Glu Glu Glu Ile Lys Thr
145                 150                 155                 160

Thr Asn Pro Val Ala Thr Glu Glu Tyr Gly Ile Val Ala Asp Asn Leu
                165                 170                 175

Gln Gln Gln Asn Thr Ala Pro Gln Ile Gly Thr Val Asn Ser Gln Gly
            180                 185                 190

Ala Leu Pro Gly Met Val Trp Gln Asn Arg Asp Val Tyr Leu Gln Gly
        195                 200                 205

Pro Ile Trp Ala Lys Ile Pro His Thr Asp Gly Asn Phe His Pro Ser
    210                 215                 220

Pro Leu Met Gly Gly Phe Gly Leu Lys His Pro Pro Gln Ile Leu
225                 230                 235                 240

Ile Lys Asn

<210> SEQ ID NO 144
<211> LENGTH: 243
<212> TYPE: PRT
<213> ORGANISM: Adeno-associated virus

<400> SEQUENCE: 144
```

```
Asn Phe Gln Phe Thr Tyr Thr Phe Glu Asp Val Pro Phe His Ser Ser
 1               5                  10                  15
Tyr Ala His Ser Gln Ser Leu Asp Arg Leu Met Asn Pro Leu Ile Asp
             20                  25                  30
Gln Tyr Leu Tyr Tyr Leu Ser Arg Thr Gln Thr Thr Gly Gly Thr Ala
         35                  40                  45
Asn Thr Gln Thr Leu Gly Phe Ser Gln Gly Gly Pro Asn Thr Met Ala
 50                  55                  60
Asn Gln Ala Lys Asn Trp Leu Pro Gly Pro Cys Tyr Arg Gln Gln Arg
 65                  70                  75                  80
Val Ser Thr Thr Thr Gly Gln Asn Asn Asn Ser Asn Phe Ala Trp Thr
                 85                  90                  95
Ala Gly Thr Lys Tyr His Leu Asn Gly Arg Asn Ser Leu Ala Asn Pro
             100                 105                 110
Gly Ile Ala Met Ala Thr His Lys Asp Asp Glu Arg Phe Phe Pro
             115                 120                 125
Ser Asn Gly Ile Leu Ile Phe Gly Lys Gln Asn Ala Ala Arg Asp Asn
 130                 135                 140
Ala Asp Tyr Ser Asp Val Met Leu Thr Ser Glu Glu Glu Ile Lys Thr
145                 150                 155                 160
Thr Asn Pro Val Ala Thr Glu Glu Tyr Gly Ile Val Ala Asp Asn Leu
                 165                 170                 175
Gln Gly Gln Arg Gln Ala Ala Gln Ile Gly Thr Val Asn Ser Gln Gly
             180                 185                 190
Ala Leu Pro Gly Met Val Trp Gln Asn Arg Asp Val Tyr Leu Gln Gly
             195                 200                 205
Pro Ile Trp Ala Lys Ile Pro His Thr Asp Gly Asn Phe His Pro Ser
 210                 215                 220
Pro Leu Met Gly Gly Phe Gly Leu Lys His Pro Pro Gln Ile Leu
225                 230                 235                 240
Ile Lys Asn

<210> SEQ ID NO 145
<211> LENGTH: 241
<212> TYPE: PRT
<213> ORGANISM: Adeno-associated virus

<400> SEQUENCE: 145

Phe Gln Phe Ser Tyr Thr Phe Glu Asp Val Pro Phe His Ser Ser Tyr
 1               5                  10                  15
Ala His Ser Gln Ser Leu Asp Arg Leu Met Asn Pro Leu Ile Asp Gln
             20                  25                  30
Tyr Leu Tyr Tyr Leu Val Arg Thr Gln Thr Thr Gly Thr Gly Gly Thr
         35                  40                  45
Gln Thr Leu Ala Phe Ser Gln Ala Gly Pro Ser Ser Met Ala Asn Gln
 50                  55                  60
Ala Arg Asn Trp Val Pro Gly Pro Cys Tyr Arg Gln Gln Arg Val Ser
 65                  70                  75                  80
Thr Thr Thr Asn Gln Asn Asn Asn Ser Asn Phe Ala Trp Thr Gly Ala
                 85                  90                  95
Ala Lys Phe Lys Leu Asn Gly Arg Asp Ser Leu Met Asn Pro Gly Val
             100                 105                 110
Ala Met Ala Ser His Lys Asp Asp Asp Arg Phe Phe Pro Ser Ser
             115                 120                 125
```

```
Gly Val Leu Ile Phe Gly Lys Gln Gly Ala Gly Asn Asp Gly Val Asp
    130                 135                 140
Tyr Ser Gln Val Leu Ile Thr Asp Glu Glu Ile Lys Ala Thr Asn
145                 150                 155                 160
Pro Val Ala Thr Glu Glu Tyr Gly Ala Val Ala Ile Asn Asn Gln Ala
                165                 170                 175
Ala Asn Thr Gln Ala Gln Thr Gly Leu Val His Asn Gln Gly Val Ile
            180                 185                 190
Pro Gly Met Val Trp Gln Asn Arg Asp Val Tyr Leu Gln Gly Pro Ile
            195                 200                 205
Trp Ala Lys Ile Pro His Thr Asp Gly Asn Phe His Pro Ser Pro Leu
210                 215                 220
Met Gly Gly Phe Gly Leu Lys His Pro Pro Gln Ile Leu Ile Lys
225                 230                 235                 240
Asn
```

<210> SEQ ID NO 146
<211> LENGTH: 243
<212> TYPE: PRT
<213> ORGANISM: Adeno-associated virus

<400> SEQUENCE: 146

```
Asn Phe Glu Phe Ser Tyr Thr Phe Glu Asp Val Pro Phe His Ser Ser
1               5                   10                  15
Tyr Ala His Ser Gln Ser Leu Asp Arg Leu Met Asn Pro Leu Ile Asp
                20                  25                  30
Gln Tyr Leu Tyr Tyr Leu Ser Arg Thr Gln Ser Thr Gly Gly Thr Gln
            35                  40                  45
Gly Thr Gln Gln Leu Leu Phe Ser Gln Ala Gly Pro Ala Asn Met Ser
        50                  55                  60
Ala Gln Ala Lys Asn Trp Leu Pro Gly Pro Cys Tyr Arg Gln Gln Arg
65                  70                  75                  80
Val Ser Thr Thr Leu Ser Gln Asn Asn Asn Ser Asn Phe Ala Trp Thr
                85                  90                  95
Gly Ala Thr Lys Tyr His Leu Asn Gly Arg Asp Ser Leu Val Asn Pro
            100                 105                 110
Gly Val Ala Met Ala Thr His Lys Asp Asp Glu Glu Arg Phe Phe Pro
        115                 120                 125
Ser Ser Gly Val Leu Met Phe Gly Lys Gln Gly Ala Gly Arg Asp Asn
130                 135                 140
Val Asp Tyr Ser Ser Val Met Leu Thr Ser Glu Glu Ile Lys Thr
145                 150                 155                 160
Thr Asn Pro Val Ala Thr Glu Gln Tyr Gly Val Val Ala Asp Asn Leu
                165                 170                 175
Gln Gln Ala Asn Thr Gly Pro Ile Val Gly Asn Val Asn Ser Gln Gly
            180                 185                 190
Ala Leu Pro Gly Met Val Trp Gln Asn Arg Asp Val Tyr Leu Gln Gly
        195                 200                 205
Pro Ile Trp Ala Lys Ile Pro His Thr Asp Gly Asn Phe His Pro Ser
210                 215                 220
Pro Leu Met Gly Gly Phe Gly Leu Lys His Pro Pro Gln Ile Leu
225                 230                 235                 240
Ile Lys Asn
```

<210> SEQ ID NO 147
<211> LENGTH: 242
<212> TYPE: PRT
<213> ORGANISM: Adeno-associated virus

<400> SEQUENCE: 147

Phe Glu Phe Ser Tyr Ser Phe Glu Asp Val Pro Phe His Ser Ser Tyr
1               5                   10                  15

Ala His Ser Gln Ser Leu Asp Arg Leu Met Asn Pro Leu Ile Asp Gln
            20                  25                  30

Tyr Leu Tyr Tyr Leu Ala Arg Thr Gln Ser Asn Pro Gly Gly Thr Ala
        35                  40                  45

Gly Asn Arg Glu Leu Gln Phe Tyr Gln Gly Pro Ser Thr Met Ala
50                  55                  60

Glu Gln Ala Lys Asn Trp Leu Pro Gly Pro Cys Phe Arg Gln Gln Arg
65                  70                  75                  80

Val Ser Lys Thr Leu Asp Gln Asn Asn Ser Asn Phe Ala Trp Thr
                85                  90                  95

Gly Ala Thr Lys Tyr His Leu Asn Gly Arg Asn Ser Leu Val Asn Pro
            100                 105                 110

Gly Val Ala Met Ala Thr His Lys Asp Glu Asp Arg Phe Phe Pro
        115                 120                 125

Ser Ser Gly Val Leu Ile Phe Gly Lys Thr Gly Ala Thr Asn Lys Thr
130                 135                 140

Thr Leu Glu Asn Val Leu Met Thr Asn Glu Glu Ile Arg Pro Thr
145                 150                 155                 160

Asn Pro Val Ala Thr Glu Glu Tyr Gly Ile Val Ser Ser Asn Leu Gln
                165                 170                 175

Ala Ala Asn Thr Ala Ala Gln Thr Gln Val Val Asn Asn Gln Gly Ala
            180                 185                 190

Leu Pro Gly Met Val Trp Gln Asn Arg Asp Val Tyr Leu Gln Gly Pro
        195                 200                 205

Ile Trp Ala Lys Ile Pro His Thr Asp Gly Asn Phe His Pro Ser Pro
210                 215                 220

Leu Met Gly Gly Phe Gly Leu Lys His Pro Pro Gln Ile Leu Ile
225                 230                 235                 240

Lys Asn

<210> SEQ ID NO 148
<211> LENGTH: 240
<212> TYPE: PRT
<213> ORGANISM: Adeno-associated virus

<400> SEQUENCE: 148

Phe Gln Phe Ser Tyr Glu Phe Glu Asn Val Pro Phe His Ser Ser Tyr
1               5                   10                  15

Ala His Ser Gln Ser Leu Asp Arg Leu Met Asn Pro Leu Ile Asp Gln
            20                  25                  30

Tyr Leu Tyr Tyr Leu Ser Lys Thr Ile Asn Gly Ser Gly Gln Asn Gln
        35                  40                  45

Gln Thr Leu Lys Phe Ser Val Ala Gly Pro Ser Asn Met Ala Val Gln
50                  55                  60

Gly Arg Asn Tyr Ile Pro Gly Pro Ser Tyr Arg Gln Gln Arg Val Ser
65                  70                  75                  80

Thr Thr Val Thr Gln Asn Asn Asn Ser Glu Phe Ala Trp Pro Gly Ala
                85                  90                  95

```
Ser Ser Trp Ala Leu Asn Gly Arg Asn Ser Leu Met Asn Pro Gly Pro
            100                 105                 110

Ala Met Ala Ser His Lys Glu Gly Glu Asp Arg Phe Phe Pro Leu Ser
            115                 120                 125

Gly Ser Leu Ile Phe Gly Lys Gln Gly Thr Gly Arg Asp Asn Val Asp
            130                 135                 140

Ala Asp Lys Val Met Ile Thr Asn Glu Glu Ile Lys Thr Thr Asn
145                 150                 155                 160

Pro Val Ala Thr Glu Ser Tyr Gly Gln Val Ala Thr Asn His Gln Ser
                165                 170                 175

Ala Gln Ala Gln Ala Gln Thr Gly Trp Val Gln Asn Gln Gly Ile Leu
            180                 185                 190

Pro Gly Met Val Trp Gln Asp Arg Asp Val Tyr Leu Gln Gly Pro Ile
            195                 200                 205

Trp Ala Lys Ile Pro His Thr Asp Gly Asn Phe His Pro Ser Pro Leu
            210                 215                 220

Met Gly Gly Phe Gly Met Lys His Pro Pro Gln Ile Leu Ile Lys
225                 230                 235                 240

<210> SEQ ID NO 149
<211> LENGTH: 240
<212> TYPE: PRT
<213> ORGANISM: Adeno-associated virus

<400> SEQUENCE: 149

Phe Gln Phe Ser Tyr Glu Phe Glu Asn Val Pro Phe His Ser Ser Tyr
1               5                   10                  15

Ala His Ser Gln Ser Leu Asp Arg Leu Met Asn Pro Leu Ile Asp Gln
            20                  25                  30

Tyr Leu Tyr Tyr Leu Ser Lys Thr Ile Asn Gly Ser Gly Gln Asn Gln
        35                  40                  45

Gln Thr Leu Lys Phe Ser Val Ala Gly Pro Ser Asn Met Ala Val Gln
    50                  55                  60

Gly Arg Asn Tyr Ile Pro Gly Pro Ser Tyr Arg Gln Gln Arg Val Ser
65                  70                  75                  80

Thr Thr Val Thr Gln Asn Asn Asn Ser Glu Phe Ala Trp Pro Gly Ala
                85                  90                  95

Ser Ser Trp Ala Leu Asn Gly Arg Asn Ser Leu Met Asn Pro Gly Pro
            100                 105                 110

Ala Met Ala Ser His Lys Glu Gly Glu Asp Arg Phe Phe Pro Leu Ser
            115                 120                 125

Gly Ser Leu Ile Phe Gly Lys Gln Gly Thr Gly Arg Asp Asn Val Asp
            130                 135                 140

Ala Asp Lys Val Met Ile Thr Asn Glu Glu Ile Lys Thr Thr Asn
145                 150                 155                 160

Pro Val Ala Thr Glu Ser Tyr Gly Gln Val Ala Thr Asn His Gln Ser
                165                 170                 175

Gly Gln Ala Gln Ala Ala Thr Gly Trp Val Gln Asn Gln Gly Ile Leu
            180                 185                 190

Pro Gly Met Val Trp Gln Asp Arg Asp Val Tyr Leu Gln Gly Pro Ile
            195                 200                 205

Trp Ala Lys Ile Pro His Thr Asp Gly Asn Phe His Pro Ser Pro Leu
            210                 215                 220

Met Gly Gly Phe Gly Met Lys His Pro Pro Gln Ile Leu Ile Lys
```

225            230            235            240

<210> SEQ ID NO 150
<211> LENGTH: 240
<212> TYPE: PRT
<213> ORGANISM: Adeno-associated virus

<400> SEQUENCE: 150

Asn Phe Glu Phe Thr Tyr Asn Phe Glu Glu Val Pro Phe His Ser Ser
1               5                   10                  15

Phe Ala Pro Ser Gln Asn Leu Phe Lys Leu Ala Asn Pro Leu Val Asp
            20                  25                  30

Gln Tyr Leu Tyr Arg Phe Val Ser Thr Asn Asn Thr Gly Gly Val Gln
        35                  40                  45

Phe Asn Lys Asn Leu Ala Gly Arg Tyr Ala Asn Thr Tyr Lys Asn Trp
    50                  55                  60

Phe Pro Gly Pro Met Gly Arg Thr Gln Gly Trp Asn Leu Gly Ser Gly
65                  70                  75                  80

Val Asn Arg Ala Ser Val Ser Ala Phe Ala Thr Thr Asn Arg Met Glu
                85                  90                  95

Leu Glu Gly Ala Ser Tyr Gln Val Pro Pro Gln Pro Asn Gly Met Thr
            100                 105                 110

Asn Asn Leu Gln Gly Ser Asn Thr Tyr Ala Leu Glu Asn Thr Met Ile
        115                 120                 125

Phe Asn Ser Gln Pro Ala Asn Pro Gly Thr Thr Ala Thr Tyr Leu Glu
    130                 135                 140

Gly Asn Met Leu Ile Thr Ser Glu Ser Glu Thr Gln Pro Val Asn Arg
145                 150                 155                 160

Val Ala Tyr Asn Val Gly Gly Gln Met Ala Thr Asn Asn Gln Ser Ser
                165                 170                 175

Thr Thr Ala Pro Ala Thr Gly Thr Tyr Asn Leu Gln Glu Ile Val Pro
            180                 185                 190

Gly Ser Val Trp Met Glu Arg Asp Val Tyr Leu Gln Gly Pro Ile Trp
        195                 200                 205

Ala Lys Ile Pro Glu Thr Gly Ala His Phe His Pro Ser Pro Ala Met
    210                 215                 220

Gly Gly Phe Gly Leu Lys His Pro Pro Met Met Leu Ile Lys Asn
225                 230                 235                 240

<210> SEQ ID NO 151
<211> LENGTH: 10
<212> TYPE: PRT
<213> ORGANISM: Artificial sequence
<220> FEATURE:
<223> OTHER INFORMATION: Synthetic sequence

<400> SEQUENCE: 151

Leu Ala Leu Ile Gln Asp Ser Met Arg Ala
1               5                   10

<210> SEQ ID NO 152
<211> LENGTH: 10
<212> TYPE: PRT
<213> ORGANISM: Artificial sequence
<220> FEATURE:
<223> OTHER INFORMATION: Synthetic sequence

<400> SEQUENCE: 152

Leu Ala Asn Gln Glu His Val Lys Asn Ala

```
1               5                   10
```

<210> SEQ ID NO 153
<211> LENGTH: 12
<212> TYPE: PRT
<213> ORGANISM: Artificial sequence
<220> FEATURE:
<223> OTHER INFORMATION: Synthetic sequence

<400> SEQUENCE: 153

```
Thr Gly Val Met Arg Ser Thr Asn Ser Gly Leu Asn
1               5                   10
```

<210> SEQ ID NO 154
<211> LENGTH: 12
<212> TYPE: PRT
<213> ORGANISM: Artificial sequence
<220> FEATURE:
<223> OTHER INFORMATION: Synthetic sequence

<400> SEQUENCE: 154

```
Thr Gly Glu Val Asp Leu Ala Gly Gly Gly Leu Ser
1               5                   10
```

<210> SEQ ID NO 155
<211> LENGTH: 12
<212> TYPE: PRT
<213> ORGANISM: Artificial sequence
<220> FEATURE:
<223> OTHER INFORMATION: Synthetic sequence

<400> SEQUENCE: 155

```
Thr Ser Pro Tyr Ser Gly Ser Ser Asp Gly Leu Ser
1               5                   10
```

<210> SEQ ID NO 156
<211> LENGTH: 12
<212> TYPE: PRT
<213> ORGANISM: Artificial sequence
<220> FEATURE:
<223> OTHER INFORMATION: Synthetic sequence

<400> SEQUENCE: 156

```
Thr Gly Gly His Asp Ser Ser Leu Asp Gly Leu Ser
1               5                   10
```

<210> SEQ ID NO 157
<211> LENGTH: 12
<212> TYPE: PRT
<213> ORGANISM: Artificial sequence
<220> FEATURE:
<223> OTHER INFORMATION: Synthetic sequence

<400> SEQUENCE: 157

```
Thr Gly Asp Gly Gly Thr Thr Met Asn Gly Leu Ser
1               5                   10
```

<210> SEQ ID NO 158
<211> LENGTH: 12
<212> TYPE: PRT
<213> ORGANISM: Artificial sequence
<220> FEATURE:
<223> OTHER INFORMATION: Synthetic sequence

<400> SEQUENCE: 158

```
Thr Gly Gly His Gly Ser Ala Pro Asp Gly Leu Ser
1               5                   10
```

```
<210> SEQ ID NO 159
<211> LENGTH: 12
<212> TYPE: PRT
<213> ORGANISM: Artificial sequence
<220> FEATURE:
<223> OTHER INFORMATION: Synthetic sequence

<400> SEQUENCE: 159

Thr Gly Met His Val Thr Met Met Ala Gly Leu Asn
1               5                   10

<210> SEQ ID NO 160
<211> LENGTH: 12
<212> TYPE: PRT
<213> ORGANISM: Artificial sequence
<220> FEATURE:
<223> OTHER INFORMATION: Synthetic sequence

<400> SEQUENCE: 160

Thr Gly Ala Ser Tyr Leu Asp Asn Ser Gly Leu Ser
1               5                   10

<210> SEQ ID NO 161
<211> LENGTH: 12
<212> TYPE: PRT
<213> ORGANISM: Artificial sequence
<220> FEATURE:
<223> OTHER INFORMATION: Synthetic sequence

<400> SEQUENCE: 161

Thr Val Val Ser Thr Gln Ala Gly Ile Gly Leu Ser
1               5                   10

<210> SEQ ID NO 162
<211> LENGTH: 12
<212> TYPE: PRT
<213> ORGANISM: Artificial sequence
<220> FEATURE:
<223> OTHER INFORMATION: Synthetic sequence

<400> SEQUENCE: 162

Thr Gly Val Met His Ser Gln Ala Ser Gly Leu Ser
1               5                   10

<210> SEQ ID NO 163
<211> LENGTH: 12
<212> TYPE: PRT
<213> ORGANISM: Artificial sequence
<220> FEATURE:
<223> OTHER INFORMATION: Synthetic sequence

<400> SEQUENCE: 163

Thr Gly Asp Gly Ser Pro Ala Ala Pro Gly Leu Ser
1               5                   10

<210> SEQ ID NO 164
<211> LENGTH: 12
<212> TYPE: PRT
<213> ORGANISM: Artificial sequence
<220> FEATURE:
<223> OTHER INFORMATION: Synthetic sequence

<400> SEQUENCE: 164

Thr Gly Ser Asp Met Ala His Gly Thr Gly Leu Ser
1               5                   10
```

<210> SEQ ID NO 165
<211> LENGTH: 17
<212> TYPE: PRT
<213> ORGANISM: Artificial sequence
<220> FEATURE:
<223> OTHER INFORMATION: Synthetic sequence

<400> SEQUENCE: 165

Thr Gly Leu Asp Ala Thr Arg Asp His Gly Leu Ser Pro Val Thr Gly
1               5                   10                  15

Thr

<210> SEQ ID NO 166
<211> LENGTH: 17
<212> TYPE: PRT
<213> ORGANISM: Artificial sequence
<220> FEATURE:
<223> OTHER INFORMATION: Synthetic sequence

<400> SEQUENCE: 166

Thr Gly Ser Asp Gly Thr Arg Asp His Gly Leu Ser Pro Val Thr Trp
1               5                   10                  15

Thr

<210> SEQ ID NO 167
<211> LENGTH: 17
<212> TYPE: PRT
<213> ORGANISM: Artificial sequence
<220> FEATURE:
<223> OTHER INFORMATION: Synthetic sequence

<400> SEQUENCE: 167

Asn Gly Ala Val Ala Asp Tyr Thr Arg Gly Leu Ser Pro Ala Thr Gly
1               5                   10                  15

Thr

<210> SEQ ID NO 168
<211> LENGTH: 17
<212> TYPE: PRT
<213> ORGANISM: Artificial sequence
<220> FEATURE:
<223> OTHER INFORMATION: Synthetic sequence

<400> SEQUENCE: 168

Thr Gly Gly Asp Pro Thr Arg Gly Thr Gly Leu Ser Pro Val Thr Gly
1               5                   10                  15

Ala

<210> SEQ ID NO 169
<211> LENGTH: 16
<212> TYPE: PRT
<213> ORGANISM: Artificial sequence
<220> FEATURE:
<223> OTHER INFORMATION: Synthetic sequence

<400> SEQUENCE: 169

Leu Gln Lys Asn Ala Arg Pro Ala Ser Thr Glu Ser Val Asn Phe Gln
1               5                   10                  15

<210> SEQ ID NO 170
<211> LENGTH: 16
<212> TYPE: PRT
<213> ORGANISM: Artificial sequence
<220> FEATURE:

```
<223> OTHER INFORMATION: Synthetic sequence

<400> SEQUENCE: 170

Leu Gln Arg Gly Val Arg Ile Pro Ser Val Leu Glu Val Asn Gly Gln
1               5                   10                  15

<210> SEQ ID NO 171
<211> LENGTH: 16
<212> TYPE: PRT
<213> ORGANISM: Artificial sequence
<220> FEATURE:
<223> OTHER INFORMATION: Synthetic sequence

<400> SEQUENCE: 171

Leu Gln Arg Gly Asn Arg Pro Val Thr Thr Ala Asp Val Asn Thr Gln
1               5                   10                  15

<210> SEQ ID NO 172
<211> LENGTH: 16
<212> TYPE: PRT
<213> ORGANISM: Artificial sequence
<220> FEATURE:
<223> OTHER INFORMATION: Synthetic sequence

<400> SEQUENCE: 172

Leu Gln Lys Ala Asp Arg Gln Pro Gly Val Val Val Asn Cys Gln
1               5                   10                  15
```